US012700475B2

(12) United States Patent
Thomson et al.

(10) Patent No.: US 12,700,475 B2
(45) Date of Patent: Aug. 4, 2026

(54) SYSTEMS AND METHODS FOR DISSECTING HETEROGENEOUS CELL POPULATIONS

(71) Applicant: California Institute of Technology, Pasadena, CA (US)

(72) Inventors: Matthew W. Thomson, Los Angeles, CA (US); Siyu Chen, Los Angeles, CA (US); Paul Rivaud, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1229 days.

(21) Appl. No.: 16/574,108

(22) Filed: Sep. 18, 2019

(65) Prior Publication Data

US 2020/0090782 A1     Mar. 19, 2020

Related U.S. Application Data

(60) Provisional application No. 62/732,664, filed on Sep. 18, 2018, provisional application No. 62/733,044, filed on Sep. 18, 2018.

(51) Int. Cl.

| | |
|---|---|
| *G16B 20/00* | (2019.01) |
| *C12Q 1/6806* | (2018.01) |
| *C12Q 1/6869* | (2018.01) |
| *G16B 30/00* | (2019.01) |
| *G16B 40/10* | (2019.01) |
| *G16B 40/20* | (2019.01) |
| *G16B 50/00* | (2019.01) |

(52) U.S. Cl.
CPC ........... *G16B 20/00* (2019.02); *C12Q 1/6806* (2013.01); *C12Q 1/6869* (2013.01); *G16B 30/00* (2019.02); *G16B 40/10* (2019.02);

*G16B 40/20* (2019.02); *G16B 50/00* (2019.02); *C12Q 2535/122* (2013.01); *C12Q 2545/113* (2013.01)

(58) Field of Classification Search
None
See application file for complete search history.

(56) References Cited

U.S. PATENT DOCUMENTS 9,637,799 B2      5/2017    Fan et al.
2020/0176080 A1*   6/2020   Newman et al.

OTHER PUBLICATIONS

Scrucca, L., Fop, M., Murphy, T. B., & Raftery, A. E. (2016). mclust 5: Clustering, Classification and Density Estimation Using Gaussian Finite Mixture Models. The R journal, 8(1), 289-317. (Year: 2016).*

(Continued)

*Primary Examiner* — Anna Skibinsky
*Assistant Examiner* — Joseph Pulliam
(74) *Attorney, Agent, or Firm* — Dickinson Wright PLLC

(57) ABSTRACT

Gene expression vectors of two samples in a gene expression space can be transformed into gene feature vectors in a gene feature space. Gaussian densities and associated weights can be determined for each sample using the corresponding gene feature vectors. Gaussian densities of one samples can be aligned to Gaussian densities of the other sample. A difference between a pair of aligned Gaussian densities of the two samples can be determined, which indicates a difference between subpopulation of cells of the two samples represented by the Gaussian densities of the pair of aligned Gaussian densities.

30 Claims, 65 Drawing Sheets
(62 of 65 Drawing Sheet(s) Filed in Color)

PopAlign probabilistic modeling framework

(56)                    References Cited

OTHER PUBLICATIONS

Wang, N., Hoffman, E. P., Chen, L., Chen, L., Zhang, Z., Liu, C., Yu, G., Herrington, D. M., Clarke, R., & Wang, Y. (2016). Mathematical modelling of transcriptional heterogeneity identifies novel markers and subpopulations in complex tissues. Scientific reports, 6, 18909. (Year: 2016).*

Satija, Rahul et al. "Spatial Reconstruction of Single-Cell Gene Expression Data." Nature biotechnology 33.5 (2015): 495-502. Web. (Year: 2015).*

Azizi, Elham et al. "Single-Cell Map of Diverse Immune Phenotypes in the Breast Tumor Microenvironment." Cell 174.5 (2018): 1293-1308.e36. Web. (Year: 2018).*

Butler, Andrew et al. "Integrating Single-Cell Transcriptomic Data Across Different Conditions, Technologies, and Species." Nature biotechnology 36.5 (2018): 411-420. Web. (Year: 2018).*

Heimberg, Graham. "Statistical Inference of a Single Cell Gene Expression Model for Heterogeneous Tissues." ProQuest Dissertations & Theses, 2018 (Mar. 2018). Print. (Year: 2018).*

Wikipedia, "RNA-Seq", https://en.wikipedia.org/wiki/RNA-Seq, Last accessed on Aug. 7, 2024, Printed in 30 Pages.

Bolzoni et al., "IL21R expressing CD14+CD16+ monocytes expand in multiple myeloma patients leading to increased osteoclasts," Haematologica 2017, 102(4), 773-784.

Botta et al., "Myeloid-derived suppressor cells in multiple myeloma: pre-clinical research and translational opportunities," Frontiers in Oncology 2014, 4(348), 1-12.

Bronte et al., "Recommendations for myeloid-derived suppressor cell nomenclature and characterization standards," Nat Comm 2016, 7(12150), 1-10.

Brown, "Immunological functions of splenic B-lymphocytes," Crit Rev Immunol. 1992, 11(6), 395-417.

Buta et al., "Reconsidering pluripotency tests: Do we still need teratoma assays?" Stem Cell Research 2013, 11, 552-562.

Butler et al., "Integrating single-cell transcriptomic data across different conditions, technologies, and species," Nat Biotechnol. 2018, 36(5), 411-420.

Cahoy et al., "A Transcriptome Database for Astrocytes, Neurons, and Oligodendrocytes: A New Resource for Understanding Brain Development and Function," The Journal of Neuroscience 2008, 28(1), 264-278.

Candes et al., "Robust Principal Component Analysis?" J. Acm 2011, 58(3), 11, 1-37.2011.

Cao et al., "The single cell transcriptional landscape of mammalian organogenesis," Nature 2019, 566(7745), 496-502. doi:10.1038/s41586-019-0969-x.

Chen et al., "Dissecting heterogeneous cell populations across drug and disease conditions with PopAlign," bioRxiv 2020, 421354, in 35 pages.

Chen et al., "Dissecting heterogeneous cell-populations across signaling and disease conditions with PopAlign," bioRxiv 2018, 421354, in 33 pages.

Cover et al., "Elements of Information Theory, Second Edition," Wiley-Interscience 2006.

Dasgupta, "Learning Mixtures of Gaussians," Foundations of computer science IEEE 1999, 634-644.

Delneste et al., "Interferon-γ switches monocyte differentiation from dendritic cells to macrophages," Blood 2003, 101(1), 143-150.

Dempster et al., "Maximum Likelihood from Incomplete Data via the EM Algorithm," Journal of the Royal Statistical Society Series B (Methodological) 1977, 39(1) 1-38.

Deuse et al., "Hypoimmunogenic derivatives of induced pluripotent stem cells evade immune rejection in fully immunocompetent allogeneic recipients," Nat Biotechnol. 2019, 37(3), 252-258. doi:10.1038/s41587-019-0016-3.

Dewitt et al., "Selection-free Genome Editing of the Sickle Mutation in Human Adult Hematopoietic Stem/Progenitor Cells," Sci Transl Med. 2016, 8(360), 360ra134.

Ding et al., "Orthogonal Nonnegative Matrix Tri-Factorizations for Clustering," kdd06 2006.

Dixit et al., "Perturb-Seq: Dissecting Molecular Circuits with Scalable Single-Cell RNA Profiling of Pooled Genetic Screens," Cell 2016, 34(11), 1145-1160.

Döhner et al., "Acute Myeloid Leukemia," New England Journal of Medicine 2015, 373, 1136-1152.

Döhner et al., "Diagnosis and management of acute myeloid leukemia in adults: recommendations from an international expert panel, on behalf of the European LeukemiaNet," Blood 2010, 115(3), 453-474.

Donoho, "Compressed Sensing," IEEE Transactions on Information Theory 2006, 52(4), 1289-1306.

Dosani et al., "Significance of the absolute lymphocyte/monocyte ratio as a prognostic immune biomarker in newly diagnosed multiple myeloma," Blood Cancer Journal 2017, 7(e579), 1-4.

Ehrchen et al., "Glucocorticoids induce differentiation of a specifically activated, anti-inflammatory subtype of human monocytes," Blood 2007, 109, 1265-1274.

Faure-André et al., "Regulation of Dendritic Cell Migration by CD74, the MHC Class II: Associated Invariant Chain," Science 2008, 322, 1705-1710.

Fiebech et al., "The two-hit hypothesis for neuroinflammation: role of exogenous ATP in modulating inflammation in the brain," Frontiers in Cellular Neuroscience 2014, 8(260), 1-11.

Förstner et al., "A Metric for Covariance Matrices," Geodesy—The Challenge of the 3rd Millennium, Springer 2003, 299-309.

Gage et al., "Survival and differentiation of adult neuronal progenitor cells transplanted to the adult brain," Proc. Natl. Acad. Sci. USA 1995, 92, 11879-11883.

Gautier et al., "Gene expression profiles and transcriptional regulatory pathways underlying mouse tissue macrophage identity and diversity," Nat Immunol. 2012, 13(11), 1118-1128.

Gehring et al., "Highly Multiplexed Single-Cell RNA-seq for Defining Cell Population and Transcriptional Spaces," bioRxiv 2018, 315333, in 19 pages.

Giladi et al., "Single-Cell Genomics: A Stepping Stone for Future Immunology Discoveries," Cell 2018, 172, 14-21.

Gordon et al., "Monocyte and Macrophage Heterogeneity," Nature Reviews 2005, 5, 953-964.

Hack et al., "Regionalization and fate specification in neurospheres: the role of Olig2 and Pax6," Mol. Cell. Neurosci. 2004, 25, 664-678.

Haghverdi et al., "Batch effects in single-cell RNA-sequencing data are corrected by matching mutual nearest neighbors," Nature biotechnology 2018, 36(5), 421-427.

Heimberg et al., "Low Dimensionality in Gene Expression Data Enables the Accurate Extraction of Transcriptional Programs from Shallow Sequencing," Cell Systems 2016, 2, 239-250.

Hinton et al., "Reducing the Dimensionality of Data with Neural Networks," Science 2006, 313(504), 1-9.

Hirsch et al., "Regeneration of the entire human epidermis by transgenic stem cells," Nature 2017, 551(7680), 327-332.

Horning, "A new cancer ecosystem," Science 2017, 355(6330), 1103.

Huber, "Projection Pursuit," The Annals of Statistics 1985, 13(2), 435-475.

International Search Report and Written Opinion dated Jan. 3, 2020 in PCT Application No. PCT/US2019/051614.

Kouchkovsky et al., "Acute myeloid leukemia: a comprehensive review and 2016 update," Blood Cancer Journal 2016, 6, e441, 1-10.

Kumar et al., "Deconstructing transcriptional heterogeneity in pluripotent stem cells," Nature 2014, 516(7529), 56-61.

Kumar et al., "Multiple myeloma," Nature Reviews Disease Primers 2017, 3, 17046.

La Manno et al., "Molecular Diversity of Midbrain Development in Mouse, Human, and Stem Cells," Cell 2016, 167, 566-580.

Lim et al., "The Principles of Engineering Immune Cells to Treat Cancer," Cell. 2017, 168(4), 724-740.

Lipshultz et al., "The Effect of Dexrazoxane on Myocardial Injury in Doxorubicin-Treated Children with Acute Lymphoblastic Leukemia," N. Engl. J. Med. 2004, 351, 145-153.

(56)                    References Cited

OTHER PUBLICATIONS

Maaten, "Visualizing Data using t-SNE," Journal of Machine Learning Research 2008, 9, 2579-2605.

Mackay, "Information Theory, Inference and Learning Algorithms," Cambridge University Press 2003.

Macosko et al., "Highly parallel genome-wide expression profiling of individual cells using nanoliter droplets," Cell. 2015, 161(5), 1202-1214.

Malek et al., "Myeloid-derived Suppressor Cells: The Green Light for Myeloma Immune Escape," Blood Rev. 2016, 30(5), 341-348.

Mcginnis et al., "Multi-seq: Scalable sample multiplexing for single-cell RNA sequencing using lipid-tagged indices," bioRxiv 2018, 387241.

Molyneaux et al., "Neuronal subtype specification in the cerebral cortex," Nature reviews Neuroscience 2007, 8(6), 427-437.

Mosser et al., "Exploring the full spectrum of macrophage activation," Nat Rev Immunol. 2008, 8(12), 958-969.

Mueller et al., "Regulation of T cell survival through coronin-1-mediated generation of inositol-1,4,5-trisphosphate and calcium mobilization after T cell receptor triggering," Nat. Immunol. 2008, 9, 424-431.

Müller et al., "Glucocorticoids Induce Effector T Cell Depolarization via ERM Proteins, Thereby Impeding Migration and APC Conjugation," J. Immunol. 2013, 190, 4360-4370.

Mumford et al., "Pattern Theory: The Stochastic Analysis of Real-World Signals," AK Peters/CRC Press 2010.

Murphy et al., "Janeway's Immunobiology, 9th edition," CRC Press 2016.

Newton et al., "Signaling in Innate Immunity and Inflammation," Cold Spring Harb Perspect Biol 2012, 4(3) pii: a006049, 1-19.

Pessoa-Magalhães et al., "Analysis of the immune system of multiple myeloma patients achieving long-term disease control by multidimensional flow cytometry," Haematologica 2012, 98(1), 79-86.

Pienta et al., "Ecological Therapy for Cancer: Defining Tumors Using an Ecosystem Paradigm Suggests New Opportunities for Novel Cancer Treatments," Translational Oncology 2008, 1(4), 158-164.

Pilarski et al., "Humoral Immune Deficiency in Multiple Myeloma Patients Due to Compromised B-Cell Function," Journal of Clinical Immunology 1986, 6(6), 491-501.

Quake, "Single-cell transcriptomic characterization of 20 organs and tissues from individual mice creates a Tabula Muris," bioRxiv 2018, 237446.

Rawstron et al., "B-lymphocyte suppression in multiple myeloma is a reversible phenomenon specific to normal B-cell progenitors and plasma cell precursors," British Journal of Haematology 1998, 100, 176-183.

Ribatti et al., "Macrophages in multiple myeloma, " Immunology Letters 2014, 161, 241-244.

Rosenberg et al., "Single-cell profiling of the developing mouse brain and spinal cord with split-pool barcoding," Science 2018, 360, 176-182.

Sanchez et al., "Stochastic models of transcription: From single molecules to single cells," Methods 2013, 62, 13-25.

Schiebinger et al., "Reconstruction of developmental landscapes by optimal-transport analysis of single-cell gene expression sheds light on cellular re-programming," bioRxiv 2017, 191056.

Setty et al., "Wishbone identifies bifurcating developmental trajectories from single-cell data," Nat Biotechnol. 2016, 34(6), 637-645.

Singer et al., "Dynamic Heterogeneity and DNA Methylation in Embryonic Stem Cells," Molecular Cell 2014, 55, 319-331.

Stubbington, "Single-cell transcriptomics to explore the immune system in health and disease," Science 2017, 358, 58-63.

Sun et al., "Inference of differentiation time for single cell transcriptomes using cell population reference data," Nature Communications 2017, 8(1586), 1-12.

Tabula Muris Consortium, "Single-cell transcriptomics of 20 mouse organs creates a Tabula Muris," Nature 2018, 562(7727), 367-372.

Takaba et al., "The Mechanisms of T Cell Selection in the Thymus," Trends in Immunology 2017, 38(11) 805-816.

Tanay et al., "Single cell genomics: from phenomenology to mechanism," Nature 2017, 541(7637), 331-338.

Tirosh et al., "Dissecting the multicellular ecosystem of metastatic melanoma by single-cell RNA-seq," Science 2016, 352(6282), 189-196.

Trapnell et al., "The dynamics and regulators of cell fate decisions are revealed by pseudotemporal ordering of single cells," Nat Biotechnol. 2014, 32(4), 381-391.

Trapnell, "Defining cell types and states with single-cell genomics," Genome Research 2015, 25, 1491-1498.

Van De Laar et al., "Regulation of dendritic cell development by GM-CSF: molecular control and implications for immune homeostasis and therapy," Blood 2012, 119(15) 3383-3393.

Villani et al., "Systems Immunology: Learning the Rules of the Immune System," Annu Rev Immunol. 2018, 36, 813-842.

Vitak et al., "Sequencing thousands of single-cell genomes with combinatorial indexing," Nature Methods 2017, 14(3), 302-309.

Wagner et al., "Revealing the vectors of cellular identity with single-cell genomics," Nat Biotechnol. 2016, 34(11), 1145-1160.

Watanabe et al., "Algebraic Geometry and Statistical Learning Theory," Cambridge University Press 2009.

Winqvist et al., "In Vivo Effects of Lenalidomide on T Cell Proliferation and Immune Checkpoint Molecules in Patients with Advanced Stage CLL: Results from a Phase II Study" Blood 2015, 126(23), 4164.

Zaheer et al., "Deep Sets," Advances in Neural Information Processing Systems 2017, 30, 3391-3401.

Zeisel et al., "Cell types in the mouse cortex and hippocampus revealed by single-cell RNA-seq," Science 2015, 347(622) 1138-1142.

Zhang et al., "Thymosin beta 10 is a key regulator of tumorigenesis and metastasis and a novel serum marker in breast cancer," Breast Cancer Res. 2017, 19, 1-15.

Zheng et al., "Massively parallel digital transcriptional profiling of single cells," Nat Comm 2016, 8(14049), 1-12.

\* cited by examiner

PopAlign probabilistic modeling framework

$$P(x) = \sum_i c_i \mathcal{N}(\mu_i, \Sigma_i)$$

RANK samples
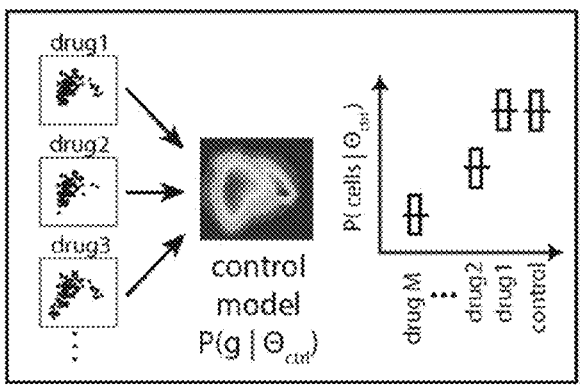
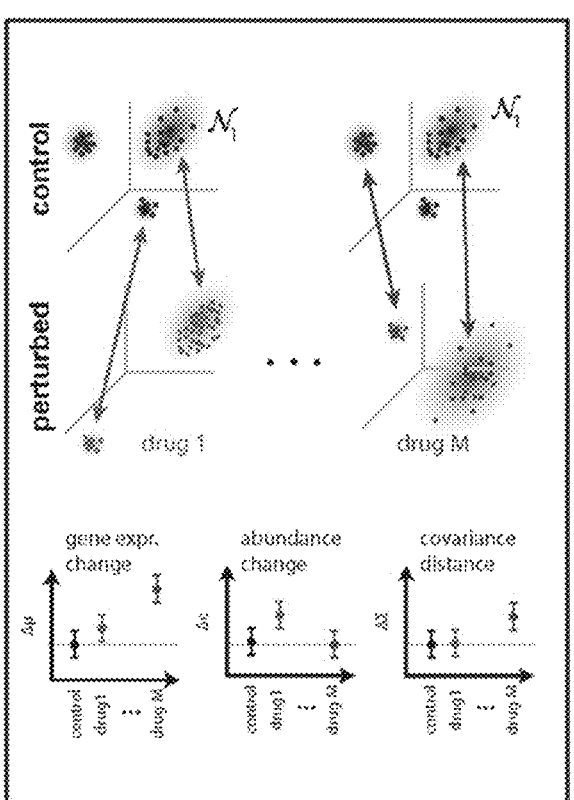
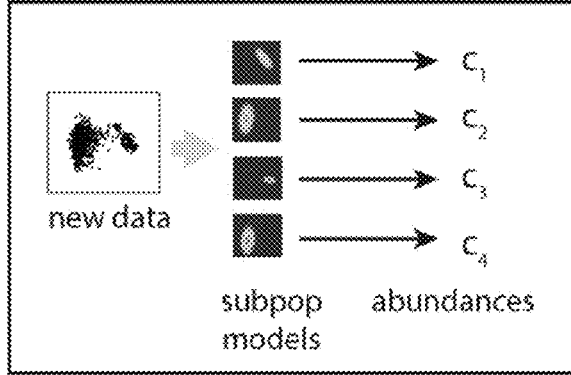
QUERY new data using reference models
ALIGN subpopulations across all
samples and quantify $\Delta\mu$, $\Delta\Sigma$, and $\Delta c$
*FIG. 1 (Cont'd)*

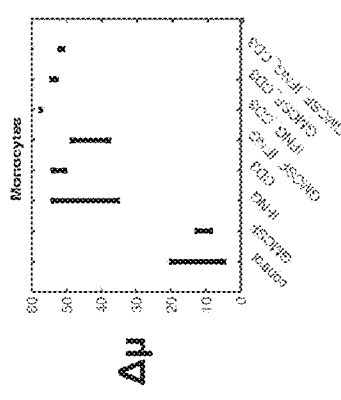
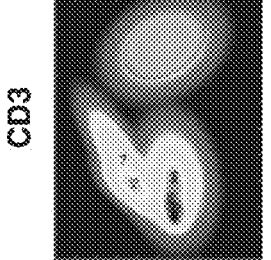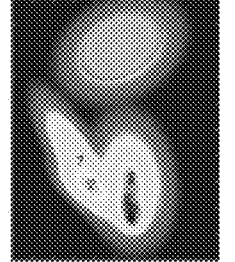
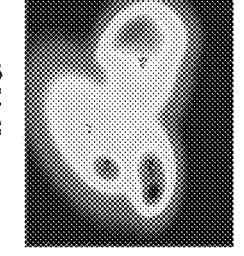
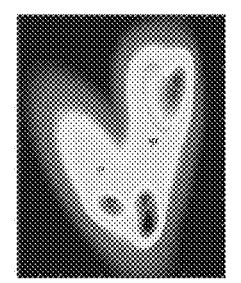
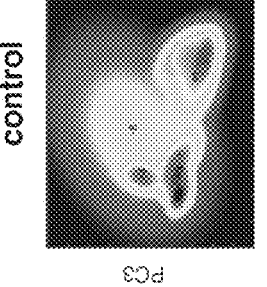
*FIG. 5*

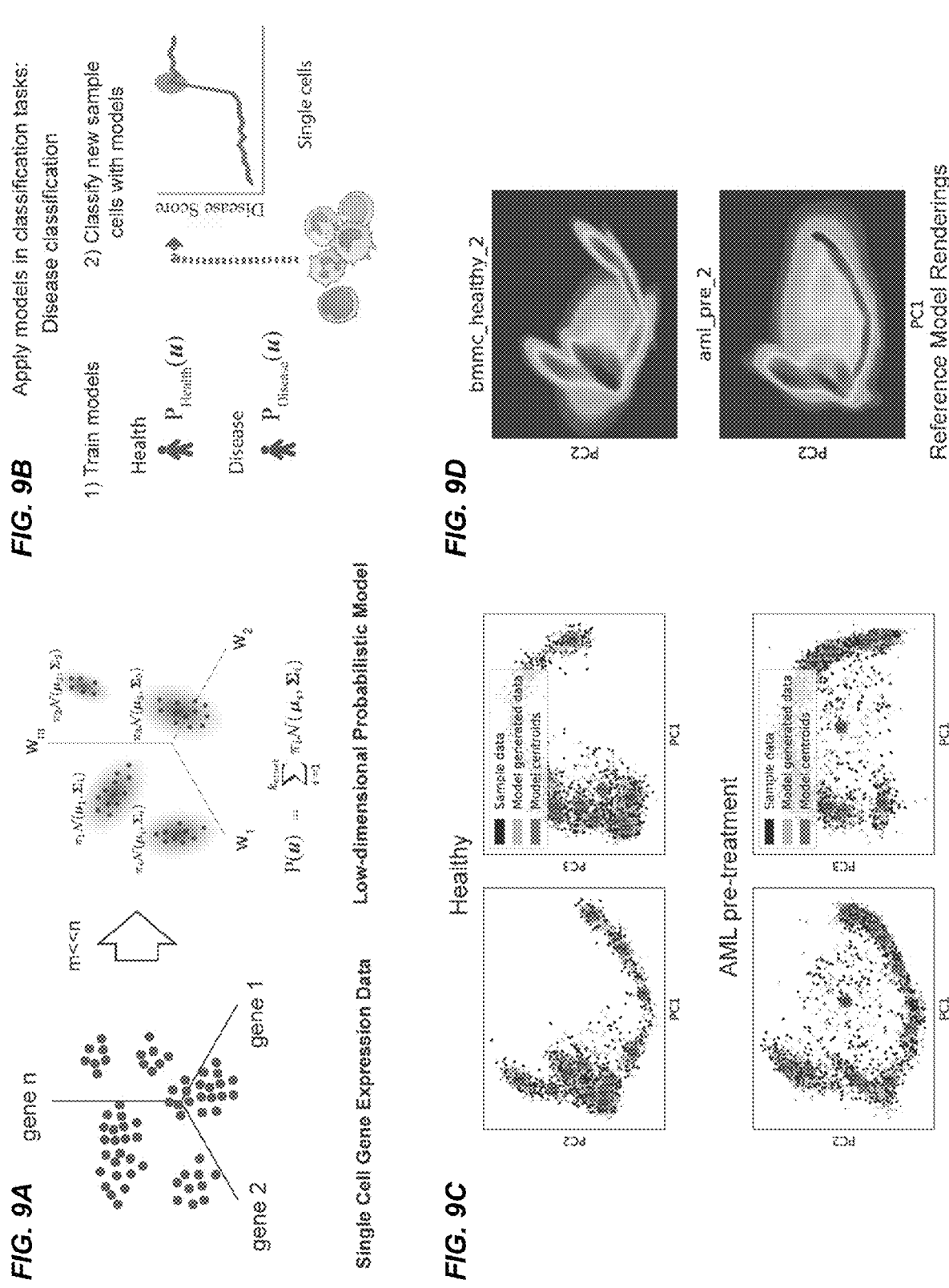

Classification of HIV patient samples

Model Renderings

Sample classification accuracy
100 iteration(s) with 10 random cell(s)

Classification of AML patient samples

Sample classification accuracy
100 iteration(s) with 10 random cell(s)

Sample classification accuracy
100 iteration(s) with 100 random cell(s)

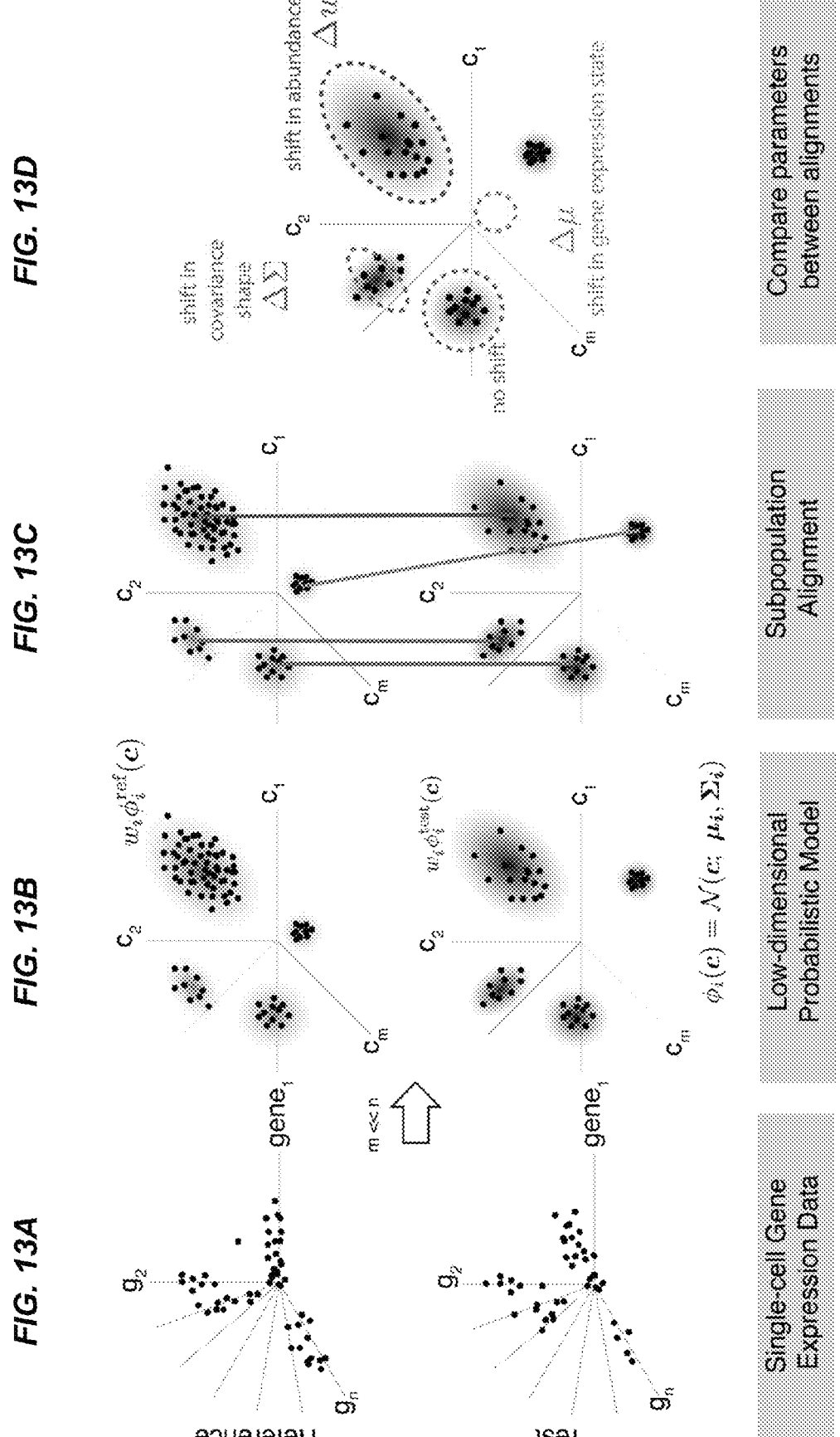

Mammary Gland

Tabula Muris Annotations:
B cell
T cell
macrophage
stromal cell
endothelial cell
basal cell
luminal epithelial cell Limb Muscle Tabula Muris Annotations:
B cell
T cell
macrophage
endothelial cell
mesenchymal stem cell
skeletal muscle satellite cell

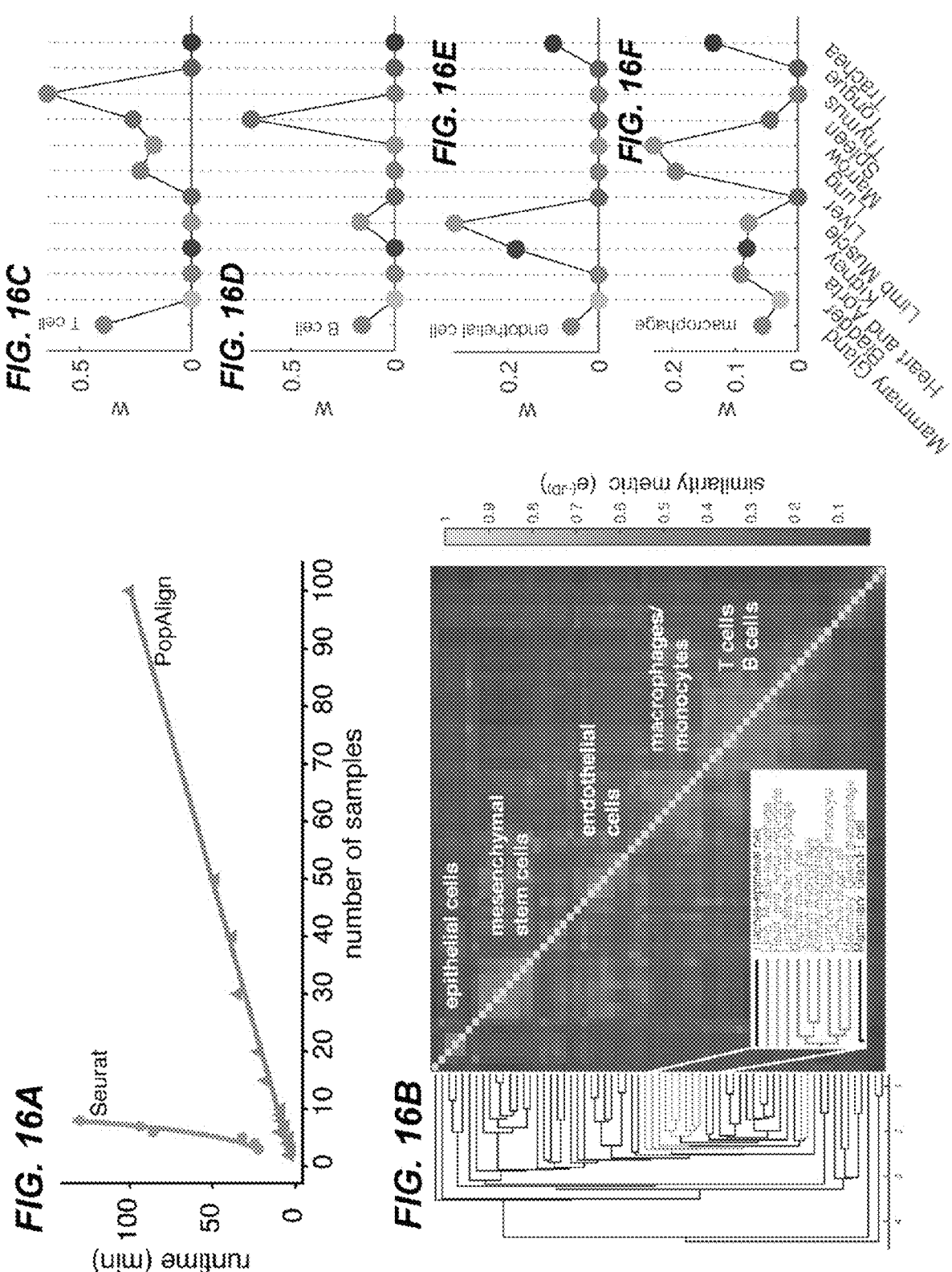

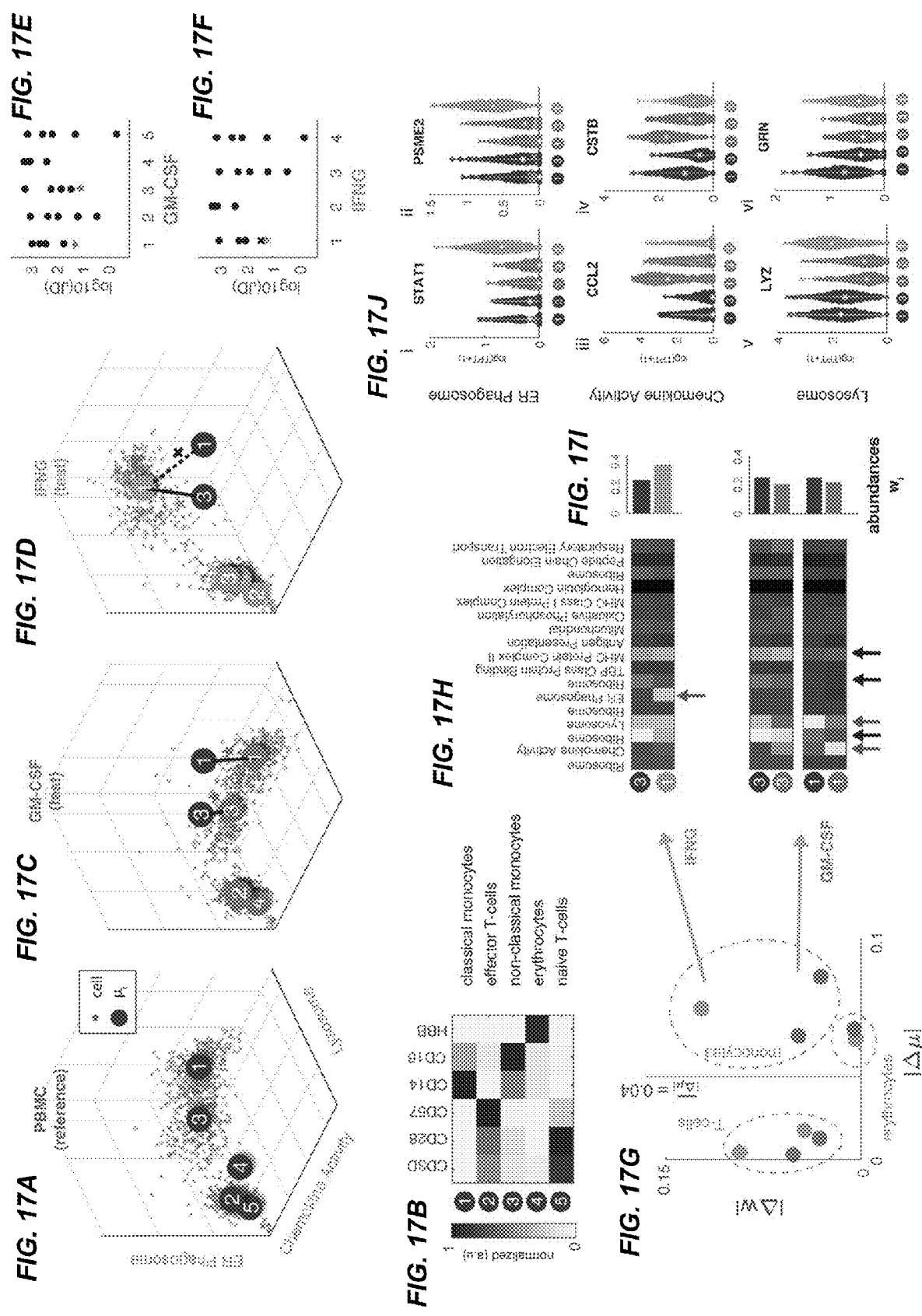

*FIG. 18G*
*FIG. 18H*
*FIG. 18K*
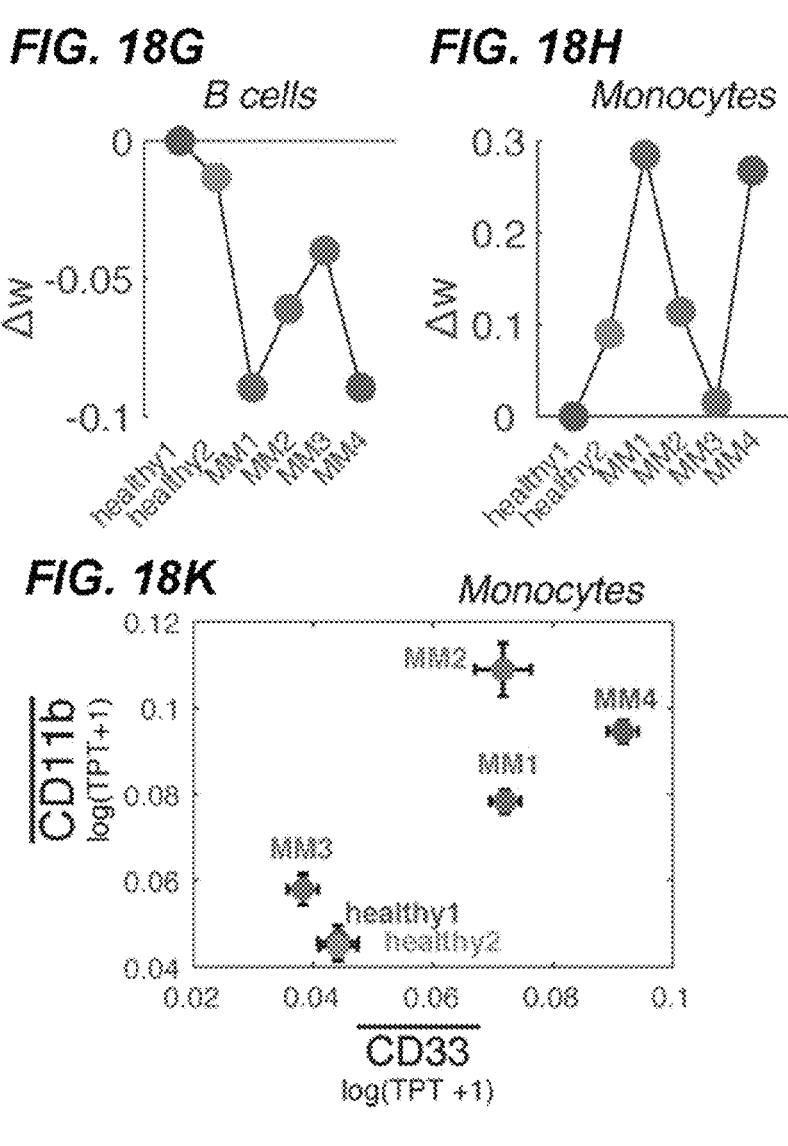
*FIG. 18O*
*FIG. 18P*
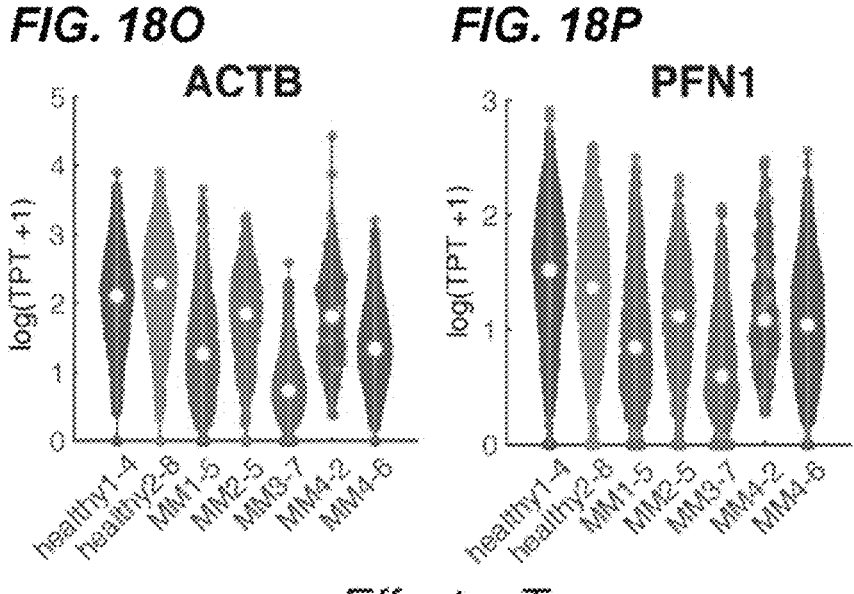
*Effector T*

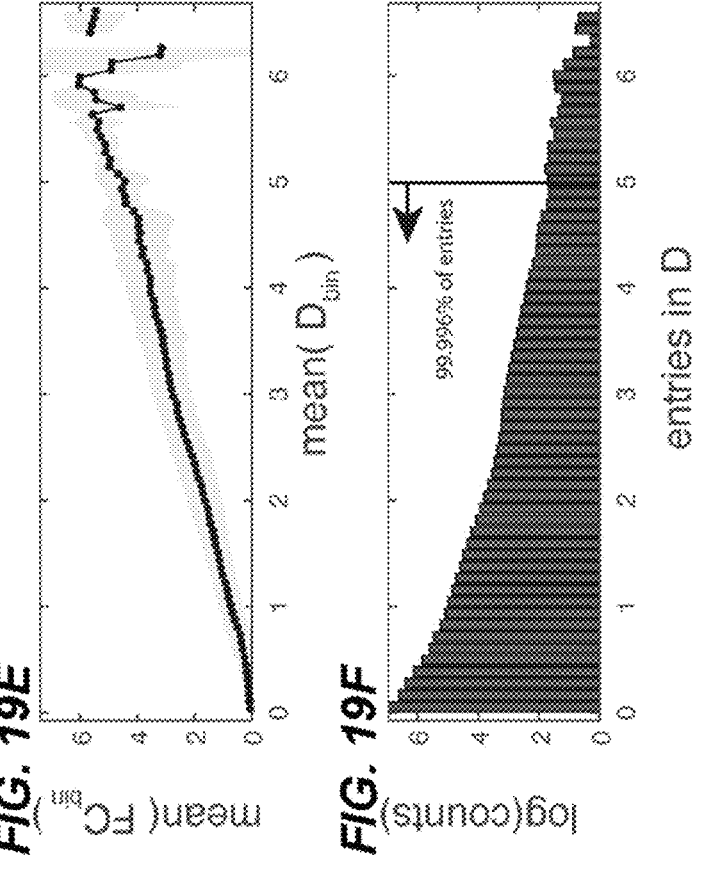
FIG. 19E
FIG. 19F
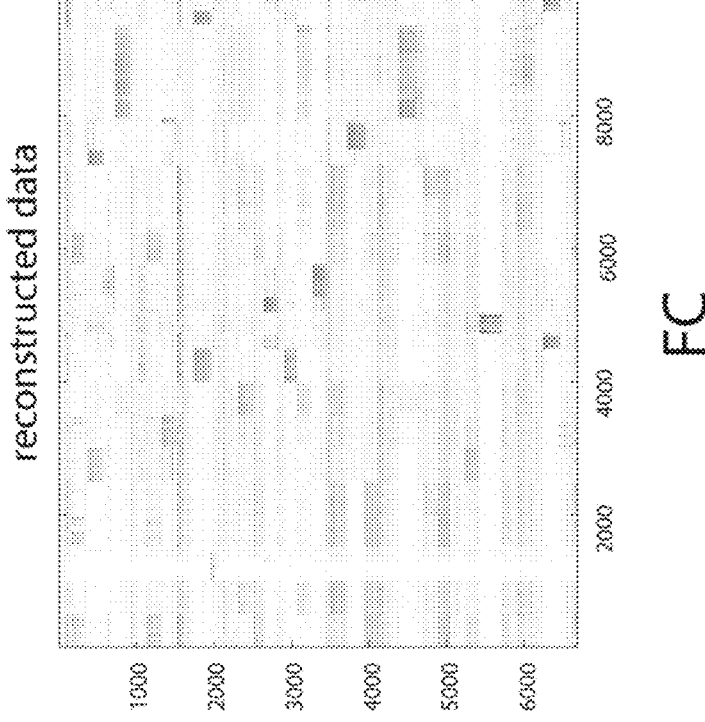
FIG. 19D

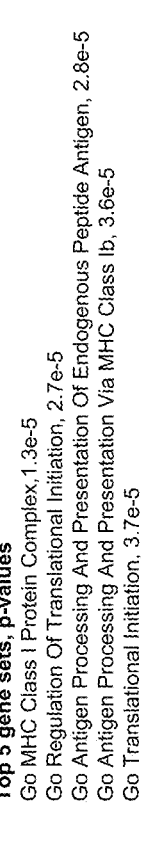

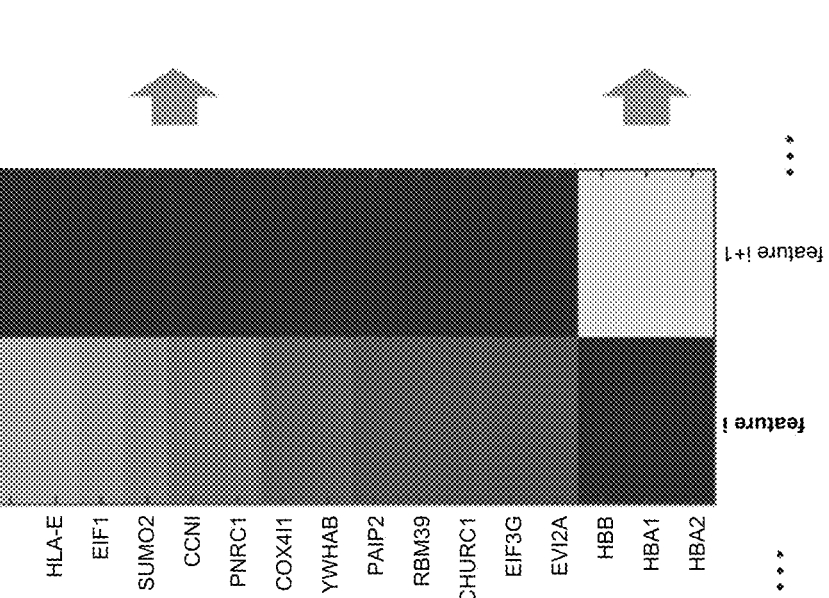

FIG. 19G

Top 5 gene sets, p-values
Go MHC Class I Protein Complex, 1.3e-5
Go Regulation Of Translational Initiation, 2.7e-5
Go Antigen Processing And Presentation Of Endogenous Peptide Antigen, 2.8e-5
Go Antigen Processing And Presentation Via MHC Class Ib, 3.6e-5
Go Translational Initiation, 3.7e-5

Top 5 gene sets, p-values
Go Hemoglobin Complex, 1e-12
Go Oxygen Transport, 3e-12
Go Gas Transport, 1.3e-11
Biocarta AHSP Pathway, 1e-9
Go Oxygen Binding, 1.7e-9

HLA-E
EIF1
SUMO2
CCNI
PNRC1
COX4I1
YWHAB
PAIP2
RBM39
CHURC1
EIF3G
EVI2A
HBB
HBA1
HBA2 feature i    feature i+1

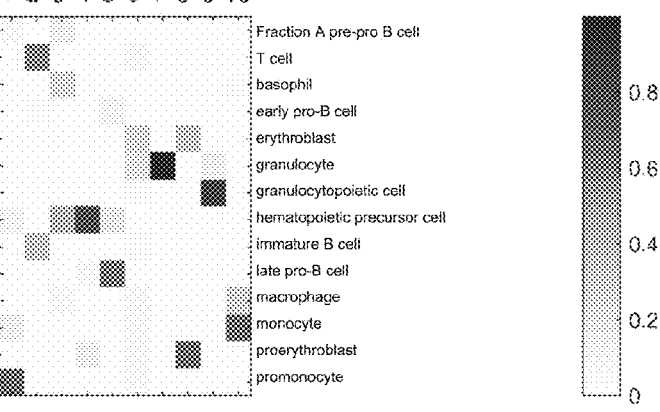
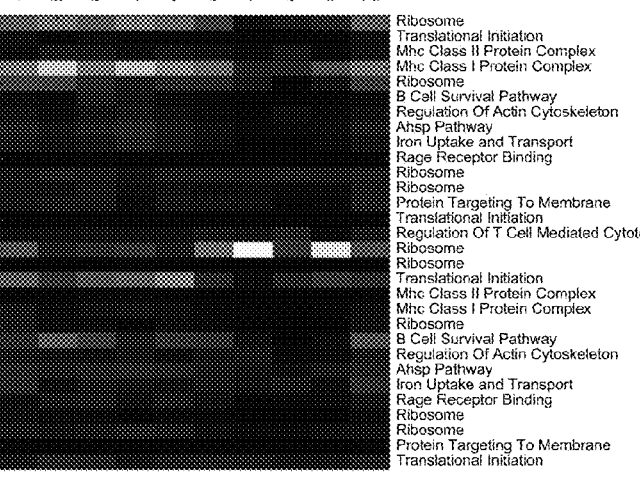
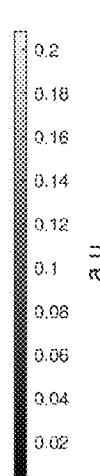
FIG. 21A

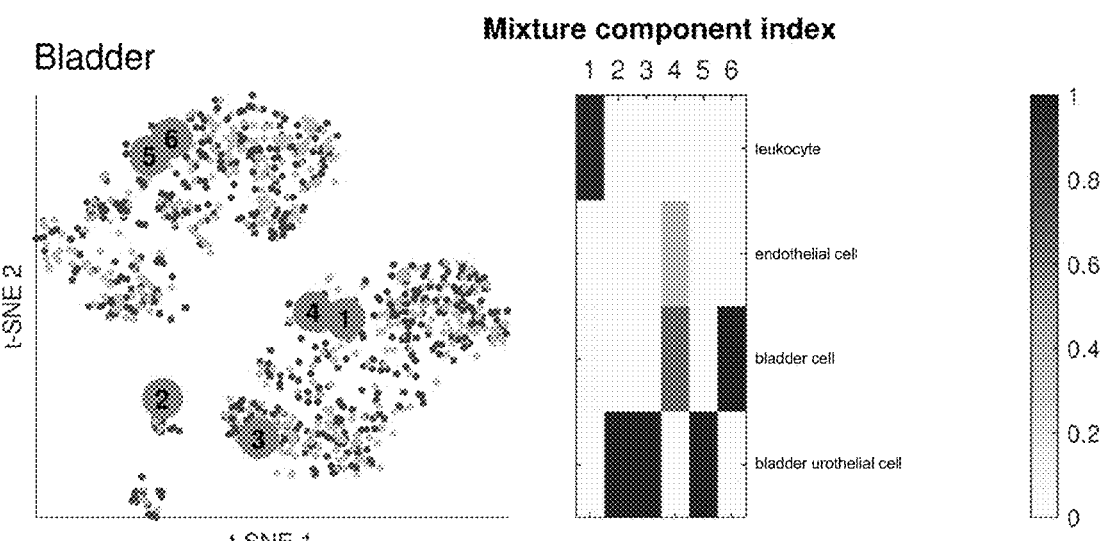
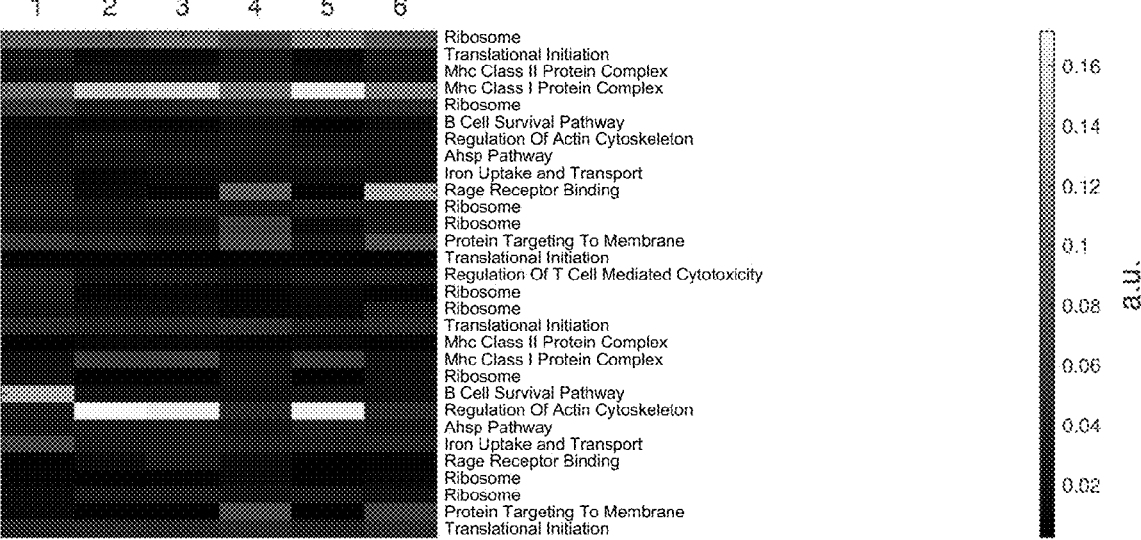
FIG. 21B

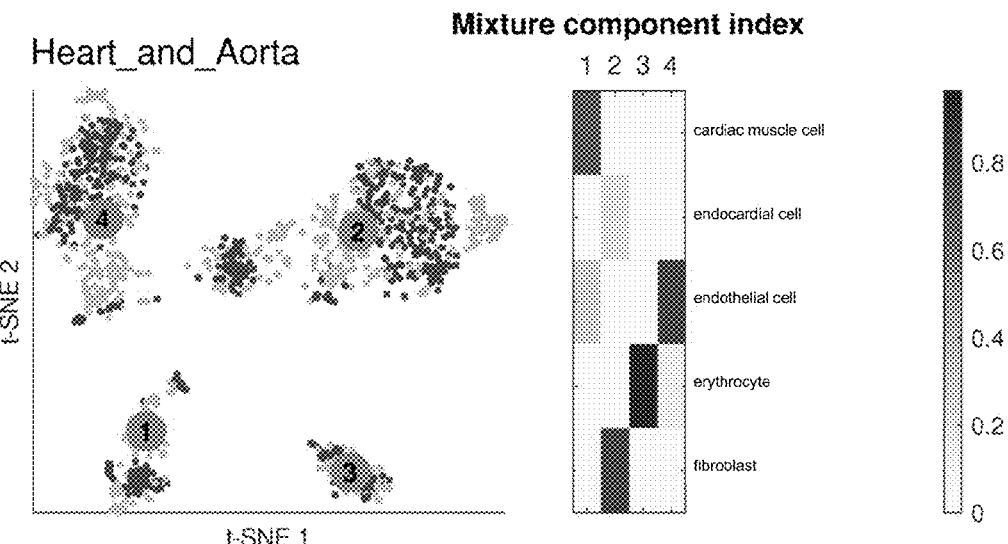
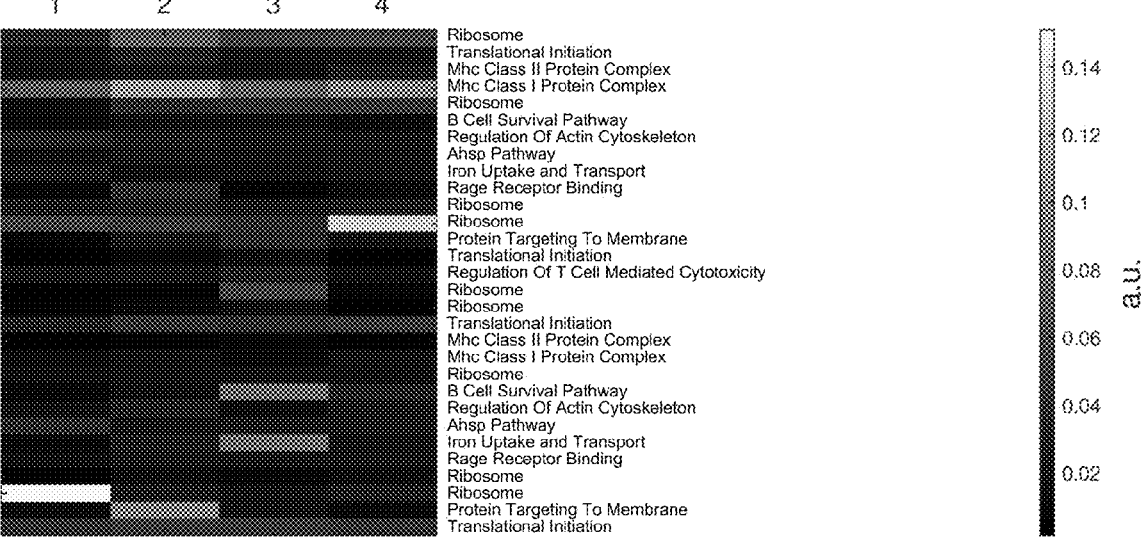
FIG. 21C

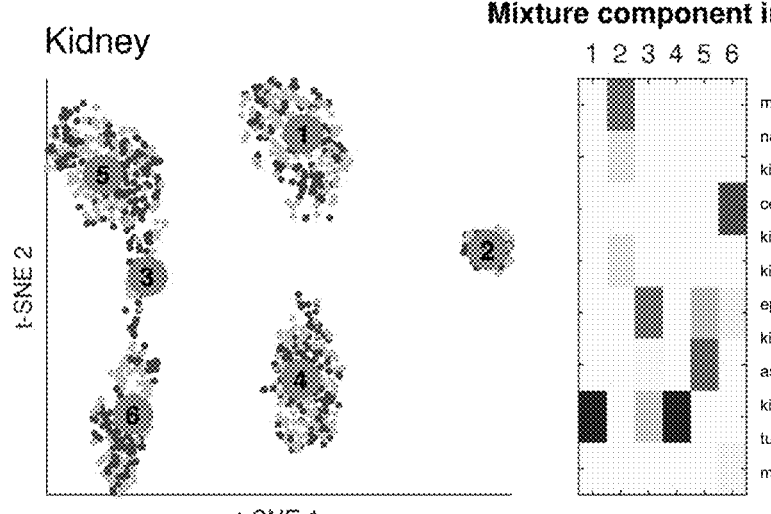
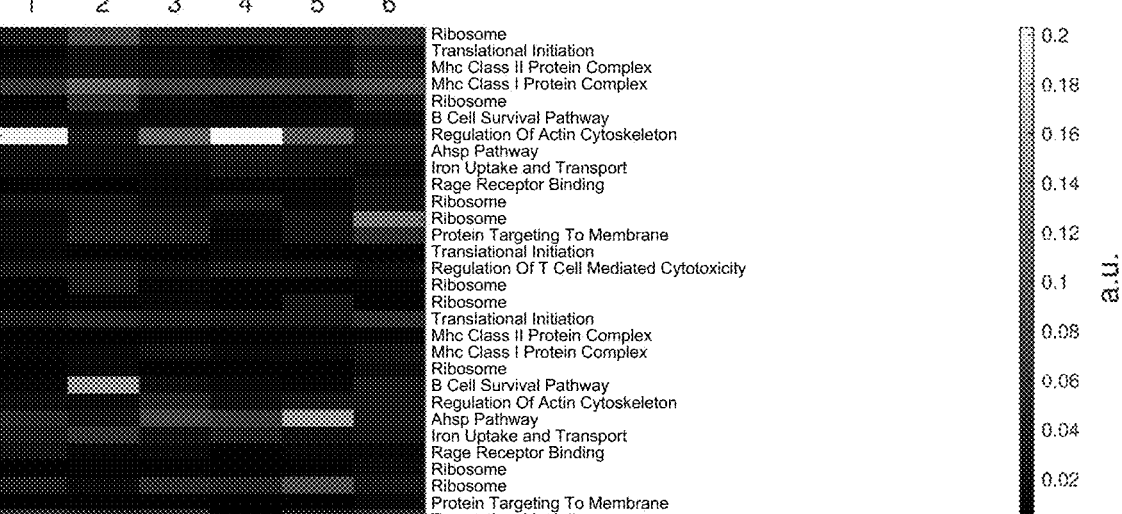
FIG. 21D

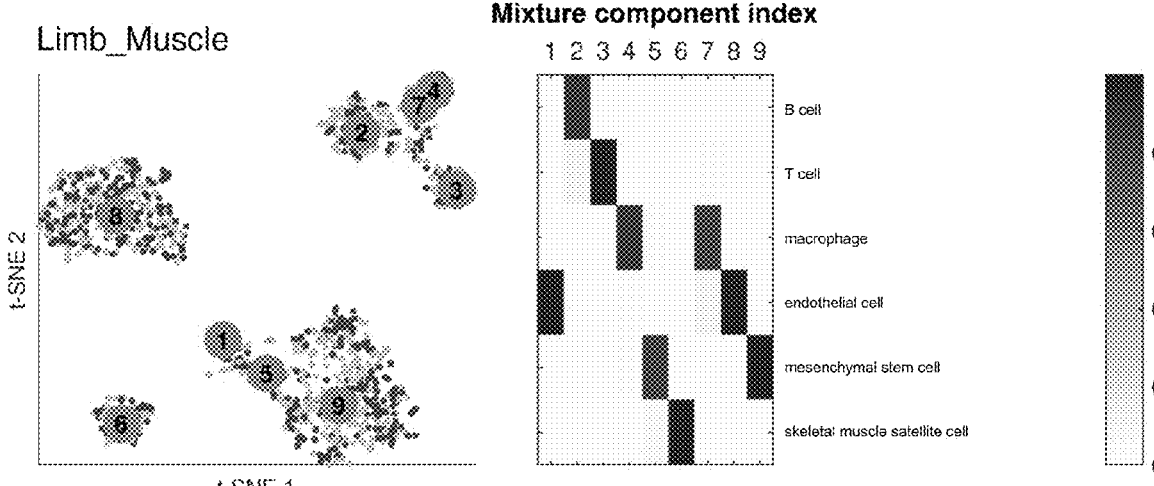
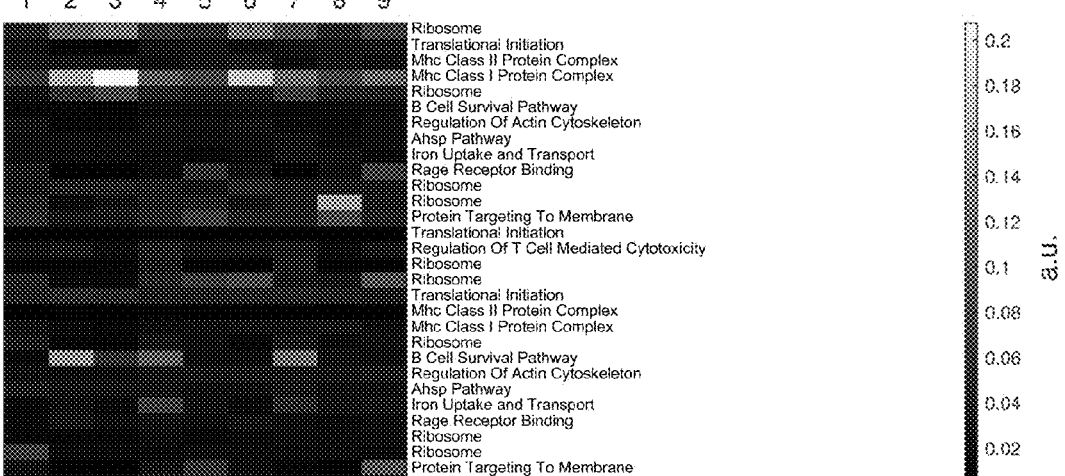
*FIG. 21E*

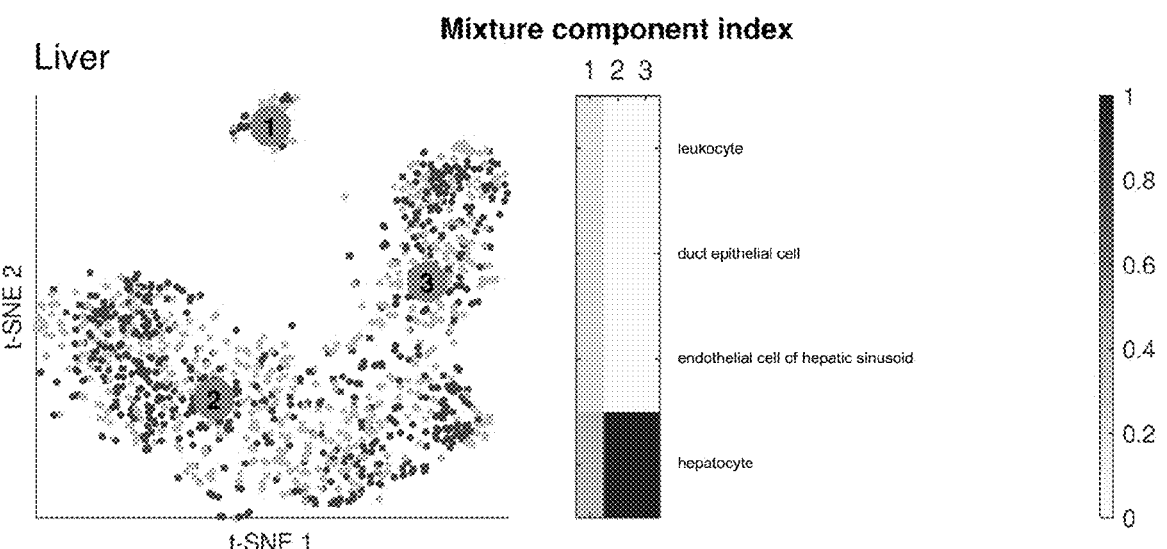
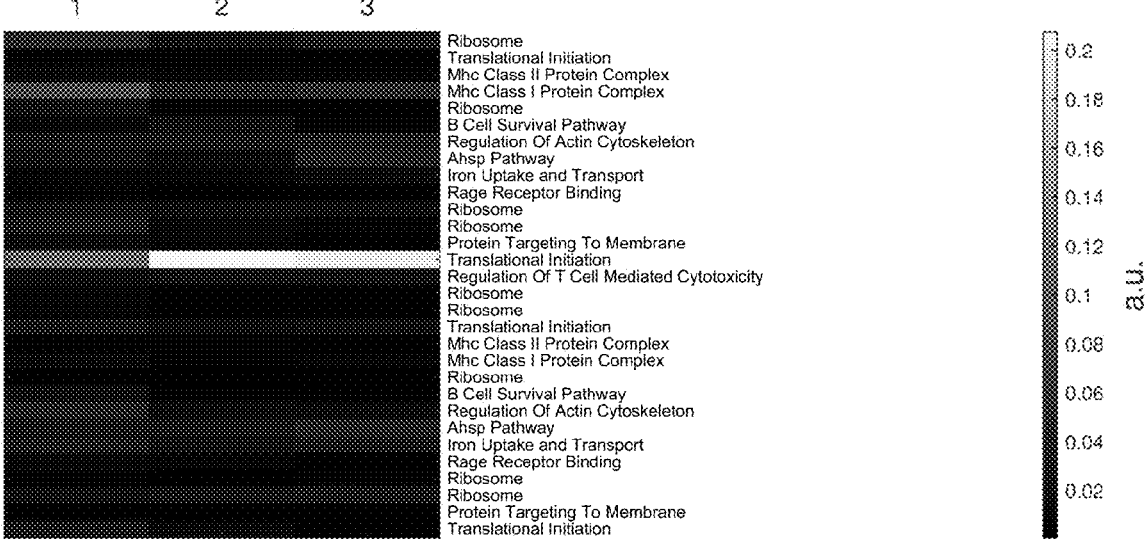
*FIG. 21F*

Lung
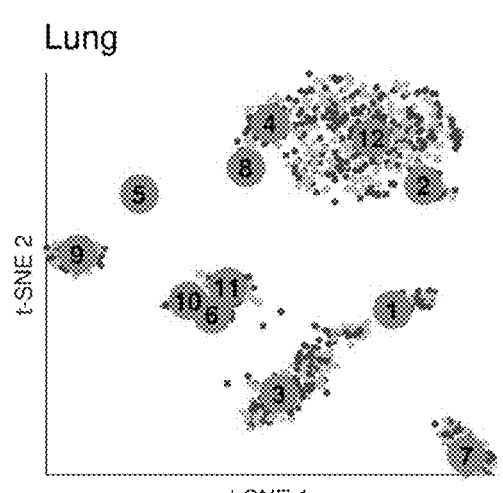
Mixture component index
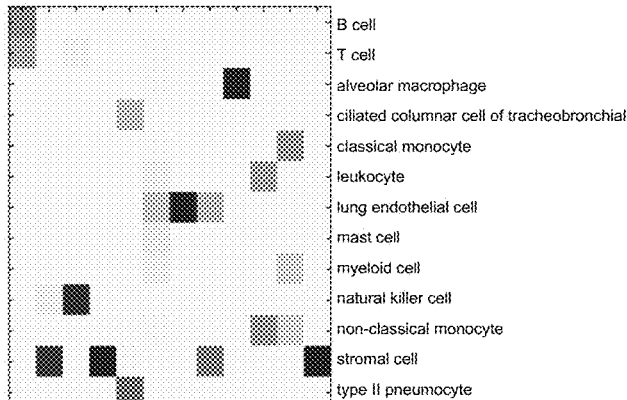
Mixture component index
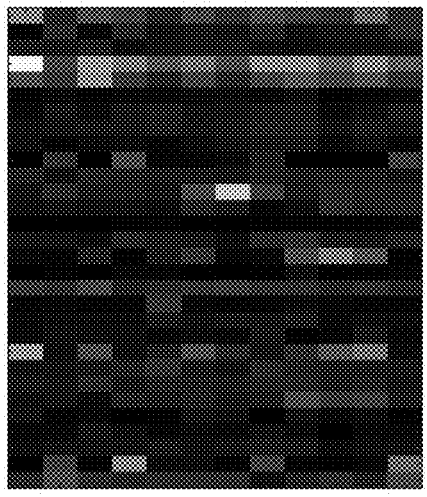
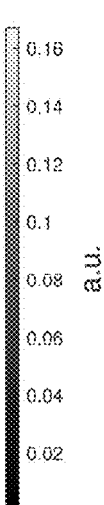
FIG. 21G Mammary_Gland
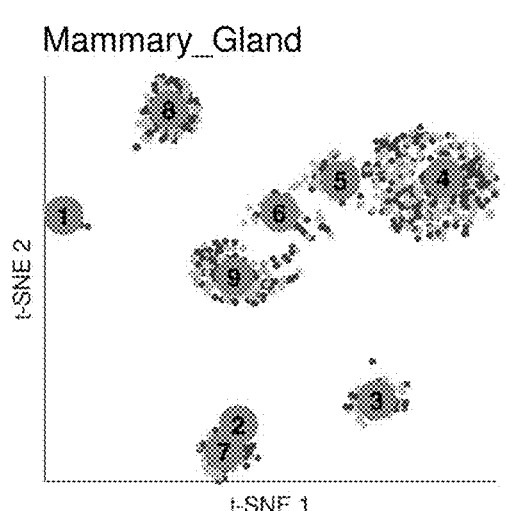
Mixture component index
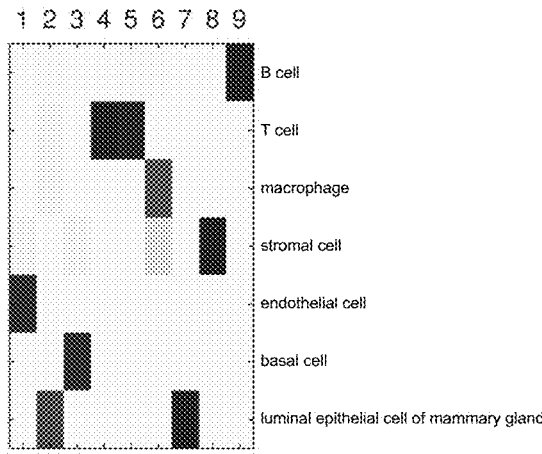
Mixture component index
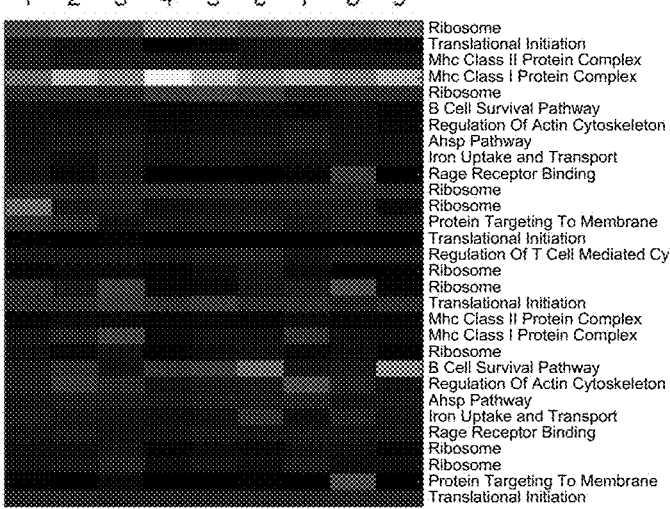
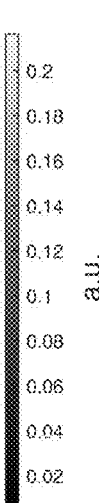
*FIG. 21H*

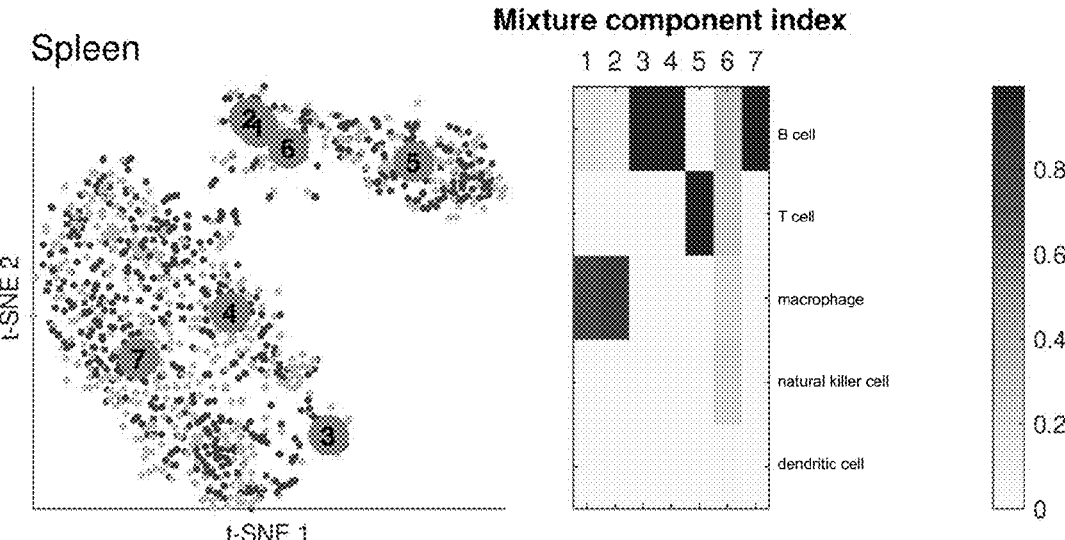
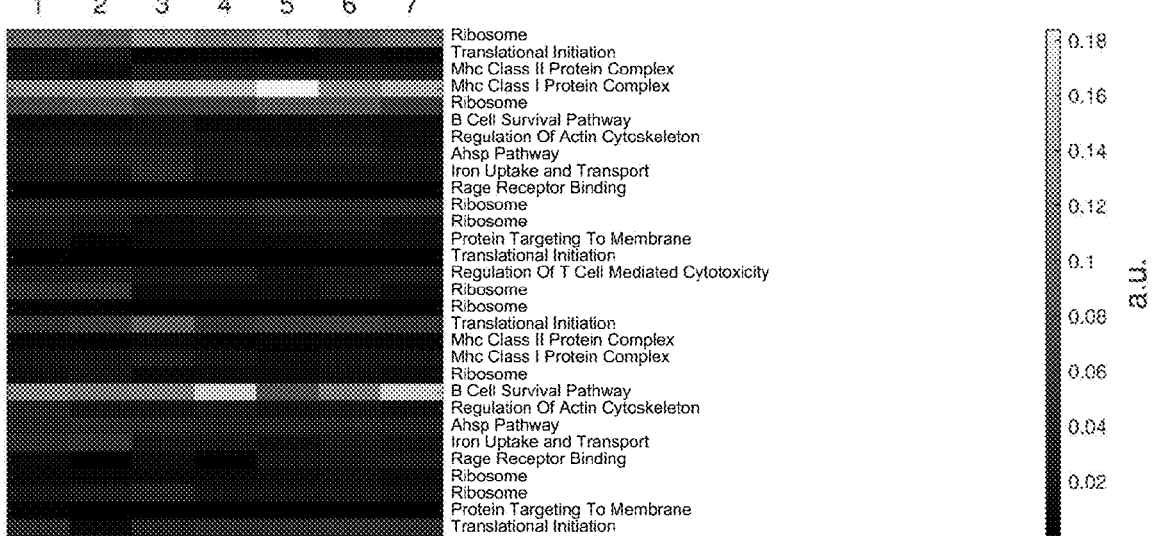
*FIG. 21I*

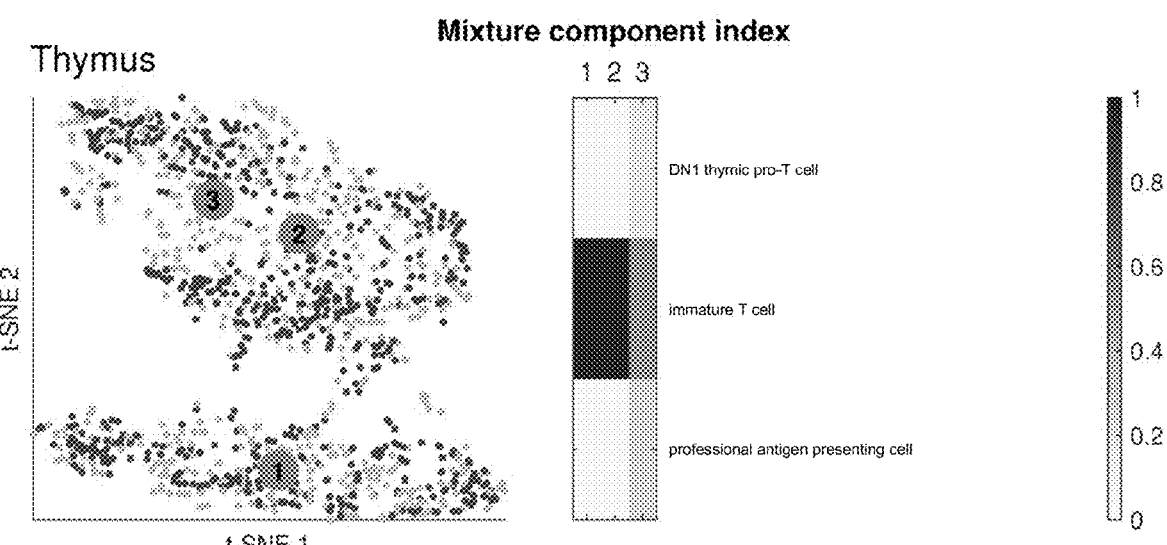
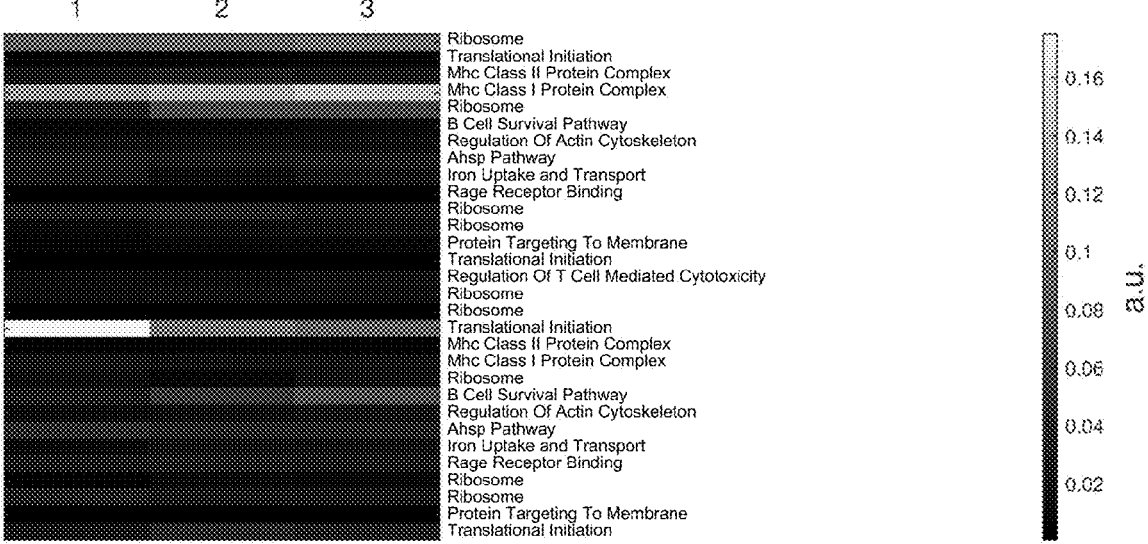
FIG. 21J

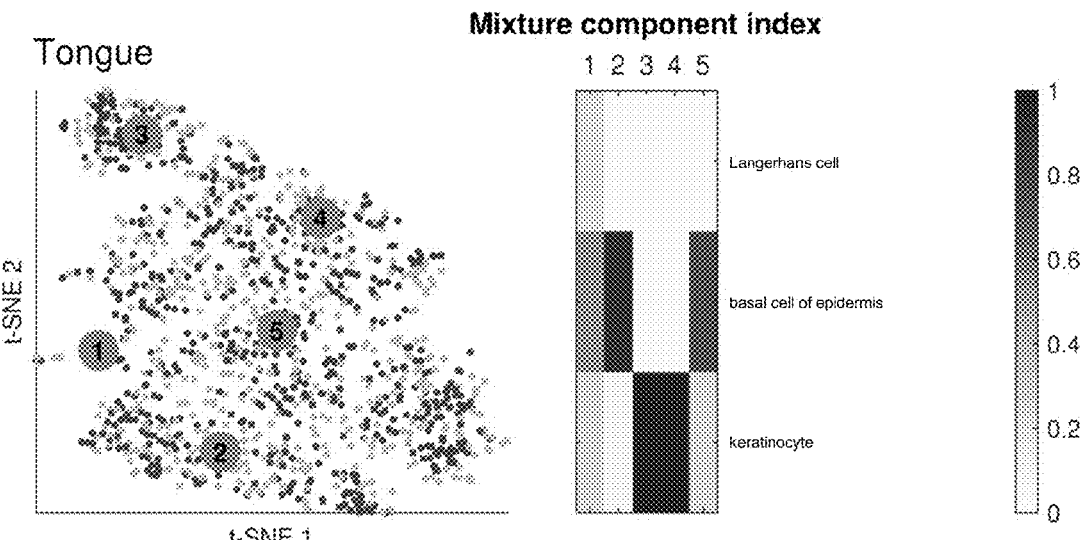
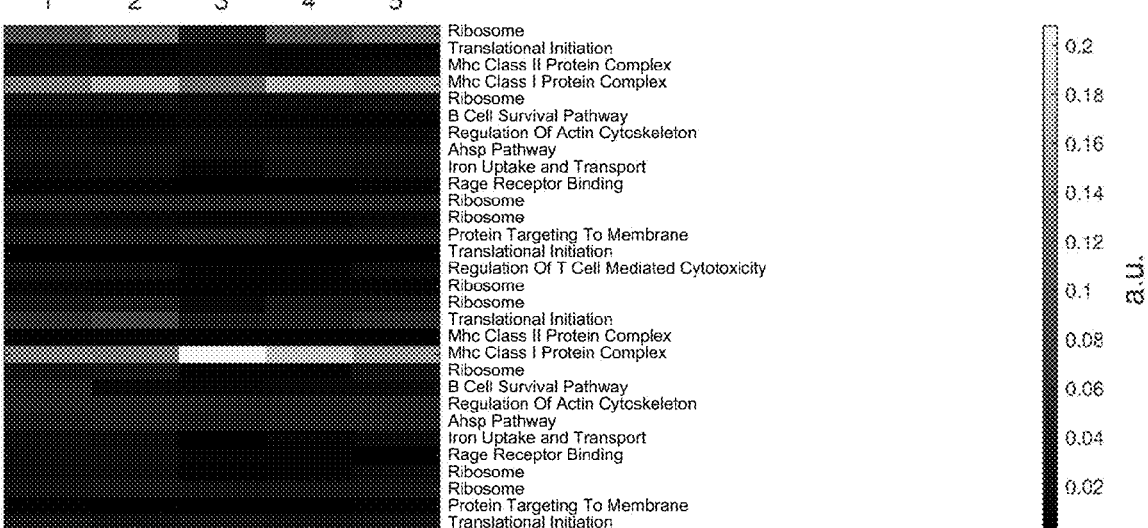
*FIG. 21K*

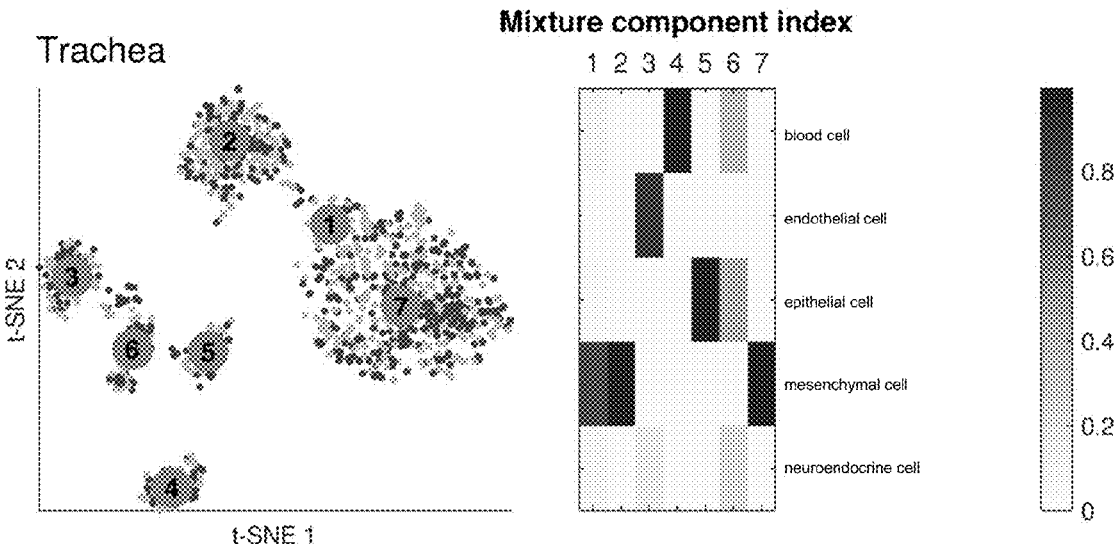
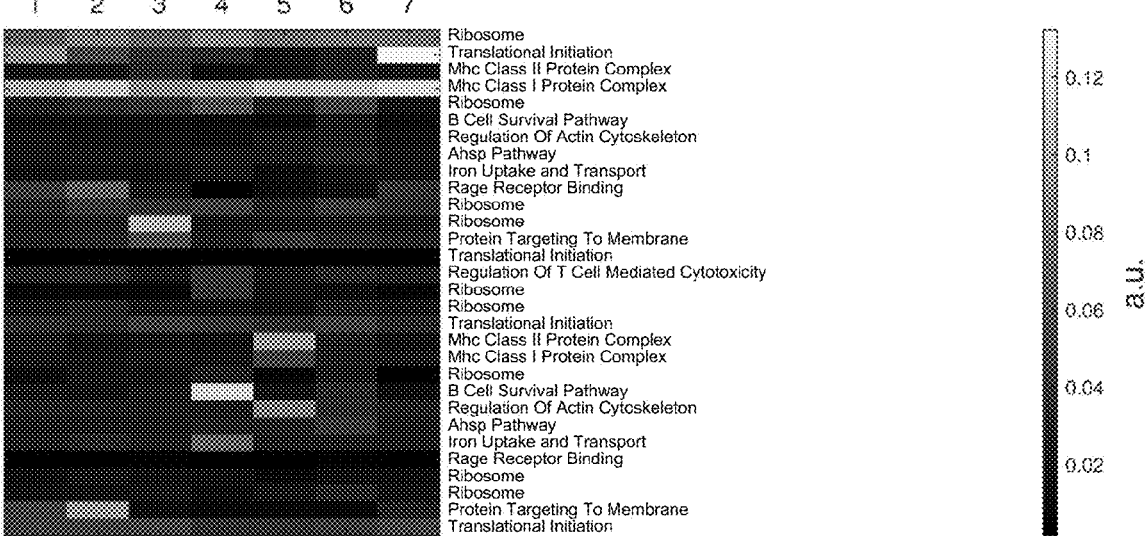
FIG. 21L

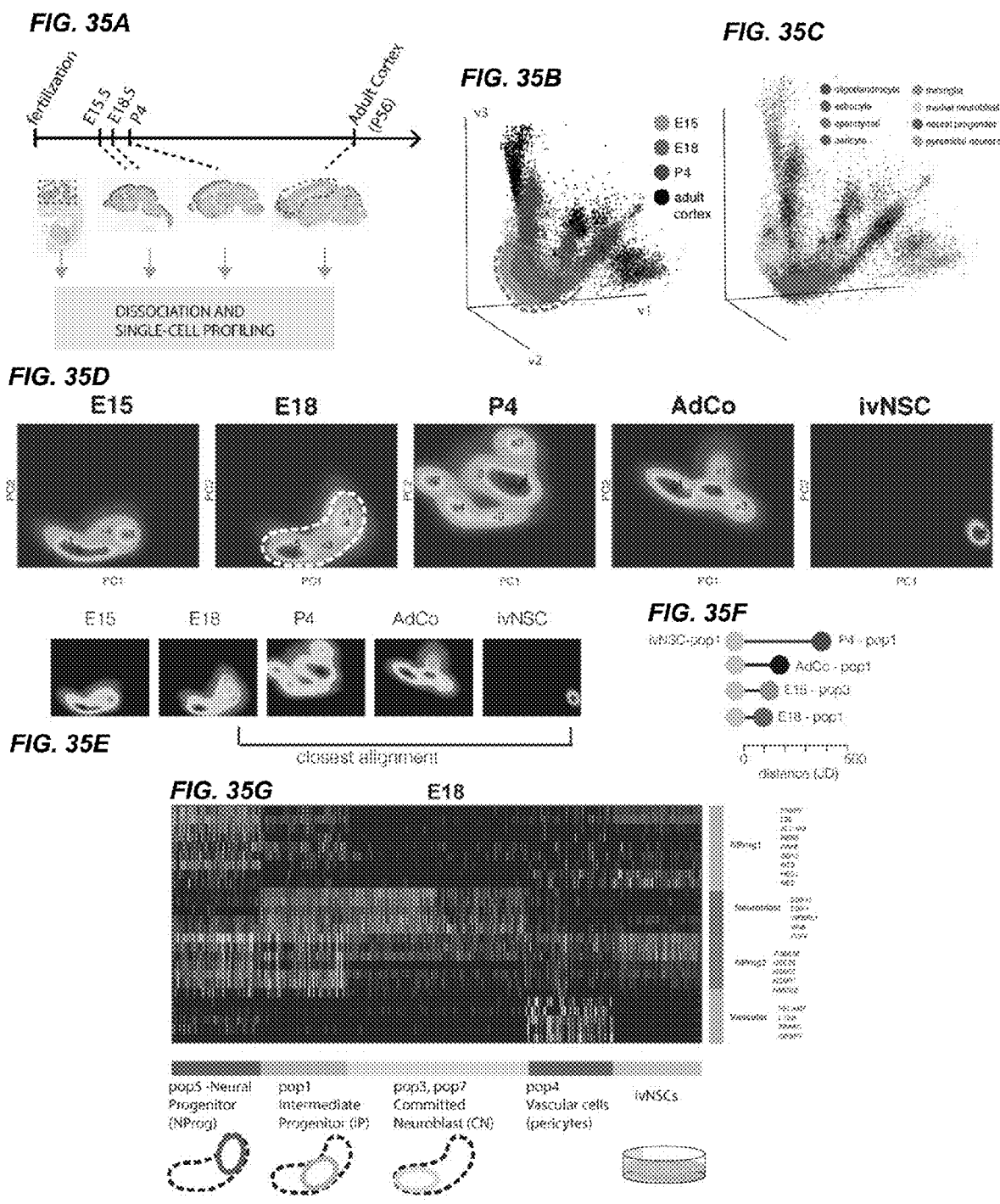

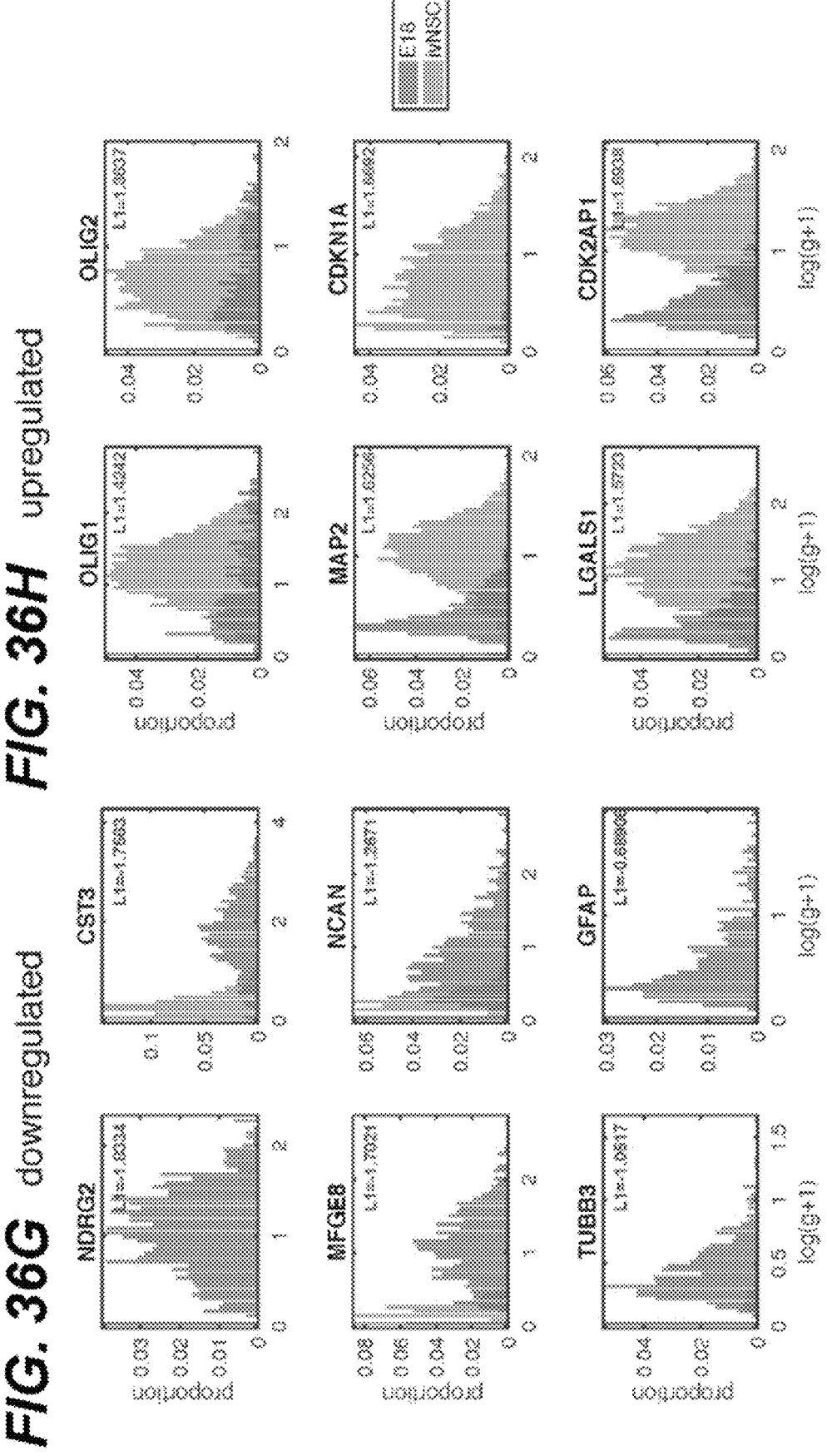

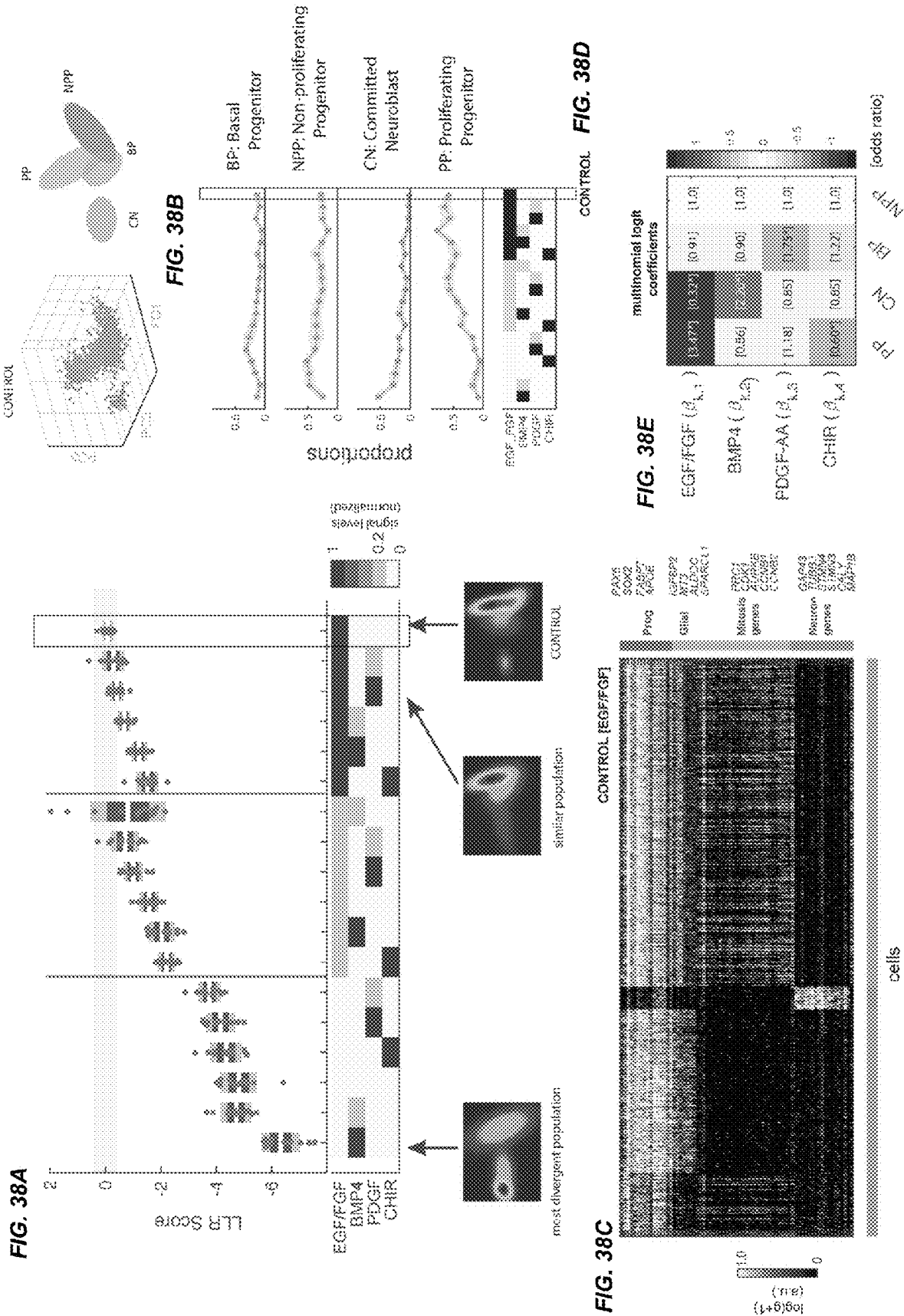

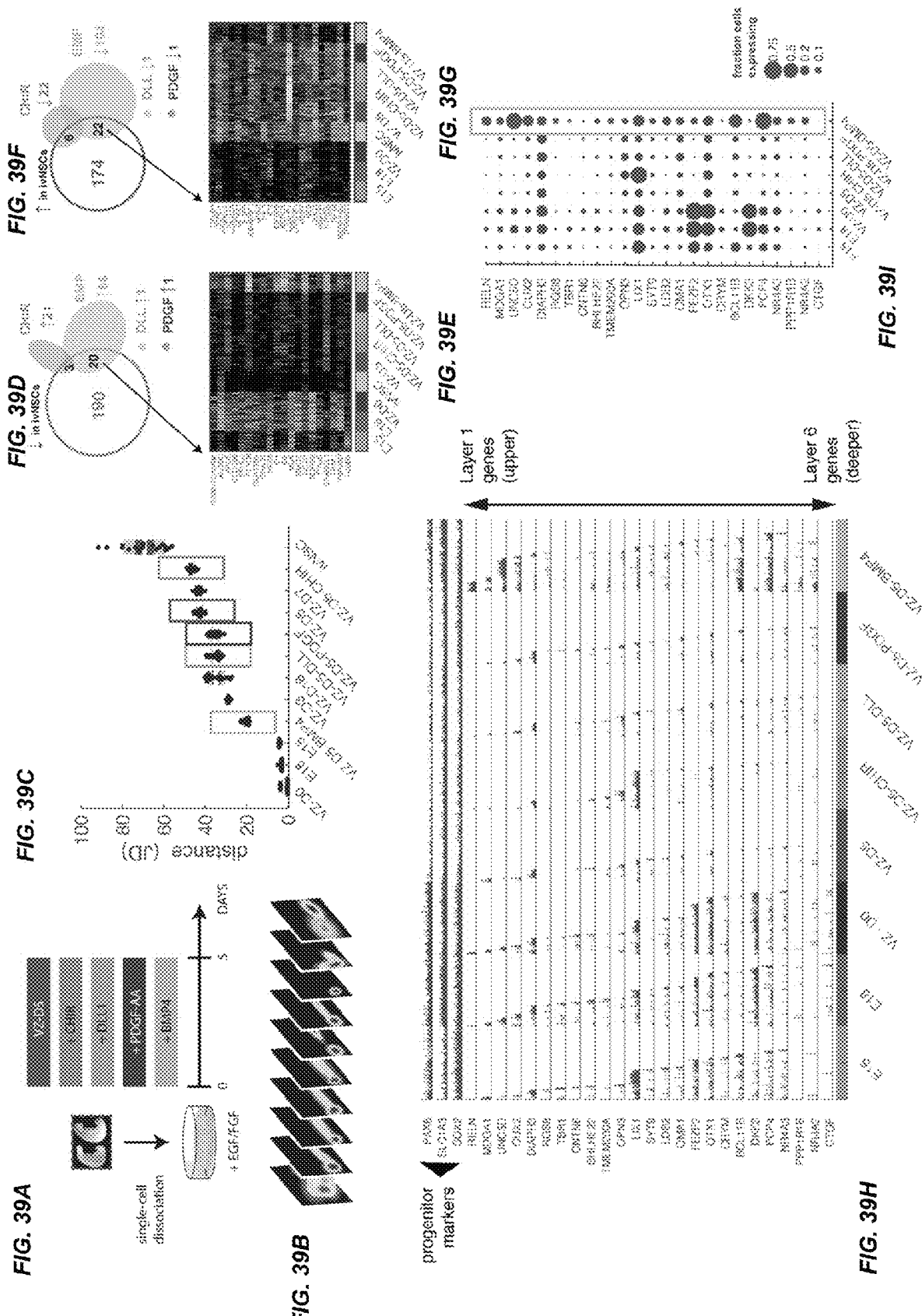

1. High Dimensional Data is projected into low-dimensional feature space
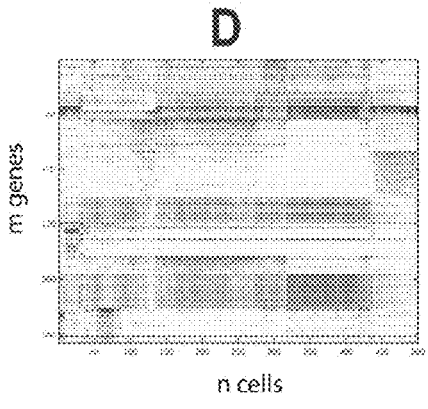
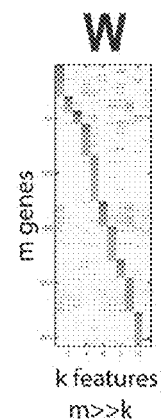
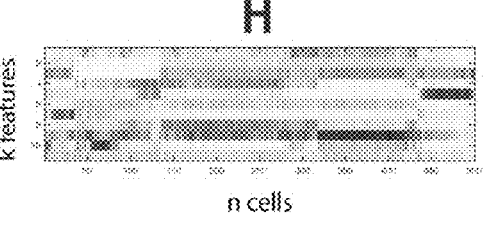
2. Reconstructed values are low-error
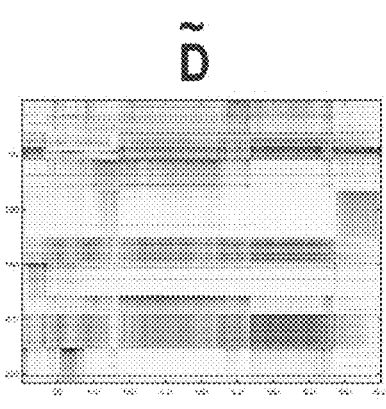
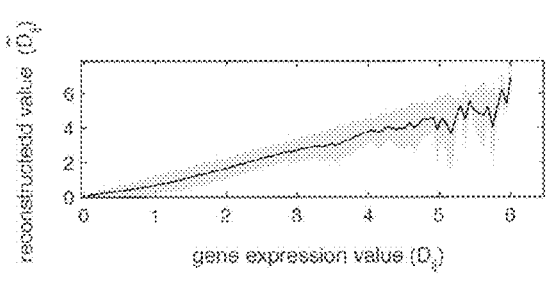
3. H vectors form clouds of points that can be fit by Gaussian Mixture Model
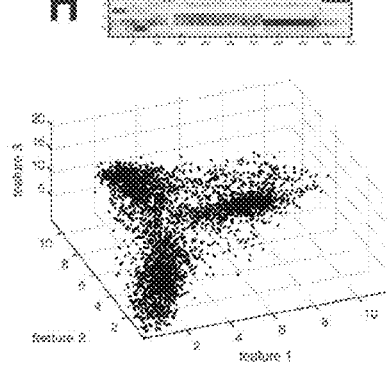
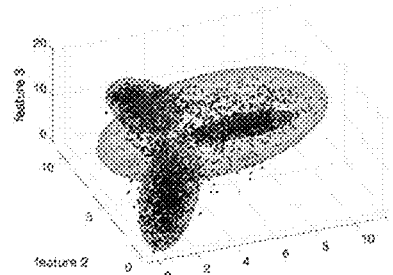
*FIG. 40*

SYSTEMS AND METHODS FOR DISSECTING HETEROGENEOUS CELL POPULATIONS

CROSS-REFERENCE TO RELATED APPLICATIONS

This application claims the benefit of priority to U.S. Patent Application No. 62/732,664, filed on Sep. 18, 2018, and U.S. Patent Application No. 62/733,044, filed on Sep. 18, 2018, and the content of each of which is incorporated herein by reference herein in its entirety.

STATEMENT REGARDING FEDERALLY SPONSORED R&D

This invention was made with government support under Grant Nos. CA199090 & OD012194 awarded by the National Institutes of Health. The government has certain rights in the invention

COPYRIGHT NOTICE

BACKGROUND

Field

This disclosure relates to relates generally to the field of single cell profiling and analysis, and more particularly to analyzing single cell profiling data.

Background

Single cell transcriptional or multiomics profiling enables thousands of single cells can be profiled. There is a need for analyzing data generated by single cell transcriptional or multiomics profiling.

SUMMARY

Disclosed herein include embodiments of a system for single cell analysis. In some embodiments, the system comprises: non-transitory memory configured to store executable instructions and single cell gene expression data comprising a plurality of reference gene expression vectors and a plurality of test gene expression vectors representing single cell gene expression profiles of a plurality of reference cells and a plurality of test cells respectively, in a gene expression space. The system can comprise: a hardware processor (or a virtual processor) in communication with the non-transitory memory, the hardware processor is programmed by the executable instructions to: for each of the plurality of reference gene expression vectors and the plurality of test gene expression vectors, normalize gene expression values of the reference gene expression vector or the test gene expression vector to generate a normalized reference gene expression vector or a normalized test gene expression vector comprising normalized gene expression values. determine (i) a gene feature matrix, comprising a plurality of gene features, and, for each of the plurality of normalized reference gene expression vectors and the plurality of normalized test gene expression vectors, (ii) reference gene feature weighting vector or a test gene feature weighting vector using a training matrix comprising a plurality normalized training gene expression vectors. The plurality of reference gene feature weighting vectors and the plurality of test gene feature weighting vectors can represent gene feature profiles of the plurality of reference cells and the plurality of test cells in a gene feature space, respectively. The hardware processor can be programmed by the executable instructions to: determine (i) a reference Gaussian mixture model comprising a plurality of reference Gaussian densities each associated with a reference weight (e.g., a scalar) and (ii) a test Gaussian mixture model comprising a plurality of test Gaussian densities each associated with a test weight (e.g., a scalar) from the plurality of reference gene feature weighting vectors and the plurality of test gene expression vectors, respectively. Each of (i) the plurality of reference Gaussian densities and associated reference weights and (ii) the plurality of test Gaussian densities and the associated test weights can represent a subpopulation of the plurality of reference cells or the plurality of test cells, respectively. The hardware processor can be programmed by the executable instructions to: aligning each of the plurality of test Gaussian densities to an aligned reference Gaussian density of the plurality of reference Gaussian densities. The hardware processor can be programmed by the executable instructions to: perform an analysis of the plurality of test cells relative to the plurality of reference cells using one, at least one, or each, of the plurality of test Gaussian densities and the aligned reference Gaussian density the test Gaussian density is aligned to.

Disclosed herein include embodiments of a system for single cell analysis. In some embodiments, the system comprises: non-transitory memory configured to store executable instructions and single cell gene expression data comprising a plurality of normalized reference gene expression vectors and a plurality of normalized test gene expression vectors representing single cell gene expression profiles of a plurality of reference cells and a plurality of test cells respectively, in a gene expression space. The hardware processor can be programmed by the executable instructions to: a hardware processor (or a virtual processor) in communication with the non-transitory memory, the hardware processor is programmed by the executable instructions to: determine (i) a gene feature matrix, comprising a plurality of gene features, and, for each of the plurality of normalized reference gene expression vectors and the plurality of normalized test gene expression vectors, (ii) reference gene feature weighting vector or a test gene feature weighting vector using a training matrix comprising a plurality normalized training gene expression vectors. The plurality of reference gene feature weighting vectors and the plurality of test gene feature weighting vectors can represent gene feature profiles of the plurality of reference cells and the plurality of test cells in a gene feature space, respectively. The hardware processor can be programmed by the executable instructions to: determine (i) a reference Gaussian mixture model comprising a plurality of reference Gaussian densities each associated with a reference weight (e.g., a scalar) and (ii) a test Gaussian mixture model comprising a plurality of test Gaussian densities each associated with a test weight (e.g., a scalar) from the plurality of reference gene feature weighting vectors and the plurality of test gene expression vectors, respectively. Each of (i) the plurality of reference Gaussian densities and associated reference weights and (ii) the plurality of test Gaussian densities and the associated test weights can represent a subpopulation of the plurality of reference cells or the plurality of test cells, respectively. The hardware processor can be programmed by the executable instructions to: align each of the plurality of test Gaussian densities to an aligned reference Gaussian density of the plurality of reference Gaussian densities. The hardware processor can be programmed by the executable instructions to: perform an analysis of the plurality of test cells relative to the plurality of reference cells using one, at least one, or each, of the plurality of test Gaussian densities and the aligned reference Gaussian density the test Gaussian density is aligned to. The hardware processor can be programmed by the executable instructions to: determine a difference of the plurality of test cells, or a subpopulation thereof, relative to the plurality of reference cells, or a subpopulation thereof, using one, at least one, or each, of the plurality of test Gaussian densities and the aligned reference Gaussian density the test Gaussian density is aligned to. The hardware processor can be programmed by the executable instructions to: determine a Gaussian density difference between one of the plurality of test Gaussian densities and the aligned reference Gaussian density the test Gaussian density is aligned to; and determine a difference between the plurality of test cells, or a subpopulation thereof, and the plurality of reference cells, or a subpopulation thereof, using the Gaussian density difference. The hardware processor can be programmed by the executable instructions to: for each of a plurality of reference gene expression vectors and a plurality of test gene expression vectors, normalize gene expression values of the reference gene expression vector or the test gene expression vector to generate a normalized reference gene expression vector or a normalized test gene expression vector comprising normalized gene expression values.

In some embodiments, the gene expression profiles comprise mRNA expression profiles and/or protein expression profiles.

In some embodiments, to normalize, the hardware processor is programmed by the executable instructions to: normalize the gene expression values of the reference gene expression vector or the test gene expression vector relative to a sum of the gene expression values to generate the normalized reference gene expression vector or the normalized test gene expression vector comprising the normalized gene expression values.

In some embodiments, to normalize, the hardware processor is programmed by the executable instructions to: adjust the gene expression values of the reference gene expression vector or the test gene expression vector with a scaling factor to generate the normalized reference gene expression vector or the normalized test gene expression vector comprising the normalized gene expression values. The scaling factor can be about a sum of the gene expression values of one of the plurality of reference gene expression vectors and the plurality of test gene expression vectors. The scaling factor can be about a smallest sum of the gene expression values of any of the plurality of reference gene expression vectors and the plurality of test gene expression vectors. The scaling factor can be about 1000.

In some embodiments, to normalize, the hardware processor is programmed by the executable instructions to: increase the gene expression values of the reference gene expression vector or the test gene expression vector by a pseudo-count value to generate the normalized reference gene expression vector or the normalized test gene expression vector comprising the normalized gene expression values. The pseudo-count value can be one.

In some embodiments, to normalize, the hardware processor is programmed by the executable instructions to: changing the gene expression values of the reference gene expression vector or the test gene expression vector to a logarithmic scale to generate the normalized reference gene expression vector or the normalized test gene expression vector comprising the normalized gene expression values.

In some embodiments, the normalized gene expression values of the plurality of reference gene expression vectors and the plurality of test gene expression vectors transition smoothly.

In some embodiments, the plurality of normalized training gene expression vectors comprises one or more the plurality of normalized reference gene expression vectors and/or one or more of the plurality of test gene expression vectors. The plurality of normalized training gene expression vectors can comprise one or more of the plurality of normalized reference gene expression vectors sampled and/ or one or more of the plurality of test gene expression vectors. The plurality of normalized training gene expression vectors can comprise two or more the plurality of normalized reference gene expression vectors randomly and/or uniformly sampled and/or two or more of the plurality of test gene expression vectors randomly and/or uniformly sampled. The plurality of normalized training gene expression vectors can comprise the plurality of normalized reference gene expression vectors and/or the plurality of test gene expression vectors.

In some embodiments, to determine the gene feature matrix, the hardware processor is programmed by the executable instructions to: determine the gene feature matrix from the plurality of normalized training gene expression vectors using machine learning. The machine learning can be based on a layered neural network.

In some embodiments, to determine the gene feature matrix, the hardware processor is programmed by the executable instructions to: determine the gene feature matrix using matrix factorization. The matrix factorization can comprise singular value decomposition. The matrix factorization can comprise principal component analysis. The matrix factorization can comprise non-negative matrix factorization. The matrix factorization can comprise sparse non-negative matrix factorization. The matrix factorization can comprise orthogonal non-negative matrix factorization.

In some embodiments, the gene feature matrix is an orthogonal matrix. Each, or at least one, element of the gene feature matrix can be greater than or equal to zero. Each, one or at least one, element of at least one of the plurality of reference gene feature weighting vectors and/or at least one of the plurality of test gene feature weighting vectors can be greater than or equal to zero.

In some embodiments, a number of the plurality of gene features is predetermined. A size of a gene expression vector of the plurality of reference gene expression vectors and the plurality of test gene expression vectors can be at most 10, 20, 30, 40, or 50. A ratio of a size of a gene expression vector of the plurality of reference gene expression vectors and the plurality of test gene expression vectors to a number of the plurality of gene features can be at least 10, 20, 30, 40, 50, 100, 500, or 1000. A size of a gene expression vector of the plurality of reference gene expression vectors and the plurality of test gene expression vectors can be at least 1000, 5000, or 1000.

In some embodiments, to determine the gene feature matrix, the hardware processor is programmed by the executable instructions to: determine the gene feature matrix comprising the plurality of gene features using a plurality normalized training gene expression vectors; and/or for each of the plurality of normalized reference gene expression vectors and the plurality of normalized test gene expression vectors, determine a reference gene feature weighting vector or a test gene feature weighting vector in a gene feature space using the gene feature matrix. To determine the gene feature matrix, the hardware processor can be programmed by the executable instructions to: determine the gene feature matrix and a gene feature weighting matrix comprising a plurality of gene feature weighting vectors using the plurality of normalized training gene expression vectors. Each, one, or at least one, element of the gene feature weighting matrix can be greater than or equal to zero.

In some embodiments, to determine the gene feature matrix and the gene feature weighting matrix, the hardware processor is programmed by the executable instructions to: determine the gene feature matrix and the gene feature weighting matrix by minimizing a loss function comprising a difference of the training matrix and a product of the gene feature matrix and the gene feature weighting matrix. To determine the gene feature matrix and the gene feature weighting matrix, the hardware processor can be programmed by the executable instructions to: determine the gene feature matrix and the gene feature weighting matrix by minimizing a loss function comprising a norm of the training matrix and a product of the gene feature matrix and the gene feature weighting matrix. To determine the gene feature matrix and the gene feature weighting matrix, the hardware processor can be programmed by the executable instructions to: determine the gene feature matrix and the gene feature weighting matrix by minimizing a loss function comprising a Frobenius norm of the training matrix and a product of the gene feature matrix and the gene feature weighting matrix.

In some embodiments, the loss function comprises a penalty comprising a number of the plurality of gene features in the gene feature matrix. The loss function can comprise a penalty comprising to a number of the plurality of gene features in the gene feature matrix exponentiated with an exponentiation factor. The exponentiation factor can be about 0.7.

In some embodiments, to determine the reference gene feature weighting vector or the test gene feature weighting vector, the hardware processor is programmed by the executable instructions to: determine the reference gene feature weighting vector or the test gene feature weighting vector in the gene feature space by minimizing a loss function comprising a difference of the corresponding normalized reference gene expression vector or normalized test gene expression vector and a product of the gene feature matrix and the reference gene feature weighting vector or the test gene feature weighting vector. To determine the reference gene feature weighting vector or the test gene feature weighting vector, the hardware processor can be programmed by the executable instructions to: determine the reference gene feature weighting vector or the test gene feature weighting vector in the gene feature space by minimizing a loss function comprising a norm of the corresponding normalized reference gene expression vector or normalized test gene expression vector and a product of the gene feature matrix and the reference gene feature weighting vector or the test gene feature weighting vector. To determine the reference gene feature weighting vector or the test gene feature weighting vector, the hardware processor can be programmed by the executable instructions to determine the reference gene feature weighting vector or the test gene feature weighting vector in the gene feature space by minimizing a loss function comprising a Frobenius norm of the corresponding normalized reference gene expression vector or normalized test gene expression vector and a product of the gene feature matrix and the reference gene feature weighting vector or the test gene feature weighting vector.

In some embodiments, to determine (i) the reference Gaussian mixture model and (ii) the test Gaussian mixture model, the hardware processor is programmed by the executable instructions to: determine (i) one or more reference parameters and the reference weight of or associated with each of the plurality of reference Gaussian densities and (ii) one or more test parameters and the test weight of each of the plurality of test Gaussian densities, respectively, from (i) the plurality of reference gene feature weighting vectors and (ii) the plurality of test gene feature weighting vectors, respectively. Each of the plurality of reference Gaussian densities and/or each of the plurality of test Gaussian densities can comprise a normal distribution, and/or parameters of the normal distribution comprises the one or more reference parameters or the one or more test parameters of the reference Gaussian density or the test Gaussian density, respectively. The one or more parameters of each, or at least one, of the plurality of reference Gaussian densities can comprise a reference centroid and a reference covariance matrix, and/or the one or more parameters of each, or at least one, of the plurality of test Gaussian densities comprises a test centroid and a test covariance matrix. The reference centroid, the reference covariance matrix, and the reference weight of or associated with a reference Gaussian density of the plurality of Gaussian densities can represent an average of reference gene features of a subpopulation of the plurality of reference cells represented by the reference Gaussian density, a spread of the reference gene features, an abundance of the subpopulation of the plurality of reference cells represented by the reference Gaussian density, and/or the test centroid, the test covariance matrix, and the test weight of or associated with a test Gaussian density of the plurality of Gaussian densities can represent an average of test gene features of a subpopulation of the plurality of test cells represented by the test Gaussian density, a spread of the test gene features, an abundance of the subpopulation of the plurality of test cells represented by the test Gaussian density.

In some embodiments, to determine (i) the reference Gaussian mixture model and (ii) the test Gaussian mixture model, the hardware processor is programmed by the executable instructions to: determine (i) the reference Gaussian mixture model and (ii) the test Gaussian mixture model using maximum likelihood estimation and a likelihood function. The maximum likelihood estimation can comprise expectation maximization. In some embodiments, a number of the plurality of reference Gaussian densities and/or a number of the plurality of test Gaussian densities is predetermined. In some embodiments, a number of the plurality of reference Gaussian densities and/or a number of the plurality of test Gaussian densities is about 10, 15, 20, 30, 40, or 50. In some embodiments, to determine (i) the reference Gaussian mixture model and (ii) the test Gaussian mixture model, the hardware processor is programmed by the executable instructions to: determine a number of the plurality of reference Gaussian densities and/or a number of the plurality of test Gaussian densities by penalizing the number of the plurality of reference Gaussian densities and/or the number of the plurality of test Gaussian densities. In some embodiments, to determine (i) the reference Gaussian mixture model and (ii) the test Gaussian mixture model, the hardware processor can be programmed by the executable instructions to: determine a number of the plurality of reference Gaussian densities and/or a number of the plurality of test Gaussian densities using Bayesian Information Criterion.

In some embodiments, to determine (i) the reference Gaussian mixture model, the hardware processor is programmed by the executable instructions to: determine a pair of reference Gaussian densities of the plurality of reference Gaussian densities with a divergence smaller than a divergence of any other pair of reference Gaussian densities of the plurality of reference Gaussian densities to be redundant in the reference Gaussian model; merge the pair reference Gaussian densities to generate a merged reference Gaussian density; determine merging the pair of reference Gaussian densities results in increasing a Bayesian Information Criterion of the reference Gaussian mixture model; and/or accept the merged reference Gaussian density. In some embodiments, to determine (i) the test Gaussian mixture model, the hardware processor is programmed by the executable instructions to: determine a pair of test Gaussian densities of the plurality of test Gaussian densities with a divergence smaller than a divergence of any other pair of test Gaussian densities of the plurality of test Gaussian densities to be redundant in the test Gaussian model; merge the pair test Gaussian densities to generate a merged test Gaussian density; determine merging the pair of test Gaussian densities results in increasing a Bayesian Information Criterion of the test Gaussian mixture model; and/or accept the merged test Gaussian density.

In some embodiments, to determine (i) the reference Gaussian mixture model, the hardware processor is programmed by the executable instructions to: iterative merge a pair of reference Gaussian densities of the plurality of reference Gaussian densities with a divergence smaller than a divergence of any other pair of reference Gaussian densities of the plurality of reference Gaussian densities to be redundant until merging the pair of reference Gaussian densities does not result in increasing a Bayesian Information Criterion of the reference Gaussian mixture model after merging. To determine (i) the test Gaussian mixture model, the hardware processor can be programmed by the executable instructions to: iterative merge a pair of test Gaussian densities of the plurality of test Gaussian densities with a divergence smaller than a divergence of any other pair of test Gaussian densities of the plurality of test Gaussian densities to be redundant until merging the pair of test Gaussian densities does not result in increasing a Bayesian Information Criterion of the test Gaussian mixture model after merging.

In some embodiments, the divergence of the pair of reference Gaussian densities or test Gaussian densities comprises a Jeffrey's divergence of the pair of reference Gaussian densities or test Gaussian densities. The divergence of the pair of reference Gaussian densities or test Gaussian densities can comprise a Kullback Leibler divergence of the pair of reference Gaussian densities or test Gaussian densities.

In some embodiments, to align each of the plurality of test Gaussian densities to the aligned reference Gaussian density of the plurality of reference Gaussian densities, the hardware processor is programmed by the executable instructions to: align each of the plurality of test Gaussian densities to an aligned reference Gaussian density of the plurality of reference Gaussian densities based on one or more test parameters of the test Gaussian density and one or more reference parameters of each of the plurality of reference Gaussian densities.

In some embodiments, to align each of the plurality of test Gaussian densities to the aligned reference Gaussian density of the plurality of reference Gaussian densities, the hardware processor is programmed by the executable instructions to: align the test Gaussian density to the aligned reference Gaussian density with a divergence smaller than a divergence between the test Gaussian density and any other of the plurality of reference Gaussian densities. The divergence between the test Gaussian density and the aligned reference Gaussian density can comprise a Jeffrey's divergence between the test Gaussian density and the reference Gaussian density. The divergence between the test Gaussian density and the aligned reference Gaussian density can comprise a Kullback Leibler divergence between the test Gaussian density and the reference Gaussian density. The hardware processor can be programmed by the executable instructions to: determine, for each of the plurality of test Gaussian densities, a probability of the divergence between the test Gaussian density and the aligned reference Gaussian density the test Gaussian density is aligned to. To determine the probability of the divergence, the hardware processor can be programmed by the executable instructions to: determine the probability of the divergence between the test Gaussian density and the aligned reference Gaussian density the test Gaussian density is aligned to using an empirical null distribution of divergence. The hardware processor can be programmed by the executable instructions to: determine the empirical null distribution of divergence using divergences of pairs of Gaussian densities.

In some embodiments, to perform the analysis, the hardware processor is programmed by the executable instructions to: perform the analysis of the plurality of test cells relative to the plurality of reference cells using one of the plurality of test Gaussian densities and the associated test weight and the aligned reference Gaussian density the test Gaussian density is aligned to and the associated reference weight.

In some embodiments, to perform the analysis, the hardware processor is programmed by the executable instructions to perform the analysis of the plurality of test cells relative to the plurality of reference cells using a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. To perform the analysis, the hardware processor is programmed by the executable instructions to: determine a centroid delta of the test centroid and the reference centroid; determine a covariance matrix delta of the test covariance matrix and the reference covariance matrix; determine a weight delta of the test weight and the reference weight; and/or perform the analysis of the plurality of test cells relative to the plurality of reference cells using the centroid delta, the covariance matrix delta, and the weight delta.

In some embodiments, to determine the difference, the hardware processor is programmed by the executable instructions to: determine the difference of the plurality of test cells and the plurality of reference cells using one of the plurality of test Gaussian densities and the associated test weight and the aligned reference Gaussian density the test Gaussian density is aligned to and the associated reference weight. To determine the difference, the hardware processor can be programmed by the executable instructions to: determine the difference between one of the plurality of test cells and to the plurality of reference cells using a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. To perform the analysis, or to determine the difference, the hardware processor can be programmed by the executable instructions to: determine a centroid delta of the test centroid and the reference centroid; determine a covariance matrix delta of the test covariance matrix and the reference covariance matrix; determine a weight delta of the test weight and the reference weight; and determine the difference between the plurality of test cells and the plurality of reference cells using the centroid delta, the covariance matrix delta, and the weight delta.

In some embodiments, to determine the Gaussian density difference, the hardware processor is programmed by the executable instructions to: determine the Gaussian density difference between one of the plurality of test Gaussian densities and the associated test weight and the aligned reference Gaussian density the test Gaussian density is aligned to and the associated reference weight. To determine the Gaussian density difference, the hardware processor can be programmed by the executable instructions to: determine the Gaussian density difference comprising a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. The Gaussian density difference can comprise a centroid delta of the test centroid and the reference centroid, and/or a weight delta of the test weight and the reference weight The centroid delta can represent a change in gene features of a subpopulation of cells represented by the test Gaussian densities or the aligned reference Gaussian density, the covariance matrix delta can represent a change in a spread of the gene features of the subpopulation of cells, and/or the weight delta can represent a change in abundance of the subpopulation of cells. The centroid delta can comprise a difference, a norm, or a Frobenius norm of the test centroid and the reference centroid, the covariance matrix delta can comprise a difference or a norm of the test covariance matrix and the reference covariance matrix, and/or a weight delta can comprise a difference or a norm of the test weight and the reference weight.

In some embodiments, wherein each, one, or at least one, of the plurality of reference cells is associated with a first annotation, and wherein the hardware processor is programmed by the executable instructions to: determine a second annotation of each, or at least one, of the plurality of reference Gaussian densities using the first annotation associated with each, or at least one, of the plurality of reference cells. The first annotation and/or the second annotation can comprise a function annotation, a pathway annotation, a cell-type annotation, and/or a tissue-type annotation. The hardware processor can be programmed by the executable instructions to: determine a third annotation of each, or at least one, of the plurality of test Gaussian densities using the second annotation associated with the aligned reference Gaussian density the test Gaussian density is aligned to.

In some embodiments, the plurality of reference cells comprises healthy cells, and/or the plurality of test cells comprises diseased cells. The plurality of reference cells can comprise cells cultured in the absence of a drug or a signal, and/or the plurality of test cells can comprise cells cultured in the presence of the drug or the signal. The plurality of reference cells can comprise cells from a first subject not treated with a drug, and/or the plurality of test cells can comprise cells from a second subject treated with the drug. The first subject can be the second subject.

In some embodiments, the plurality of reference cells comprises cells from a first tissue type, and wherein the plurality of test cells comprises cells from a second tissue type. To perform the analysis, the hardware processor can be programmed by the executable instructions to: determine similarities of and difference between the plurality of reference cells and the plurality of test cells. To perform the analysis, the hardware processor can be programmed by the executable instructions to: determine a gene feature of the plurality of gene features absent or present in the plurality of reference cells is present or absent in the plurality of test cells. To perform the analysis, the hardware processor can be programmed by the executable instructions to: determining a similarity between the plurality of reference cells and the plurality of test cells using a log-likelihood ratio score of (i) one, at least one, or each of, the plurality of reference Gaussian mixtures and associated reference weights and (ii) one, at least one, or each of, the plurality of test Gaussian mixtures and associated test weights.

In some embodiments, the single cell gene expression data comprises a plurality of second reference gene expression vectors representing single cell gene expression profiles of a plurality of second reference cells. To normalize, the hardware processor can be programmed by the executable instructions to: for each of the plurality of second reference gene expression vectors, normalize gene expression values of the second reference gene expression vector to generate a normalized second reference gene expression vector comprising normalized gene expression values. To determine the gene feature matrix, the hardware processor can be programmed by the executable instructions to: for each of the plurality of normalized second reference gene expression vectors, determine a second reference gene feature weighting vector using the training matrix, wherein the plurality of second reference gene feature weighting vectors represent second gene feature profiles of the plurality of second reference cells. To determine (i) the reference Gaussian mixture model, the hardware processor can be programmed by the executable instructions to: determine a second reference Gaussian mixture model comprising a plurality of second reference Gaussian densities each associated with a second reference weight, wherein each of the plurality of second reference Gaussian densities and associated reference weights represents a second subpopulation of the plurality of second reference cells. To perform the analysis, the hardware processor can be programmed by the executable instructions to: perform the analysis of the plurality of test cells relative to the plurality of reference cells and the plurality of second reference cells using the plurality of reference Gaussian densities, the plurality of second reference Gaussian densities, and the plurality of test Gaussian densities.

In some embodiments, the plurality of gene expression vectors comprises a plurality of (first) reference gene expression vectors and a plurality of second reference gene expression vectors representing single cell gene expression profiles of a plurality of (first) reference cells and a plurality of second reference cells of the plurality of cells.

In some embodiments, the plurality of (first) reference cells comprises healthy cells, and the plurality of second reference cells comprises diseased cells. The plurality of (first) reference cells can be from a (first) tissue, and/or the plurality of second reference cells can be from a second tissue. The (first) tissue and the second tissue can be of different tissue types. In some embodiments, to perform the analysis, the hardware processor is programmed by the executable instructions to: determine a (first) similarity between the plurality of (first) reference cells and the plurality of test cells using a (first) log-likelihood ratio score of (i) one, at least one, or each of, the plurality of (first) reference Gaussian mixtures and associated (first) reference weights and (ii) one, at least one, or each of, the plurality of test Gaussian mixtures and associated test weights; determine a second similarity between the plurality of second reference cells and the plurality of test cells using a second log-likelihood ratio score of (i) one, at least one, or each of, the plurality of second reference Gaussian mixtures and associated second reference weights and (ii) one, at least one, or each of, the plurality of test Gaussian mixtures and associated test weights; and/or determine the plurality of test cells to be more similar to the plurality of (first) reference cells and the plurality of second reference cells based on the (first) similarity and the second similarity.

In some embodiments, to perform the analysis, the hardware is processor is programmed by the executable instructions to: determine a probability of the plurality of test cells, or a subpopulation thereof, to be a (first) reference cell type of the plurality of (first) reference cells, or a subpopulation thereof, relative to the a second reference cell type of the plurality of second reference cells, or a subpopulation thereof, with respect to a difference in a (first) condition for culturing the plurality of (first) reference cells and a second condition for culturing the plurality of second reference cells. To determine the probability, the hardware can be processor programmed by the executable instructions to: determine the probability using multinomial logistic regression.

In some embodiments, the plurality of (first) reference cells comprises a (first) reference type of cells and is associated with a (first) reference label. The plurality of second reference cells can comprise a second reference type of cells and is associated with a second reference label. To perform the analysis, the hardware processor is programmed by the executable instructions to: determine a probability of the plurality of test cells to be the reference type of cells using (i) the plurality of (first) reference Gaussian densities and/or the associated (first) reference weights and (ii) the plurality of test Gaussian densities and/or the associated test weights; determine a probability of the plurality of test cells to be the second reference type of cells using (i) the plurality of second reference Gaussian densities and/or the associated second reference weights and (ii) the plurality of test Gaussian densities and/or the associated test weights; and/or determine a test label of the plurality of test cells to be the reference label or the second reference label based on the probability and the second probability.

In some embodiments, the single cell gene expression data comprises a plurality of second test gene expression vectors representing single cell gene expression profiles of a plurality of second test cells. To normalize, the hardware processor can be programmed by the executable instructions to: for each of the plurality of second test gene expression vectors, normalize gene expression values of the second test gene expression vector to generate a normalized second test gene expression vector comprising normalized gene expression values. To determine the gene feature matrix, the hardware processor can be programmed by the executable instructions to: for each of the plurality of normalized second test gene expression vectors, determine a second test gene feature weighting vector using the training matrix, wherein the plurality of second test gene feature weighting vectors represent second gene feature profiles of the plurality of second test cells. To determine (i) the reference Gaussian mixture model, the hardware processor can be programmed by the executable instructions to: determine a second test Gaussian mixture model comprising a plurality of second test Gaussian densities each associated with a second test weight, wherein each of the plurality of second test Gaussian densities and associated test weights represents a second subpopulation of the plurality of second test cells. To perform the analysis, the hardware processor can be programmed by the executable instructions to: perform an analysis of the plurality of second test cells relative to the plurality of reference cells using the plurality of reference Gaussian densities and the plurality of second test Gaussian densities. To perform the analysis, the hardware processor can be programmed by the executable instructions to: perform an analysis of the plurality of test cells relative to the plurality of second test cells using the plurality of test Gaussian densities and the plurality of second test Gaussian densities.

In some embodiments, the plurality of gene expression vectors comprises a plurality of first test gene expression vectors and a plurality of second test gene expression vectors representing single cell gene expression profiles of a plurality of first test cells and a plurality of second test cells of the plurality of cells.

In some embodiments, to perform the analysis, the hardware processor is programmed by the executable instructions to: perform an analysis of the plurality of (first) test cells and the plurality of second test cells relative to the plurality reference cells using the plurality of reference Gaussian densities and a plurality of (first) test Gaussian densities and the plurality of second test Gaussian densities of the plurality of test Gaussian densities. The plurality of (first) test cells can be originally of a (first) test cell type or from a (first) test tissue type and cultured under a (first) test condition, the plurality of second test cells can be originally of a second test cell type or from a second test tissue type and cultured under a second test condition, and/or the plurality of reference cells can be originally of a reference cell type or from a reference tissue type and cultured under a reference condition. The plurality of (first) test cells can be cultured under a (first) test condition and of a (first) test cell type and, the plurality of second test cells can be cultured under a second test condition and of a second test cell type, and wherein the plurality of reference cells is cultured under a reference condition and of a reference cell type. The (first) test cell type, the second test cell type, and/or the reference cell type are identical, the (first) tissue type, the second test tissue type, and/or the reference tissue type are identical, and/or the (first) test condition, the second test condition, and/or the reference condition are identical. The (first) test cell type, the second test cell type, and/or the reference cell type can be different, the (first) tissue type, the second test tissue type, and/or the reference tissue type can be different, and/or the (first) test condition, the second test condition, and/or the reference condition can be different. The (first) test condition can comprise presence of a (first) drug, signal, or environmental condition, wherein the second test condition comprises presence of a second drug, signal, or environmental condition. The reference condition can comprise no (first) drug, signal, and environmental condition and/or no second drug, signal, and environmental condition. The (first) test condition, second test condition, and/or the reference condition can comprise different concentrations or extents of a drug, signal, or environmental condition. The plurality of (first) test cells can be from a (first) sample of a subject at a (first) time, and the plurality of second test cells can be from a second sample of the subject at a second time. To perform the analysis, the hardware processor can be programmed by the executable instructions to: determine a (first) similarity between the plurality of (first) test cells and the plurality of reference cells using a (first) log-likelihood ratio score of (i) one, at least one, or each of, the plurality of (first) test Gaussian mixtures and associated (first) test weights and (ii) one, at least one, or each of, the plurality of reference Gaussian mixtures and associated reference weights; determine a second similarity between the plurality of second test cells and the plurality of reference cells using a second log-likelihood ratio score of (i) one, at least one, or each of, the plurality of second test Gaussian mixtures and associated second test weights and (ii) one, at least one, or each of, the plurality of reference Gaussian mixtures and associated reference weights; and/or determine the plurality of (first) test cells or the plurality of second test cells to be more similar to the plurality of reference cells based on the (first) similarity and the second similarity. The hardware processor can be programmed by the executable instructions to: demix of the plurality of test gene expression vectors to generate a plurality of (first) test gene expression vectors and a plurality of second gene expression vectors.

In some embodiments, the hardware processor is programmed by the executable instructions to: determine a reference diversity comprising a reference heterogeneity of the plurality of reference cells or a subpopulation of the plurality of reference cells and/or a test diversity comprising a test heterogeneity of the plurality of test cells or a subpopulation of the plurality of test cells. The reference heterogeneity can comprise (i) an entropy of one, at least one, or each, of the plurality of reference Gaussian mixtures and/or associated reference weights and/or (ii) a reference covariance matrix of one, at least one, or each, the plurality of reference Gaussian mixtures, and/or the test heterogeneity can comprise (i) an entropy of one, at least one, or each, of the plurality of test Gaussian mixtures and/or associated test weights and/or (ii) a test covariance matrix of one, at least one, or each, the plurality of test Gaussian mixtures.

In some embodiments, the hardware processor is programmed by the executable instructions to: determine a gene is upregulated or downregulated in a subpopulation of the plurality of test cells relative to a subpopulation of the plurality of reference cells. To determine the gene is upregulated or downregulated, the hardware processor can be programmed by the executable instructions to: determine the gene is upregulated or downregulated in a subpopulation of the plurality of test cells relative to a subpopulation of the plurality of reference cells using a L1 distance between a test distribution of the single cell gene expression profiles of the gene in the subpopulation of the plurality of test cells and a reference distribution of the single cell gene expression profiles of the gene in the subpopulation of the plurality of reference cells. In some embodiments, the subpopulation of the plurality of reference cells comprises 50%, 60%, 70%, 80%, 90%, 95%, 99%, or 100 cells of a cell type, and/or wherein the subpopulation of the plurality of test cells comprises 50%, 60%, 70%, 80%, 90%, 95%, 99%, or 100 cells of a cell type.

In some embodiments, a run time of the hardware processor increases linearly or non-exponentially as a number of the plurality of reference gene expression vectors and/or the plurality of test gene expression vectors increases.

Disclosed herein include embodiments of a method for single cell analysis. In some embodiments, the method is under control of a hardware processor (or a virtual processor) and comprises: receiving single cell gene expression data comprising a plurality of reference gene expression vectors and a plurality of test gene expression vectors representing single cell gene expression profiles of a plurality of reference cells and a plurality of test cells respectively, in a gene expression space. The method can comprise: for each of the plurality of reference gene expression vectors and the plurality of test gene expression vectors, normalizing gene expression values of the reference gene expression vector or the test gene expression vector to generate a normalized reference gene expression vector or a normalized test gene expression vector comprising normalized gene expression values. The method can comprise: determining (i) a gene feature matrix, comprising a plurality of gene features, and, for each of the plurality of normalized reference gene expression vectors and the plurality of normalized test gene expression vectors, (ii) a reference gene feature weighting vector or a test gene feature weighting vector using a training matrix comprising a plurality normalized training gene expression vectors. The plurality of reference gene feature weighting vectors and the plurality of test gene feature weighting vectors can represent gene feature profiles of the plurality of reference cells and the plurality of test cells in a gene feature space, respectively. The method can comprise: determining (i) a reference Gaussian mixture model comprising a plurality of reference Gaussian densities each associated with a reference weight (e.g., a scalar) and (ii) a test Gaussian mixture model comprising a plurality of test Gaussian densities each associated with a test weight (e.g., a scalar) from the plurality of reference gene feature weighting vectors and the plurality of test gene expression vectors, respectively. Each of (i) the plurality of reference Gaussian densities and associated reference weights and (ii) the plurality of test Gaussian densities and the associated test weights can represent a subpopulation of the plurality of reference cells or the plurality of test cells, respectively. The method can comprise: performing an analysis of the plurality of test cells relative to the plurality of reference cells using the plurality of reference Gaussian densities and the plurality of test Gaussian densities.

Disclosed herein include embodiments of a method for single cell analysis. In some embodiments, the method is under control of a hardware processor (or a virtual processor) and comprises: receiving single cell gene expression data comprising a plurality of normalized reference gene expression vectors and a plurality of normalized test gene expression vectors representing single cell gene expression profiles of a plurality of reference cells and a plurality of test cells respectively, in a gene expression space. The method can comprise: determining (i) a gene feature matrix, comprising a plurality of gene features, and, for each of the plurality of normalized reference gene expression vectors and the plurality of normalized test gene expression vectors, (ii) a reference gene feature weighting vector or a test gene feature weighting vector using a training matrix comprising a plurality normalized training gene expression vectors. The plurality of reference gene feature weighting vectors and the plurality of test gene feature weighting vectors can represent gene feature profiles of the plurality of reference cells and the plurality of test cells in a gene feature space, respectively. The method can comprise: determining (i) a reference Gaussian mixture model comprising a plurality of reference Gaussian densities each associated with a reference weight (e.g., a scalar) and (ii) a test Gaussian mixture model comprising a plurality of test Gaussian densities each associated with a test weight (e.g., a scalar) from the plurality of reference gene feature weighting vectors and the plurality of test gene expression vectors, respectively. Each of (i) the plurality of reference Gaussian densities and associated reference weights and (ii) the plurality of test Gaussian densities and the associated test weights can represent a subpopulation of the plurality of reference cells or the plurality of test cells, respectively. The method can comprise: performing an analysis of the plurality of test cells relative to the plurality of reference cells using the plurality of reference Gaussian densities and the plurality of test Gaussian densities. In some embodiments, receiving the single cell gene expression data comprises: receiving single cell gene expression data comprising a plurality of reference gene expression vectors and a plurality of test gene expression vectors representing single cell gene expression profiles of a plurality of reference cells and a plurality of test cells respectively, in a gene expression space. Receiving the single cell gene expression data can comprise: for each of the plurality of reference gene expression vectors and the plurality of test gene expression vectors, normalizing gene expression values of the reference gene expression vector or the test gene expression vector to generate a normalized reference gene expression vector or a normalized test gene expression vector comprising normalized gene expression values. The method can comprise: determining a difference between the plurality of test cells, or a subpopulation thereof, and the plurality of reference cells, or a subpopulation thereof, using the plurality of reference Gaussian densities and the plurality of test Gaussian densities. The method can comprise: determining a difference between one of the plurality of test Gaussian densities the reference Gaussian density the test Gaussian density is aligned to, wherein the difference indicates a difference between the plurality of test cells, or a subpopulation thereof, and the plurality of reference cells, or a subpopulation thereof.

In some embodiments, the gene expression profiles comprise mRNA expression profiles and/or protein expression profiles. The receiving can comprise: performing single cell gene expression profiling to obtain the single cell gene expression data.

In some embodiments, the normalizing comprises: normalizing the gene expression values of the reference gene expression vector or the test gene expression vector relative to a sum of the gene expression values to generate the normalized reference gene expression vector or the normalized test gene expression vector comprising the normalized gene expression values. In some embodiments, the normalizing comprises: adjusting the gene expression values of the reference gene expression vector or the test gene expression vector with a scaling factor to generate the normalized reference gene expression vector or the normalized test gene expression vector comprising the normalized gene expression values. The scaling factor can be about a sum of the gene expression values of one of the plurality of reference gene expression vectors or one the plurality of test gene expression vectors. The scaling factor can be about a smallest sum of the gene expression values of any of the plurality of reference gene expression vectors and any of the plurality of test gene expression vectors. The scaling factor can be about 1000.

In some embodiments, the normalizing comprises: increasing the gene expression values of the reference gene expression vector or the test gene expression vector by a pseudo-count value to generate the normalized reference gene expression vector or the normalized test gene expression vector comprising the normalized gene expression values. The pseudo-count value can be one. The normalizing can comprise: changing the gene expression values of the reference gene expression vector or the test gene expression vector to a logarithmic scale to generate the normalized reference gene expression vector or the normalized test gene expression vector comprising the normalized gene expression values. In some embodiments, the normalized gene expression values of the plurality of reference gene expression vectors and the plurality of test gene expression vectors transition smoothly.

In some embodiments, the plurality of normalized training gene expression vectors comprises: one or more the plurality of normalized reference gene expression vectors and/or one or more of the plurality of test gene expression vectors. In some embodiments, the plurality of normalized training gene expression vectors comprises one or more of the plurality of normalized reference gene expression vectors sampled and/or one or more of the plurality of test gene expression vectors. In some embodiments, the plurality of normalized training gene expression vectors comprises two or more the plurality of normalized reference gene expression vectors randomly and/or uniformly sampled and/or two or more of the plurality of test gene expression vectors randomly and/or uniformly sampled. In some embodiments, the plurality of normalized training gene expression vectors comprises the plurality of normalized reference gene expression vectors and/or the plurality of test gene expression vectors.

In some embodiments, determining the gene feature matrix comprises determining the gene feature matrix from the plurality of normalized training gene expression vectors using machine learning. The machine learning can be based on a layered neural network. In some embodiments, determining the gene feature matrix comprises: determining the gene feature matrix using matrix factorization. In some embodiments, the matrix factorization comprises singular value decomposition. The matrix factorization can comprise principal component analysis. The matrix factorization can comprise non-negative matrix factorization. The matrix factorization can comprise sparse non-negative matrix factorization. The matrix factorization can comprise orthogonal non-negative matrix factorization.

In some embodiments, the gene feature matrix is an orthogonal matrix. Each, one, or at least one, element of the gene feature matrix is greater than or equal to zero. Each, one, or at least one, element of at least one of the plurality of reference gene feature weighting vectors and/or at least one of the plurality of test gene feature weighting vectors is greater than or equal to zero.

In some embodiments, a number of the plurality of gene features is predetermined. A size of a gene expression vector of the plurality of reference gene expression vectors and the plurality of test gene expression vectors can be at most 10, 20, 30, 40, or 50. A ratio of a size of a gene expression vector of the plurality of reference gene expression vectors and the plurality of test gene expression vectors to a number of the plurality of gene features can be at least 10, 20, 30, 40, 50, 100, 500, or 1000. A size of a gene expression vector of the plurality of reference gene expression vectors and the plurality of test gene expression vectors can be at least 1000, 5000, or 1000.

In some embodiments, determining the gene feature matrix comprises: determining the gene feature matrix comprising the plurality of gene features using a plurality normalized training gene expression vectors. Determining the gene feature matrix can comprise: for each of the plurality of normalized reference gene expression vectors and the plurality of normalized test gene expression vectors, determining a reference gene feature weighting vector or a test gene feature weighting vector in a gene feature space using the gene feature matrix. Determining the gene feature matrix can comprise: determining the gene feature matrix and a gene feature weighting matrix comprising a plurality of gene feature weighting vectors using the plurality of normalized training gene expression vectors. Each, one, or at least one, element of the gene feature weighting matrix can be greater than or equal to zero.

In some embodiments, determining the gene feature matrix and the gene feature weighting matrix comprises: determining the gene feature matrix and the gene feature weighting matrix by minimizing a loss function comprising a difference of the training matrix and a product of the gene feature matrix and the gene feature weighting matrix. Determining the gene feature matrix and the gene feature weighting matrix can comprise: determining the gene feature matrix and the gene feature weighting matrix by minimizing a loss function comprising a norm of the training matrix and a product of the gene feature matrix and the gene feature weighting matrix. Determining the gene feature matrix and the gene feature weighting matrix can comprise: determining the gene feature matrix and the gene feature weighting matrix by minimizing a loss function comprising a Frobenius norm of the training matrix and a product of the gene feature matrix and the gene feature weighting matrix. In some embodiments, the loss function comprises a penalty comprising a number of the plurality of gene features in the gene feature matrix. The loss function can comprise a penalty comprising to a number of the plurality of gene features in the gene feature matrix exponentiated with an exponentiation factor. The exponentiation factor can be about 0.7.

In some embodiments, determining the reference gene feature weighting vector or the test gene feature weighting vector comprises: determining the reference gene feature weighting vector or the test gene feature weighting vector in the gene feature space by minimizing a loss function comprising a difference of the corresponding normalized reference gene expression vector or normalized test gene expression vector and a product of the gene feature matrix and the reference gene feature weighting vector or the test gene feature weighting vector. Determining the reference gene feature weighting vector or the test gene feature weighting vector can comprise: determining the reference gene feature weighting vector or the test gene feature weighting vector in the gene feature space by minimizing a loss function comprising a norm of the corresponding normalized reference gene expression vector or normalized test gene expression vector and a product of the gene feature matrix and the reference gene feature weighting vector or the test gene feature weighting vector. Determining the reference gene feature weighting vector or the test gene feature weighting vector can comprise: determining the reference gene feature weighting vector or the test gene feature weighting vector in the gene feature space by minimizing a loss function comprising a Frobenius norm of the corresponding normalized reference gene expression vector or normalized test gene expression vector and a product of the gene feature matrix and the reference gene feature weighting vector or the test gene feature weighting vector.

In some embodiments, determining (i) the reference Gaussian mixture model and (ii) the test Gaussian mixture model comprises: determining (i) one or more reference parameters and the reference weight of or associated with each of the plurality of reference Gaussian densities and (ii) one or more test parameters and the test weight of each of the plurality of test Gaussian densities, respectively, from (i) the plurality of reference gene feature weighting vectors and (ii) the plurality of test gene feature weighting vectors, respectively. Each, one, or at least one, of the plurality of reference Gaussian densities and/or each, one, or at least one, of the plurality of test Gaussian densities comprises a normal distribution, and wherein parameters of the normal distribution comprises the one or more reference parameters or the one or more test parameters of the reference Gaussian density or the test Gaussian density, respectively. The one or more can parameters of each, one, or at least one, of the plurality of reference Gaussian densities comprise a reference centroid and a reference covariance matrix. The one or more parameters of each, one, or at least one, of the plurality of test Gaussian densities can comprise a test centroid and a test covariance matrix. The reference centroid, the reference covariance matrix, and the reference weight of or associated with a reference Gaussian density of the plurality of Gaussian densities can represent an average of reference gene features of a subpopulation of the plurality of reference cells represented by the reference Gaussian density, a spread of the reference gene features, an abundance of the subpopulation of the plurality of reference cells represented by the reference Gaussian density. The test centroid, the test covariance matrix, and the test weight of or associated with a test Gaussian density of the plurality of Gaussian densities can represent an average of test gene features of a subpopulation of the plurality of test cells represented by the test Gaussian density, a spread of the test gene features, an abundance of the subpopulation of the plurality of test cells represented by the test Gaussian density.

In some embodiments, determining (i) the reference Gaussian mixture model and (ii) the test Gaussian mixture model comprises: determining (i) the reference Gaussian mixture model and (ii) the test Gaussian mixture model by maximum likelihood estimation and a likelihood function. The maximum likelihood estimation can comprise an expectation maximization method.

In some embodiments, a number of the plurality of reference Gaussian densities and/or a number of the plurality of test Gaussian densities is predetermined. In some embodiments, a number of the plurality of reference Gaussian densities and/or a number of the plurality of test Gaussian densities is about 10, 15, 20, 30, 40, or 50. In some embodiments, determining (i) the reference Gaussian mixture model and (ii) the test Gaussian mixture model comprises determining a number of the plurality of reference Gaussian densities and/or a number of the plurality of test Gaussian densities by penalizing the number of the plurality of reference Gaussian densities and/or the number of the plurality of test Gaussian densities. Determining (i) the reference Gaussian mixture model and (ii) the test Gaussian mixture model can comprise: determining a number of the plurality of reference Gaussian densities and/or a number of the plurality of test Gaussian densities using Bayesian Information Criterion.

In some embodiments, determining (i) the reference Gaussian mixture model comprises: determining a pair of reference Gaussian densities of the plurality of reference Gaussian densities with a divergence smaller than a divergence of any other pair of reference Gaussian densities of the plurality of reference Gaussian densities to be redundant in the reference Gaussian model; merging the pair reference Gaussian densities to generate a merged reference Gaussian density; determining merging the pair of reference Gaussian densities results in increasing a Bayesian Information Criterion of the reference Gaussian mixture model; and/or accepting the merged reference Gaussian density. Determining (i) the test Gaussian mixture model can comprise: determining a pair of test Gaussian densities of the plurality of test Gaussian densities with a divergence smaller than a divergence of any other pair of test Gaussian densities of the plurality of test Gaussian densities to be redundant in the test Gaussian model; merging the pair test Gaussian densities to generate a merged test Gaussian density; determining merging the pair of test Gaussian densities results in increasing a Bayesian Information Criterion of the test Gaussian mixture model; and/or accepting the merged test Gaussian density.

In some embodiments, determining (i) the reference Gaussian mixture model comprises: iterative merging a pair of reference Gaussian densities of the plurality of reference Gaussian densities with a divergence smaller than a divergence of any other pair of reference Gaussian densities of the plurality of reference Gaussian densities to be redundant until merging the pair of reference Gaussian densities does not result in increasing a Bayesian Information Criterion of the reference Gaussian mixture model after merging. Determining (i) the test Gaussian mixture model can comprise: iterative merging a pair of test Gaussian densities of the plurality of test Gaussian densities with a divergence smaller than a divergence of any other pair of test Gaussian densities of the plurality of test Gaussian densities to be redundant until merging the pair of test Gaussian densities does not result in increasing a Bayesian Information Criterion of the test Gaussian mixture model after merging. The divergence of the pair of reference Gaussian densities can comprises a Jeffrey's divergence of the pair of reference Gaussian densities. The divergence of the pair of test Gaussian densities can comprises a Jeffrey's divergence of the pair of test Gaussian densities. The divergence of the pair of reference Gaussian densities can comprise a Kullback Leibler divergence of the pair of reference Gaussian densities. The divergence of the pair of test Gaussian densities can comprise a Kullback Leibler divergence of the pair of test Gaussian densities.

In some embodiments, the performing comprises: aligning each of the plurality of test Gaussian densities to an aligned reference Gaussian density of the plurality of reference Gaussian densities; and/or performing an analysis of the plurality of test cells relative to the plurality of reference cells using one, at least one, or each, of the plurality of test Gaussian densities and the aligned reference Gaussian density the test Gaussian density is aligned to.

In some embodiments, aligning each of the plurality of test Gaussian densities to the aligned reference Gaussian density of the plurality of reference Gaussian densities comprises: aligning each of the plurality of test Gaussian densities to an aligned reference Gaussian density of the plurality of reference Gaussian densities based on one or more test parameters of the test Gaussian density and one or more reference parameters of each of the plurality of reference Gaussian densities.

In some embodiments, aligning each of the plurality of test Gaussian densities to the aligned reference Gaussian density of the plurality of reference Gaussian densities comprises: aligning the test Gaussian density to the aligned reference Gaussian density with a divergence smaller than a divergence between the test Gaussian density and any other of the plurality of reference Gaussian densities. The divergence between the test Gaussian density and the aligned reference Gaussian density can comprise a Jeffrey's divergence between the test Gaussian density and the reference Gaussian density. The divergence between the test Gaussian density and the aligned reference Gaussian density can comprise a Kullback Leibler divergence between the test Gaussian density and the reference Gaussian density. The method can comprise: determining, for each of the plurality of test Gaussian densities, a probability of the divergence between the test Gaussian density and the aligned reference Gaussian density the test Gaussian density is aligned to. Determining the probability of the divergence can comprise: determining the probability of the divergence between the test Gaussian density and the aligned reference Gaussian density the test Gaussian density is aligned to using an empirical null distribution of divergence. The method can comprise: determining the empirical null distribution of divergence using divergences of pairs of Gaussian densities.

In some embodiments, performing the analysis comprises: performing the analysis of the plurality of test cells relative to the plurality of reference cells using one of the plurality of test Gaussian densities and the associated test weight and the aligned reference Gaussian density the test Gaussian density is aligned to and the associated reference weight.

In some embodiments, performing the analysis comprises: performing the analysis of the plurality of test cells relative to the plurality of reference cells using a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. Performing the analysis can comprise: determining a centroid delta of the test centroid and the reference centroid; determining a covariance matrix delta of the test covariance matrix and the reference covariance matrix; determining a weight delta of the test weight and the reference weight; and/or performing the analysis of the plurality of test cells relative to the plurality of reference cells using the centroid delta, the covariance matrix delta, and the weight delta.

In some embodiments, determining the difference comprises: determining the difference using one of the plurality of test Gaussian densities and the associated test weight and the aligned reference Gaussian density the test Gaussian density is aligned to and the associated reference weight. Determining the difference can comprise: determining the difference between the plurality of test cells and the plurality of reference cells using a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. Determining the difference can comprise: determining a centroid delta of the test centroid and the reference centroid; determining a covariance matrix delta of the test covariance matrix and the reference covariance matrix; determining a weight delta of the test weight and the reference weight; and determining the difference of the plurality of test cells relative to the plurality of reference cells using the centroid delta, the covariance matrix delta, and the weight delta.

In some embodiments, the Gaussian model difference comprises a difference between one of the plurality of test Gaussian densities and the associated test weight and one of the reference Gaussian densities and the associated reference weight. The Gaussian density difference can comprise a difference between a test centroid and a reference centroid, a test covariance matrix and a reference covariance matrix, and the associated test weights of one of the plurality of test Gaussian densities and of one of the plurality of reference Gaussian densities. The Gaussian density difference comprises a centroid delta of the test centroid and the reference centroid, a covariance matrix delta of the test covariance matrix and the reference covariance matrix, and/or a weight delta of the test weight and the reference weight The centroid delta can represent a change in gene features of a subpopulation of cells represented by the test Gaussian densities or the aligned reference Gaussian density. The covariance matrix delta can represent a change in a spread of the gene features of the subpopulation of cells, and wherein the weight delta represents a change in abundance of the subpopulation of cells. The centroid delta can comprise a difference, a norm, or a Frobenius norm of the test centroid and the reference centroid. The covariance matrix delta can comprise a difference or a norm of the test covariance matrix and the reference covariance matrix, and a weight delta comprises a difference or a norm of the test weight and the reference weight.

In some embodiments, each, one, or at least one, of the plurality of reference cells is associated with a first annotation. The method can comprise: determining a second annotation of each, one, or at least one, of the plurality of reference Gaussian densities using the first annotation associated with each, one, or at least one, of the plurality of reference cells. The first annotation and/or the second annotation can comprise a function annotation, a pathway annotation, a cell-type annotation, and/or a tissue-type annotation. The method can comprise: determining a third annotation of each, or at least one, of the plurality of test Gaussian densities using the second annotation associated with the aligned reference Gaussian density the test Gaussian density is aligned to.

In some embodiments, the plurality of reference cells comprises healthy cells. The plurality of test cells can comprise diseased cells and/or the plurality of reference cells can comprise cells cultured in the absence of a drug or a signal, and/or the plurality of test cells can comprise cells cultured in the presence of the drug or the signal. The plurality of reference cells can comprise cells from a first subject not treated with a drug, and/or the plurality of test cells can comprise cells from a second subject treated with the drug. The first subject can be the second subject. The plurality of reference cells can comprise cells from a first tissue type, and/or the plurality of test cells can comprise cells from a second tissue type.

In some embodiments, performing the analysis comprises: determining similarities of and difference between the plurality of reference cells and the plurality of test cells. Performing the analysis can comprise: determining a gene feature of the plurality of gene features absent or present in the plurality of reference cells is present or absent in the plurality of test cells. Performing the analysis can comprise: determining a similarity between the plurality of reference cells and the plurality of test cells using a log-likelihood ratio score of (i) one, at least one, or each of, the plurality of reference Gaussian mixtures and associated reference weights and (ii) one, at least one, or each of, the plurality of test Gaussian mixtures and associated test weights.

In some embodiments, the single cell gene expression data comprises a plurality of second reference gene expression vectors representing single cell gene expression profiles of a plurality of second reference cells. The normalizing can comprise: for each of the plurality of second reference gene expression vectors, normalizing gene expression values of the second reference gene expression vector to generate a normalized second reference gene expression vector comprising normalized gene expression values. Determining the gene feature matrix can comprise: for each of the plurality of normalized second reference gene expression vectors, determining a second reference gene feature weighting vector using the training matrix, wherein the plurality of second reference gene feature weighting vectors represent second gene feature profiles of the plurality of second reference cells. Determining (i) the reference Gaussian mixture model can comprise: determining a second reference Gaussian mixture model comprising a plurality of second reference Gaussian densities each associated with a second reference weight, wherein each of the plurality of second reference Gaussian densities and associated reference weights represents a second subpopulation of the plurality of second reference cells. The performing can comprise: performing the analysis of the plurality of test cells relative to the plurality of reference cells and the plurality of second reference cells using the plurality of reference Gaussian densities, the plurality of second reference Gaussian densities, and/or the plurality of test Gaussian densities. In some embodiments, the plurality of gene expression vectors comprises a plurality of first reference gene expression vectors and a plurality of second reference gene expression vectors representing single cell gene expression profiles of a plurality of first reference cells and a plurality of second reference cells of the plurality of cells.

In some embodiments, the plurality of (first) reference cells can comprise healthy cells, and/or wherein the plurality of second reference cells comprises diseased cells. The plurality of (first) reference cells can from a first tissue, and/or the plurality of second reference cells is from a second tissue. The first tissue and the second tissue can be of different tissue types.

In some embodiments, the performing comprises: determining a first similarity between the plurality of (first) reference cells and the plurality of test cells using a first log-likelihood ratio score of (i) one, at least one, or each of, the plurality of (first) reference Gaussian mixtures and associated (first) reference weights and (ii) one, at least one, or each of, the plurality of test Gaussian mixtures and associated test weights; determining a second similarity between the plurality of second reference cells and the plurality of test cells using a second log-likelihood ratio score of (i) one, at least one, or each of, the plurality of second reference Gaussian mixtures and associated second reference weights and (ii) one, at least one, or each of, the plurality of test Gaussian mixtures and associated test weights; and/or determining the plurality of test cells to be more similar to the plurality of (first) reference cells and the plurality of second reference cells based on the first similarity and the second similarity. The performing can comprise: determining a probability of the plurality of test cells, or a subpopulation thereof, to be a (first) reference cell type of the plurality of (first) reference cells, or a subpopulation thereof, relative to the a second reference cell type of the plurality of second reference cells, or a subpopulation thereof, with respect to a difference in a first condition for culturing the plurality of (first) reference cells and a second condition for culturing the plurality of second reference cells. Determining the probability can comprise determining the probability using multinomial logistic regression.

In some embodiments, the plurality of (first) reference cells comprises a (first) reference type of cells and is associated with a (first) reference label. The plurality of second reference cells can comprise a second reference type of cells and is associated with a second reference label. The performing can comprise: determining a probability of the plurality of test cells to be the reference type of cells using (i) the plurality of (first) reference Gaussian densities and/or the associated (first) reference weights and (ii) the plurality of test Gaussian densities and/or the associated test weights; determining a probability of the plurality of test cells to be the second reference type of cells using (i) the plurality of second reference Gaussian densities and/or the associated second reference weights and (ii) the plurality of test Gaussian densities and/or the associated test weights; and/or determining a test label of the plurality of test cells to be the reference label or the second reference label based on the probability and the second probability.

In some embodiments, the single cell gene expression data comprises a plurality of second test gene expression vectors representing single cell gene expression profiles of a plurality of second test cells. The normalizing can comprise: for each of the plurality of second test gene expression vectors, normalizing gene expression values of the second test gene expression vector to generate a normalized second test gene expression vector comprising normalized gene expression values. Determining the gene feature matrix can comprise: for each of the plurality of normalized second test gene expression vectors, determining a second test gene feature weighting vector using the training matrix, wherein the plurality of second test gene feature weighting vectors represent second gene feature profiles of the plurality of second test cells. Determining (i) the reference Gaussian mixture model can comprise: determining a second test Gaussian mixture model comprising a plurality of second test Gaussian densities each associated with a second test weight, wherein each of the plurality of second test Gaussian densities and associated test weights represents a second subpopulation of the plurality of second test cells. The performing can comprise: performing an analysis of the plurality of second test cells relative to the plurality of reference cells using the plurality of reference Gaussian densities and the plurality of second test Gaussian densities. The performing can comprise: performing an analysis of the plurality of test cells relative to the plurality of second test cells using the plurality of test Gaussian densities and the plurality of second test Gaussian densities. In some embodiments, the plurality of gene expression vectors comprises a plurality of first test gene expression vectors and a plurality of second test gene expression vectors representing single cell gene expression profiles of a plurality of first test cells and a plurality of second test cells of the plurality of cells.

In some embodiments, the performing comprises: performing an analysis of the plurality of (first) test cells and the plurality of second test cells relative to the plurality reference cells using the plurality of reference Gaussian densities and a plurality of (first) test Gaussian densities and the plurality of second test Gaussian densities of the plurality of test Gaussian densities. The plurality of (first) test cells can be originally of a (first) test cell type or from a (first) test tissue type and cultured under a (first) test condition, the plurality of second test cells can be originally of a second test cell type or from a second test tissue type and cultured under a second test condition, and/or the plurality of reference cells can be originally of a reference cell type or from a reference tissue type and cultured under a reference condition. The plurality of (first) test cells can be cultured under a (first) test condition and of a (first) test cell type and, the plurality of second test cells can be cultured under a second test condition and of a second test cell type, and wherein the plurality of reference cells can be cultured under a reference condition and of a reference cell type. The (first) test cell type, the second test cell type, and/or the reference cell type can be identical, the (first) tissue type, the second test tissue type, and/or the reference tissue type can be identical, and/or the (first) test condition, the second test condition, and/or the reference condition can be identical. The (first) test cell type, the second test cell type, and/or the reference cell type can be different, the (first) tissue type, the second test tissue type, and/or the reference tissue type can be different, and/or wherein the (first) test condition, the second test condition, and/or the reference condition can be different. The (first) test condition can comprise presence of a (first) drug, signal, or environmental condition, wherein the second test condition comprises presence of a second drug, signal, or environmental condition. The reference condition can comprise no (first) drug, signal, and environmental condition and/or no second drug, signal, and environmental condition. The (first) test condition, second test condition, and/or the reference condition can comprise different concentrations or extents of a drug, signal, or environmental condition. The plurality of (first) test cells can be from a (first) sample of a subject at a (first) time, and the plurality of second test cells can be from a second sample of the subject at a second time.

In some embodiments, performing the analysis comprises: determining a (first) similarity between the plurality of (first) test cells and the plurality of reference cells using a (first) log-likelihood ratio score of (i) one, at least one, or each of, the plurality of (first) test Gaussian mixtures and associated (first) test weights and (ii) one, at least one, or each of, the plurality of reference Gaussian mixtures and associated reference weights; determining a second similarity between the plurality of second test cells and the plurality of reference cells using a second log-likelihood ratio score of (i) one, at least one, or each of, the plurality of second test Gaussian mixtures and associated second test weights and (ii) one, at least one, or each of, the plurality of reference Gaussian mixtures and associated reference weights; and determining the plurality of (first) test cells or the plurality of second test cells to be more similar to the plurality of reference cells based on the (first) similarity and the second similarity.

In some embodiments, the method can comprise: demixing of the plurality of test gene expression vectors to generate a plurality of (first) test gene expression vectors and a plurality of second gene expression vectors.

In some embodiments, the method comprises: determining a reference diversity comprising a reference heterogeneity of the plurality of reference cells or a subpopulation of the plurality of reference cells and/or a test diversity comprising a test heterogeneity of the plurality of test cells or a subpopulation of the plurality of test cells. The reference heterogeneity can comprise (i) an entropy of one, at least one, or each, of the plurality of reference Gaussian mixtures and/or associated reference weights and/or (ii) a reference covariance matrix of one, at least one, or each, the plurality of reference Gaussian mixtures. The test heterogeneity can comprise (i) an entropy of one, at least one, or each, of the plurality of test Gaussian mixtures and/or associated test weights and/or (ii) a test covariance matrix of one, at least one, or each, the plurality of test Gaussian mixtures. The method can comprise: determining a gene is upregulated or downregulated in a subpopulation of the plurality of test cells relative to a subpopulation of the plurality of reference cells. Determining the gene is upregulated or downregulated can comprise: determining the gene is upregulated or downregulated in a subpopulation of the plurality of test cells relative to a subpopulation of the plurality of reference cells using a L1 distance between a test distribution of the single cell gene expression profiles of the gene in the subpopulation of the plurality of test cells and a reference distribution of the single cell gene expression profiles of the gene in the subpopulation of the plurality of reference cells. In some embodiments, the subpopulation of the plurality of reference cells comprises 50%, 60%, 70%, 80%, 90%, 95%, 99%, or 100 cells of a cell type, and/or wherein the subpopulation of the plurality of test cells comprises 50%, 60%, 70%, 80%, 90%, 95%, 99%, or 100 cells of a cell type.

In some embodiments, a run time of the hardware processor increases linearly or non-exponentially as a number of the plurality of reference gene expression vectors and/or the plurality of test gene expression vectors increases.

Disclosed herein include embodiments of a computer readable medium comprising executable instructions that, when executed by a hardware processor, cause the hardware processor to perform any of the methods disclosed herein.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 shows PopAlign and plot changes. Subpopulations are automatically aligned to a population in the control sample. Then changes in mean ($\mu$) are plotted.

FIGS. 9A-9D show a non-limiting exemplary probabilistic modeling framework.

FIGS. 13A-13D: Summary of PopAlign framework.

FIG. 14A: Experimental data for ~3600 bone marrow cells projected into an m=15 dimensional gene feature space. 2D plots show single cells projected along gene feature pairs ($c_i$, $c_j$), and a single selected 3D projection (inset) is shown. Blue axis denote shared axis between 2D and 3D plot. FIG. 14B: Model generated data for the same 2D and 3D feature space projections shown in FIG. 14A. In the 3D projection (inset), each larger circle denotes the centroid ($\mu$) of a Gaussian mixture component where the circle radius is proportional to $w_i$, the mixture weight. In all cases, the model generated data replicates the qualitative geometric structures in the experimental data. FIG. 14C: Model error across 2D projections from FIG. 14A and FIG. 14B quantified by analyzing percent deviation in point density for experimental vs model generated data. Quantification of error is performed using a numerical error metric based on binning the 2D projections (See Methods—Analysis of model error). The quantitative error in model-generated is on average 11.3% (red line) compared with 8.5% error when comparing random subsamples of experimental data (blue line).

FIGS. 15C-15D: For models from both tissues, mixture components (x-axis) are scored using cell type annotations supplied by Tabula Muris (y-axis). Each cell of the heatmap represents the percentage of cells associated with each mixture component that have a specific cell type label. Columns (but not rows) sum to 1. FIG. 15E: Alignments between mixture component centroids ($\mu$) from the reference population (Mammary Gland) and the test population (Limb Muscle) are shown as connecting lines. All m-dimensional $\mu$ vectors are transformed using principal components analysis (PCA) and plotted using the first 3 PCS. Width of each line is inversely proportional to the p-value associated with the alignment (see Legend). FIG. 15F: Null distribution of Jeffrey's divergence used to calculate p-values. Jeffrey's divergence was calculated for all possible pairs of mixture components from models of all tissues from Tabula Muris. FIG. 15G: Aligned subpopulations were rank in terms of maximum $\Delta w$ and show top two pairs. These subpopulations are identified as T cells and endothelial cells, and are highlighted using a blue dotted oval on the top left and top right in FIG. 15E. It was found that T cells are highly abundant in Mammary gland while endothelial cells are highly abundant in muscle. FIG. 15H: Comparing subpopulation centroids ($\mu$) for macrophages in terms of gene expression features. Macrophages in Mammary gland and Limb Muscle share common features (black font), but also have tissue-specific features (red font). Corresponding alignments are highlighted in FIG. 15E with a gray dotted oval on the middle left.

FIGS. 16A-16G: PopAlign can perform global comparisons of cell states across dozens to hundreds of experimental samples. FIG. 16A: Computational runtime versus number of samples for PopAlign (blue) vs Seurat (red). PopAlign scaled linearly with the number of samples, while Seurat scaled exponentially and encountered an out-of-memory error when applied to >8 samples. Samples were bootstrapped from all 12 samples of the mouse tissue survey Tabula Muris. Benchmarking tests performed on typical workstation (8 cores, 64 GB RAM). FIG. 16B: Heatmap of a pairwise similarity metric between subpopulations from all 12 tissues demonstrates PopAlign can identify cogent cell-type specific clusters even when applied on very disparate tissue types. The similarity metric is defined as $e^{-JD}$ where JD is the Jeffrey's Divergence between two subpopulations. Inset highlights subpopulations clustered as macrophages, displaying tissue and cell type labels extracted from Tabula Muris annotations. FIGS. 16C-16F: Models for all tissues are aligned to a reference model (Mammary Gland) and corresponding abundances (w) are plotted for selected subpopulations classified as (FIG. 16C) T cells (FIG. 16D) B cells (FIG. 16E) endothelial cells (FIG. 16F) macrophages. FIG. 16G: Mean gene expression state (p) for macrophage across all tissues show variation in key immune pathways (highlighted in red).

FIGS. 17A-17J: PopAlign identifies cell-type specific signaling responses in primary human immune cells. FIG. 17A: Experimental data from reference PBMC sample (~1300 cells) are projected into a 17-dimensional feature space, but are plotted in a 3D subset of features that are found to be impacted by signals. Mixture model centroids (p) are indicated as numbered disks. FIG. 17B: Classification of mixture model components using mean gene expression values for canonical markers of immune cells. Classical monocytes are CD14+, non-classical monocytes are CD14low/CD16+, effector T cells are CD3D+/CD57+, naive T cells are CD3D+/CD28+, B cells are CD19+, and Erythrocytes are HBB+. All gene means were calculated across cells scored by that mixture component, and independently scaled by its max value across all mixture component means (including subpopulations for signaling conditions). FIG. 17C: Experimental data from cells exposed to GM-CSF, with mixture component centroids denoted. FIG. 17D: Experimental data from cells exposed to IFNG, with mixture component centroids denoted in light blue. Both test samples (GM-CSF and IFNG) were aligned to the reference population, with specific alignments for reference mixture components that classified as monocytes (overlaid and shown with connected lines). Shifts in the position of the mixture component $\mu$ revealed how GM-CSF and IFNG exerted differential effects on monocyte populations. FIGS. 17E-17F: For each mixture component from test samples (x-axis), Jeffrey's divergence against all reference components is plotted on a log 10 scale, with lowest divergence values giving the best alignment. Symbols correspond to alignments displayed in FIG. 17C and FIG. 17D. Black cross in FIGS. 17D and 17F denotes a high secondary alignment for IFNG mixture 1, suggesting that both PBMC-1 and PBMC-3 converge to the same final population in response to IFNG. FIG. 17G: Scatterplot of parameter changes $\Delta\mu$ and $\Delta w$ for all subpopulation alignments across both test samples. Monocytes were above average ($\Delta\mu \geq 0.04$) for both test samples. FIG. 17H: Heatmap of aligned monocyte mixture component centroids ($\mu$) in terms of gene expression features. IFNG (upper) induced expression of an ER Phagosome feature (blue arrow). GM-CSF altered expression of two features (Chemokine Activity and Lysosome) but did not affect each subpopulation's baseline levels for 3 monocyte specific features (black arrows). FIG. 17I: Abundances (w) are shown for both sets of aligned subpopulations. FIG. 17J: Gene expression distributions for all monocyte subpopulations for specific genes from FIG. 17J that were affected by signals (blue arrows): (i) STAT1, a signal transducer (ii) PSME2, a proteasome activator, (iii) CCL2, an inflammatory chemokine, (iv) CSTB, a protease inhibitor, (v) LYZ, an antimicrobial enzyme, and (vi) GRN, a lysosomal protein.

FIGS. 18A-18F, 18G, 18H, 18I, 18J, 18K, 18M, 18N, 18O, and 18P: Discovering signatures of disease and treatment in PBMCs from multiple myeloma patients. FIG. 18A-18F: Experimental single cell mRNA-seq data from two healthy donors and four multiple myeloma patients (MM1-4) are projected into 16-dimensional gene feature space. 3D plots show single cells in a subset of three gene features that highlight separation between different immune cell types. Mixture model centroids ($\mu$) are indicated as numbered disks. Subpopulations in test samples are aligned to the reference (FIG. 18A) and changes in abundance ($\Delta w$)

are plotted for (FIG. 18G) B cells, (FIG. 18H) monocytes, (FIG. 18I) naive T cells, and (FIG. 18J) effector T cells, showing general and patient specific changes. FIG. 18K: Mean gene expression levels for two markers of myeloid derived suppressor cells (MDSC), CD33 and CD11b, are plotted for all monocyte subpopulations. Error bars denote confidence interval of the mean. FIG. 18M: $|\Delta\mu|$ for naive T cell and effector T cell populations relative to healthy1. FIG. 18N: Heatmap of mixture component $\mu$ vectors in terms of feature coefficients $c_i$ for aligned naive and effector T cells across samples. MM subpopulations exhibit reduced expression of two features (red font): Leukocyte motility and Cytotoxic Lymphocyte Killing. FIG. 18O: Distribution of beta-actin (ACTB) expression for all effector T cell subpopulations across samples. Violin shows distribution, and mean is denoted by white circle. FIG. 18P: Distribution of perforin 1 (PFN1) expression for all effector T cell subpopulations across samples. For single gene plots in FIGS. 18K, 18O, and 18P, units are in terms of normalized and transformed gene expression (log(TPT+1)) where TPT denotes transcripts per thousands.

FIGS. 19A-19G: Orthogonal NMF produces low-error reconstruction Orthogonal nonnegative matrix factorization factors each (FIG. 19A) gene expression data matrix into (FIG. 19B) F, a set of orthogonal linear feature vectors, and (FIG. 19C) C, a matrix of coefficients. For FIG. 19B, the genes were ordered according to their weight in each feature, only genes with greater >4$\sigma$ for each feature were kept. This ordering highlights the orthogonality of features. FIG. 19D: The reconstructed data F C is a denoised version of the original data matrix. FIG. 19E: Data values from the original data matrix are partitioned into bins, and their means are plotted against corresponding data values from the reconstructed data matrix (F C). Bin width ~0.1. Shaded area indicates the standard deviation between original values and reconstructed values within each bin. (See Methods—oNMF error analysis). FIG. 19F Histogram of the entries in normalized data matrix D, with log(counts) on y-axis. 99.996% of data values are less than 5, which is also the linear regime of FIG. 19E. FIG. 19G: Zoomed in view of white inset from FIG. 19C, showing specific genes that have high weights for two features, as well as their top gene set results from gene set enrichment analysis.

FIGS. 21A-21L. PopAlign models for all 12 tissues of Tabula Muris. For each tissue, the following is plotted: (upper left) joint t-SNE plot of experimental single-cell data (black), PopAlign model-generated data (teal), and mixture model centroids (p) as numbered disks, (upper right) Heatmap of the proportion of cells classified by each mixture model component against their annotated labels. Each column sums to 1. (lower) Heatmap of mixture component centroids (mu) in terms of their expression level of features. For all tissues, a universal 30D feature set was used determined using sampled data from all tissues within the collection.

(FIG. 31A) PBMC, (FIG. 31B) GM-CSF, and (FIG. 31C) IFNG. Mixture component p's (disks) for PBMC mixture components 1 and 3 overlaid on plots FIG. 31B and FIG. 31C to aid interpretation. PopAlign generated alignments for monocyte mixtures from figure (3) are indicated as lines. tSNE was performed on data pooled from all experiments, but experimental conditions are shown individually for clarity. Plot shows that gene expression changes due to signaling can result in relative cluster shifts within the tSNE plots that obscure subpopulation alignment. For example, in FIG. 31B the monocyte populations aligned by PopAlign (FIGS. 16A-16G) become separated by a cluster of T-cells (mixture components 3 and 4).

FIG. 32A: PopAlign probabilistic modeling framework. PopAlign was validated on Tabula Muris. Data showing that the model accurately reproduces experimental data (FIG. 32B), and the model automatically finds subpopulations agreeing with expert annotations (FIG. 32C). FIG. 32D: PopAlign can compare any two samples by using probabilistic distance to align subpopulations (FIG. 32D), and then computes subpopulation-specific differences across aligned groups. Gene expression program changes for aligned macrophages are shown in FIG. 32E. PopAlign used statistical metrics (Jeffrey's Divergence JD) to automatically extract common populations across all 12 tissues of Tabula Muris (FIG. 32F). These alignments were then used to discover global signatures, such as the high abundance of macrophages in the Lung and Marrow (FIG. 32G). PopAlign models are low-error (FIG. 32H), and compress single-cell data by 50-100×, enabling scalable comparisons of data. PopAlign compares data 15× faster than Seurat and can compare >10× as many samples (FIG. 32I).

FIGS. 33A-33C: Cell types and drug conditions in large-scale single-cell drug screen. FIG. 33A: Cell types present in RESTING context [no CD3/CD28]. FIG. 33B: Cell types present in ACTIVATED context [+CD3/CD28]. FIG. 33C: 42,423 cells across 93 separate drug conditions. Some example drugs are highlighted.

FIG. 34A: RESTING [No CD3/CD28]. FIG. 34B: ACTIVATED [+CD3/CD28]. FIG. 34C: PopAlign identifies that GCs generate new and specific subpopulations of macrophages. FIG. 34D: PopAlign found that an inflammatory context disrupts specific immunosuppressive functions of glucocorticoids on macrophages.

FIGS. 35A-35G illustrate non-limiting exemplary mapping of neural stem cells to a developmental reference atlas. FIG. 35A is a non-limiting exemplary experimental scheme showing timepoints at which mouse brains were collected for single-cell profiling. FIG. 35B is a non-limiting exemplary scatter plot of all cells, labeled by timepoint, on first 3 principal components (PCs). Progenitor cells are shown to have formed a cup at the base of the three main branches (dashed line). FIG. 35C is a non-limiting exemplary plot corresponding to the plot in FIG. 35B with cells classified using labeled transcriptional profiles from an expert annotated dataset. Mature neurons (pink), oligodendrocytes (red), and astrocytes (blue) label the tips of the main branches. FIG. 35D show non-limiting exemplary renderings of model distributions for each timepoint built in a twelve-dimensional (12D) space. Renderings were projected into a two-dimensional (2D) PC space. Each subpopulation is labeled with a dot denoting the abundance of the subpopulation. FIG. 35E are non-limiting exemplary renderings showing that PopAlign found closest subpopulation alignment for ivNSC subpopulation within each timepoint of the reference map which is highlighted in plots. FIG. 35F show distances (measured in terms of Jeffrey's Divergence) for each of the closest alignments, showing that the best alignment was in the E18 brain. FIG. 35G is a non-limiting exemplary heatmap displaying gene programs for subpopulations present within the E18 brain. ivNSCs matched E18-pop5 in the expression of two Neural Progenitor programs, while not expressing Neuroblast or Vascular genes.

FIGS. 36A-36I show neural stem cells grown in vitro (ivNSCs) lost diversity of function compared to embryonic day 18 (E18) neuronal progenitors (NProgs). FIG. 36A is a non-limiting exemplary plot showing whole population entropy estimated using PopAlign framework for normal mouse brains at various stages of development and ivNSCs (which had the lowest population entropy). FIG. 36B is a non-limiting exemplary plot showing single entropies for each subpopulation (Gaussians) plotted for each stage of development. Highlighted in red circles are subpopulations aligned to the NSC population, showing that even at the subpopulation level, NSCs grown in vitro have less entropy than subpopulations in the developing brain. FIGS. 36C-36D show covariance matrix (E) of ivNSC-pop2 to closest aligned subpopulation—E18-pop5. The E18 subpopulation had high variance along several feature dimensions (arrows), while the ivNSC subpopulation had low variance along all dimensions. FIG. 36E is a non-limiting exemplary plot of L1-norm error metric vs. log 10 (mean) for highly variable genes between E18-pop5 and ivNSC-pop2. Selected genes are highlighted on the plot. FIG. 36F shows top genes from the L1-norm analysis displayed as a heatmap using cells sampled from both subpopulations. FIG. 36G show non-limiting exemplary distributions of positive L1-norm error genes. FIG. 36H show non-limiting exemplary distributions of negative L1-norm error genes. FIG. 36I shows gene set enrichment analysis applied to upregulated (blue) genes and downregulated (red) genes. Upregulated gene sets include EGF/FGF pathways and Mitosis. However, downregulated gene sets include pathways across diverse functions including: glutamine and amino acid synthesis tubulin folding pathways, oligodendrocyte and glial cell differentiation pathways.

FIGS. 37A-37E illustrate stem cells derived from the mouse brain underwent rapid population collapse and transcriptional drift. FIG. 37A is a schematic illustration showing cells were dissociated from the ventricular zone (VZ) into single cells and either immediately profiled, or grown in culture in EGF/FGF-containing media. FIG. 37B are non-limiting exemplary renderings of models built for each timepoint in timecourse. The day 0 (D0) sample served as the reference population, and other timepoints were associated to that population using PopAlign. Neuroblast populations—dashed ovals in red (the dashed ovals encircling "4" and "2" at the bottom left in the VZ-D0 and VZ-D3 renderings respectively). Intermediate Progenitors—dashed ovals in blue (the dashed ovals encircling "3," "3," "2," "3," and "4" in the VZ-D0, VZ-D3, VZ-D5, VZ-D7, and VZ-D18 renderings respectively). Neural Progenitor populations—the dashed ovals in white (the remaining dashed ovals in the VZ-D0, VZ-D3, VZ-D5, VZ-D7, VZ-D18, and ivNSC renderings). FIG. 37C is a non-limiting exemplary plot showing the total entropy of the population declines over time. FIG. 37D are non-limiting exemplary plots showing proportions of the different subpopulations across the timepoint that were aligned to subpopulations found in the VZ-D0 sample. These proportions were bootstrapped by building many models (20 models) for each time point, aligning them to a single reference model, and then extracting changes in abundance from the model parameters. All subpopulations declined rapidly except the progenitor population (D0-pop2), which dominated the culture after 3-5 days. FIG. 37E is a non-limiting exemplary heatmap showing transcriptional changes in the progenitor population happens quickly in <3 days.

FIGS. 38A-38E show signaling factor combinations titrated population balance between different progenitor subpopulations. FIG. 38A is a plot showing log-likelihood ratio (LLR) scores for each sample against the control population—20 ng/mL EGF/FGF condition. The more a population of cells differed from the control sample, the lower its LLR score. For each sample, 20 models were built and the LLR computed for each model using data from that sample. White line: mean, dark gray: 95% CI for the mean, light gray: standard deviation. The lowest ranked population had both low EGF/FGF (0.8 ng/mL), as well as high BMP4 (20 ng/mL). FIG. 38B shows a PCA plot of twelve-dimensional (12D) data from control population, showing that the population separates into four subpopulations—neuroblasts (CN), as well intermediate progenitors (IP), proliferating progenitors (PP) and non-proliferating progenitors (NPP). FIG. 38C illustrates a non-limiting exemplary heatmap showing gene expression differences between subpopulations, with specific genes listed for each program. FIG. 38D illustrate non-limiting exemplary plots showing subpopulation abundances, determined using the PopAlign query function and plotted across samples. The PP proportion went up with EGF/FGF, and that CN proportion decreased with EGF/FGF. With the addition of BMP and low EGF/FGF, committed neuroblasts (CN) can comprise almost 50% of the population. FIG. 38E is a non-limiting exemplary heatmap of coefficients from multinomial logistic regression of subpopulation abundances with respect to the signals as predictor variables. The shading is scaled according to the value of the coefficient, while the numerical text corresponds to the odds ratio (which is equal to $e^{\beta_{m,k}}$). Starred values denote coefficients for which the p-value <0.05. For FIG. 38A and FIG. 38D, the signal concentration heatmaps show relative levels of each signal scaled to the maximum used within that signal [maximums: EGF/FGF—combined with 20 ng/mL each, BMP4—20 ng/mL, PDGF-AA—20 ng/mL, CHIR—3 uM]. Each "unit" in the logistic regression corresponds to the maximum for each signal.

FIGS. 39A-39I show additional signals rescued transcriptional defects of cultured ivNSCs and reinvigorates layer-specific genes. FIG. 39A is a non-limiting exemplary experimental scheme. FIG. 39B shows non-limiting exemplary renderings showing subpopulations from all samples that were aligned to neural progenitor population from VZ-D0. FIG. 39C is a plot showing distances (Jeffrey's Divergence) of aligned subpopulations shown in FIG. 39B. E18, and E15 progenitor populations were close to the VZ-D0 brain. In vitro culture (ivNSC, VZ timecourse) produced populations that had high divergence. The addition of BMP4 produced subpopulations that were closest to the progenitor population from the in vivo brain. FIG. 39D is a non-limiting exemplary Venn diagram of downregulated genes in ivNSCs (from FIGS. 36A-36I) and how they overlapped with upregulated genes in response to signals. BMP4 re-induced 20 genes that were downregulated in ivNSCs). FIG. 39E is a non-limiting exemplary heatmap of 20 genes from FIG. 39C in neural progenitor subpopulation across samples. BMP4 generated progenitors with a matched profile to VZ-D0. FIG. 39F is a non-limiting exemplary Venn diagram of upregulated genes in ivNSCs (from FIGS. 36A-36I) and how the upregulated genes overlapped with downregulated genes in response to signals. BMP4 suppressed 22 genes that were upregulated in ivNSCs. FIG. 39G is a non-limiting exemplary heatmap of 22 genes from FIG. 39E in neural progenitor subpopulation across samples. BMP4 generated progenitors with a matched profile to VZ-D0. FIG. 39H shows expression levels cortical-layer specific genes in neural progenitor cells across samples. Cells are along the x axis, and are sorted in a staircase pattern for visual clarity. Top 3 genes (PAX6, SLC1A3 and SOX2) are stem cell markers. In ivNSCs, expression of these genes was almost entirely lost. BMP4 reinvigorated the expression of cortical specific genes to match that of progenitors in the E15, E18, and VZ-D0 subpopulations. FIG. 39I shows bubble plots showing the fraction of cells that express each layer specific gene. Relative to the unstimulated control (VZ-D5), BMP4 increased expression of many layer-specific genes, including FEZF2, BCL11B (CTIP2), and PCP4.

FIG. 40 illustrates non-limiting exemplary feature space and model building.

Figure 41B:
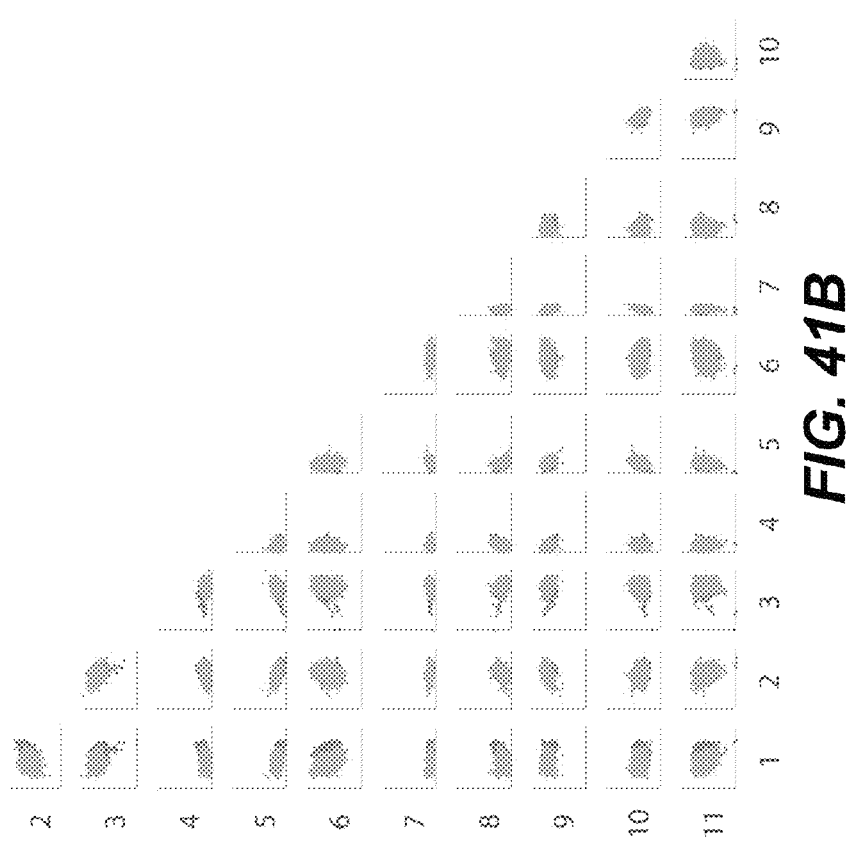
Figure 41A:
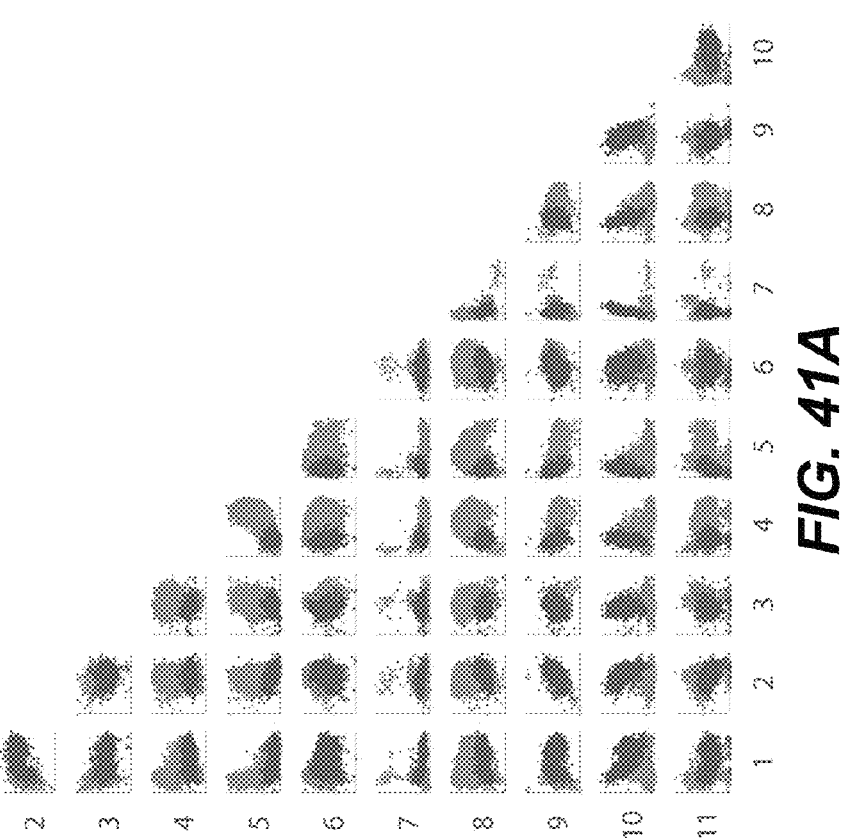

FIGS. 41A-41B illustrate non-limiting exemplary arrays of 2D renderings of data from E18 and ivNSC samples showing that ivNSCs were less heterogeneous in the feature space. FIG. 41A shows that E18 data with NProg cells (pop1) highlighted. FIG. 41B shows ivNSC data with the corresponding subpopulation (pop1) highlighted. For each plot tile, the feature number is displayed on the axis. Corresponding plots in both arrays are matched in terms of both the x- and y-axis scale.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Single-cell transcriptional profiling can be used as an engine for learning how to engineer cells and tissues. For example, perturbations (genes, drugs, etc.) can be used to stimulate a heterogeneous population or cells (such as blood immune cells) for learning the cell responses. Learning these responses can facilitate drug design or design treatments that can coax the correct functions out of a complex tissue, such as the immune system in our blood. However, each cell population contains many different cell types, and each of the cell types or each of the single cells can respond to the perturbation differently. Thus, there is a need to automate the detection of subtype specific responses.

Disclosed herein include embodiments of a method for single cell analysis. In some embodiments, the method is under control of a hardware processor (or a virtual processor) and comprises: receiving single cell gene expression data comprising a plurality of normalized reference gene expression vectors and a plurality of normalized test gene expression vectors representing single cell gene expression profiles of a plurality of reference cells and a plurality of test cells respectively, in a gene expression space. The method can comprise: determining (i) a gene feature matrix, comprising a plurality of gene features, and, for each of the plurality of normalized reference gene expression vectors and the plurality of normalized test gene expression vectors, (ii) a reference gene feature weighting vector or a test gene feature weighting vector using a training matrix comprising a plurality normalized training gene expression vectors. The plurality of reference gene feature weighting vectors and the plurality of test gene feature weighting vectors can represent gene feature profiles of the plurality of reference cells and the plurality of test cells in a gene feature space, respectively. The method can comprise: determining (i) a reference Gaussian mixture model comprising a plurality of reference Gaussian densities each associated with a reference weight (e.g., a scalar) and (ii) a test Gaussian mixture model comprising a plurality of test Gaussian densities each associated with a test weight (e.g., a scalar) from the plurality of reference gene feature weighting vectors and the plurality of test gene expression vectors, respectively. Each of (i) the plurality of reference Gaussian densities and associated reference weights and (ii) the plurality of test Gaussian densities and the associated test weights can represent a subpopulation of the plurality of reference cells or the plurality of test cells, respectively. The method can comprise: performing an analysis of the plurality of test cells relative to the plurality of reference cells using the plurality of reference Gaussian densities and the plurality of test Gaussian densities. In some embodiments, receiving the single cell gene expression data comprises: receiving single cell gene expression data comprising a plurality of reference gene expression vectors and a plurality of test gene expression vectors representing single cell gene expression profiles of a plurality of reference cells and a plurality of test cells respectively, in a gene expression space. Receiving the single cell gene expression data can comprise: for each of the plurality of reference gene expression vectors and the plurality of test gene expression vectors, normalizing gene expression values of the reference gene expression vector or the test gene expression vector to generate a normalized reference gene expression vector or a normalized test gene expression vector comprising normalized gene expression values. The method can comprise: determining a difference between the plurality of test cells, or a subpopulation thereof, and the plurality of reference cells, or a subpopulation thereof, using the plurality of reference Gaussian densities and the plurality of test Gaussian densities. The method can comprise: determining a difference between one of the plurality of test Gaussian densities the reference Gaussian density the test Gaussian density is aligned to, wherein the difference indicates a difference between the plurality of test cells, or a subpopulation thereof, and the plurality of reference cells, or a subpopulation thereof.

Disclosed herein include embodiments of a system for single cell analysis. In some embodiments, the system comprises: non-transitory memory configured to store executable instructions and single cell gene expression data comprising a plurality of normalized reference gene expression vectors and a plurality of normalized test gene expression vectors representing single cell gene expression profiles of a plurality of reference cells and a plurality of test cells respectively, in a gene expression space. The hardware processor can be programmed by the executable instructions to: a hardware processor (or a virtual processor) in communication with the non-transitory memory, the hardware processor is programmed by the executable instructions to: determine (i) a gene feature matrix, comprising a plurality of gene features, and, for each of the plurality of normalized reference gene expression vectors and the plurality of normalized test gene expression vectors, (ii) reference gene feature weighting vector or a test gene feature weighting vector using a training matrix comprising a plurality normalized training gene expression vectors. The plurality of reference gene feature weighting vectors and the plurality of test gene feature weighting vectors can represent gene feature profiles of the plurality of reference cells and the plurality of test cells in a gene feature space, respectively. The hardware processor can be programmed by the executable instructions to: determine (i) a reference Gaussian mixture model comprising a plurality of reference Gaussian densities each associated with a reference weight (e.g., a scalar) and (ii) a test Gaussian mixture model comprising a plurality of test Gaussian densities each associated with a test weight (e.g., a scalar) from the plurality of reference gene feature weighting vectors and the plurality of test gene expression vectors, respectively. Each of (i) the plurality of reference Gaussian densities and associated reference weights and (ii) the plurality of test Gaussian densities and the associated test weights can represent a subpopulation of the plurality of reference cells or the plurality of test cells, respectively. The hardware processor can be programmed by the executable instructions to: align each of the plurality of test Gaussian densities to an aligned reference Gaussian density of the plurality of reference Gaussian densities. The hardware processor can be programmed by the executable instructions to: perform an analysis of the plurality of test cells relative to the plurality of reference cells using one, at least one, or each, of the plurality of test Gaussian densities and the aligned reference Gaussian density the test Gaussian density is aligned to. The hardware processor can be programmed by the executable instructions to: determine a difference of the plurality of test cells, or a subpopulation thereof, relative to the plurality of reference cells, or a subpopulation thereof, using one, at least one, or each, of the plurality of test Gaussian densities and the aligned reference Gaussian density the test Gaussian density is aligned to. The hardware processor can be programmed by the executable instructions to: determine a Gaussian density difference between one of the plurality of test Gaussian densities and the aligned reference Gaussian density the test Gaussian density is aligned to; and determining a difference between the plurality of test cells, or a subpopulation thereof, and the plurality of reference cells, or a subpopulation thereof, using the Gaussian density difference. The hardware processor can be programmed by the executable instructions to: for each of a plurality of reference gene expression vectors and a plurality of test gene expression vectors, normalize gene expression values of the reference gene expression vector or the test gene expression vector to generate a normalized reference gene expression vector or a normalized test gene expression vector comprising normalized gene expression values.

Throughout the drawings, reference numbers may be re-used to indicate correspondence between referenced elements. The drawings are provided to illustrate example embodiments described herein and are not intended to limit the scope of the disclosure.

LOWMIX

A modeling architecture, framework, platform, system, and method, LOWMIX, is described herein for performing "cell population" classification tasks using probabilistic models. LOWMIX can be used for inferring statistical models of gene expression distributions within a cell population. LOWMIX can be applied to perform disease classification from single cell mRNA-seq data. LOWMIX can overcome the mathematical challenges associated with high-dimensionality by building probabilistic models over a gene expression vectors rather than single genes. Gaussian Mixtures (GMMs) can be used to model the resulting distribution of cellular states within the lower dimensional feature space, and provide an effective and semantically meaningful class of functions for modeling a heterogeneous cell populations. Latent structure in data can be used to embed cell populations within a low dimensional space where probabilistic models are efficiently constructed using reference cell populations (e.g., health, disease) and then models can applied to classify new populations against these labels. The method can be applied to a series of cell populations classification tests including tissue type identification and disease state classification. The low dimensional probabilistic modeling framework provides a general computational platform for classifying and diagnosing human disease across tissues and disease states using high throughput single cell data.

A framework, referred to herein as LOWMIX, can be used for building a probabilistic model of the gene expression distribution generated by a heterogeneous population of single cells. The probabilistic models can be used to perform population-state classification tasks. The method has two main steps: (1) cells are represented as a linear combination of gene expression basis vectors (i.e., gene expression features) that are extracted from training data; and (2) Following projection of single cell data into a lower dimensional feature space, the cell populations are modeled as a mixture of Gaussian densities in this space. Gaussian mixture models can be trained on cell populations in health and disease and, then, applied to new data to classify the physiological state of new samples.

Mathematical Formulation

The transcriptional state of a single cell can be represented as an n dimensional vector, $g=(g_1, g_2, \ldots, g_n)$, where $g_i$ is the abundance of mRNA species i in a single cell, and n is the number of total mRNA species encoded in the genome. While raw mRNA-seq measurements generate integer valued gene count data, due to measurement noise and data normalization, g can be considered to be embedded in an n dimensional Euclidean vector space, gene expression space, $g \in \mathbb{R}^n$. For the human genome n ~20,000. The high dimensional nature of gene expression space can pose a key challenge for construction and interpretation of statistical models.

Mathematically, a cell population can be considered a set of gene expression vectors, $S=\{g_k\}$, where the index k indexes single cells. The gene expression vectors. $g_k$, can be considered as being distributed according to an underlying probability density function. P(g), that quantifies the probability of observing a particular joint gene expression state, $g=(g_1, g_2, \ldots, g_n)$. in a given cell population. P(g) the gene expression distribution, can be generated by the underlying cell population.

A statistical model of P(g) can be estimated based upon independent and identically distributed single cell measurements. To construct a statistical model, a standard statistical technique, such as maximum likelihood estimation, can be used to estimate the parameters of a Gaussian Mixture model. Probabilistic models can be constructed across a series of cell populations (e.g. P(g|health) and P(g|disease)). and then statistical measures can be applied to classify cells from a new sample according to these models.

Dimensionality Reduction: Single Cells as Linear Combinations of Gene Features

LOWMIX can overcome the challenge of model estimation in the high dimensional nature of gene expression space. To construct statistical models, the curse of dimensionality can be circumvented by building models in a low-dimensional space defined by gene expression features or programs. Mathematically, the transcriptional state of each single cell, g, can be represented as a linear combination of gene expression feature vectors, $w_i$:

$$g = \sum_{i=1}^{m} c_i w_i$$

where $w_i \in \mathbb{R}^n$ specifies a gene expression feature, and $c_i$ is a coefficient that encodes the weighting of vector $w_i$ in g. A cell's gene expression state, g can be represented as a linear combination of m gene expression module vectors, $w_i$ where $m \ll n$. For example, m can be, 5, 10, 15, 20, 30, or more, and n can be 1000, 5000, 10000, 15000, 20000, or more. A low dimensional representation of a cell population can be constructed and use to estimate statistical models within the low dimensional space.

A set of gene expression basis vectors, $w_i$ can be determined using a range of matrix factorization techniques. Singular value decomposition (SVD) is a canonical and pedagogical example. To apply SVD to define a basis set of gene expression vectors for classification, a compendium of training data, D sampled uniformly at random can be first constructed from the datasets to be classified. Then, SVD can provide a factorization of the training data into three matrices:

$$D = W S V^T \qquad (1.1)$$

where W is an n×n matrix of gene expression feature vectors, and S $V^T$ is an n×k matrix that contains the coefficients for W across all the cells in the training data.

Feature vectors W can be extracted and, then, the first m singular vectors were selected as gene feature vectors for model construction. W can be used to represent a single cell as a linear combination of gene features. The training data D can be sampled from a large dataset, and so cells that have not formally been included in the SVD that generates W can be represented.

Any cell's gene expression state, g can be represented as:

$$u = W_m g, \qquad (1.2)$$

where $W_m$ contains the m first features in W, and u is the representation of g in gene feature space. A range of techniques can be applied to extract gene expression feature vectors, including non-negative matrix factorization (NNMF). orthogonal NNMF, and sparse NNMF.

A cell population, S={g}, can be mapped from an n ~20,000 dimensional gene expression space into a gene feature space that is often of order 10-20 dimensions:

$$S = \{g_i\} \rightarrow \{\{u_i\},$$

where $\{u_i\}$ are m×1 dimensional vectors that represent the cell population in the reduced gene feature space.

Representing a Cell Population as a Gaussian Mixture Modeling in Gene Feature Space Following the feature based representation, a statistical model of the cell population within the reduced space can be constructed. A probability distribution in gene expression space can be exchanged for or transformed into a probability distribution in gene feature space:

$$P(g) \rightarrow P(u), \qquad (1.3)$$

and a statistical model of P(u) can be estimated.

As the second main step in cell population classification, the cell population can be represented as a mixture of Gaussian densities. For a given cell population S, the following can be constructed:

$$\widehat{P(\mathbf{u})} = \sum_{i=1}^{l} \pi_i \mathcal{N}(u; \mu_i, \Sigma_i) \qquad (1.4)$$

where $\widehat{P(\mathbf{u})}$ encodes the gene expression distribution of a given cell population as a mixture of Gaussian densities, $\mathcal{N}(c; \mu_i, \Sigma_i)$, with centroid, pi; covariance matrix, $\Sigma_i$ and scalar weighting $\pi_i$. l is the number of Gaussian mixtures or components in the statistical model.

The Gaussian mixture model (GMM) represents a cell populations as a mixture of individual Gaussian densities. Biologically, each density can be considered as parameterizing a sub-population of cells. The GMM provide a natural set of basis functions for modeling a cell population as a collection of densities (cell-states) in gene expression space.

To construct a Gaussian Mixture model from data, the parameters $\mu_i$, $\Sigma_i$, and $w_i$ can be estimated based upon training data, using maximum likelihood estimation with likelihood function:

$$\mathcal{L}(\mu_i, \Sigma_i, \pi_i | S') = \sum_{i=1}^{k} \log P(u_i; \{\mu_i, \Sigma_i, w_i\}), \qquad (1.5)$$

where $u_i$ are single cell profiles drawn from S', and k is the number of single cells in the cell population S'. This function can be maximized approximately using expectation maximization. To select a number of mixtures needs to be selected to use in the model construction, the Bayesian information criteria (BIC) which is a statistical measure that balances model accuracy with model complexity can be used. The number of SVD dimensions can be selected to maximize classification accuracy on the training data for tasks of interest.

Applications of Mixture Models to Population Classification Tasks

Given an estimated probabilistic model, a range of statistical tasks can be performed. Statistical models can be estimated from a series of labeled cell populations, $S_{health}$ and $S_{disease}$ to yield P(u|health) and P(u|disease).

Given these probabilistic models, the probability that a set of single cell, $u_i$, came from $S_{health}$ or $S_{disease}$ can be estimated as:

$$R = \sum_{k=1}^{k} \log \frac{P(u_i | Disease)}{P(u_i | Health)} \qquad (1.6)$$

Given a set of q classes, the class that maximizes the below can be determined:

$$\text{argmax}_{Class} = \sum_{i=1}^{k} \log P(u|class), \qquad (1.7)$$

Equations (1.1-1.4) provide a generalized procedure for constructing a statistical a model of a cell population from single cell mRNA-seq data (or single cell multiomics data, such as transcriptomics data. proteomics data, epigenomics data, and microbiomics data). The procedure can have four steps: (a) Build a dictionary of gene expression features from training data with (b) Represent cells in an analysis data set within this basis set, (c) Parameterize a Gaussian Mixture model of the analysis population within the feature space, and (d) Perform classification based analysis using models of samples in health and disease.

PopAlign

Disclosed herein includes a modeling architecture, framework, platform, system, and method, PopAlign, for analyzing large-scale single-cell RNA-seq datasets by constructing and comparing probabilistic models which provide a low-error, compressed representation of single cell data that has well-defined statistical metrics. Probabilistic modeling of cell populations can provide conceptual and practical advances that enables multi-scale analysis of single cell datasets across samples, subpopulations, and individual cells. Mathematically, PopAlign can model the distribution of gene expression states within a heterogeneous cell population, by representing subpopulations of cells as independent Gaussian densities. Probabilistic modeling can be enabled by a novel low dimensional representation of cell-state in terms of a set of gene expression features learned from data. For each large-scale dataset, PopAlign can learn probabilistic models and use them to perform a number of tasks and analyses: (a) classifying and ranking samples based on statistical distance, (b) querying samples against a universal set of reference populations, (c) aligning subpopulation models across experimental conditions, and (d) quantifying changes in cell abundance and gene expression for aligned subpopulations across samples.

PopAlign can be used to automatically rank and classify experimental samples, identify and align subpopulations of cells, and track abundance and gene expression changes within subpopulations across experimental conditions. PopAlign can be used to interpret data hierarchically, from samples to tracking quantitative changes within specific subpopulations of cells to comparing the expression level of single genes.

Using probabilistic models to represent single-cell data can provide both a conceptual and practical advance. One key conceptual value of the probabilistic model it is the probabilistic model produces a semantically meaningful, modular representation of a cell population. By modeling the distribution of gene expression states as a mixture of independent probability densities, a formal mathematical definition of a population and its constituent subpopulations was constructed. This mathematical definition can be used to generate new instances of single-cell data, for model validation and prediction. Practically, probabilistic models are powerful because they enable quantitative statistical metrics, such as the divergence between two models, or the likelihood of a model given data. These metrics form the basis for essential tasks such as sample classification and quantifying shifts in abundance or gene expression across samples. Unlike PopAlign, geometric methods based on global cell clustering do not provide a natural language for mathematically representing a subpopulation of cells or statistical metrics for quantifying shifts in population structure across experimental samples.

PopAlign can fulfill a fundamental need for comparative analysis methods that can scale to hundreds of experimental samples, because probabilistic models provide a reduced representation of single-cell data. For a typical 10,000-cell experimental sample, the probabilistic model can reduce the memory footprint by 50-100x. PopAlign runtime can scale linearly with the number of samples because computations are performed on probabilistic models rather than on raw single cell data (methods). Further, down-stream computations including population alignment can be performed on the models themselves, often reducing the number of computations by an order of magnitude.

The PopAlign method can have three main steps: probabilistic mixture model construction, model alignment, and parameter analysis. PopAlign can be applied to analyze gene expression and population structure changes in heterogeneous populations of cells as they respond to signals, drugs, and disease conditions. PopAlign provides a scalable method for deconstructing quantitative changes in population structure including cell-state abundance and gene expression across many single cell experimental samples. PopAlign can be used for the analysis of large-scale experimental screens of drugs and genetic perturbations on heterogeneous cell populations extracted from primary human tissue samples. PopAlign can (i) identify and aligns cell-states across paired populations of single cells (a reference population and a test population), and then (ii) quantify shifts in cell-state abundance and gene expression between aligned populations. PopAlign can provide a scalable method for deconstructing quantitative changes in population structure including cell-state abundance and gene expression across many single cell experimental samples. A probabilistic mixture model of PopAlign can be an accurate and interpretable decomposition of the underlying cell states. PopAlign models can represent experimental data with high qualitative and quantitative accuracy. The mixture models decomposed the cell populations into a biologically interpretable set of cellular subpopulations represented by individual mixture components. Through alignment of model components across tissues, PopAlign can enable high-level comparisons of tissue composition. PopAlign can compare large numbers of samples. PopAlign can be used to study heterogeneous cell populations, for example, in the human body (or an animal, such as a mammal). PopAlign can extract and quantify population level changes in the signaling data set that are obscured by existing geometric techniques like tSNE. PopAlign can be applied to study underlying changes in cell state due to a disease process. PopAlign can identify several common global signatures in the samples at the level of cell-type abundance and gene expression.

PopAlign can be used for tracking changes in gene expression state and cell abundance in a heterogeneous cell populations across experimental conditions. The PopAlign method uses a probabilistic modeling framework that represents a cell population as a mixture of Gaussian probability densities within a low dimensional space of gene expression features. Models can be aligned and compared across experimental samples, and by analyzing shifts in model parameters, gene expression and cell abundance changes in individual cell populations can be identified. PopAlign can be used to track changes within complex cell populations. Since human diseases like cancer and neurodegeneration arise due to interactions between a wide variety of cell-types within a tissue, population level models can be important for building a single cell picture of human disease and for understanding how disease interventions like drug treatments impact the wide range of cell-types within a tissue.

By considering a single-cell population as a probability distribution in gene expression space, discrete mathematical objects whose parameters can be interpreted, and which can be used to explicitly calculate quantitative statistical metrics for subpopulation alignment is defined. The probabilistic representation described herein allows quick and scalable learning of drug responses even on a complex mixture of cells, in "one shot." Computationally, PopAlign scales to analyze many samples that each contain thousands of single cells. The PopAlign method can be used to analyze data from drug screens where the goal is to identify cell-population specific transcriptional responses.

PopAlign can be used as a part of a work-bench for single cell analysis and treatment of human disease. PopAlign can be used for identifying drug/signal targets and for deconstructing single cell disease states. PopAlign can be used to identify cell-type specific signatures of disease treatment in multiple patients before and/or after treatment. PopAlign can be used for guiding treatment interventions by exposing the spectrum of transcriptional states within a diseased tissue and revealing the impact of drug treatments on diseased cell-states as well as the cellular microenvironment and immune cell-types. Such insights can lead to single cell targeting of drug combinations to treat human disease as an essentially population level phenomena.

Two populations of cells, a test and a reference population, ($D^{test}$ and $D^{ref}$), that care profiled with single cell mRNA-seq (or single cell multiomics data, such as transcriptomics data. proteomics data, epigenomics data, and microbiomics data) can be considered. Profiling of each population generates a set of gene expression vectors, e.g.

$$D^{Test} = \{g_i\}_{i=1}^k$$

where $g=(g_1, g_2, \ldots, g_n)$, is an n dimensional gene expression vector that quantifies the abundance of each mRNA species in single cell g and k is the number of profiled single cells.

To compare the reference and test cell populations, a probabilistic model of the gene expression distribution can be first constructed for each set of cells (or for all sets of cells). To simplify the inference and interpretation of probabilistic models, each cell can be represented, not as a vector of genes, but as a vector of gene expression programs or gene expression features that are extracted from the data, so that each single cell is represented as a vector $c=(c_1, c_2 \ldots c_m)$ of m feature coefficients, $c_i$, which weight the magnitude of gene expression programs in a given cell. These gene features can be extracted using a particular matrix factorization method, such as orthogonal non-negative matrix factorization (oNMF) that produces a useful set of features represented as vectors are positive and composed of largely non-overlapping genes. This may allow consideration of a cell's transcriptional state as a linear sum of different positive gene expression programs.

Following dimensionality reduction, for a given cell population, cell states can be considered as being sampled from an underlying joint probability distribution over this feature space, P(c), that specifies the probability of observing a specific combination of gene expression features/programs, c, in the cell population. A probabilistic model, $P^{test}(c)$ and $P^{ref}(c)$, can be estimated for the reference and test cell populations that intrinsically factors each population into a set of distinct subpopulations each represented by a Gaussian probability density:

$$P(c) = \sum_{i=1}^{l} w_i \phi_i(c) \text{ where} \quad (2.1)$$

$$\phi_i(c) = N\left(c; \mu_i, \sum_i\right),$$

where $N$ (c; $\mu_i$, $\Sigma_i$) are multivariate normal distributions with weight $w_i$; centroids $\mu_i$ and covariance matrices $\Sigma_i$. The distributions $$\phi_i^{test}(c) = N(c; \mu_i, \Sigma_i),$$

mixture components, represent individual subpopulations of cells; l is the number of Gaussian densities in the model. The parameters of the mixture model ($\{\mu_i, \Sigma_i, w_i\}$) from single cell data can be estimated using the expectation-maximization algorithm with an additional step to merge redundant mixture components to compensate for fitting instabilities.

The parameters associated with each Gaussian density, ($\mu_i$, $\Sigma_i$, $w_i$), have a natural correspondence to the biological structure and semantics of a cellular subpopulation. The relative abundance of each subpopulation corresponds to the weight $w_i \in [0,1]$; the average cell gene expression state of each subpopulation corresponds to the (m dimensional) Gaussian centroid vector $\mu_i$, and the shape or spread of the subpopulation is captured by the covariance matrix $\Sigma_i$. Intuitively, the local Gaussian densities provide a natural "language" for comparisons between samples. Each Gaussian is a region of high density in gene feature space, and cell populations can be compared by asking how the density of cells shifts across experimental conditions.

Statistical Alignment of Cellular Subpopulations Between Samples

To compare the test and reference models, each mixture component in the test population model, $$\phi_i^{test}(c) \in \{\phi_i^{test}(c)\},$$

can be aligned to a mixture component, $$\{\phi_i^{ref}(c)\},$$

in the reference population model. Alignment can be performed by finding the "closest" reference mixture component in gene feature space. To define closeness, a statistical metric of similarity on probability distributions, such as Jeffrey's divergence, can be used. Jeffrey's divergence is symmetric while also having a convenient parametric form. Specifically, for each $$\phi_i^{test} \in \{\phi_i^{test}(c)\}, \text{ an } \phi_j^{ref} \in \{\phi_j(c)\}^{ref},$$

the closest mixture in the reference set can be determined:

$$\text{argmin}_{\phi_j^{ref}(c) \in \{\phi_j^{ref}(c)\}} D_{JD}(\phi_i^{test}(c) \| \phi_j^{ref}(c)), \quad (22)$$

where the minimization is performed over each $$\{\phi_i^{ref}(c)\}$$

in the set of reference mixtures, and $D_{JD}$ is the Jeffrey's divergence. Intuitively, for each test mixture, the reference mixture $\phi_j$ can be found to be closest in terms of position and shape in feature space. For each alignment, an explicit p-value can be then calculated from an empirical null distribution $P(D_{JD})$ that estimates the probability of observing a given value of $D_{JD}$ in an empirical data set of all subpopulation pairs within a single cell tissue database.

Tracking Cell-State Shifts Through Mixture Model Parameters

Following mixture alignment, quantitative differences in mixture parameters can be analyzed between the reference and test models to track shifts in gene expression state, gene expression covariance, and cellular abundances across the identified subpopulations of cells. For each aligned mixture pair, $$\left(\phi_i^{test},\ \phi_j^{ref}\right)$$

with parameters $$\left\{\mu_i^{ref},\ \Sigma_i^{ref},\ w_i^{ref}\right\} \text{ and } \left\{\mu_j^{test},\ \Sigma_j^{test},\ w_j^{test}\right\},$$

the following can be calculated:

$$\Delta\mu_i = \left\| \mu_i^{ref} - \mu_j^{test} \right\|_2, \qquad (2.3)$$

$$\Delta\Sigma_i = D_C\!\left(\Sigma_i^{ref},\ \Sigma_j^{test}\right), \text{ and} \qquad (2.4)$$

$$\Delta w_i = \left| w_i^{ref} - w_j^{test} \right|, \qquad (2.5)$$

where $\Delta\mu_i$ measures shifts in mean gene expression; $\Delta w_i$ quantifies shifts in cell-state abundance; $\Delta\Sigma_i$ quantifies shifts in the shape of each mixture including rotations and changes in gene expression variance. These shifts in parameters can be calculated for all mixture pairs to assess the impact of signaling conditions or environmental changes on the underlying cell population.

Mathematical Framework.

Two populations of cells, a reference population and a test population ($D^{ref}$ and $D^{test}$) can be considered. Following profiling by single cell mRNA-seq, each population of cells is a set of gene expression vectors, $$D = \{g_i\}_{i=1}^k,$$

where k is the number of cells in the population, and $g=(g_1, g_2, \ldots, g_n)$, is an n dimensional vector that quantifies the abundance of each mRNA species. While raw mRNA-seq measurements (or multiomics measurements) generate integer valued gene count data, due to measurement noise and data normalization, g can be considered to be embedded in an n dimensional Euclidean vector space, gene expression space, $g \in \mathbb{R}^n$;

The gene expression vectors, $\{g_k\}$ can considered as being distributed according to an underlying probability density function, $P(g)$, that quantifies the probability of observing a particular joint gene expression state, $g=(g_1, g_2, \ldots, g_n)$, in a given cell population. A statistical model of $P(g)$, can be estimated based upon single cell measurements. The model provides a parametric representation of the gene expression density in each condition. This representation can be used to track changes in the structure of the cell population across conditions.

The number of parameters in the probabilistic models described herein scales quadratically with n, and mixture model learning has data requirements that are exponential in n. Therefore, the dimensionality of the problem first reduced by building models in a common low dimensional space defined by gene expression programs discovered from pooled data across all samples.

Data Normalization.

Single cell gene expression data can be normalized to (1) to account for the variation in the number of transcripts captured per cell and (2) to balance the wide disparity in the scale of values across different genes due to measurement noise and gene drop-out.

The total number of transcripts captured for each single cell can vary from for example, 1000 to 100,000 unique transcripts per cell. Technical variability in reagents and library prep steps can have a large impact on the number of transcripts retrieved per cell. To scale out these differences, each gene expression value $g_i$ can be divided by the total number of transcripts and then multiply by a scaling factor $\beta$.

Additionally, across genes, mean transcript values can span 5 orders of magnitude. Transforming the data using the logarithm brings values across all genes close in scale, while also reducing the skew in the data distributions. The equation for transforming a raw gene expression value $g_i$ (for a single gene) into a normalized gene expression value, $g_i'$ is:

$$g_i' = \log\!\left(\beta\frac{g_i}{\sum_i^n g_i} + 1\right), \qquad (2.6)$$

where n is the total number of genes, and P is a scaling factor, and a 1 pseudo-count was added to each gene expression value. It was found that by setting $\beta=1000$ to be roughly the minimum number of total transcript counts in a cell (1000 transcripts), a smooth transition was achieved in the distribution of transformed $g_i'$ when raw $g_i$ values step from 0 to 1. Gene expression values are thus denoted in units of log(TPT+1) where TPT is transcripts per thousand.

Extraction of Gene Feature Vectors with Matrix Factorization.

The curse of dimensionality can be circumvented by building models in a common low-dimensional space defined by gene expression features or programs. The transcriptional state of each single cell, g, can be represented as a linear combination of gene expression feature vectors, $\{f_i\}$:

$$g = \Sigma_{i=1}^m c_i f_i \qquad (2.7)$$

where $f_i \in \mathbb{R}^n$ specifies a gene expression feature, and $c_i$ is a coefficient that encodes the weighting of vector $f_i$ in g, the gene expression state of a single cell. A cell's gene expression state, g can be represented as a linear combination of m gene expression module vectors, $f_i$ where m<<n. Thus, a low dimensional representation of a cell population can be constructed and, then used to estimate statistical models within the low dimensional space.

Figures 19A, 19B, 19C:
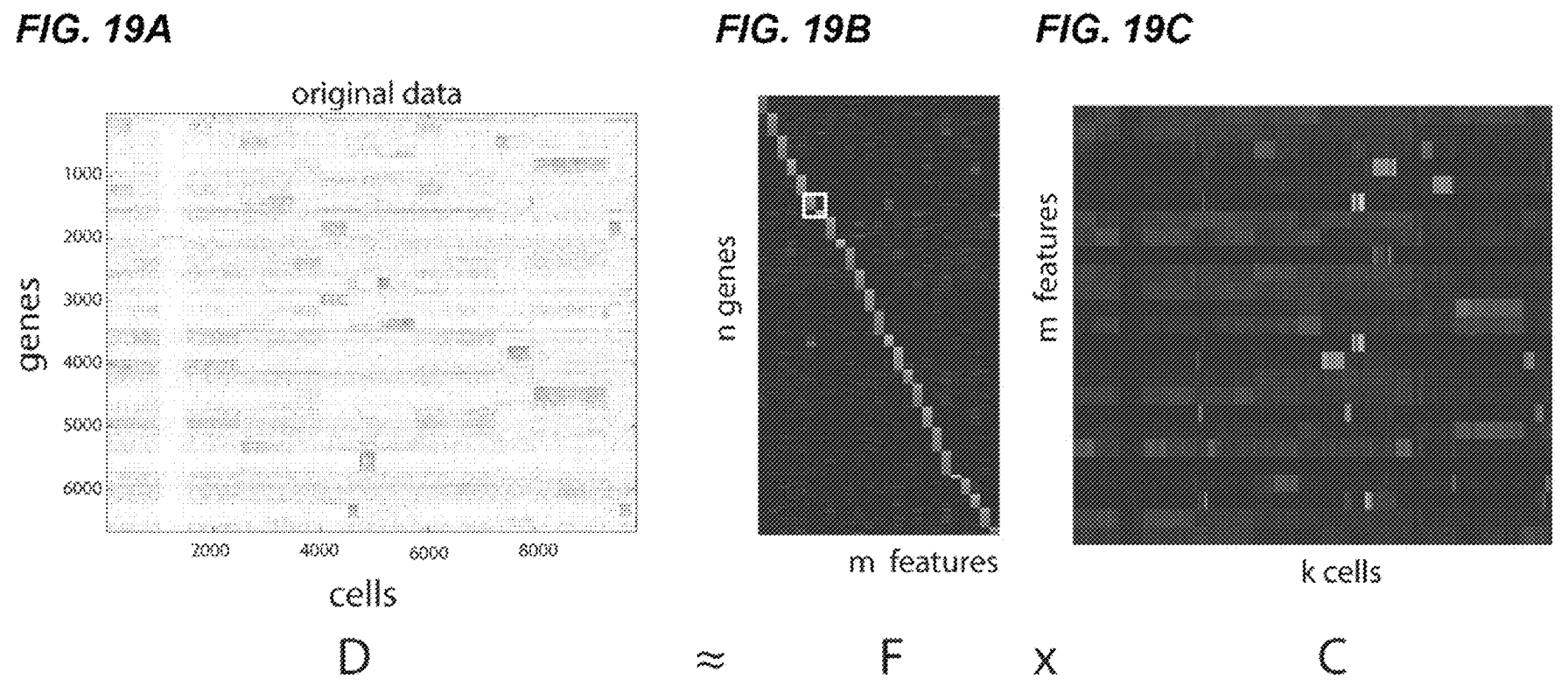

The gene features, $\{f_i\}$ can be extracted using a wide range of matrix factorization and machine learning techniques, such as Singular Value Decomposition, and its matrix factorization relatives like sparse PCA as well as methods like layered neural networks. A technique called orthogonal non-negative matrix factorization (oNMF) can be used to define a space of orthogonal gene expression features vectors. Like other linear dimensionality reduction techniques, such as PCA, oNMF factors the original data matrix, $D^{train}$ into two matrices $D \approx F$ C (FIGS. 19B-19C). Factorization can occur through minimization of an objective function with positivity and orthogonality constraints:

$$\text{argmin}_{F,C} \|D^{train} - FC\|_2 \text{ subject to } F^T F = I, C_{ij} \geq 0, F_{ij} \geq 0, \quad (2.8)$$

The optimization minimizes the (Frobenius) norm of the difference between the training data, $D^{train}$, and its factored representation FC. The columns of F contain gene features, $f_i$. The matrix C is m by k, where k is the number of single cells in $D^{train}$. Each column of C encodes the weighting of the m gene features across a given single cell. The entries of F and C; are constrained to be positive, and the columns of F (the gene features) are constrained to be orthogonal. F is an n by m matrix (genes by features). Each column contains n weights where each weight corresponds to the weight of a given gene in that feature, $f_i$. Because feature vectors have positive entries, the gene expression state of a cell, g, can be considered as being assembled as a linear sum of positive gene expression programs.

In some embodiments of PopAlign, orthogonality in F is incorporated as a secondary constraint to aid interpretation. Orthogonality can aid in interpretation of the features as well as in model construction because the orthogonal gene expression features are interpretable as non-overlapping sets of genes that can individually be analyzed by gene set enrichment analysis. Second, orthogonality can force individual cell states to be represented by more than one feature which aided stability during model parameter estimation.

To perform oNMF, m, the number of features to be extracted can be selected through an optimization that balances accuracy and dimensionality explicitly. In oNMF (as opposed to PCA and SVD), m is a parameter given to the optimization. Choosing m involves balancing the tension between the "expressiveness" in the feature set and its dimensionality. Higher m reduces the error in the representation while also breaking up blocks of genes into smaller modules that represent independent gene expression pathways with finer granularity. However, as m increases, the typical computational and sampling challenges associated with high dimensionality emerge.

This tension can be balanced in PopAlign by constructing a loss function with a penalty that increases with m:

$$\text{argmin}_m f(m) = \|D^{train} - F_m C_m\|_2 + m^\alpha. \quad (2.9)$$

For each value of m, oNMF can be performed on $D^{train}$ yielding $F_m$ and $C_m$, and thus an error $\|D^{train} - F_m C_m\|^2$. This error can be incremented by the term ma which penalizes higher values of m and hence the dimensionality of the feature set. $\alpha = 0.7$ (or 0.1, 0.2, 0.3, 0.4, 0.5, 0.6, 0.7, 0.8, 0.9, 1, 2, 3, or more) can be set based upon numerical experimentation on model data sets. For any choice of m, the accuracy of the representation can be estimated by plotting reconstructed data FC against normalized data D.

In some embodiments, given data sampled a set of cell populations, (e.g., $D^{test_1}$, $D^{test_2}$, $D^{ref}$) data can be pool from all cell populations into a training data set, $D^{train}$, and oNMF can be performed on $D^{train}$. In analyzing a large number of data sets or sets with many single cells, $D^{train}$ can be generated by sampling, for example, 500-1,000 cells uniformly at random from the reference and test cell populations and selecting a m using Equation 2.9.

The complete dataset can be recasted into the feature space using a non-negative least squares. Specifically, for each gene expression profile, $g_i$, $c_i$ is found via:

$$\text{argmin}_{c_i} \|g_i - F c_i\|_2 \quad (2.10)$$

$$c_i \geq 0$$

where F is a fixed feature set learned from oNMF on $D^{train}$. The gene expression vector $g_i$ is thus compressed into a m-dimensional vector $c_i$ that provides a high-level programmatic representation of cell state in terms of gene expression "features." Finally, the biological meaning of the feature vectors can be interpreted in terms of annotated gene expression programs using gene set enrichment analysis.

Using matrix factorization, a cell population, $D = \{g_i\}$, can be mapped from an n ~20,000 dimensional gene expression space into a gene feature space that is often of order 10-20 dimensions $$D = \{g_i\} \rightarrow \{c_i\},$$

where $\{c_i\}$ are m×1 dimensional vectors that now represent the cell population in the reduced gene feature space.
Gene Set Enrichment Analysis.

To interpret the gene features in terms of annotated gene sets, gene set enrichment analysis can be performed using the cumulative hypergeometric distribution. Each feature vector can be defined by the collection of genes that have weightings greater than 4 times the standard deviation ($>4\sigma$). Using this collection of genes, the null probability of drawing k genes ($P(X>k)$) can then be calculated from a specific annotated gene set using the hypergeometric cumulative probability distribution:

$$P(X > k) = \sum_{k=1}^{k} \frac{\binom{Y}{i}\binom{N-Y}{Z-i}}{\binom{N}{Z}},$$

where N is the total number of genes, Z is the number of genes in the feature that are $>4\sigma$, Y is the number of genes in each annotated gene set, and k is the number of genes that overlap with annotated gene set. Gene sets can be sorted by their associated null probability.
oNMF Error Analysis.

The error associated with each feature set $F_m$ can be assessed by comparing data entries between a cross validation dataset $D_x$ and its reconstructed matrix $F_m C_x$. The data in $D_x$ can be binned into bins of equal width ~0.1 (in units of $\log(TPT+1)$). Data values were retrieved from each bin, $(D_x)_{bin}$, and then their means can be plotted against the means of corresponding data values in the reconstructed matrix, $(F_m C_x)_{bin}$. The standard error in each bin can be calculated as the mean squared deviation of the reconstructed data from the original data:

$$\sigma_{bin} = \sqrt{\frac{\sum_k^n ((F_m C_x)_i - (D_x)_i)^2}{n}}, \forall\, i \in bin$$

To quantify the amount of dispersion relative to the mean, the coefficient of variation for each bin can be calculated:

$$CV_{bin} = \frac{\sigma_{bin}}{(D_x)_i}, \forall\, i \in \text{bin}.$$

Representing a Cell Population as a Gaussian Mixture Model in Gene Feature Space.

Following the feature based representation, a statistical model of each can be constructed given cell population within the reduced gene feature space. A probability distribution in gene expression space can be exchanged for or transformed into a probability distribution in gene feature space:

$$P(g) \rightarrow P(c), \tag{2.11}$$

where g is n×1 and c is m×1, and m<<n. A statistical model of P(c) can now be estimated.

To account for the heterogeneity of cell-states within a tissue, cell-populations were modeled using Gaussian mixture models. Gaussian densities provide a natural representation of a transcriptional state in gene expression space which is consistent with measured gene expression distributions as well as empirical models of transcription. Theoretical models of stochastic transcription commonly yield univariate gene expression distributions where mRNA counts are Poisson or Gamma distributed. Normal distributions provide a reasonable approximation to these distributions with a computationally tractable inference procedure.

The cell population can be represented as a mixture of Gaussian densities, so that for a given cell population D, it was constructed:

$$\overline{P(\mathbf{c})} = \sum_{k=1}^l w_i \phi_i(c) \tag{2.12}$$

$$\phi(c) = \mathcal{N}(c; \mu_i, \Sigma_i)$$

where $\overline{P(\mathbf{c})}$ is a mixture of Gaussian densities, $\mathcal{N}(c; \mu_i, \Sigma_i)$, with centroid, $\mu_i$; covariance matrix, $\Sigma_i$; and scalar weighting $w_i$. $\mu_i$ is a vector in the m dimensional feature space, and $\Sigma_i$ is a symmetric m×m matrix. l is the number of Gaussian mixtures or components in the statistical model. The Gaussian mixture model (GMM) represents a cell population as a mixture of individual Gaussian densities. Biologically, each density can be considered as parameterizing a subpopulation of cells.

The parameters $\mu_i$, $\Sigma_i$, and $w_i$ can be estimated based upon training data, using maximum likelihood estimation with likelihood function:

$$\mathcal{L}(\{\mu_i, \Sigma_i, \pi_i\} | D') = \sum_{j=1}^k \log P(c_j; \{\mu_i, \Sigma_i, w_i\}), \tag{2.13}$$

where $c_j$ are single cell profiles drawn from a cell population D' and cast into feature space; k is the number of single cells in the cell population D'. For a given experimental data set, $\mathcal{L}$ defines a function over the space of model parameters. To select model parameters given data, the value of $\mathcal{L}$ can be maximized. $\mathcal{L}$ can be maximized approximately using expectation maximization (EM).

Expectation-maximization is a heuristic algorithm that finds (local) maximum likelihood parameters. Fitting instabilities could be overcome by algorithmically merging components. The variance of individual mixtures was regularized to constrain variance to be non-zero to avoid fitting instabilities. Mixtures number can be determined through the Bayesian Information Criterion (BIC) which optimizes a trade-off between model complexity and accuracy on training data.

Merging of Redundant Mixture Components.

PopAlign can algorithmically merge redundant mixtures using the Jeffrey's divergence. For multivariate Gaussian distributions, the Jeffrey's divergence has a closed analytic form.

$$D_{JD}(\phi_i \| \phi_j) = \frac{1}{2}(D_{KL}(\phi_i \| \phi_j) + D_{KL}(\phi_j \| \phi_i)), \tag{2.14}$$

where $\phi_0$ and $\phi_1$ are two independent components from the same mixture model, and $\mu$ and $\Sigma$ are their associated parameters. $D_{KL}$ is the Kullback Leibler divergence and has a convenient parametric form for Gaussian distributions:

$$D_{KL}\left(\mathcal{N}_i\left(c; \mu_i, \sum_i\right) \middle\| \mathcal{N}_j\left(c; \mu_j, \sum_j\right)\right) =$$

$$\frac{1}{2}\left(tr\left(\sum_i^{-1} \sum_j\right) + (\mu_i - \mu_j)^T \sum_i^{-1} (\mu_i - \mu_j) - k + \ln\left(\frac{\det\sum_i}{\det\sum_j}\right)\right).$$

For each mixture model, iterative attempts can be made to merge component pairs with the lowest Jeffrey's divergence and mergers that increase the BIC of the model given the data can be accepted. With each merge step, model parameters for candidate pair can be recalculated, and the updated model can be accepted or rejected based on the new BIC. Mergers can be performed until the first rejection. This procedure can remove redundant mixture components from the model.

Sampling Data from Gaussian Mixture Models.

Given parameters, $$\left\{\left(\mu_i, \sum_i, w_i\right)\right\}_{i=1}^l$$

for a given mixture model. synthetic data can be generated from the model through a simple sampling procedure. A given model has, l mixtures, and a mixture from the set of l mixtures was first selected with probabilities weighted by $w_i$. Following selection of a mixture, j, standard methods were used to draw a "point" in the m dimensional feature space from $\mathcal{N}_j(c, \mu_j, \Sigma_j)$.

Analysis of Model Error.

Model error can be assessed by comparing the distribution of model generated data to the empirical data. To avoid under-sampling, error analysis can be performed within two dimensional projections of the data and averaged error over all (or some) projections. Briefly, each projection can be binned into 25 bins (or 10, 20, 30, 40, 50, or more). In each bin, the deviation between the model generated data and empirical data can be calculated in terms of percent error in each bin. Total error within each projection can be calculated as a weighted average of this percent error over all bins in a projection:

$$\text{error} = \sum_i \frac{N_i}{N_T} \frac{|N_i - \hat{N}_i|}{N_i},$$

where $N_i$ is the number of experimental data points in bin i, $\hat{N}_i$ is the number of model generated data points in bin i and, $N_T$ is the total number of experimental data points. This metric weights the per-bin fractional error by the probability density of each binned region in the projection.

Alignment of Models Across Reference and Test Populations.

To compare the test and reference models, each mixture component in the test population model, $$\phi_i^{test}(c) \in \{\phi_i^{test}(c)\},$$

can be aligned to a mixture component, $$\{\phi_i^{ref}(c)\},$$

in the reference population model (FIG. 19C). Alignment can be performed by finding the "closest" reference mixture in gene feature space. To define closeness, a statistical metric of similarity on probability distributions, such as Jeffrey's divergence, can be used. Specifically, for each $$\phi_i^{test} \in \{\phi_i^{test}(c)\}, \text{ an } \phi_j^{ref} \in \{\phi_j(c)\}^{ref},$$

the closest mixture in the reference set, can be found:

$$\underset{\phi_j^{ref}(c) \in \{\phi_j^{ref}(c)\}}{\text{argmin}} D_{JD}\big(\phi_i^{test}(c) \parallel \phi_j^{ref}(c)\big), \quad (2.15)$$

where the minimization is performed over each $$\{\phi_i^{ref}(c)\}$$

in the set of reference mixtures, and $D_{JD}$ is the Jeffrey's divergence (JD). For each test mixture, the reference mixture $\phi_j$ that is closest in terms of position and shape in feature space can be found.

For each alignment, an explicit p-value can be calculated from an empirical null distribution $P(D_{JD})$ that estimates the probability of observing a given value of $D_{JD}$ in an empirical data set of all subpopulation pairs within a single cell tissue database. Aligning subpopulations using Jeffrey's divergence incorporates information about the shape and position of the probability distributions (i.e., covariance), while disregarding the relative abundance of each subpopulation.

Scoring Alignments.

To assign a p-value to alignments, the probability of observing two cell-states with a given Jeffrey's divergence by chance can be calculated using an empirical null distribution generated from a data set (e.g., a large dataset of RNA-seq data). Specifically, a mixture model for all tissue pairs can be constructed form the data set. Then, all pairwise Jeffrey's divergence scores can be calculated for all the underlying mixtures. This calculation provides a global distribution over $D_{JD}$ for cell-states in the mouse. This distribution provides a null distribution for typical statistical closeness between cell-states in feature space.

Model Interpretation Through Parameter Analysis.

Following mixture alignment, quantitative differences in mixture parameters between the reference and test sample can be analyzed to track shifts in gene expression state, gene expression covariance, and cellular abundances across the identified cell-states in the cell population.

Specifically, for each aligned mixture pair, $$\big(\phi_i^{test}, \phi_j^{ref}\big)$$

with parameters $$\big\{\mu_i^{ref}, \Sigma_i^{ref}, w_i^{ref}\big\} \text{ and } \big\{\mu_j^{test}, \Sigma_j^{test}, w_j^{test}\big\},$$

the below can be calculated:

$$\Delta\mu_i = \|\mu_i^{ref} - \mu_j^{test}\|_2,$$

$$\Delta\Sigma_i = D_C\big(\Sigma_i^{ref}, \Sigma_j^{test}\big), \text{ and}$$

$$\Delta w_i = \big|w_i^{ref} - w_j^{test}\big|,$$

where $\Delta\mu_i$ measures shifts in mean gene expression; $\Delta w_i$ quantifies shifts in cell-state abundance; $\Delta\Sigma_i$ quantifies shifts in the shape of each mixture including rotations and changes in gene expression variance. These shift parameters can be calculated for all mixture pairs, and then the shifts can be analyzed to assess the impact of signaling conditions or environmental changes on the underlying cell population.

$$D_C(\Sigma_i, \Sigma_j) = \sqrt{\sum_{z=1}^m \ln^2 \lambda_z(\Sigma_i, \Sigma_j)},$$

where $\lambda_z$ is a generalized eigenvalue of $\Sigma_i$ and $\Sigma_j$ or a solution to $\Sigma_i v = \lambda_z \Sigma_j v$, and m is the number of gene features.

Example PopAlign Implementation

There are challenges for the automated detection due to the structure of the data. For example, the data is high-dimensional: 20,000 genes×10,000 up to 1 million cells. Also, many different subtypes of cells exist in the data at varying abundances. Moreover, Perturbations can change cells so much, and the cells can become a new cluster. Thus, cells from different experiments cannot be clustered together (because they will cluster separately).

Figure 1:
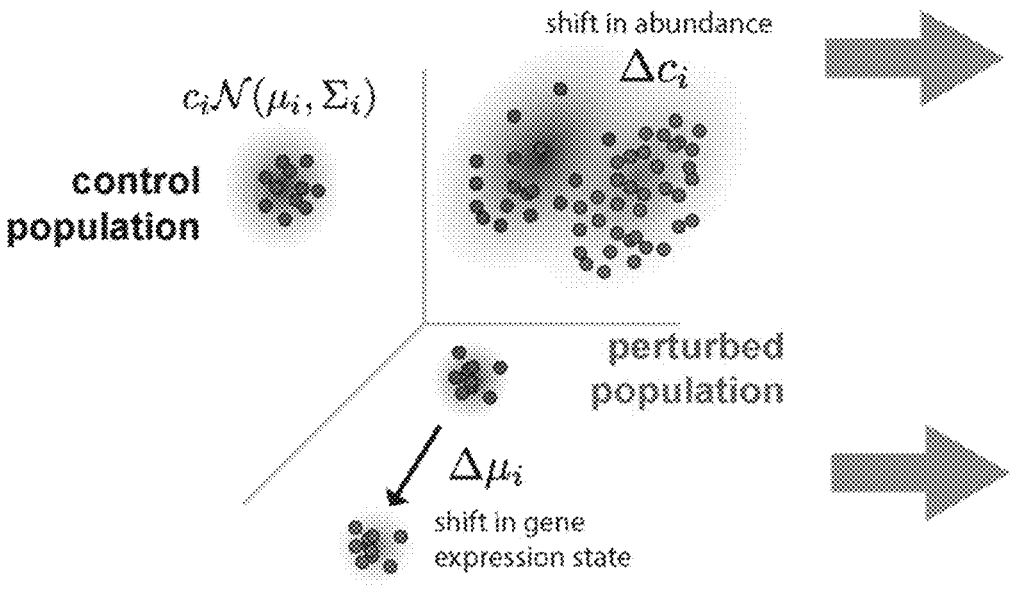
FIG. 1 illustrates an overview of PopAlign framework.
Figure 2:
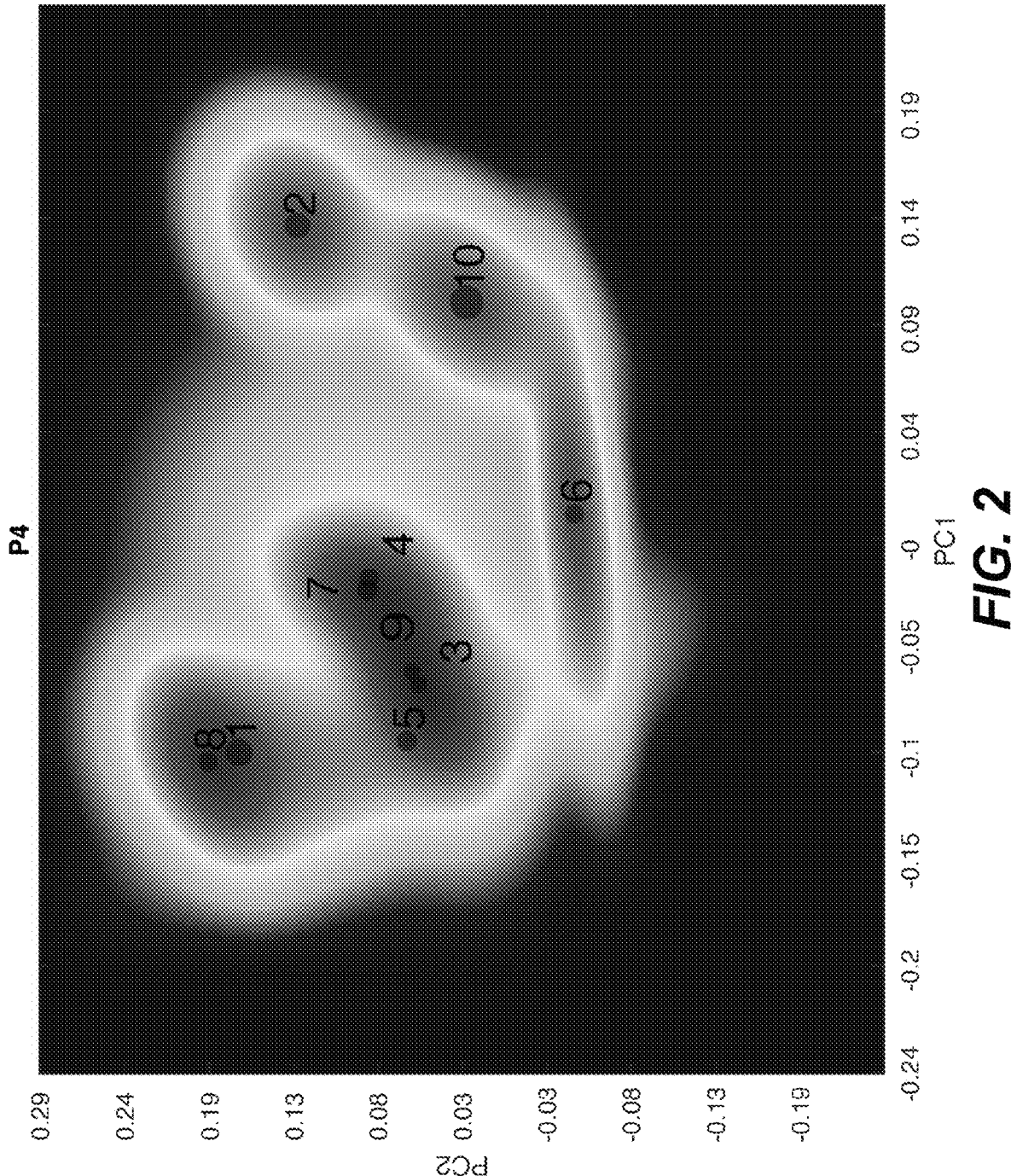
FIG. 2 shows a rendering of a model (neural development data).
Figure 3:
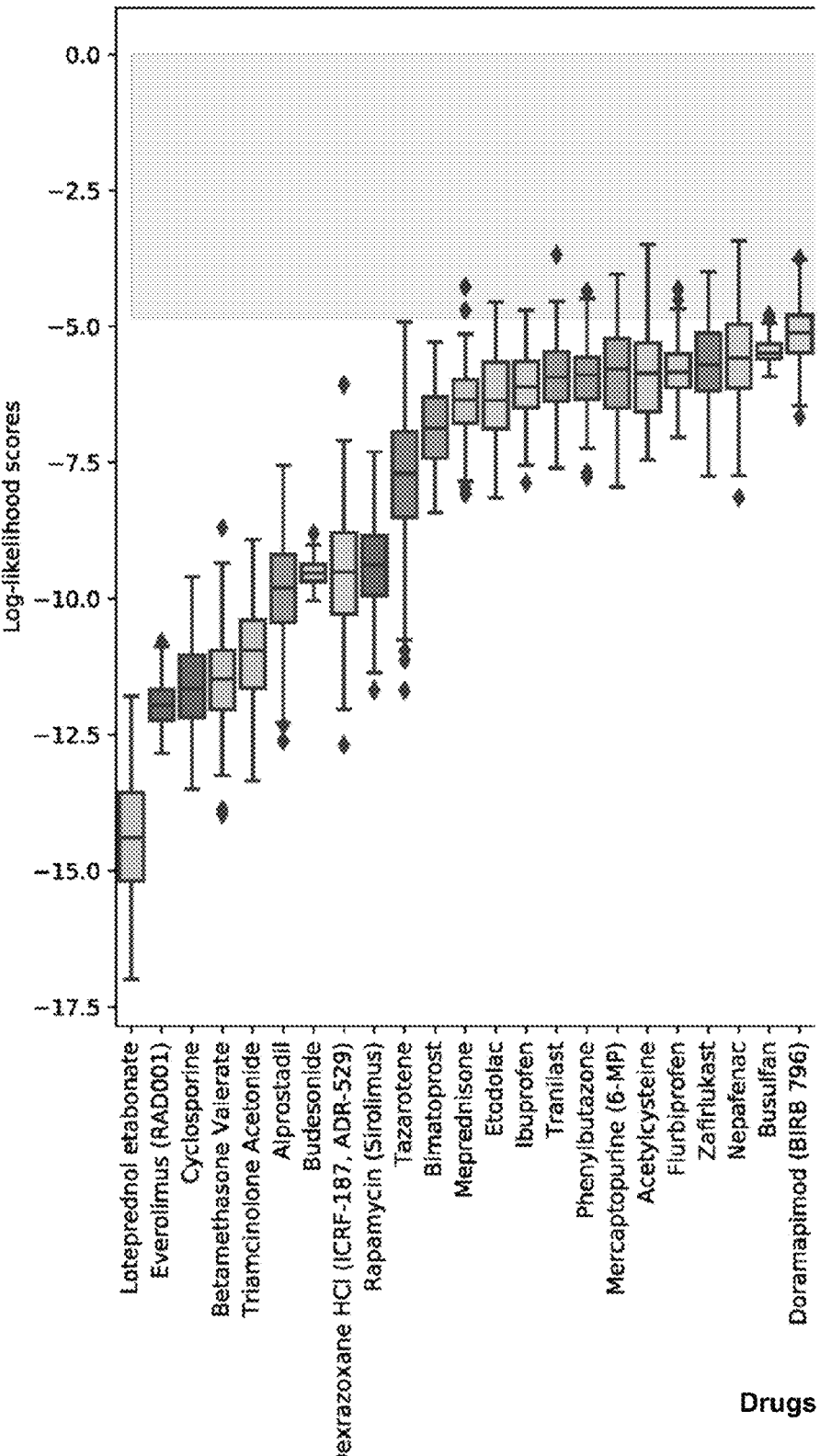
FIG. 3 shows a ranking plot for sample scores against CD3+ CTRL sample.
Figure 3:
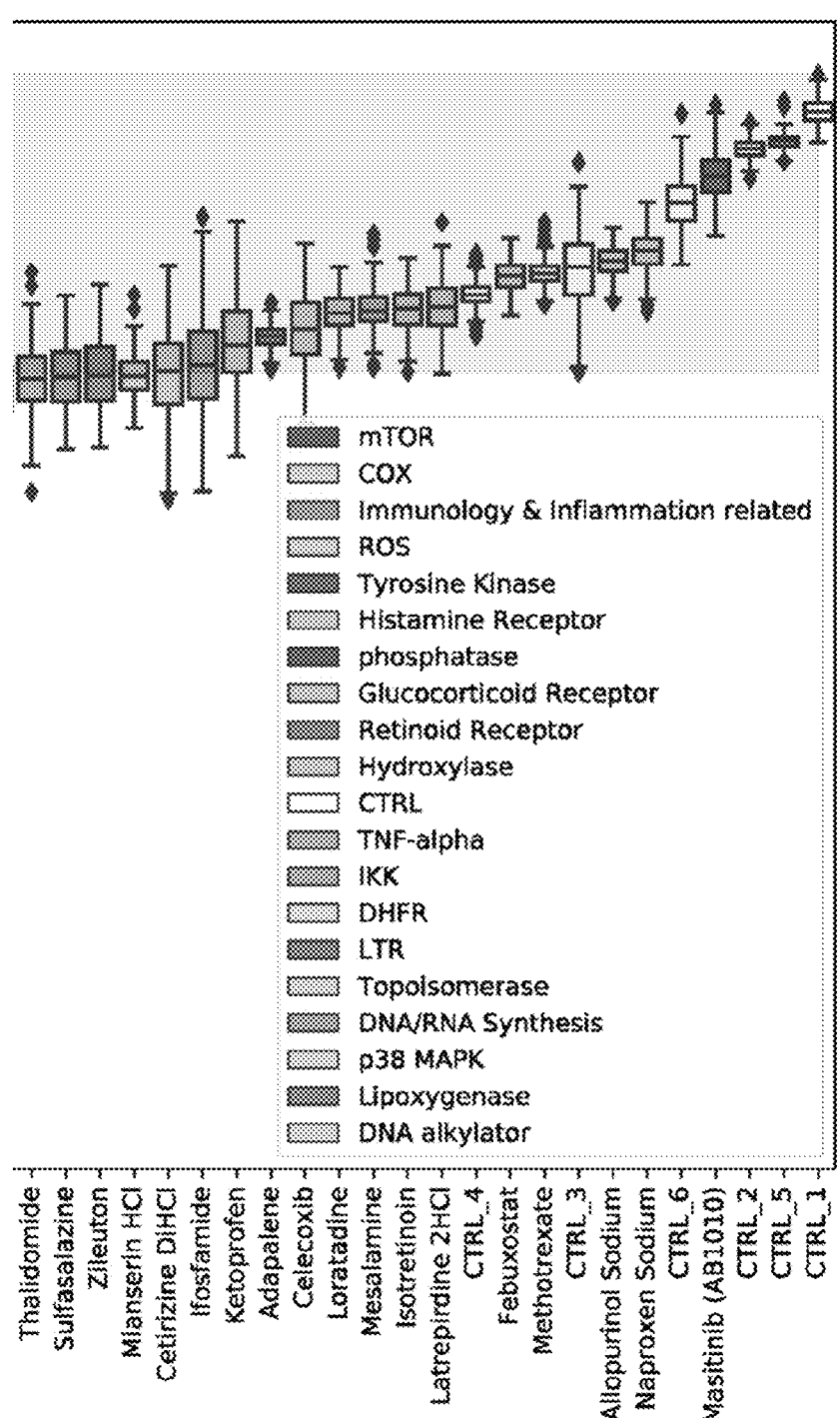
Figure 4:
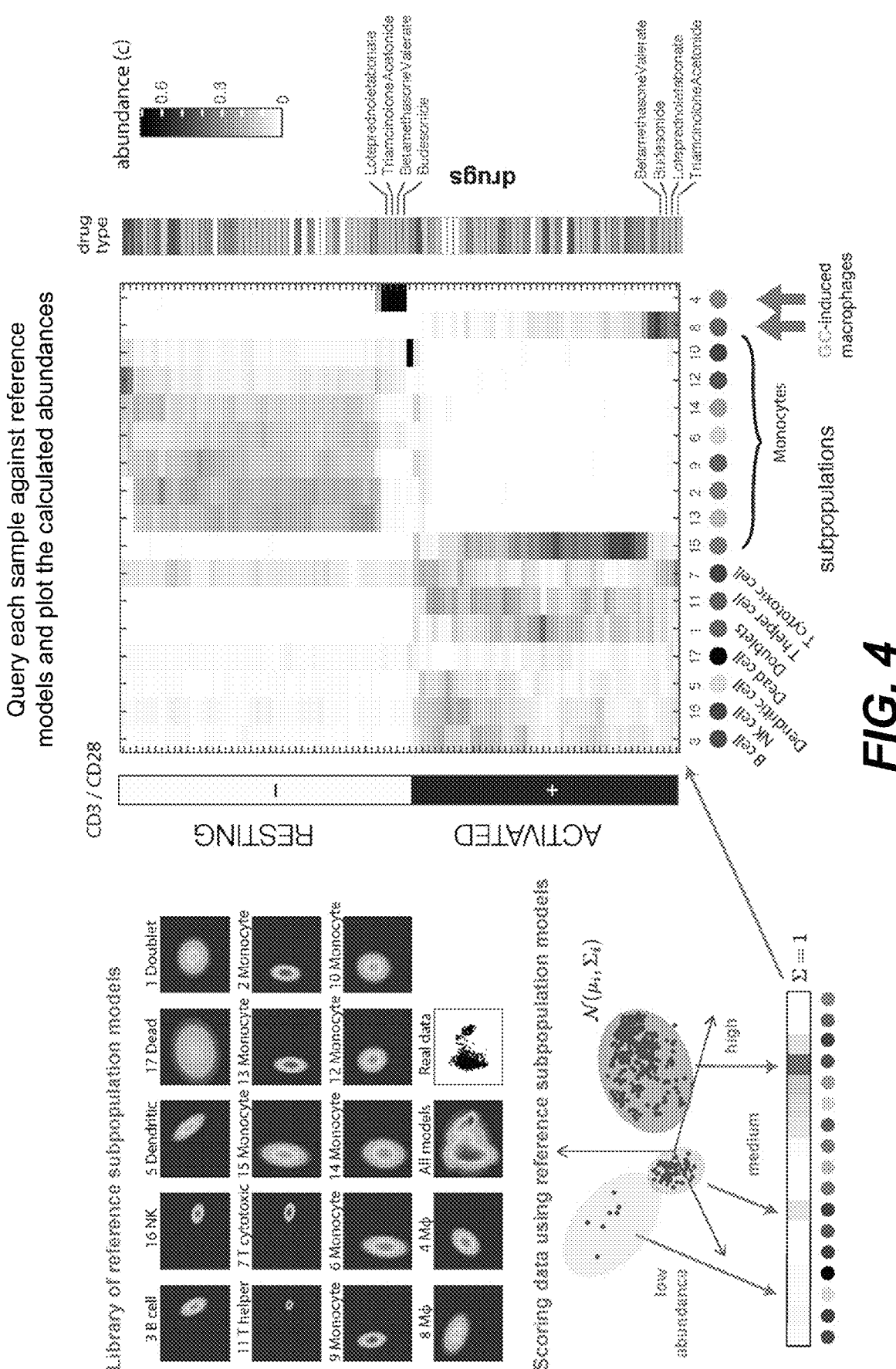
FIG. 4 shows a query plot.
Figure 6:
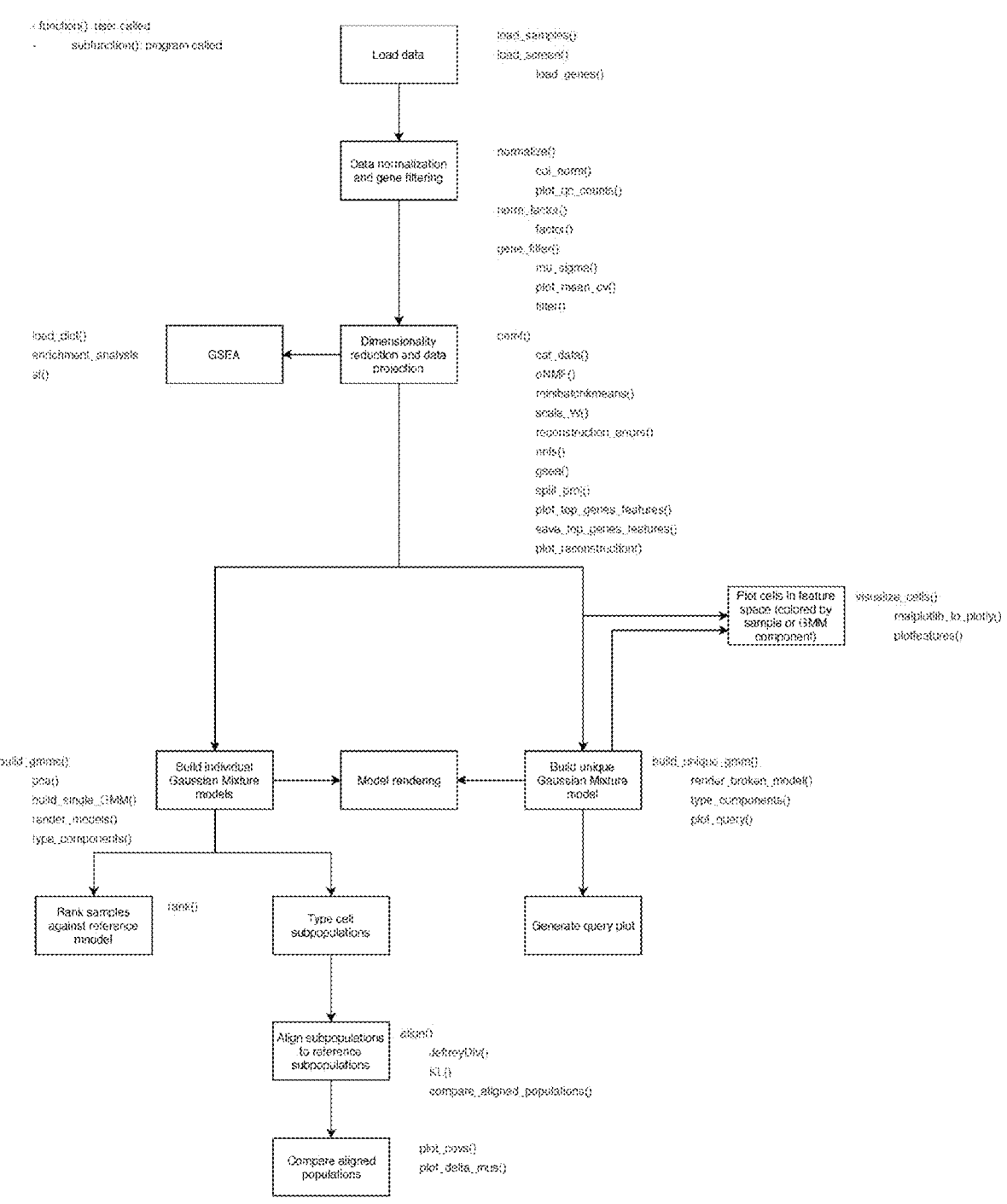
FIG. 6 is a non-limiting exemplary software flow chart.

Mathematical and computational methods are described herein can overcome these challenges by using probabilistic models. Single-cell data are modeled as a probability distribution within gene expression space. Specifically, a Gaussian mixture model which represents distinct cell types can be used as independent Gaussians. The parameters of each Gaussian are meaningful and can be directly compared (for example, the mean gene expression state, and the covariance matrix represents each subpopulations' spread).
FIG. 1 illustrates an overview of PopAlign framework.

By using probabilistic models, a number of powerful statistical metrics from classic information theory (for example, likelihood, divergence, and entropy) can be used. For example, a notion of statistical distance, the divergence between two distributions, can be used to align subpopulations across different samples. This alignment provides information on which subpopulations should be compared to each other to find gene expression differences.

Software Overview

There are three main tasks that one PopAlign package can perform:

1. Rank drugs or perturbations by how much they change the population globally.

2. Query experimental samples against a reference set of subpopulations.

3. PopAlign: Build models for each experimental sample, dissect the subpopulations into independent Gaussians, and then align subpopulations between each perturbation and the control sample. The subpopulations that have the lowest divergence relative to each other, are the ones that are likely the same "cell type."

3A. Once it is known which subpopulations are aligned, the changes for each aligned pair can be calculated, including:

3Ai. Change in mean gene expression state (mu)

3Aii. Change in abundance (c)

3Aiii. Change in the shape of the covariance matrix (Sigma)

There are two core steps to the model building procedure: First, the data are compressed into roughly 3-15 dimensions using some type of dimensionality reduction technique. In the framework, both principal component vectors (PCA) and orthogonal non-negative matrix factorization (oNMF) are used. oNMF has a number of useful features including biological interpretability. oNMF has been implemented in Python already.

The second step involves learning the probability distribution using a Gaussian Mixture Model. Learning these models are done using the standard Expectation Maximization algorithm because of its high speek and to avoid a number of problems (e.g., weak guarantees for convergence) that EM has. Some custom code has been developed to check the accuracy of the models based on looking at univariate projections.

Type of Data to be Ingested

Gene expression matrix as a sparse matrix—matrix.mtx: Up to 50,000-100,000 cells per experiment List of genes—features.tsv: 20,000-30,000 gene IDs Metadata—meta.csv: Metadata (one line per cell) containing sample information. Drug or signaling protein name and concentration.

Cell barcodes—barcodes.tsv: One barcode per cell. Each barcode is a 16 bp string (ATCG, etc)

Language

For example, Python. There is codebase for this method written in Python scripts (roughly 50 scripts). It is advantageous in some embodiments to reproduce the analysis on present data as well as on new data. We'd like code review to focus on the following things:

Functions

Load Raw Data: Loads in raw data from input files above Normalize Data: Normalize data by transcript number Filter Data: Filter out highly variable genes Find Features: Use NMF or PCA to define linear features Gene Set Enrichment Analysis: Use hypergeometric test and gene sets to define the Project Data: Project remaining data into feature space Build Models: Build GMM models Render Models: Project high-dimensional models into 2D space and plot rendered probability distribution Rank Models: Rank data against a control model by ranking the likelihoods calculated using control model Query Models: Build a single model for all data and query each sample against those data Pop Align: Align subpopulations within each sample against a reference model (control experiment)

Cell Typing: Takes in a list of marker genes and types each subpopulation for the reference data based on expression of those markers Plot Changes: Plot changes in mean (mu), covariance (Sigma), and abundance (c)

Example List of Dependencies and Functions:

```
import os import csv
import numpy as np import pandas as pd
from multiprocessing import Pool from scipy import io as sio
from scipy import sparse as ss from scipy import optimize as so from scipy import stats
from scipy.stats import linregress
from sklearn.utils.sparsefuncs import mean_variance_axis from sklearn.metrics import mean_squared_error
from sklearn.decomposition import PCA import sklearn.mixture as smix
from sklearn import cluster as sc import matplotlib
from matplotlib import pyplot as plt import seaborn as sns
from scipy.stats import multivariate_normal as mvn
import adjustText
```

Misc Functions

```
mkdir(str)
cat_data(pop, name)
show_samples(pop) factors(n)
```

Load Functions

```
load_genes(genes)
load_samples(samples, genes)
```

Normalization and Filtering Functions

```
col_norm(M)
plot_qc_counts(pop)
normalize(pop)
factor(M, normfactor)
norm_factor(pop, normfactor)
mu_sigma(M, pop)
plot_mean_cv(lognzcv, lognzmean, pop)
filter(pop)
gene_filter(pop)
```

Gene Set Enrichment Analysis Functions

```
load_dict(dic)
sf(k, size_total, n, N)
enrichment_analysis(d,genelist,size_total)
gsea(pop, geneset='c5')
```

Dimensionality Reduction Functions

```
minibatchkmeans(m, k)
oNMF(X, k, n_iter=500, verbose=1, residual=1e-4, tof=1e-4)
nnls(W, V)
reconstruction_errors(M_norm, q)
split_proj(pop, proj)
save_top_genes_features(pop, stds, stdfactor)
plot_top_genes_features(pop)
plot_reconstruction(pop)
scale_W(W)
onmf(pop, ncells=500, nfeats=[5,7,9], nreps=3, niter=300)
pca(pop, fromspace='genes')
render_model(pop, name)
render_models(pop, mode='grouped')
```

GMM Functions

```
build_single_GMM(k, C)
build_gmms(pop, ks=(5,20), nreps=3)
build_unique_gmm(pop, ks=(5,20), nreps=3)
```

Figure 7:
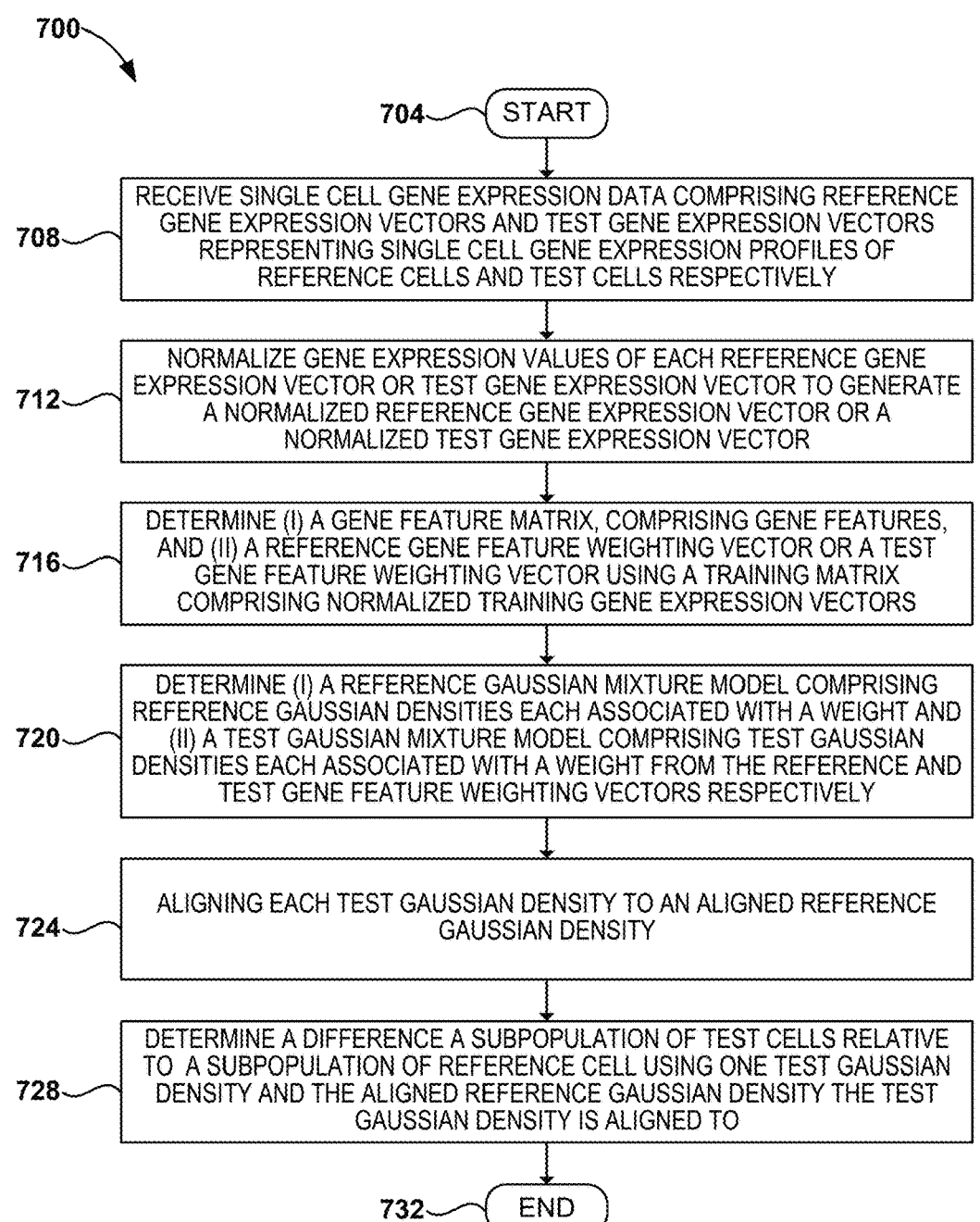
FIG. 7 is a flow diagram showing an exemplary method of single cell analysis method.

Align Functions
    KL(mu1, cov1, mu2, cov2)
    JeffreyDiv(mu1, cov1, mu2, cov2)
    align(pop, ref=None)
Rank Functions
    rank(pop, ref=None, k=100, niter=200, mincells=50)
Query Functions
    plot_query(pop)
Example Single Cell Analysis Method FIG. 7 is a flow diagram showing an exemplary method 700 of single cell analysis. The method 700 may be embodied in a set of executable program instructions stored on a computer-readable medium, such as one or more disk drives, of a computing system. For example, the computing system 800 shown in FIG. 8 and described in greater detail below can execute a set of executable program instructions to implement the method 700. When the method 700 is initiated, the executable program instructions can be loaded into memory, such as RAM, and executed by one or more processors of the computing system 800. Although the method 700 is described with respect to the computing system 800 shown in FIG. 8, the description is illustrative only and is not intended to be limiting. In some embodiments, the method 700 or portions thereof may be performed serially or in parallel by multiple computing systems.

After the method 700 begins at block 704, the method 700 proceeds to block 708, where a computing system can receive single cell gene expression data (or single cell multiomics data, such as transcriptomics data, proteomics data, epigenomics data, and microbiomics data) comprising a plurality of reference gene expression vectors and a plurality of test gene expression vectors representing single cell gene expression profiles of a plurality of reference cells and a plurality of test cells respectively, in a gene expression space. In some embodiments, the gene expression profiles comprise mRNA expression profiles and/or protein expression profiles.

The method 700 proceeds from block 708 to block 712, where the computing system can, for each of the plurality of reference gene expression vectors and the plurality of test gene expression vectors, optionally normalize gene expression values of the reference gene expression vector or the test gene expression vector to generate a normalized reference gene expression vector or a normalized test gene expression vector comprising normalized gene expression values. In some embodiments, the normalized gene expression values of the plurality of reference gene expression vectors and the plurality of test gene expression vectors transition smoothly.

In some embodiments, to normalize, the computing system can: normalize the gene expression values of the reference gene expression vector or the test gene expression vector relative to a sum of the gene expression values to generate the normalized reference gene expression vector or the normalized test gene expression vector comprising the normalized gene expression values. In some embodiments, to normalize, the computing system can: adjust the gene expression values of the reference gene expression vector or the test gene expression vector with a scaling factor to generate the normalized reference gene expression vector or the normalized test gene expression vector comprising the normalized gene expression values. The scaling factor can be about a sum of the gene expression values of one of the plurality of reference gene expression vectors and the plurality of test gene expression vectors. The scaling factor can be about a smallest sum of the gene expression values of any of the plurality of reference gene expression vectors and the plurality of test gene expression vectors. The scaling factor can be, be about, be at least, or be at most, 100, 1000, 10000, or more. In some embodiments, to normalize, the computing system can: increase the gene expression values of the reference gene expression vector or the test gene expression vector by a pseudo-count value to generate the normalized reference gene expression vector or the normalized test gene expression vector comprising the normalized gene expression values. The pseudo-count value can be, be about, be at least, or be at most, 1, 2, 5, 10, or more. In some embodiments, to normalize, the computing system can: changing the gene expression values of the reference gene expression vector or the test gene expression vector to a logarithmic scale to generate the normalized reference gene expression vector or the normalized test gene expression vector comprising the normalized gene expression values.

After normalizing gene expression vectors at block 712, the method 700 proceeds to block 716, where the computing system can determine (i) a gene feature matrix, comprising a plurality of gene features, and, for each of the plurality of normalized reference gene expression vectors and the plurality of normalized test gene expression vectors, (ii) reference gene feature weighting vector or a test gene feature weighting vector using a training matrix comprising a plurality normalized training gene expression vectors. The plurality of reference gene feature weighting vectors and the plurality of test gene feature weighting vectors can represent gene feature profiles of the plurality of reference cells and the plurality of test cells in a gene feature space, respectively.

In some embodiments, the plurality of normalized training gene expression vectors comprises one or more the plurality of normalized reference gene expression vectors and/or one or more of the plurality of test gene expression vectors. The plurality of normalized training gene expression vectors can comprise one or more of the plurality of normalized reference gene expression vectors sampled and/or one or more of the plurality of test gene expression vectors. The plurality of normalized training gene expression vectors can comprise two or more the plurality of normalized reference gene expression vectors randomly and/or uniformly sampled and/or two or more of the plurality of test gene expression vectors randomly and/or uniformly sampled. The plurality of normalized training gene expression vectors can comprise the plurality of normalized reference gene expression vectors and/or the plurality of test gene expression vectors.

In some embodiments, to determine the gene feature matrix, the computing system can: determine the gene feature matrix from the plurality of normalized training gene expression vectors using machine learning. The machine learning can be based on a layered neural network. In some embodiments, to determine the gene feature matrix, the computing system can: determine the gene feature matrix using matrix factorization. The matrix factorization can comprise singular value decomposition. The matrix factorization can comprise principal component analysis. The matrix factorization can comprise non-negative matrix factorization. The matrix factorization can comprise sparse non-negative matrix factorization. The matrix factorization can comprise orthogonal non-negative matrix factorization.

In some embodiments, the gene feature matrix is an orthogonal matrix. Each, or at least one, element of the gene feature matrix can be greater than or equal to zero. Each, one or at least one, element of at least one of the plurality of reference gene feature weighting vectors and/or at least one of the plurality of test gene feature weighting vectors can be greater than or equal to zero.

In some embodiments, a number of the plurality of gene features is predetermined. A size of a gene expression vector of the plurality of reference gene expression vectors and the plurality of test gene expression vectors can be, be about, be at least, or be at most, 10, 20, 30, 40, or 50. A ratio of a size of a gene expression vector of the plurality of reference gene expression vectors and the plurality of test gene expression vectors to a number of the plurality of gene features can be, be about, be at least, or be at most, 10, 20, 30, 40, 50, 100, 500, or 1000. A size of a gene expression vector of the plurality of reference gene expression vectors and the plurality of test gene expression vectors can be, be about, be at least, or be at most, 1000, 5000, or 1000.

In some embodiments, to determine the gene feature matrix, the computing system can: determine the gene feature matrix comprising the plurality of gene features using a plurality normalized training gene expression vectors; and/or for each of the plurality of normalized reference gene expression vectors and the plurality of normalized test gene expression vectors, determine a reference gene feature weighting vector or a test gene feature weighting vector in a gene feature space using the gene feature matrix. To determine the gene feature matrix, the computing system can determine the gene feature matrix and a gene feature weighting matrix comprising a plurality of gene feature weighting vectors using the plurality of normalized training gene expression vectors. Each, one, or at least one, element of the gene feature weighting matrix can be greater than or equal to zero.

In some embodiments, to determine the gene feature matrix and the gene feature weighting matrix, the computing system can: determine the gene feature matrix and the gene feature weighting matrix by minimizing a loss function comprising a difference of the training matrix and a product of the gene feature matrix and the gene feature weighting matrix. To determine the gene feature matrix and the gene feature weighting matrix, the computing system can determine the gene feature matrix and the gene feature weighting matrix by minimizing a loss function comprising a norm of the training matrix and a product of the gene feature matrix and the gene feature weighting matrix. To determine the gene feature matrix and the gene feature weighting matrix, the computing system can determine the gene feature matrix and the gene feature weighting matrix by minimizing a loss function comprising a Frobenius norm of the training matrix and a product of the gene feature matrix and the gene feature weighting matrix.

In some embodiments, the loss function comprises a penalty comprising a number of the plurality of gene features in the gene feature matrix. The loss function can comprise a penalty comprising to a number of the plurality of gene features in the gene feature matrix exponentiated with an exponentiation factor. The exponentiation factor can be about 0.7.

In some embodiments, to determine the reference gene feature weighting vector or the test gene feature weighting vector, the computing system can: determine the reference gene feature weighting vector or the test gene feature weighting vector in the gene feature space by minimizing a loss function comprising a difference of the corresponding normalized reference gene expression vector or normalized test gene expression vector and a product of the gene feature matrix and the reference gene feature weighting vector or the test gene feature weighting vector. To determine the reference gene feature weighting vector or the test gene feature weighting vector, the computing system can determine the reference gene feature weighting vector or the test gene feature weighting vector in the gene feature space by minimizing a loss function comprising a norm of the corresponding normalized reference gene expression vector or normalized test gene expression vector and a product of the gene feature matrix and the reference gene feature weighting vector or the test gene feature weighting vector. To determine the reference gene feature weighting vector or the test gene feature weighting vector, the hardware processor can be programmed by the executable instructions to determine the reference gene feature weighting vector or the test gene feature weighting vector in the gene feature space by minimizing a loss function comprising a Frobenius norm of the corresponding normalized reference gene expression vector or normalized test gene expression vector and a product of the gene feature matrix and the reference gene feature weighting vector or the test gene feature weighting vector.

The method 700 proceeds from block 716 to block 720, where the computing system determine (i) a reference Gaussian mixture model comprising a plurality of reference Gaussian densities each associated with a reference weight (e.g., a scalar) and (ii) a test Gaussian mixture model comprising a plurality of test Gaussian densities each associated with a test weight (e.g., a scalar) from the plurality of reference gene feature weighting vectors and the plurality of test gene expression vectors, respectively. Each of (i) the plurality of reference Gaussian densities and associated reference weights and (ii) the plurality of test Gaussian densities and the associated test weights can represent a subpopulation of the plurality of reference cells or the plurality of test cells, respectively. In some embodiments, the subpopulation of the plurality of reference cells comprises, comprises about, comprises at least, or comprises at most, 50%, 60%, 70%, 80%, 90%, 95%, 99%, or 100 cells of a cell type, and/or wherein the subpopulation of the plurality of test cells comprises, comprises about, comprises at least, or comprises at most, 50%, 60%, 70%, 80%, 90%, 95%, 99%, or 100 cells of a cell type.

In some embodiments, to determine (i) the reference Gaussian mixture model and (ii) the test Gaussian mixture model, the computing system can: determine (i) one or more reference parameters and the reference weight of or associated with each of the plurality of reference Gaussian densities and (ii) one or more test parameters and the test weight of each of the plurality of test Gaussian densities, respectively, from (i) the plurality of reference gene feature weighting vectors and (ii) the plurality of test gene feature weighting vectors, respectively. Each of the plurality of reference Gaussian densities and/or each of the plurality of test Gaussian densities can comprise a normal distribution, and/or parameters of the normal distribution comprises the one or more reference parameters or the one or more test parameters of the reference Gaussian density or the test Gaussian density, respectively. The one or more parameters of each, or at least one, of the plurality of reference Gaussian densities can comprise a reference centroid and a reference covariance matrix, and/or the one or more parameters of each, or at least one, of the plurality of test Gaussian densities comprises a test centroid and a test covariance matrix. The reference centroid, the reference covariance matrix, and the reference weight of or associated with a reference Gaussian density of the plurality of Gaussian densities can represent an average of reference gene features of a subpopulation of the plurality of reference cells represented by the reference Gaussian density, a spread of the reference gene features, an abundance of the subpopulation of the plurality of reference cells represented by the reference Gaussian density, and/or the test centroid, the test covariance matrix, and the test weight of or associated with a test Gaussian density of the plurality of Gaussian densities can represent an average of test gene features of a subpopulation of the plurality of test cells represented by the test Gaussian density, a spread of the test gene features, an abundance of the subpopulation of the plurality of test cells represented by the test Gaussian density.

In some embodiments, to determine (i) the reference Gaussian mixture model and (ii) the test Gaussian mixture model, the computing system can: determine (i) the reference Gaussian mixture model and (ii) the test Gaussian mixture model using maximum likelihood estimation and a likelihood function. The maximum likelihood estimation can comprise expectation maximization. In some embodiments, a number of the plurality of reference Gaussian densities and/or a number of the plurality of test Gaussian densities is predetermined. In some embodiments, a number of the plurality of reference Gaussian densities and/or a number of the plurality of test Gaussian densities can be, be about, be at least, or be at most, 10, 15, 20, 30, 40, or 50. In some embodiments, to determine (i) the reference Gaussian mixture model and (ii) the test Gaussian mixture model, the computing system can: determine a number of the plurality of reference Gaussian densities and/or a number of the plurality of test Gaussian densities by penalizing the number of the plurality of reference Gaussian densities and/or the number of the plurality of test Gaussian densities. In some embodiments, to determine (i) the reference Gaussian mixture model and (ii) the test Gaussian mixture model, the computing system can determine a number of the plurality of reference Gaussian densities and/or a number of the plurality of test Gaussian densities using Bayesian Information Criterion.

In some embodiments, to determine (i) the reference Gaussian mixture model, the computing system can: determine a pair of reference Gaussian densities of the plurality of reference Gaussian densities with a divergence smaller than a divergence of any other pair of reference Gaussian densities of the plurality of reference Gaussian densities to be redundant in the reference Gaussian model; merge the pair reference Gaussian densities to generate a merged reference Gaussian density; determine merging the pair of reference Gaussian densities results in increasing a Bayesian Information Criterion of the reference Gaussian mixture model; and/or accept the merged reference Gaussian density. In some embodiments, to determine (i) the test Gaussian mixture model, the computing system can: determine a pair of test Gaussian densities of the plurality of test Gaussian densities with a divergence smaller than a divergence of any other pair of test Gaussian densities of the plurality of test Gaussian densities to be redundant in the test Gaussian model; merge the pair test Gaussian densities to generate a merged test Gaussian density; determine merging the pair of test Gaussian densities results in increasing a Bayesian Information Criterion of the test Gaussian mixture model; and/or accept the merged test Gaussian density.

In some embodiments, to determine (i) the reference Gaussian mixture model, the computing system can: iterative merge a pair of reference Gaussian densities of the plurality of reference Gaussian densities with a divergence smaller than a divergence of any other pair of reference Gaussian densities of the plurality of reference Gaussian densities to be redundant until merging the pair of reference Gaussian densities does not result in increasing a Bayesian Information Criterion of the reference Gaussian mixture model after merging. To determine (i) the test Gaussian mixture model, the computing system can iterative merge a pair of test Gaussian densities of the plurality of test Gaussian densities with a divergence smaller than a divergence of any other pair of test Gaussian densities of the plurality of test Gaussian densities to be redundant until merging the pair of test Gaussian densities does not result in increasing a Bayesian Information Criterion of the test Gaussian mixture model after merging.

In some embodiments, the divergence of the pair of reference Gaussian densities or test Gaussian densities comprises a Jeffrey's divergence of the pair of reference Gaussian densities or test Gaussian densities. The divergence of the pair of reference Gaussian densities or test Gaussian densities can comprise a Kullback Leibler divergence of the pair of reference Gaussian densities or test Gaussian densities.

After determining Gaussian density models at block 720, the method 700 proceeds to block 724, where the computing system can align each of the plurality of test Gaussian densities to an aligned reference Gaussian density of the plurality of reference Gaussian densities. In some embodiments, to align each of the plurality of test Gaussian densities to the aligned reference Gaussian density of the plurality of reference Gaussian densities, the computing system can: align each of the plurality of test Gaussian densities to an aligned reference Gaussian density of the plurality of reference Gaussian densities based on one or more test parameters of the test Gaussian density and one or more reference parameters of each of the plurality of reference Gaussian densities.

In some embodiments, to align each of the plurality of test Gaussian densities to the aligned reference Gaussian density of the plurality of reference Gaussian densities, the computing system can: align the test Gaussian density to the aligned reference Gaussian density with a divergence smaller than a divergence between the test Gaussian density and any other of the plurality of reference Gaussian densities. The divergence between the test Gaussian density and the aligned reference Gaussian density can comprise a Jeffrey's divergence between the test Gaussian density and the reference Gaussian density. The divergence between the test Gaussian density and the aligned reference Gaussian density can comprise a Kullback Leibler divergence between the test Gaussian density and the reference Gaussian density. The computing system can determine, for each of the plurality of test Gaussian densities, a probability of the divergence between the test Gaussian density and the aligned reference Gaussian density the test Gaussian density is aligned to. To determine the probability of the divergence, the computing system can determine the probability of the divergence between the test Gaussian density and the aligned reference Gaussian density the test Gaussian density is aligned to using an empirical null distribution of divergence. The computing system can determine the empirical null distribution of divergence using divergences of pairs of Gaussian densities.

The method 700 proceeds from block 724 to block 728, where the computing system can determine a difference of the plurality of test cells, or a subpopulation thereof, relative to the plurality of reference cells, or a subpopulation thereof, using one, at least one, or each, of the plurality of test Gaussian densities and the aligned reference Gaussian density the test Gaussian density is aligned to. The computing system can perform an analysis of the plurality of test cells relative to the plurality of reference cells using one, at least one, or each, of the plurality of test Gaussian densities and the aligned reference Gaussian density the test Gaussian density is aligned to. The computing system can determine a difference of the plurality of test cells, or a subpopulation thereof, relative to the plurality of reference cells, or a subpopulation thereof, using one, at least one, or each, of the plurality of test Gaussian densities and the aligned reference Gaussian density the test Gaussian density is aligned to. The computing system can determine a Gaussian density difference between one of the plurality of test Gaussian densities and the aligned reference Gaussian density the test Gaussian density is aligned to; and determine a difference between the plurality of test cells, or a subpopulation thereof, and the plurality of reference cells, or a subpopulation thereof, using the Gaussian density difference.

In some embodiments, to perform the analysis, the computing system can: perform the analysis of the plurality of test cells relative to the plurality of reference cells using one of the plurality of test Gaussian densities and the associated test weight and the aligned reference Gaussian density the test Gaussian density is aligned to and the associated reference weight.

In some embodiments, to perform the analysis, the computing system can perform the analysis of the plurality of test cells relative to the plurality of reference cells using a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. To perform the analysis, the computing system can: determine a centroid delta of the test centroid and the reference centroid; determine a covariance matrix delta of the test covariance matrix and the reference covariance matrix; determine a weight delta of the test weight and the reference weight; and/or perform the analysis of the plurality of test cells relative to the plurality of reference cells using the centroid delta, the covariance matrix delta, and the weight delta.

In some embodiments, to determine the difference, the computing system can: determine the difference of the plurality of test cells and the plurality of reference cells using one of the plurality of test Gaussian densities and the associated test weight and the aligned reference Gaussian density the test Gaussian density is aligned to and the associated reference weight. To determine the difference, the computing system can determine the difference between one of the plurality of test cells and to the plurality of reference cells using a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. To perform the analysis, or to determine the difference, the computing system can determine a centroid delta of the test centroid and the reference centroid; determine a covariance matrix delta of the test covariance matrix and the reference covariance matrix; determine a weight delta of the test weight and the reference weight; and determine the difference between the plurality of test cells and the plurality of reference cells using the centroid delta, the covariance matrix delta, and the weight delta.

In some embodiments, to determine the Gaussian density difference, the computing system can: determine the Gaussian density difference between one of the plurality of test Gaussian densities and the associated test weight and the aligned reference Gaussian density the test Gaussian density is aligned to and the associated reference weight. To determine the Gaussian density difference, the computing system can determine the Gaussian density difference comprising a test centroid and a test covariance matrix of one of the plurality of test Gaussian densities and the associated test weight and a reference centroid and a reference covariance matrix of the aligned reference Gaussian density the test Gaussian mixture component is aligned to and the associated reference weight. The Gaussian density difference can comprise a centroid delta of the test centroid and the reference centroid, and/or a weight delta of the test weight and the reference weight The centroid delta can represent a change in gene features of a subpopulation of cells represented by the test Gaussian densities or the aligned reference Gaussian density, the covariance matrix delta can represent a change in a spread of the gene features of the subpopulation of cells, and/or the weight delta can represent a change in abundance of the subpopulation of cells. The centroid delta can comprise a difference, a norm, or a Frobenius norm of the test centroid and the reference centroid, the covariance matrix delta can comprise a difference or a norm of the test covariance matrix and the reference covariance matrix, and/or a weight delta can comprise a difference or a norm of the test weight and the reference weight.

Applications

In some embodiments, wherein each, one, or at least one, of the plurality of reference cells is associated with a first annotation, and wherein the computing system can: determine a second annotation of each, or at least one, of the plurality of reference Gaussian densities using the first annotation associated with each, or at least one, of the plurality of reference cells. The first annotation and/or the second annotation can comprise a function annotation, a pathway annotation, a cell-type annotation, and/or a tissue-type annotation. The computing system can determine a third annotation of each, or at least one, of the plurality of test Gaussian densities using the second annotation associated with the aligned reference Gaussian density the test Gaussian density is aligned to.

In some embodiments, the plurality of reference cells comprises healthy cells, and/or the plurality of test cells comprises diseased cells. The plurality of reference cells can comprise cells cultured in the absence of a drug or a signal, and/or the plurality of test cells can comprise cells cultured in the presence of the drug or the signal. The plurality of reference cells can comprise cells from a first subject not treated with a drug, and/or the plurality of test cells can comprise cells from a second subject treated with the drug. The first subject can be the second subject.

In some embodiments, the plurality of reference cells comprises cells from a first tissue type, and the plurality of test cells comprises cells from a second tissue type. To perform the analysis, the computing system can: determine similarities of and difference between the plurality of reference cells and the plurality of test cells. To perform the analysis, the computing system can: determine a gene feature of the plurality of gene features absent or present in the plurality of reference cells is present or absent in the plurality of test cells. To perform the analysis, the computing system can: determining a similarity between the plurality of reference cells and the plurality of test cells using a log-likelihood ratio score of (i) one, at least one, or each of, the plurality of reference Gaussian mixtures and associated reference weights and (ii) one, at least one, or each of, the plurality of test Gaussian mixtures and associated test weights.

In some embodiments, the single cell gene expression data comprises a plurality of second reference gene expression vectors representing single cell gene expression profiles of a plurality of second reference cells. To normalize, the computing system can for each of the plurality of second reference gene expression vectors, normalize gene expression values of the second reference gene expression vector to generate a normalized second reference gene expression vector comprising normalized gene expression values. To determine the gene feature matrix, the computing system can for each of the plurality of normalized second reference gene expression vectors, determine a second reference gene feature weighting vector using the training matrix, wherein the plurality of second reference gene feature weighting vectors represent second gene feature profiles of the plurality of second reference cells. To determine (i) the reference Gaussian mixture model, the computing system can determine a second reference Gaussian mixture model comprising a plurality of second reference Gaussian densities each associated with a second reference weight, wherein each of the plurality of second reference Gaussian densities and associated reference weights represents a second subpopulation of the plurality of second reference cells. To perform the analysis, the computing system can perform the analysis of the plurality of test cells relative to the plurality of reference cells and the plurality of second reference cells using the plurality of reference Gaussian densities, the plurality of second reference Gaussian densities, and the plurality of test Gaussian densities.

In some embodiments, the plurality of gene expression vectors comprises a plurality of (first) reference gene expression vectors and a plurality of second reference gene expression vectors representing single cell gene expression profiles of a plurality of (first) reference cells and a plurality of second reference cells of the plurality of cells.

In some embodiments, the plurality of (first) reference cells comprises healthy cells, and the plurality of second reference cells comprises diseased cells. The plurality of (first) reference cells can be from a (first) tissue, and/or the plurality of second reference cells can be from a second tissue. The (first) tissue and the second tissue can be of different tissue types. In some embodiments, to perform the analysis, the computing system can: determine a (first) similarity between the plurality of (first) reference cells and the plurality of test cells using a (first) log-likelihood ratio score of (i) one, at least one, or each of, the plurality of (first) reference Gaussian mixtures and associated (first) reference weights and (ii) one, at least one, or each of, the plurality of test Gaussian mixtures and associated test weights; determine a second similarity between the plurality of second reference cells and the plurality of test cells using a second log-likelihood ratio score of (i) one, at least one, or each of, the plurality of second reference Gaussian mixtures and associated second reference weights and (ii) one, at least one, or each of, the plurality of test Gaussian mixtures and associated test weights; and/or determine the plurality of test cells to be more similar to the plurality of (first) reference cells and the plurality of second reference cells based on the (first) similarity and the second similarity.

In some embodiments, to perform the analysis, the hardware is processor is programmed by the executable instructions to: determine a probability of the plurality of test cells, or a subpopulation thereof, to be a (first) reference cell type of the plurality of (first) reference cells, or a subpopulation thereof, relative to the a second reference cell type of the plurality of second reference cells, or a subpopulation thereof, with respect to a difference in a (first) condition for culturing the plurality of (first) reference cells and a second condition for culturing the plurality of second reference cells. To determine the probability, the hardware can be processor programmed by the executable instructions to: determine the probability using multinomial logistic regression.

In some embodiments, the plurality of (first) reference cells comprises a (first) reference type of cells and is associated with a (first) reference label. The plurality of second reference cells can comprise a second reference type of cells and is associated with a second reference label. To perform the analysis, the computing system can: determine a probability of the plurality of test cells to be the reference type of cells using (i) the plurality of (first) reference Gaussian densities and/or the associated (first) reference weights and (ii) the plurality of test Gaussian densities and/or the associated test weights; determine a probability of the plurality of test cells to be the second reference type of cells using (i) the plurality of second reference Gaussian densities and/or the associated second reference weights and (ii) the plurality of test Gaussian densities and/or the associated test weights; and/or determine a test label of the plurality of test cells to be the reference label or the second reference label based on the probability and the second probability.

In some embodiments, the single cell gene expression data comprises a plurality of second test gene expression vectors representing single cell gene expression profiles of a plurality of second test cells. To normalize, the computing system can for each of the plurality of second test gene expression vectors, normalize gene expression values of the second test gene expression vector to generate a normalized second test gene expression vector comprising normalized gene expression values. To determine the gene feature matrix, the computing system can for each of the plurality of normalized second test gene expression vectors, determine a second test gene feature weighting vector using the training matrix, wherein the plurality of second test gene feature weighting vectors represent second gene feature profiles of the plurality of second test cells. To determine (i) the reference Gaussian mixture model, the computing system can determine a second test Gaussian mixture model comprising a plurality of second test Gaussian densities each associated with a second test weight, wherein each of the plurality of second test Gaussian densities and associated test weights represents a second subpopulation of the plurality of second test cells. To perform the analysis, the computing system can perform an analysis of the plurality of second test cells relative to the plurality of reference cells using the plurality of reference Gaussian densities and the plurality of second test Gaussian densities. To perform the analysis, the computing system can perform an analysis of the plurality of test cells relative to the plurality of second test cells using the plurality of test Gaussian densities and the plurality of second test Gaussian densities.

In some embodiments, the plurality of gene expression vectors comprises a plurality of first test gene expression vectors and a plurality of second test gene expression vectors representing single cell gene expression profiles of a plurality of first test cells and a plurality of second test cells of the plurality of cells.

In some embodiments, to perform the analysis, the computing system can: perform an analysis of the plurality of (first) test cells and the plurality of second test cells relative to the plurality reference cells using the plurality of reference Gaussian densities and a plurality of (first) test Gaussian densities and the plurality of second test Gaussian densities of the plurality of test Gaussian densities. The plurality of (first) test cells can be originally of a (first) test cell type or from a (first) test tissue type and cultured under a (first) test condition, the plurality of second test cells can be originally of a second test cell type or from a second test tissue type and cultured under a second test condition, and/or the plurality of reference cells can be originally of a reference cell type or from a reference tissue type and cultured under a reference condition. The plurality of (first) test cells can be cultured under a (first) test condition and of a (first) test cell type and, the plurality of second test cells can be cultured under a second test condition and of a second test cell type, and wherein the plurality of reference cells is cultured under a reference condition and of a reference cell type. The (first) test cell type, the second test cell type, and/or the reference cell type are identical, the (first) tissue type, the second test tissue type, and/or the reference tissue type are identical, and/or the (first) test condition, the second test condition, and/or the reference condition are identical. The (first) test cell type, the second test cell type, and/or the reference cell type can be different, the (first) tissue type, the second test tissue type, and/or the reference tissue type can be different, and/or the (first) test condition, the second test condition, and/or the reference condition can be different. The (first) test condition can comprise presence of a (first) drug, signal, or environmental condition, wherein the second test condition comprises presence of a second drug, signal, or environmental condition. The reference condition can comprise no (first) drug, signal, and environmental condition and/or no second drug, signal, and environmental condition. The (first) test condition, second test condition, and/or the reference condition can comprise different concentrations or extents of a drug, signal, or environmental condition. The plurality of (first) test cells can be from a (first) sample of a subject at a (first) time, and the plurality of second test cells can be from a second sample of the subject at a second time. To perform the analysis, the computing system can determine a (first) similarity between the plurality of (first) test cells and the plurality of reference cells using a (first) log-likelihood ratio score of (i) one, at least one, or each of, the plurality of (first) test Gaussian mixtures and associated (first) test weights and (ii) one, at least one, or each of, the plurality of reference Gaussian mixtures and associated reference weights; determine a second similarity between the plurality of second test cells and the plurality of reference cells using a second log-likelihood ratio score of (i) one, at least one, or each of, the plurality of second test Gaussian mixtures and associated second test weights and (ii) one, at least one, or each of, the plurality of reference Gaussian mixtures and associated reference weights; and/or determine the plurality of (first) test cells or the plurality of second test cells to be more similar to the plurality of reference cells based on the (first) similarity and the second similarity. The computing system can demix of the plurality of test gene expression vectors to generate a plurality of (first) test gene expression vectors and a plurality of second gene expression vectors.

In some embodiments, the computing system can: determine a reference diversity comprising a reference heterogeneity of the plurality of reference cells or a subpopulation of the plurality of reference cells and/or a test diversity comprising a test heterogeneity of the plurality of test cells or a subpopulation of the plurality of test cells. The reference heterogeneity can comprise (i) an entropy of one, at least one, or each, of the plurality of reference Gaussian mixtures and/or associated reference weights and/or (ii) a reference covariance matrix of one, at least one, or each, the plurality of reference Gaussian mixtures, and/or the test heterogeneity can comprise (i) an entropy of one, at least one, or each, of the plurality of test Gaussian mixtures and/or associated test weights and/or (ii) a test covariance matrix of one, at least one, or each, the plurality of test Gaussian mixtures.

In some embodiments, the computing system can: determine a gene is upregulated or downregulated in a subpopulation of the plurality of test cells relative to a subpopulation of the plurality of reference cells. To determine the gene is upregulated or downregulated, the computing system can determine the gene is upregulated or downregulated in a subpopulation of the plurality of test cells relative to a subpopulation of the plurality of reference cells using a L1 distance between a test distribution of the single cell gene expression profiles of the gene in the subpopulation of the plurality of test cells and a reference distribution of the single cell gene expression profiles of the gene in the subpopulation of the plurality of reference cells.

In some embodiments, a run time of the hardware processor increases linearly or non-exponentially as a number of the plurality of reference gene expression vectors and/or the plurality of test gene expression vectors increases. The method 700 ends at block 732.

Execution Environment

Figure 8:
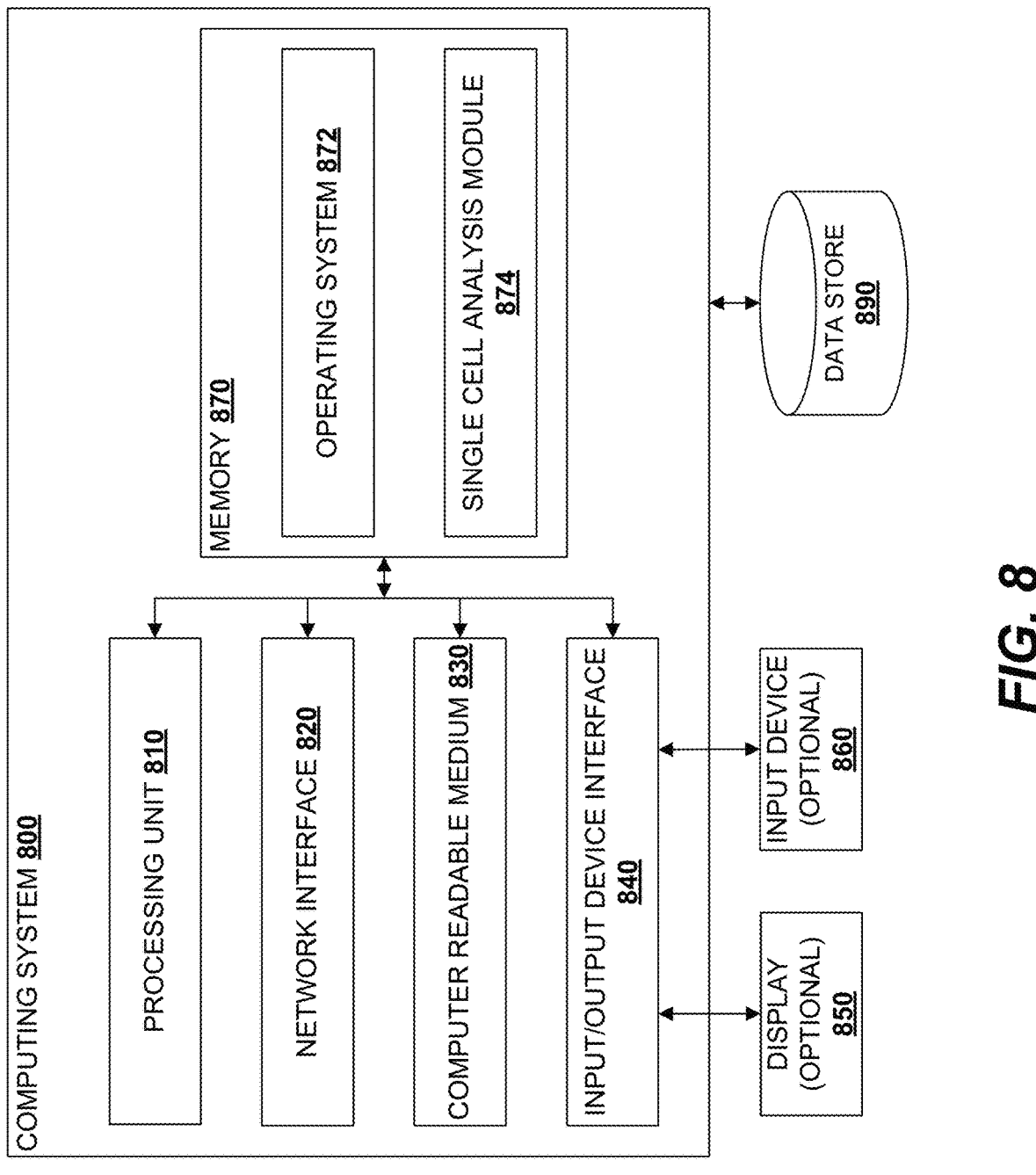
FIG. 8 is a block diagram of an illustrative computing system configured to implement single cell analysis.

In FIG. 8 depicts a general architecture of an example computing device 800 configured to implement the metabolite, annotation and gene integration system disclosed herein. The general architecture of the computing device 800 depicted in FIG. 8 includes an arrangement of computer hardware and software components. The computing device 800 may include many more (or fewer) elements than those shown in FIG. 8. It is not necessary, however, that all of these generally conventional elements be shown in order to provide an enabling disclosure. As illustrated, the computing device 800 includes a processing unit 810, a network interface 820, a computer readable medium drive 830, an input/output device interface 840, a display 850, and an input device 860, all of which may communicate with one another by way of a communication bus. The network interface 820 may provide connectivity to one or more networks or computing systems. The processing unit 810 may thus receive information and instructions from other computing systems or services via a network. The processing unit 810 may also communicate to and from memory 870 and further provide output information for an optional display 850 via the input/output device interface 840. The input/output device interface 840 may also accept input from the optional input device 860, such as a keyboard, mouse, digital pen, microphone, touch screen, gesture recognition system, voice recognition system, gamepad, accelerometer, gyroscope, or other input device.

The memory 870 may contain computer program instructions (grouped as modules or components in some embodiments) that the processing unit 810 executes in order to implement one or more embodiments. The memory 870 generally includes RAM, ROM and/or other persistent, auxiliary or non-transitory computer-readable media. The memory 870 may store an operating system 872 that provides computer program instructions for use by the processing unit 810 in the general administration and operation of the computing device 800. The memory 870 may further include computer program instructions and other information for implementing aspects of the present disclosure.

For example, in one embodiment, the memory 870 includes a single cell analysis module 874 for analyzing single cell data, such as the single cell analysis method 700 described with reference to FIG. 7, and embodiments LOW-MIX or PopAlign.

EXAMPLES

Some aspects of the embodiments discussed above are disclosed in further detail in the following examples, which are not in any way intended to limit the scope of the present disclosure.

Example 1

Low-Dimensional Probabilistic Models Classify Disease State from Single-Cell Data Human diseases including cancer and neurodegeneration are increasingly viewed as population level phenomena involving a range of different cell types (for example both immune and non-immune cells) that drive disease progression. Single cell transcriptional profiling methods have scaled to the point that thousands of single cells can be profiled at the genome wide scale in a single experiment. Thus, single cell measurements can be used to probe and diagnose human disease by examining the full distribution of gene expression states that exist in a tissue across a range of healthy and diseased conditions.

Single cell measurement techniques can now profile gene expression in thousands of individual cells within human tissues across physiological states of health and disease. There is an urgent need for developing mathematical frameworks that can classify the disease "state" of a heterogeneous tissue or cell population based upon a set of single cell transcriptional profiles to enable clinical treatment and diagnostic applications that determine the disease state and stage of tissues including human tumors using single cell data given the data scale and heterogeneity. Each single cell in a tissue can express thousands of different genes, and tissues are composed of heterogeneous populations of many single cells. Mathematically, a cell population is a distribution in the high dimensional space of cellular gene expression, and new methods are required to construct models of gene expression distributions and to apply these models for population level classification tasks like disease classification. Therefore, single cell disease characterization and classification require new computational methods that can model the underlying heterogeneity of cell states within a tissue, and perform statistical tasks like classification on cell populations.

A mathematical framework, LOWMIX, is described herein for performing "cell population" classification tasks using probabilistic models. LOWMIX can be used for inferring statistical models of gene expression distributions within a cell population. LOWMIX can be applied to perform disease classification from single cell mRNA-seq data. LOWMIX can overcome the mathematical challenges associated with high-dimensionality by building probabilistic models over a gene expression vectors rather than single genes. Gaussian Mixtures (GMMs) were used to model the resulting distribution of cellular states within the lower dimensional feature space, and found to provide an effective and semantically meaningful class of functions for modeling a heterogeneous cell populations. Latent structure in data was used to embed cell populations within a low dimensional space where probabilistic models were efficiently constructed using reference cell populations (health, disease) and then models were applied to classify new populations against these labels. The method was applied to a series of cell populations classification tests including tissue type identification and disease state classification for Acute Myeloid Leukemia (AML) and HIV. The low dimensional probabilistic modeling framework provides a general computational platform for classifying and diagnosing human disease across tissues and disease states using high throughput single cell data.

LOWMIX provides a new capability in single cell analysis. Standard methods for mRNA-seq data analysis including geometrical methods like tSNE that embedded data points within a low dimensional space but do not naturally function as statistical models and do not provide a formal statistical for estimating the probability that a single cell came from a healthy or diseased cell population. Machine learning methods, including deep neural networks, can build generative models and can function as classifiers, but neural nets have an architecture and semantics which lacks directly interpretable biology meaning. Further, neural networks methods have very large data requirements that currently make application to patient data difficult.

As described in this example, LOWMIX was applied to a series of example tasks: disease state classification in two human disease and cell population demixing task. The method was shown to have high accuracy and generalize across samples, and allow a procedure for extracting a minimal set of genes for use in disease classification. LOW-MIX can enable a wide range of population classification applications.

Mathematical Framework Summary

A framework, referred to herein as LOWMIX, was developed for building a probabilistic model of the gene expression distribution generated by a heterogeneous population of single cells (FIGS. 9A-9B). The probabilistic models were used to perform population-state classification tasks. The method has two main steps: (1) To overcome challenges associated with the high dimensional nature of gene expression data, cells were represented as a linear combination of gene expression basis vectors (i.e., gene expression features) that were extracted from training data; and (2) Following projection of single cell data into a lower dimensional feature space, the cell populations were modeled as a mixture of Gaussian densities in this space (FIG. 9A). Gaussian mixture models were trained on cell populations in health and disease and, then, applied to new data to classify the physiological state of new samples (FIG. 9B).

Mathematical Formulation

The transcriptional state of a single cell was represented as an n dimensional vector, $g=(g_1, g_2, \ldots, g_n)$, where $g_i$ is the abundance of mRNA species i in a single cell, and n is the number of total mRNA species encoded in the genome. While raw mRNA-seq measurements generate integer valued gene count data, due to measurement noise and data normalization, g was considered to be embedded in an n dimensional Euclidean vector space, gene expression space, $g \in \mathbb{R}^n$. For the human genome n~20,000. The high dimensional nature of gene expression space poses a key challenge for construction and interpretation of statistical models.

Mathematically, a cell population is a set of gene expression vectors. $S=\{g_k\}$, where the index k indexes single cells. The gene expression vectors, $g_k$, can be considered as being distributed according to an underlying probability density function, P(g), that quantifies the probability of observing a particular joint gene expression state, $g=(g_1, g_2, \ldots, g_n)$, in a given cell population. P(g) the gene expression distribution, was generated by the underlying cell population.

One objective was to estimate a statistical model of P(g). based upon independent and identically distributed single cell measurements. To construct a statistical model, a standard statistical technique, maximum likelihood estimation. was used to estimate the parameters of a Gaussian Mixture model. Probabilistic models were constructed across a series of cell populations (e.g. P(g|health) and P(g|disease)). and then statistical measures were applied to classify cells from a new sample according to these models.

Dimensionality Reduction: Single Cells as Linear Combinations of Gene Features

A present mathematical challenge is model estimation in the high dimensional nature of gene expression space. Raw gene expression space was of order n~20,000 dimension. Data requirements scale exponentially with the size of the embedding space, and current measurements methods can probe thousands of single cells per experiment.

FIGS. 9A-9D: Probabilistic modeling framework. FIG. 9A: Single-cell mRNA-seq data collected from a cell population. Each data point represents a single cell embedded in an n dimensional gene expression space. In the framework described herein, high dimensional data are, first, projected into an m dimensional gene feature space, and, second, a Gaussian mixture model is estimated in this space. The mixture model is a probabilistic model of the underlying cell population. FIG. 9B: Models were constructed from cell populations drawn from healthy and diseased patient samples, and then models were applied to classify new cell populations from naive patients as healthy or diseased. FIG. 9C: Plots show PCA projections of model generated (pink) and experimental data (black) for Healthy and AML patient samples. FIG. 9D: Renderings of parameterized low dimensional mixture model for Healthy and AML patient samples.

To construct statistical models, the curse of dimensionality was circumvented by building models in a low-dimensional space defined by gene expression features or programs. Mathematically, the transcriptional state of each single cell, g, was represented as a linear combination of gene expression feature vectors, $w_i$:

$$g = \sum_{i=1}^{m} c_i w_i$$

where $w_i \in \mathbb{R}^n$ specifies a gene expression feature, and $c_i$ is a coefficient that encodes the weighting of vector $w_i$ in g. A cell's gene expression state, g can be represented as a linear combination of m gene expression module vectors, $w_i$ where m<<n. This insight allowed construction of a low dimensional representation of a cell population and, then, to estimate statistical models within the low dimensional space.

A set of gene expression basis vectors, $w_i$ can be determined using a range of matrix factorization techniques. Singular value decomposition (SVD) is a canonical and pedagogical example. To apply SVD to define a basis set of gene expression vectors for classification, a compendium of training data, D sampled uniformly at random was first constructed from the datasets to be classified. Then, SVD provides a factorization of the training data into three matrices:

$$D = W S V^T \tag{1.1}$$

where W is an n×n matrix of gene expression feature vectors, and S $V^T$ is an n×k matrix that contains the coefficients for W across all the cells in the training data.

Feature vectors W was extracted and, then, the first m singular vectors were selected as gene feature vectors for model construction. W can be used to represent a single cell as a linear combination of gene features. The training data D can be sampled from a large dataset, and so cells that have not formally been included in the SVD that generates W can be represented.

Now, any cell's gene expression state, g can be represented as:

$$u = W_m g, \tag{1.2}$$

where $W_m$ contains the m first features in W, and u is the representation of g in gene feature space. A range of techniques was applied to extract gene expression feature vectors including non-negative matrix factorization (NNMF). orthogonal NNMF. and sparse NNMF.

Thus, a cell population, S={g}, was mapped from an n~20,000 dimensional gene expression space into a gene feature space that is often of order 10-20 dimensions:

$$S = \{g_i\} \rightarrow \{\{u_i\},$$

where $\{u_i\}$ are m×1 dimensional vectors that now represent the cell population in the reduced gene feature space.

Representing a Cell Population as a Gaussian Mixture Modeling in Gene Feature Space Following the feature based representation, a statistical model of the cell population within the reduced space was constructed. A probability distribution in gene expression space was exchanged for or transformed into a probability distribution in gene feature space:

$$P(g) \rightarrow P(u), \tag{1.3}$$

and a statistical model of P(u) was estimated.

As the second main step in cell population classification, the cell population was represented as a mixture of Gaussian densities. Thus, for a given cell population d, the following was constructed:

$$\widehat{P(\mathbf{u})} = \sum_{i=1}^{l} \pi_i \mathcal{N}(u; \mu_i, \Sigma_i) \tag{1.4}$$

where $\widehat{P(\mathbf{u})}$ encodes the gene expression distribution of a given cell population as a mixture of Gaussian densities, $\mathcal{N}$ (c; $\mu_i$, $\Sigma_i$), with centroid, p; covariance matrix, $\Sigma_i$; and scalar weighting $\pi_i$. l is the number of Gaussian mixtures or components in the statistical model.

The Gaussian mixture model (GMM) represents a cell populations as a mixture of individual Gaussian densities. Biologically, each density can be considered as parameterizing a sub-population of cells. The GMM provide a natural set of basis functions for modeling a cell population as a collection of densities (cell-states) in gene expression space.

To construct a Gaussian Mixture model from data, the parameters $\mu_i$, $\Sigma_i$, and $w_i$ were estimated based upon training data, using maximum likelihood estimation with likelihood function:

$$\mathcal{L}(\mu_i, \Sigma_i, \pi_i | S') = \sum_{i=1}^{k} \log P(u_i; \{\mu_i, \Sigma_i, w_i\}), \qquad (1.5)$$

where $u_i$ are single cell profiles drawn from S', and k is the number of single cells in the cell population S'. This function can be maximized approximately using expectation maximization. Practically, there are two issues in the fitting of the Gaussian mixture model. First, a number of mixtures needs to be selected to use in the model construction. The Bayesian information criteria (BIC) which is a statistical measure that balances model accuracy with model complexity was used. Second, the number of dimensions needs to be selected in the projection. The number of SVD dimensions was selected to maximize classification accuracy on the training data for tasks of interest.

Applications of Mixture Models to Population Classification Tasks

Given an estimated probabilistic model, a range of statistical tasks was performed. Statistical models was estimated from a series of labeled cell populations, $S_{health}$ and $S_{disease}$ to yield $P(u|health)$ and $P(u|disease)$.

Given these probabilistic models, the probability that a set of single cell, $u_i$, came from $S_{health}$ or $S_{disease}$ was estimated as:

$$R = \sum_{i=1}^{k} \log \frac{P(u_i | \text{Disease})}{P(u_i | \text{Health})} \qquad (1.6)$$

Given a set of q classes, the class that maximizes the below was determined:

$$\text{argmax}_{Class} = \sum_{i=1}^{k} \log P(u | \text{class}), \qquad (1.7)$$

Equations (1.1-1.4) provide a generalized procedure for constructing a statistical a model of a cell population from single cell mRNA-seq data. The procedure has four steps: (a) Build a dictionary of gene expression features from training data with (b) Represent cells in an analysis data set within this basis set, (c) Parameterize a Gaussian Mixture model of the analysis population within the feature space, and (d) Perform classification based analysis using models of samples in health and disease.

LOWMIX was implemented within a Python based software package that can run in a cloud computing environment.

Applications

The LOWMIX modeling framework was applied to two different human disease state classification tasks: Acute Myeloid Leukemia (AML) and HIV detection. High performance of the method was demonstrated on both tasks, showing that low dimensional probabilistic models can discriminate populations of cells based upon class labels.

Detection of Acute Myeloid Leukemia from Single Cell Profiles of Bone Marrow Derived Cells.

AML is a myeloid cell cancer that is resident in the bone marrow of patients. A recent public study profiled thousands of single cells from bone marrow across 6 patient samples The data sets comprise bone marrow derived mononucleated cells (BDMCs) for 2 healthy. 2 AML patients pre-treatment, and 2 post treatment.

The LOWMIX software platform was first applied to construct probabilistic models of a reference healthy and reference AML patient (FIGS. 9C-9D). Cells across all samples were pooled to define an m=6 dimensional feature space with SVD, and Gaussian mixture models were constructed on the individual cell populations from the healthy and AML patient sample. Renderings of the mixture models for healthy and AML are shown in the figure. Synthetic data generated from the model has good qualitative agreement with model generated data (FIG. 9C).

The probabilistic models were then applied to classify single cells from held out healthy and AML test samples. Sampling 10 cells from each held out patient (FIG. 10A), the models classified healthy as well as AML samples (pre and post treatment) with ≥80% accuracy. With 100 single cells, models performed with 100% accuracy across 100 random trials. These results show that low dimensional probabilistic models can function as highly accurate disease classifiers.

Classification of Patients as HIV or Healthy Using Peripheral Blood Cells.

To demonstrate the generality of the framework, the method was extended to a set of new patient samples collected. The samples consist of single peripheral blood cells profiled from healthy and HIV positive patients.

Figures 10A, 10B, 10C, 10D:
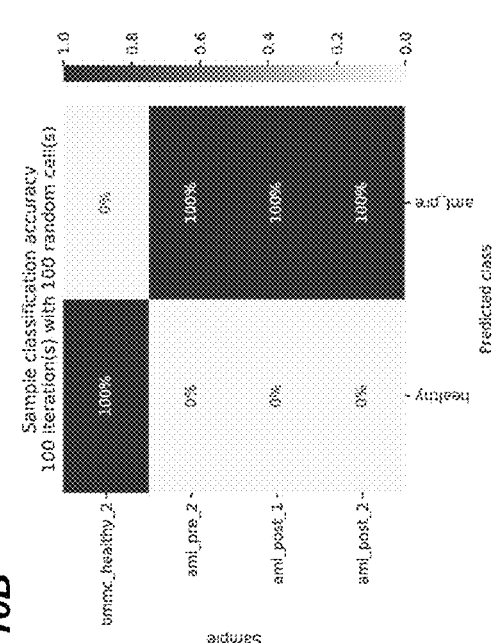
FIGS. 10A-10D illustrate single cell detection of human disease states with low dimensional mixture models.

As in AML, LOWMIX was applied to construct and render mixture models. Mixture model renderings are shown in FIG. 10C for both reference and test samples. The renderings show qualitative similarity between the Healthy (WT) and disease (HIV) cell populations. In the case of HIV, the classifier performs with 100% accuracy in classifying a patient sample as HIV with only 10 cells.

Using Models to Detect Tissue of Origin in Cell Mixtures.

Beyond disease classification, probabilistic models can be applied for a wide range of diagnostic tasks. In cancer diagnosis, a common challenge is determining the organ of origin for tumor cells detected within the peripheral blood or within a metastatic site in the body. The probabilistic models described herein have been demonstrated for their applicability to perform organ of origin classification within a mixed cell population.

FIGS. 10A-10D: Single cell detection of human disease states with low dimensional mixture models. FIG. 10A: Classification of healthy, AML, and post-treatment AML single cell samples with healthy and AML probabilistic models using a single cell. FIG. 10B: Classification accuracy using 100 single cells. FIG. 10C: Reference and test models generated using HIV patient data. FIG. 10D: Classification of HIV samples using 100 randomly sampled cells.

Figures 11A, 11B, 11C, 11D:
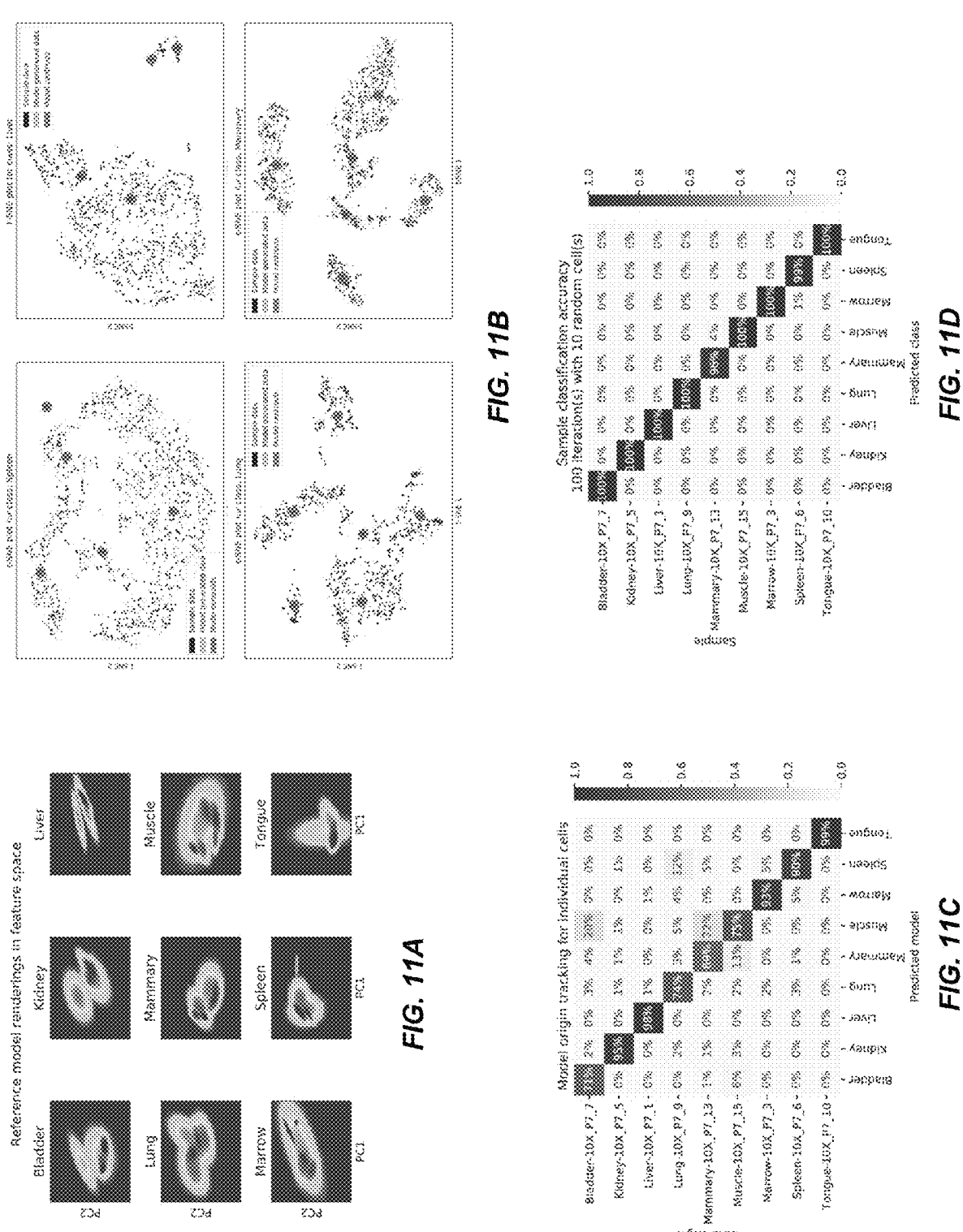
FIGS. 11A-11D illustrate tissue of origin classification from single cell mRNA-seq data.

FIGS. 11A-11D: Tissue of origin classification from single cell mRNA-seq data. FIG. 11A: Renderings of probabilistic GMM model for 9 tissues in the Tabula Muris data set. FIG. 11B: tSNE plot of experimental and model generated data for Spleen, Lung, Liver, and Mammary tissues showing accuracy of model generated data. FIG. 11C: Classification accuracy for single cells from held out test samples in reference models. FIG. 11D: Classification accuracy for groups of 10 cells drawn at random from test samples.

To show a proof of principle for this application, a public data set that profiled cell populations from 9 tissues using high throughput single cell profiling (FIGS. 11A-11B) was used. Models had high accuracy across all studied tissues.

Next, the LOWMIX framework was applied to build probabilistic models of each tissue in the data set and showed that single cells from unseen reference samples can be classified with high-accuracy. Using the reference models, classification of single cells sampled from each of the 9 test tissues was performed. Cells were sampled uniformly at random from each data set. Single cell and cell population accuracy is shown in the table in FIG. 11C. At the single cell level, the models classified single cells sampled from the test samples with accuracy ranging from 99% to 69% on a cell by cell level (FIG. 11C). For single cells, less than 100% accuracy was expected because tissues share common cell populations, for example, immune cell populations like T-cell, B-cells, and macrophages are found across different tissue types. FIG. 11D shows that classification accuracy improves to nearly 100% across tissues when classification is performed on 10 single cells.

Figures 12A, 12B, 12C, 12D:
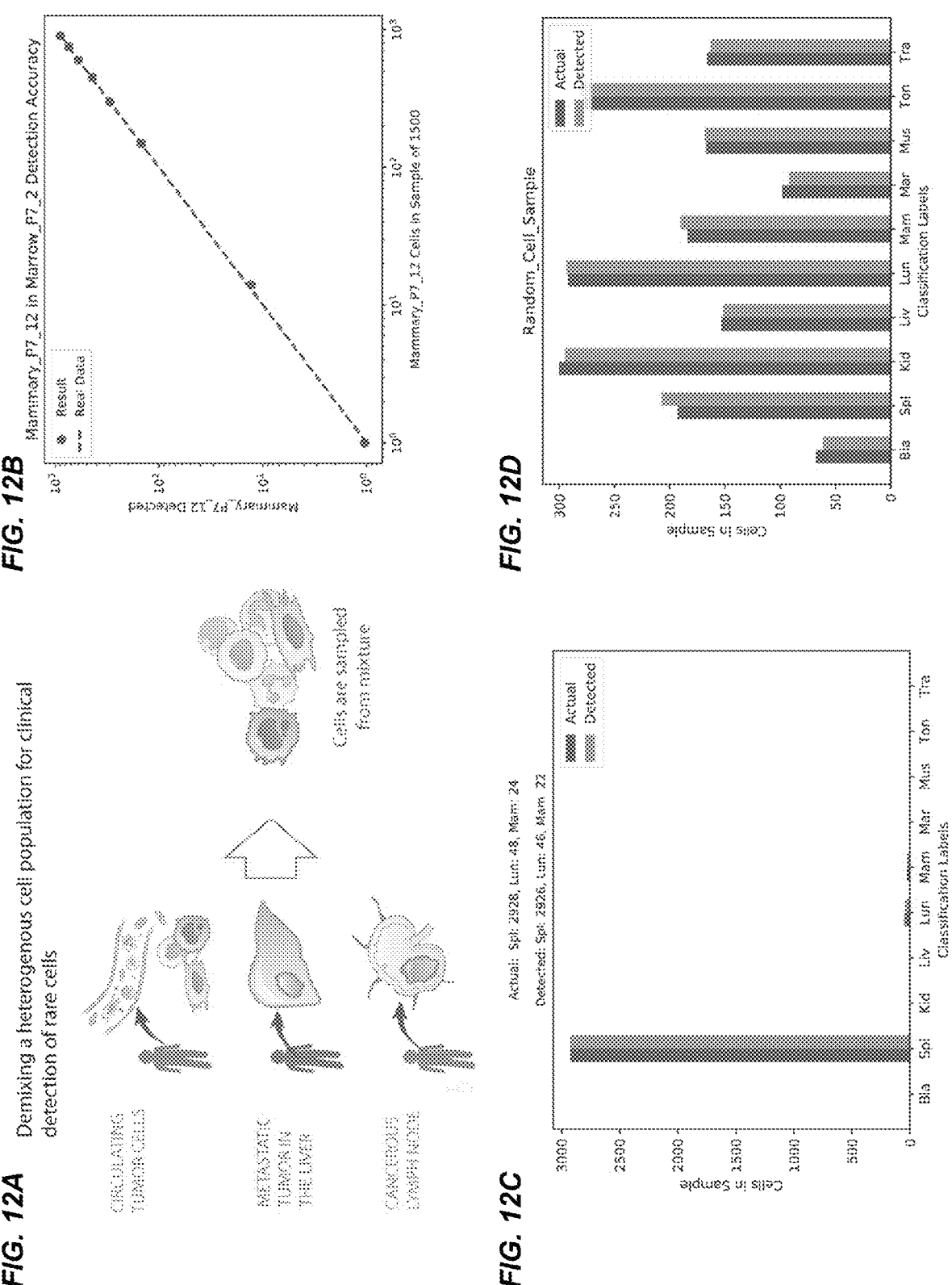
FIGS. 12A-12D illustrate classifying mixtures of single cells by organ of origin with LOWMIX.

Using the probabilistic models, a linear demixing strategy for determining the composition of a mixed cell mixture was developed. The models can be used to solve a set of related problems in cancer detection (FIG. 12A). For example, the detection of cancer cells within circulating blood cells or the classification of foreign cells within a metastatic site can both be addressed through single cell mixture dissection.

Linear demixing was performed because at the single cell level, the probabilistic models classified cells from each of the 9 tissues with the accuracy rates show in FIG. 11C. This classification matrix can be used to design a demixing strategy in the following way.

A mixture of cells drawn independently from the 9 tissues was considered in the data set. A 9×1 vector, N, was defined, where $N_i$ is the number of cells from tissue i in the mixture. Given a mixture, the probabilistic models can be applied to classify each single cell within the mixture. The models, thus, give as an estimate, $\hat{N}$ of the mixture composition. The "true" composition of the cell mixture can be inferred by solving the following linear system of equations and constraints.

$$QN = \hat{N}$$

$$\sum_i N_i = N_{total}$$

$$N_i \geq 0$$

where entries, $Q_{ij}$ in the 9×9 matrix Q encode the probability that a cell from tissue i is classified as tissue j by the classifier. This matrix is shown in FIG. 11C. The constraints ensure that (i) the total number of cells in N is the same as the measured number of cells $N_{total}$ and (ii) that all entries in $N_i$ are greater than or equal to 0. Given Q and $\hat{N}$, these equations can be solved for N using least squares with a positivity constraint.

Solving this linear system of equations on synthetic cell populations enabled solving a series of synthetic tasks designed to simulate various clinical tasks in cancer detection (FIG. 12A). Tumor cells, in cancer, commonly migrate to distant sites in the body including the peripheral blood (circulating tumor cells) as well as metastatic sites including lymph node and liver.

Using the Tabula Muris data, a set of synthetic tasks was designed to mimic these diagnostic applications by mixing cells from different tissues into a mixture. FIG. 12B shows that the LOWMIX strategy described herein can detect as few as a single mammary gland cell within a mixture of 1500 bone marrow cells. FIG. 12C shows detection of 48 lung and 22 mammary cells within a background of almost 3000 spleen cells with an error of ±2 cells in each case. FIG. 12D shows high performance on calling a mixture constructed through i.i.d random draws from the 9 cell types.

FIGS. 12A-12D: Classifying mixtures of single cells by organ of origin with LOWMIX. FIG. 12A: In cancer detection, a common problem is determining the origin of a circulating cancer cell or metastasis. The tissue modeling framework described herein allows classification of single cells by organ of origin. Thus, a small number of foreign cells can be detected within the background of larger cell populations, and the origin of these cells can be predicted using the probabilistic models described herein. FIG. 12B: Plot shows true vs detected number of mammary gland cells within a background of 1500 bone marrow2 cells. FIG. 12C: Detected vs. actual number of cells for a three component demixing tasks. The synthetic cell population has cells from lung, mammary gland, and spleen. FIG. 12D: Demixing of a random sample of cells drawn from the 9 cell-types in the Tabula Muris study.

Together, this example shows that probabilistic models and linear demixing can be applied to separate mixtures of single cells and to label small numbers of cells within a mixture by their organ origin.

Discussion

This example described a newly developed mathematical framework and software package (LOWMIX) for classifying populations of single cells using probabilistic models. LOWMIX allowed representation of single cells within a low dimensional gene feature space. and constructing parametric Gaussian Mixture models within this space. LOWMIX provided a simple but powerful framework for building population level cell classifiers that can be applied for disease studies. Instead of comparing the expression profiles of individual cells, a density function that represents each tissue was inferred and these functions were compare across a series or samples.

As more data is collected across larger cohorts, the modeling framework described herein can allow building probabilistic models across large patient data sets. Such models can be applied to diagnose new patient samples by classifying new samples against the library of models. The framework is computationally efficient and the feature space can be rebuilt continuously as samples are collected. Once a tissue sample is represented within the feature-space and GMM framework, models from a database of samples can be simply and efficiently stored, searched and retrieved.

As shown in AML, iteratively search can be done for the smallest set of genes for classification, which means that the classifier output can be implemented in an experimental format like FISH that does not require genome wide profiling.

Example 2

Probabilistic Models Reveal that Signaling Context Disrupts Drug Responses in a High-Throughput Single-Cell Screen All physiological processes in the body are driven by heterogeneous populations of single cells. The response of a cell population to a new input, whether that is a new environmental condition, a new physiological state or a drug treatment, is mediated by the response of single cells to the input as well as interactions that occur between cells within a community. Single cell measurement technologies can now profile gene expression in thousands of cells from heterogeneous cell populations across different tissues, physiological conditions, and disease states. Single cell data, thus, can enable dissecting how heterogeneous tissues respond to treatments in a cell-type specific manner and understanding of how cellular communities respond to novel physiological states. Insights from the single cell measurements can allow designing of new precision medicines that target specific cell types in the body.

However, converting single-cell data into models that provide a population-level understanding of processes like an immune response to infection or cancer progression remains a fundamental challenge. As single-cell datasets scale to include increasing numbers of patients and experimental samples, new conceptual and mathematical frameworks are required to model and track subpopulations of cells across large numbers of heterogeneous samples. New mathematical and computational methods are needed to represent, analyze and compare heterogeneous mixtures of cells as they respond to signals, drugs, or disease states. This example describes a mathematical modeling platform, PopAlign, for analyzing large-scale single-cell RNA-seq datasets by constructing and comparing probabilistic models which provide a low-error, compressed representation of single cell data that has well-defined statistical metrics. Probabilistic modeling of cell populations provides conceptual and practical advances that enables multi-scale analysis of single cell datasets across samples, subpopulations, and individual cells. Mathematically, PopAlign models the distribution of gene expression states within a heterogeneous cell population, by representing subpopulations of cells as independent Gaussian densities. Probabilistic modeling is enabled by a novel low dimensional representation of cell-state in terms of a set of gene expression features learned from data. For each large-scale dataset, PopAlign learns probabilistic models and uses them to perform a number of fundamental tasks and analyses: (a) classifying and ranking samples based on statistical distance, (b) querying samples against a universal set of reference populations, (c) aligning subpopulation models across experimental conditions, and (d) quantifying changes in cell abundance and gene expression for aligned subpopulations across samples.

These properties enable PopAlign to automatically rank and classify experimental samples, identify and align subpopulations of cells, and track abundance and gene expression changes within subpopulations across experimental conditions. PopAlign can be used to interpret data hierarchically, from samples to tracking quantitative changes within specific subpopulations of cells to comparing the expression level of single genes. PopAlign was applied to analyze the impact of 42 different immunomodulatory compounds on a heterogeneous population of donor-derived human immune cells in both a resting and a T cell-activated (CD3/CD28+) context. It was found that an activated signaling context broadly amplifies immune responses to drugs, and can specifically disrupt the ability of glucocorticoids to generate anti-inflammatory M2c macrophages, which highlights that physiological environment can play a critical role in regulating drug function, while also providing a powerful computational framework for revealing how populations of cells can respond to drugs across a wide range of physiological contexts.

Using probabilistic models to represent single-cell data can provide both a conceptual and practical advance. One key conceptual value of the probabilistic model it is the probabilistic model produces a semantically meaningful, modular representation of a cell population. By modeling the distribution of gene expression states as a mixture of independent probability densities, a formal mathematical definition of a population and its constituent subpopulations was constructed. This mathematical definition can be used to generate new instances of single-cell data, for model validation and prediction. Practically, probabilistic models are powerful because they enable quantitative statistical metrics, such as the divergence between two models, or the likelihood of a model given data. These metrics form the basis for essential tasks such as sample classification and quantifying shifts in abundance or gene expression across samples. Unlike PopAlign, geometric methods based on global cell clustering do not provide a natural language for mathematically representing a subpopulation of cells or statistical metrics for quantifying shifts in population structure across experimental samples.

PopAlign can fulfill a fundamental need for comparative analysis methods that can scale to hundreds of experimental samples, because probabilistic models provide a reduced representation of single-cell data. For a typical 10,000-cell experimental sample, the probabilistic model reduces the memory footprint by 50-100×. Fundamentally, PopAlign runtime scales linearly with the number of samples because computations are performed on probabilistic models rather than on raw single cell data (methods). Further, down-stream computations including population alignment are performed on the models themselves, often reducing the number of computations by an order of magnitude. In contrast methods based on extraction of geometric features (clusters) from single cell data either by clustering (Louvain) or tSNE rely on pairwise computations between individual cells, which is compute-intensive, and requires storing of many raw single cell data sets in memory.

The accuracy and generality of PopAlign were assessed using twelve datasets from a mouse tissue survey (Tabula Muris) as well as new experiments on human peripheral blood cells, including a combinatorial signaling screen and a comparison of healthy patients to disease (multiple myeloma). As shown here, PopAlign can identify and track cell-states across a diverse range of tissues, signaling experiments, and human disease states. The probabilistic models have high representational accuracy and identify biologically meaningful cell-states from data. An experimental screen was performed for 30 unique combinations of immune cytokines applied to primary human immune cells, and the PopAlign procedure was used to dissect the signaling responses at both a sample- and subpopulation-specific level. A signaling hierarchy where CD3/CD28 stimulation was identified as dominant, as well as dose-dependent combinatorial responses. PopAlign was also used to extract general and treatment-specific signatures of disease progression from multiple myeloma patient samples. PopAlign can be used for the analysis of large-scale experimental screens of drugs and genetic perturbations on heterogeneous cell populations extracted from primary human tissue samples.

In this example, applications of the PopAlign method to data sets from mouse tissues and primary human cells demonstrates accuracy of models and ability to track cell-state specific gene expression changes in response to signals and disease states.

Results

PopAlign Represents Heterogeneous Cell Populations with Probabilistic Mixture Models PopAlign (i) identified and aligns cell-states across paired populations of single cells (a reference population and a test population), and then (ii) quantified shifts in cell-state abundance and gene expression between aligned populations (FIGS. 13A-13D). The method has three main steps: probabilistic mixture model construction, model alignment, and parameter analysis. PopAlign can be applied to analyze gene expression and population structure changes in heterogeneous populations of cells as they respond to signals, drugs, and disease conditions.

PopAlign provides a scalable method for deconstructing quantitative changes in population structure including cell-state abundance and gene expression across many single cell experimental samples. FIG. 13A: Users input PopAlign single-cell gene expression data from a "Reference" sample, and at least one "Test" sample, which are each a collection of n-dimensional gene expression vectors g, shown as single dots. FIG. 13B: For each sample, PopAlign estimates a low-dimensional probabilistic model that represents the distribution of gene expression states as a mixture of local Gaussian densities $\phi_i$ with parameters encoding subpopulation abundance ($w_i$), mean gene expression state ($\mu_i$), and population spread ($\Sigma_i$). PopAlign reduces the dimensionality of the input data by representing each gene expression vector as set of m gene expression features (m=10-20), thus representing each cell as an m-dimensional vector of coefficients c. FIG. 13C: Each $$\phi_i^{test}$$

in the test population is aligned to the closest $$\phi_i^{ref}$$

in the Reference sample by minimizing Jeffrey's divergence. FIG. 13D: Following alignment, the parameters of aligned subpopulation pairs are compared to identify subpopulation-specific shifts in cellular abundance $\Delta w$, shifts in mean gene expression state $\Delta \mu$ and shifts in subpopulation shape $\Delta \Sigma$.

Two populations of cells, a test and a reference population, ($D^{test}$ and $D^{ref}$), that were profiled with single cell mRNA-seq were considered (FIG. 13A). Profiling of each population generates a set of gene expression vectors, e.g.

$$D^{Test} = \{g_i\}_{i=1}^{k}$$

where $g=(g_1, g_2, \ldots, g_n)$, is an n dimensional gene expression vector that quantifies the abundance of each mRNA species in single cell g and k is the number of profiled single cells.

To compare the reference and test cell populations, a probabilistic model of the gene expression distribution was first constructed for each set of cells (FIG. 13B). The high dimensional nature of gene expression (n~20,000) space makes the inference and interpretation of probabilistic models challenging. Therefore, each cell was represented, not as a vector of genes, but as a vector of gene expression programs or gene expression features that are extracted from the data, so that each single cell is represented as a vector $c=(c_1, C_2 \ldots c_m)$ of m feature coefficients, $c_i$, which weight the magnitude of gene expression programs in a given cell (See Methods—Extraction of gene feature vectors using matrix factorization). These gene features were extracted using a particular matrix factorization method called orthogonal non-negative matrix factorization (oNMF) that produces a useful set of features because all vectors are positive and composed of largely non-overlapping genes (See FIGS. 19B and 19G). This allows consideration of a cell's transcriptional state as a linear sum of different positive gene expression programs.

Following dimensionality reduction, for a given cell population, cell states are considered as being sampled from an underlying joint probability distribution over this feature space, P(c), that specifies the probability of observing a specific combination of gene expression features/programs, c, in the cell population. A probabilistic model, $P^{test}(c)$ and $P^{ref}(c)$, was estimated for the reference and test cell populations that intrinsically factors each population into a set of distinct subpopulations each represented by a Gaussian probability density (density depicted as individual "clouds" in FIG. 13B):

$$P(c) = \sum_{i=1}^{l} w_i \phi_i(c) \qquad (2.1)$$
$$\text{where } \phi_i(c) = \mathcal{N}(c; \mu_i, \Sigma_i),$$

where $\mathcal{N}(c; \mu_i, \Sigma_i)$ are multivariate normal distributions with weight $w_i$; centroids $\mu_i$ and covariance matrices $\Sigma_i$. The distributions $$\phi_i^{test}(c) = \mathcal{N}(c; \mu_i, \Sigma_i),$$

mixture components, represent individual subpopulations of cells; l is the number of Gaussian densities in the model. The parameters of the mixture model ($\{\mu_i, \Sigma_i, w_i\}$) from single cell data was estimated using the expectation-maximization algorithm with an additional step to merge redundant mixture components to compensate for fitting instabilities (See Methods—Merging of redundant mixture components).

The parameters associated with each Gaussian density, ($\mu_i, \Sigma_i, w_i$), have a natural correspondence to the biological structure and semantics of a cellular subpopulation. The relative abundance of each subpopulation corresponds to the weight $w_i \in [0,1]$; the average cell gene expression state of each subpopulation corresponds to the (m dimensional) Gaussian centroid vector $\mu_i$, and the shape or spread of the subpopulation is captured by the covariance matrix $\Sigma_i$. Intuitively, the local Gaussian densities provide a natural "language" for comparisons between samples. Each Gaussian is a region of high density in gene feature space. Cell populations were compared by asking how the density of cells shifts across experimental conditions.

Statistical Alignment of Cellular Subpopulations Between Samples

To compare the test and reference models, each mixture component in the test population model, $$\phi_i^{test}(c) \in \{\phi_i^{test}(c)\},$$

was aligned to a mixture component, $$\{\phi_i^{ref}(c)\},$$

in the reference population model (FIG. 13C). Alignment was performed by finding the "closest" reference mixture component in gene feature space. Mathematically, to define closeness, Jeffrey's divergence, a statistical metric of similarity on probability distributions was used. Jeffrey's divergence was chosen in this embodiment over other metrics because Jeffrey's divergence is symmetric while also having a convenient parametric form (see Methods).

Specifically, for each $$\phi_i^{test} \in \{\phi_i^{test}(c)\}, \text{ an } \phi_j^{ref} \in \{\phi_j(c)\}^{ref},$$

the closest mixture in the reference set was found:

$$\underset{\phi_j^{ref}(c) \in \{\phi_j^{ref}(c)\}}{\text{argmin}} D_{JD}\big(\phi_i^{test}(c) \parallel \phi_j^{ref}(c)\big), \qquad (2.2)$$

where the minimization is performed over each $$\{\phi_i^{ref}(c)\}$$

in the set of reference mixtures, and $D_{JD}$ is the Jeffrey's divergence. Intuitively, for each test mixture, the reference mixture $\phi_j$ was found to be closest in terms of position and shape in feature space. For each alignment, an explicit p-value was then calculated from an empirical null distribution $P(D_{JD})$ that estimates the probability of observing a given value of $D_{JD}$ in an empirical data set of all subpopulation pairs within a single cell tissue database (See Methods—Scoring alignments).

Tracking Cell-State Shifts Through Mixture Model Parameters

Following mixture alignment, quantitative differences in mixture parameters were analyzed between the reference and test models to track shifts in gene expression state, gene expression covariance, and cellular abundances across the identified subpopulations of cells (FIG. 13D). Mathematically, for each aligned mixture pair, $$(\phi_i^{test}, \phi_j^{ref})$$

with parameters $$\{\mu_i^{ref}, \Sigma_i^{ref}, w_i^{ref}\}$$

and $$\{\mu_j^{test}, \Sigma_j^{test}, w_j^{test}\},$$

the following were calculated:

$$\Delta\mu_i = \left\| \mu_i^{ref} - \mu_j^{test} \right\|_2, \qquad (2.3)$$

$$\Delta\Sigma_i = D_C\big(\Sigma_i^{ref}, \Sigma_j^{test}\big), \text{ and} \qquad (2.4)$$

$$\Delta w_i = \left| w_i^{ref} - w_j^{test} \right|, \qquad (2.5)$$

where $\Delta\mu_i$ measures shifts in mean gene expression; $\Delta w_i$ quantifies shifts in cell-state abundance; $\Delta\Sigma_i$ quantifies shifts in the shape of each mixture including rotations and changes in gene expression variance (see Methods). These shifts in parameters were calculated for all mixture pairs to assess the impact of signaling conditions or environmental changes on the underlying cell population.

PopAlign Identifies and Aligns Cell-States Across Disparate Mouse Tissues

To test the accuracy and generality of PopAlign, probabilistic models were first constructed and aligned across a wide range of mouse tissues from a recent public study (Tabula Muris). The Tabula Muris study contains single cell data collected from 12 different tissue samples with ~40,000 cells total.

Figures 14A, 14B, 14C:
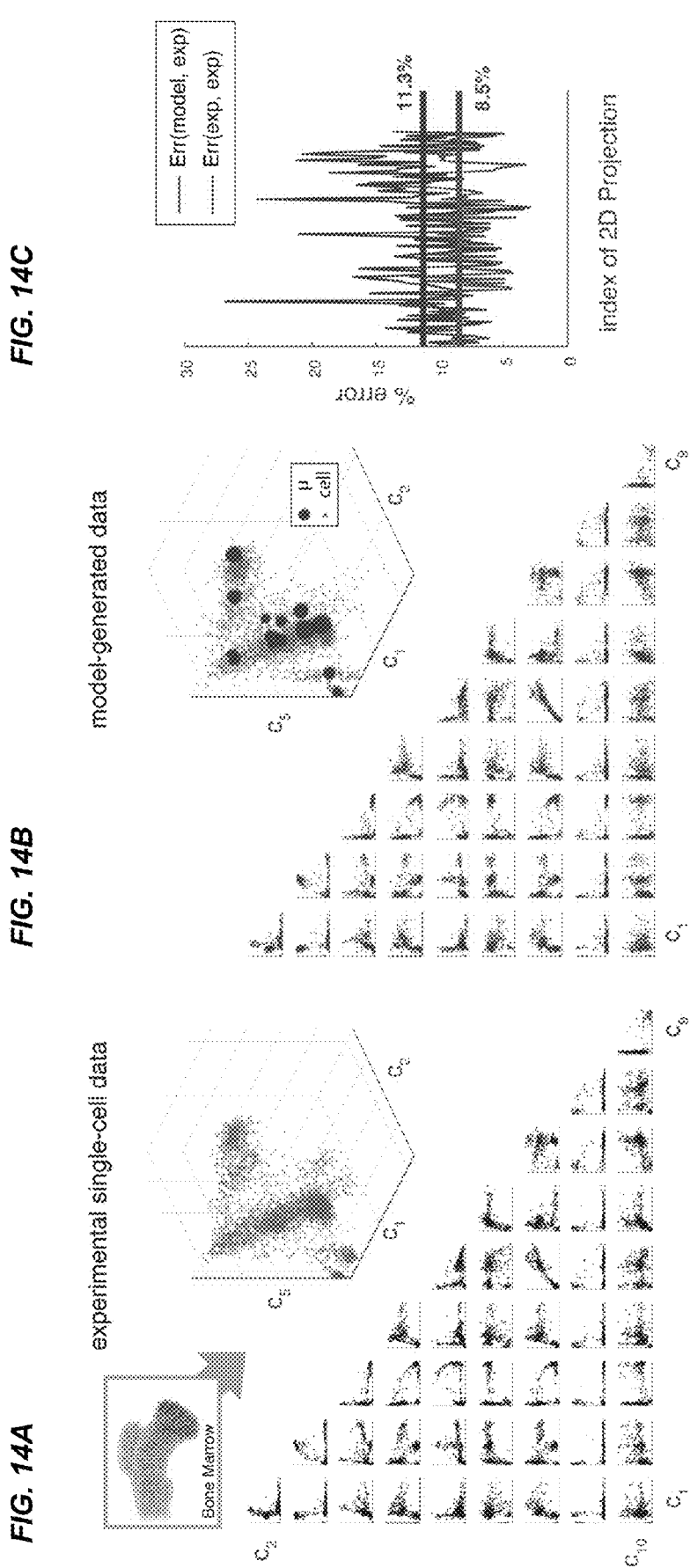
FIGS. 14A-14C: PopAlign models represent experimental data with high qualitative and quantitative accuracy.
Figures 15A, 15B, 15C, 15D, 15E, 15F, 15G, 15H:
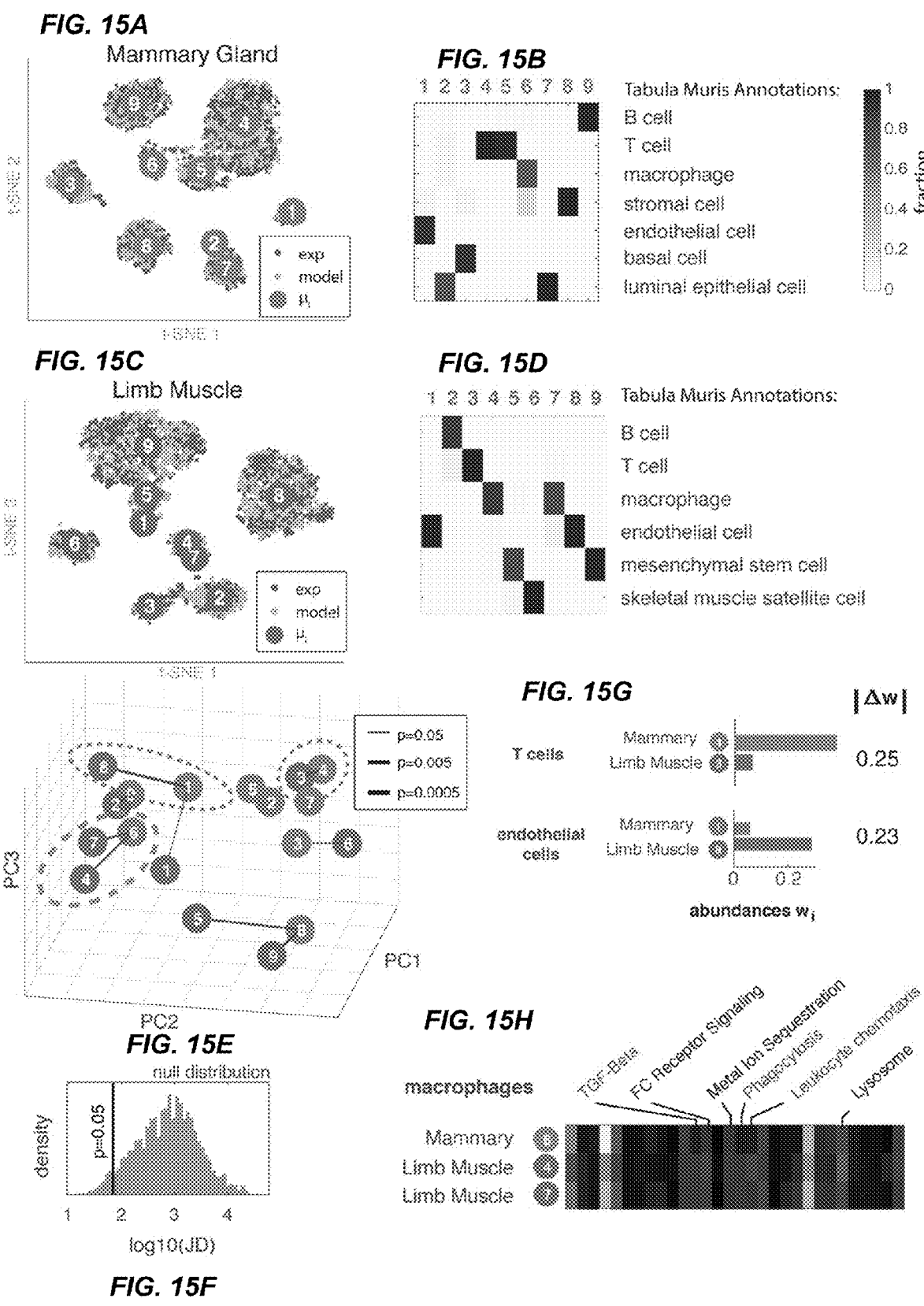
FIGS. 15A-15H: Probabilistic models identify, align, and dissect cellular subpopulations across disparate tissues. Experimental single-cell data (black) for two tissues, mammary gland (FIG. 15A) and limb muscle (FIG. 15B), are plotted together with PopAlign model-generated data (teal) using a 2D t-SNE transformation. Both experimental datasets contain ~3600 cells. For each tissue, mixture model centroids ($\mu$) are indicated as numbered disks.

For all tissues analyzed, the probabilistic mixture models produced an accurate and interpretable decomposition of the underlying cell states (FIGS. 21A-21L). Accuracy of the models can be assessed by comparing the synthetic (model generated) data to raw experimental data held out from model training. PopAlign models generated synthetic data that replicated the geometric structures and statistical variations found in the tissue data in tSNE or PCA plots with quantitative error of ~12% (See methods; FIG. 14A-14C; FIGS. 15A-15B; Tissues in FIGS. 21A-21L; see methods).

PopAlign models represent experimental data with high qualitative and quantitative accuracy. FIG. 14A: Experimental data for ~3600 bone marrow cells projected into an m=15 dimensional gene feature space. 2D plots show single cells projected along gene feature pairs ($c_i$, $c_j$), and a single selected 3D projection (inset) is shown. Blue axis denote shared axis between 2D and 3D plot. FIG. 14B: Model generated data for the same 2D and 3D feature space projections shown in FIG. 14A. In the 3D projection (inset), each larger circle denotes the centroid ($\mu$) of a Gaussian mixture component where the circle radius is proportional to $w_i$, the mixture weight. In all cases, the model generated data replicates the qualitative geometric structures in the experimental data. FIG. 14C: Model error across 2D projections from FIG. 14A and FIG. 14B quantified by analyzing percent deviation in point density for experimental vs model generated data. Quantification of error is performed using a numerical error metric based on binning the 2D projections (See Methods—Analysis of model error). The quantitative error in model-generated is on average 11.3% (red line) compared with 8.5% error when comparing random subsamples of experimental data (blue line).

In addition to providing an accurate representation, the mixture models decomposed the cell populations into a biologically interpretable set of cellular subpopulations represented by individual $\phi_i(c)$, the mixture components (FIGS. 15C-15D). The PopAlign mixture components, $\{\phi_i(c)\}$ commonly contained cells of a single cell "type" as defined by labels supplied by the Tabula Muris project. In example tissues, PopAlign extracted known tissue resident cell-types including (FIGS. 15C-15D) basal cells, luminal cells, macrophages, and T-cells (in mammary gland) and skeletal muscle cells, mesenchymal stem cells, endothelial cells, and macrophages (in limb muscle). Broadly, across all tissue models, 70% of the mixture components classified for a single cell-type provided by Tabula Muris (FIGS. 21A-21L).

Figure 22:
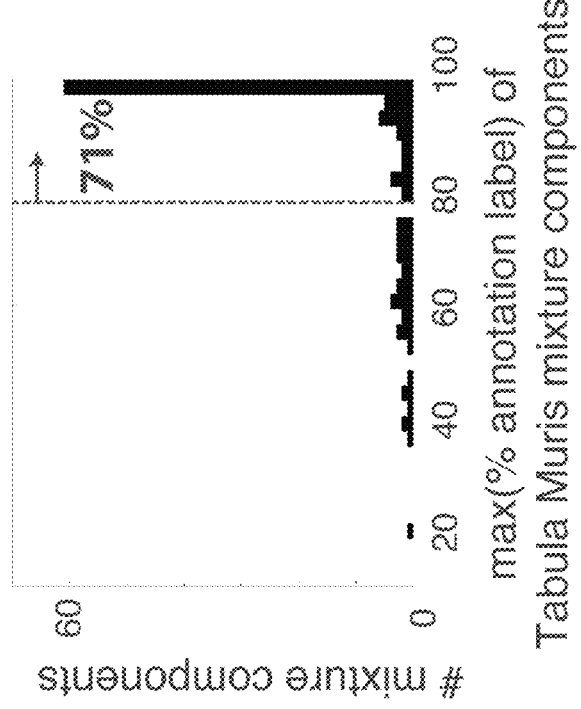
FIG. 22. Mixture components across Tabula Muris tissues are highly specific for single cell type Histogram of each mixture component's highest score for an annotated label. These highest scores as taken as the max of each column in FIGS. 15C and 15D and analogous cell annotation heatmaps for all tissues in FIGS. 15A-15H. Most mixture components score for a single annotated label uniquely.
Figure 23:
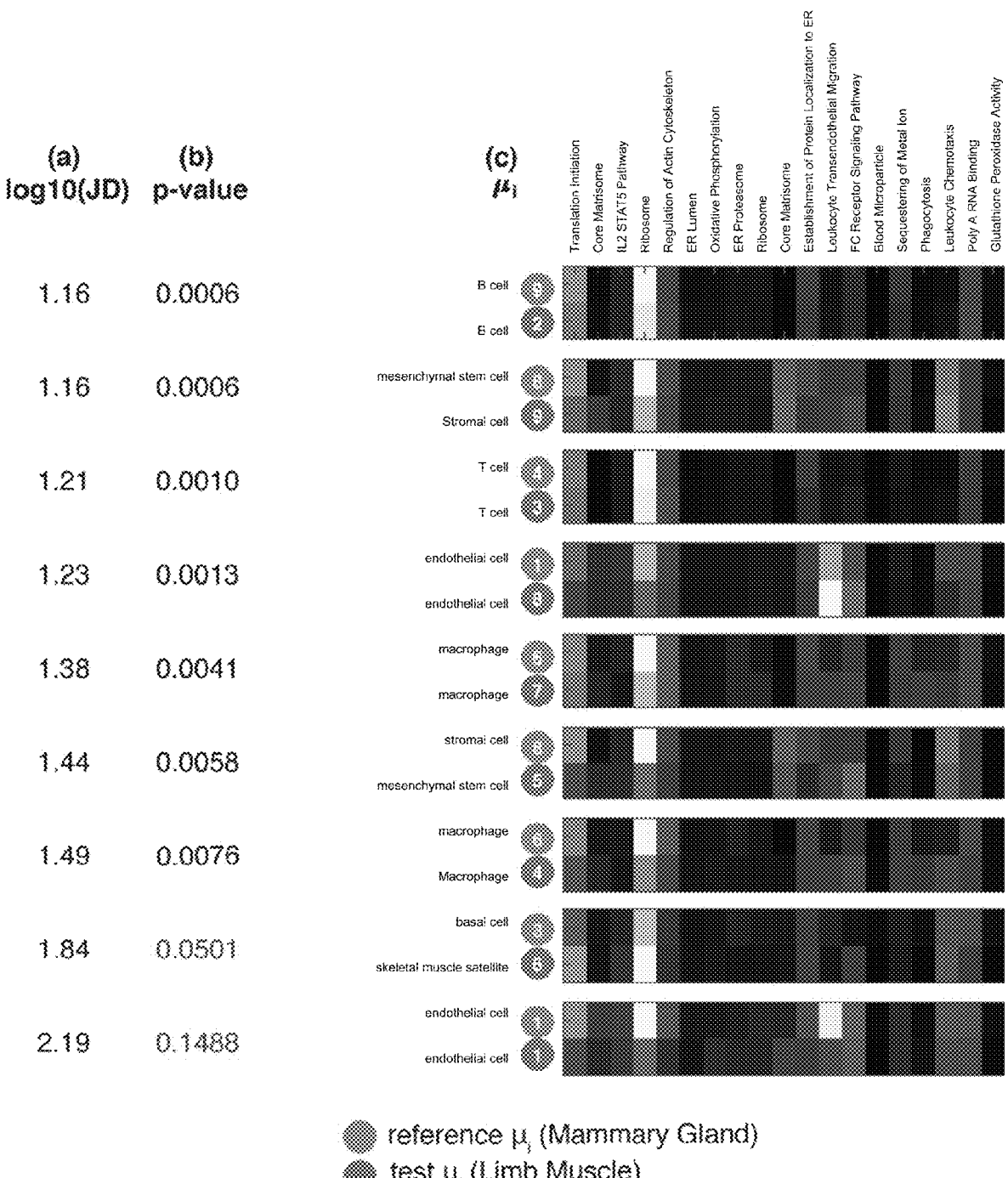
FIG. 23. Pairwise alignments between PopAlign models of Mammary Gland and Limb Muscle can be dissected in terms of Δw, Δμ, ΔΣ Aligned subpopulations between the reference tissue, Mammary Gland, and the test tissue, Limb Muscle, are ranked by their Jeffrey's Divergence (a). For each aligned pair, the following are displayed: (b) associated p-value, (c) mean gene expression states (μ$_i$) in terms of annotated features, (d) shifts in abundance (Δw), (e) shifts in mean gene expression state (Δμ), (f) shifts in population spread (ΔΣ).
Figure 24:
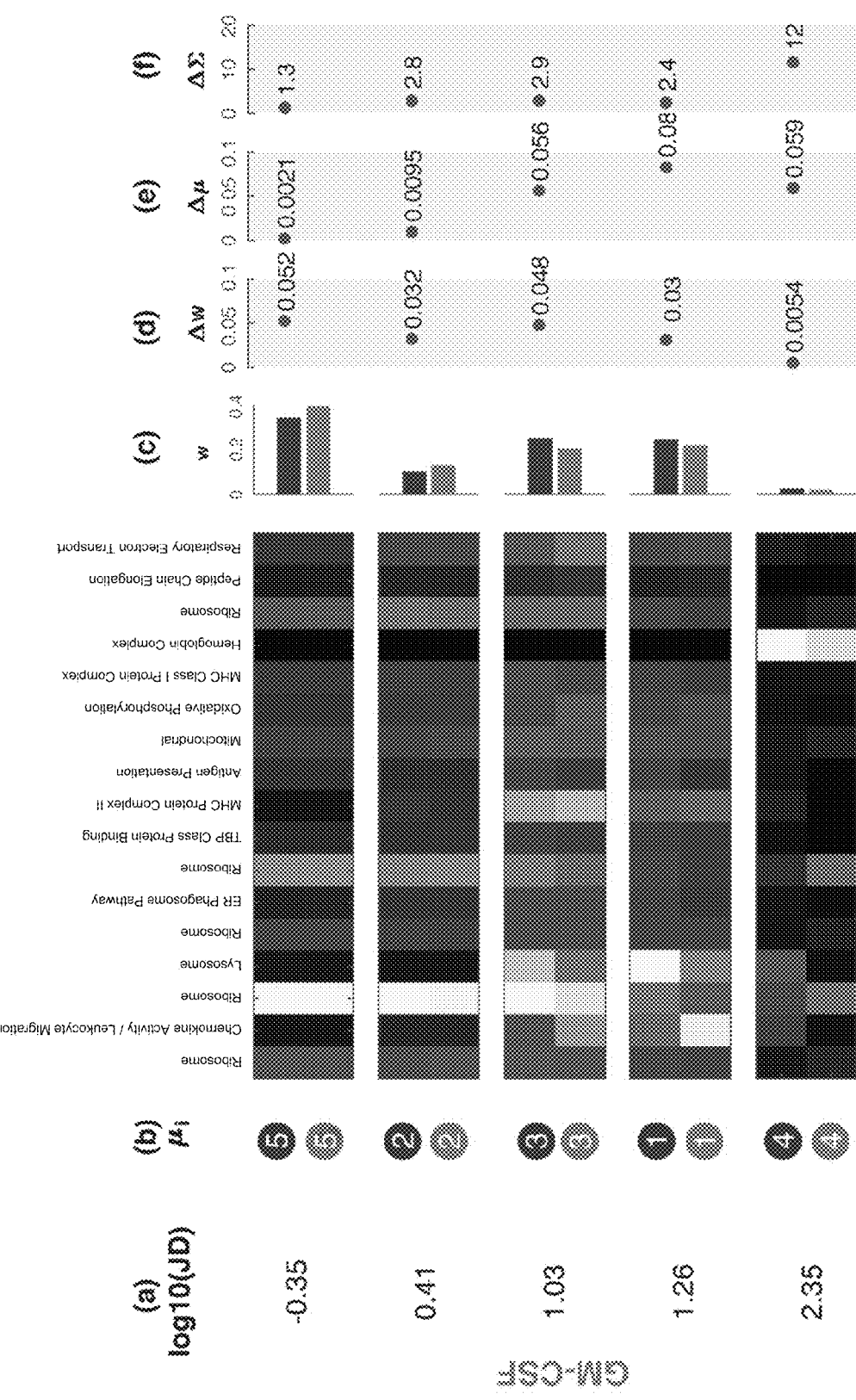
FIG. 24: Pairwise alignments between PopAlign models of immune cells and signal conditions (IFNG, GM-CSF) can be dissected in terms of Δw, Δμ, ΔΣ Aligned subpopulations between the reference PBMC sample and each test sample, GM-CSF and IFNG, are ranked by their Jeffrey's Divergence (a). For each aligned pair, the following are displayed: (b) mean gene expression states (μ$_i$) in terms of annotated features, (c) shifts in abundance (Δw), (d) shifts in mean gene expression state (Δμ), (e) shifts in population spread (ΔΣ).
Figure 24:
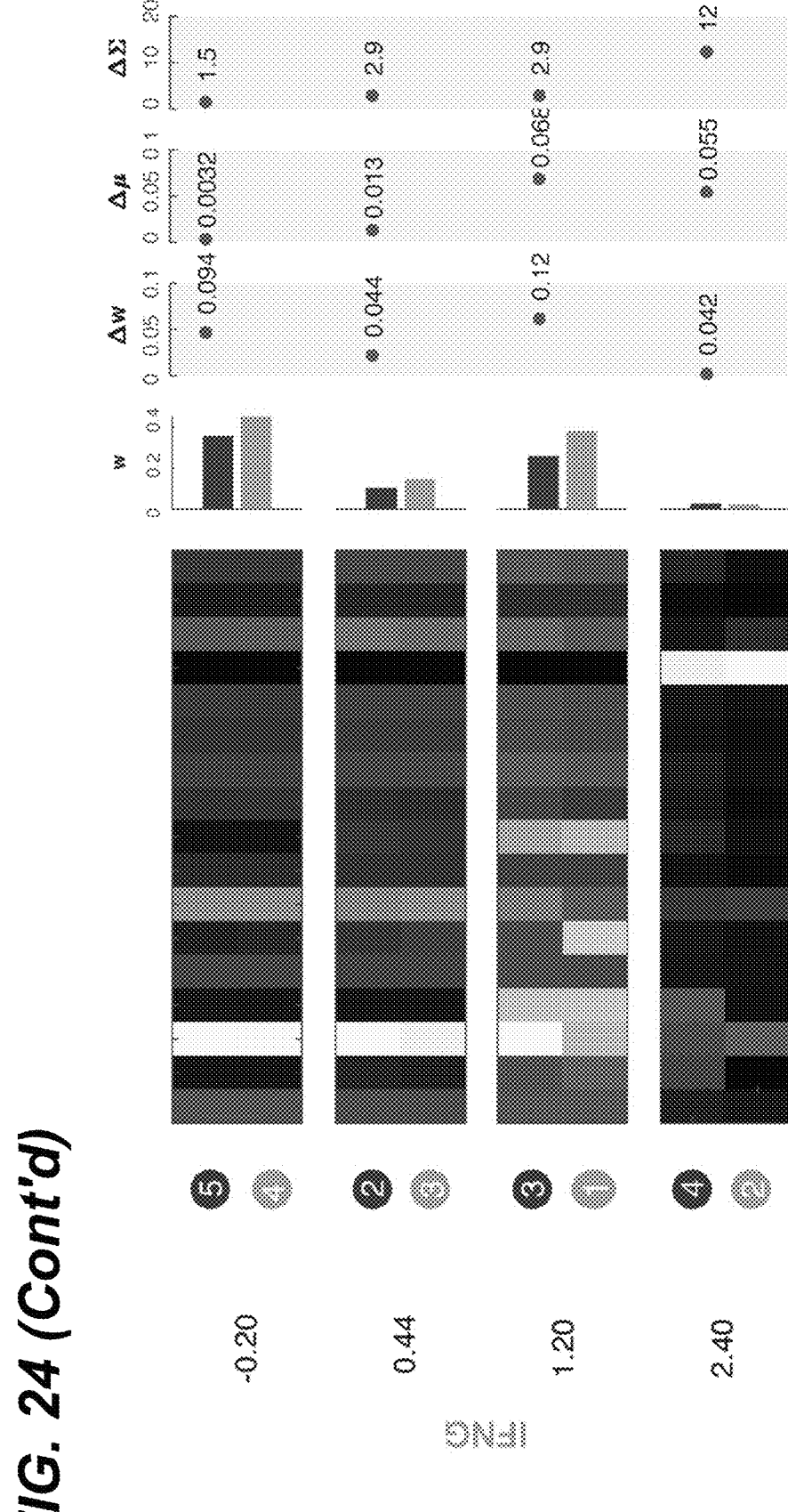
Figure 25:
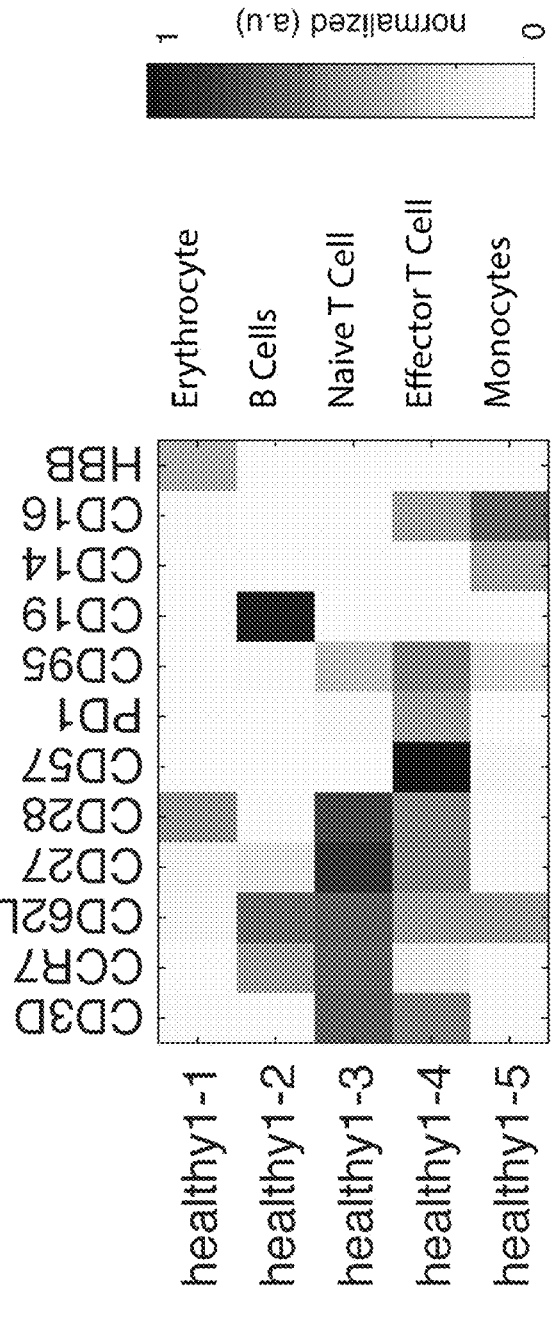
FIG. 25: Classification of reference patient population (healthy1) using canonical immune system markers. Cells were classified using heatmap of mean gene expression values for cells from each reference subpopulation from healthy1. Each gene is independently scaled by its max value across all subpopulation means. Erythrocytes are HBB+, T cells are CD3D+, naive T cells are CCR+/CD62L+/CD27+/CD28+, effector T cells are CD57+/PD1+/CD95+, B cells are CD19+, and monocytes are CD14+/CD16+.
Figure 26:
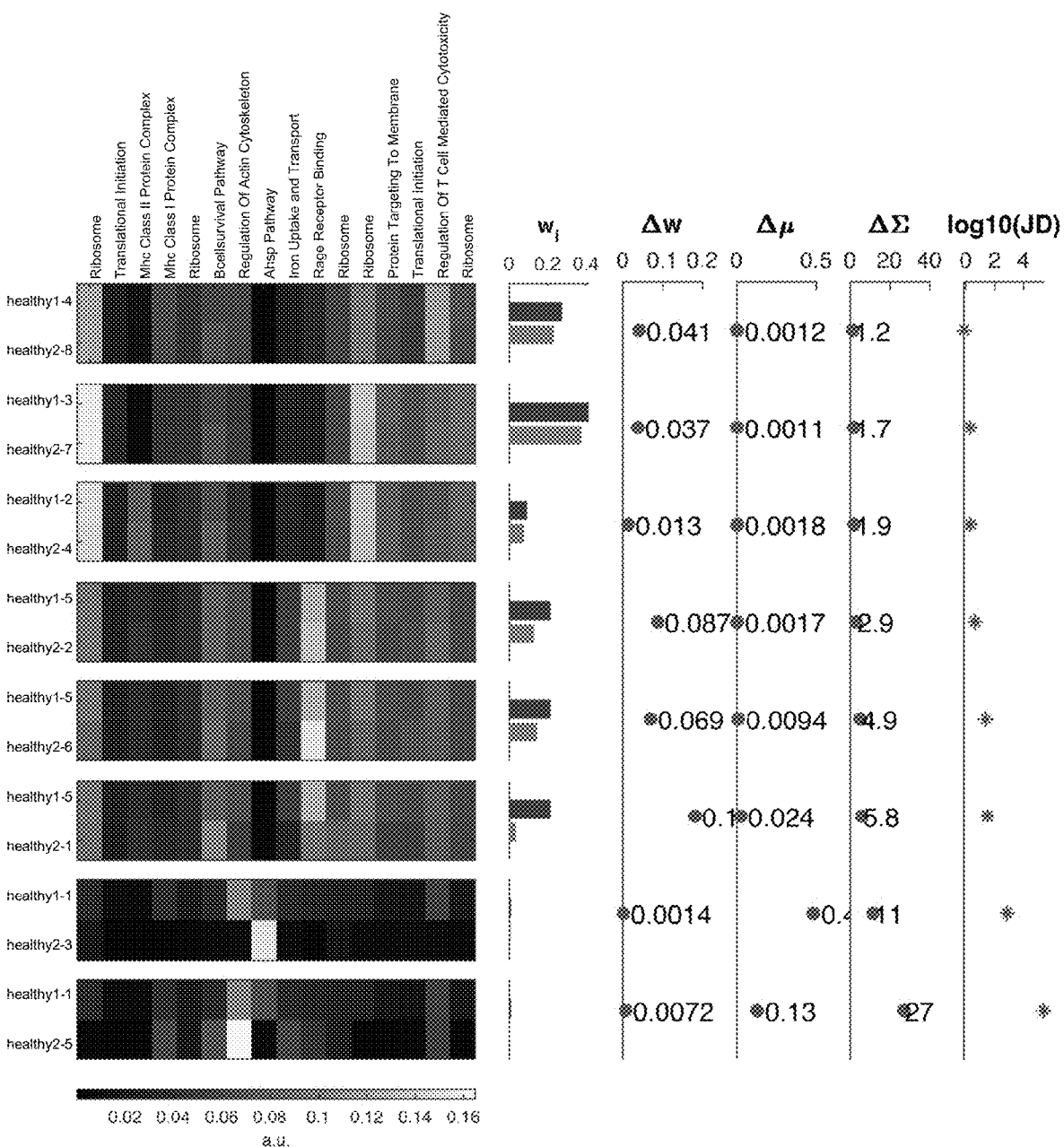
FIG. 26: Pairwise alignments between PopAlign models of healthy1 and healthy2 Aligned subpopulations between the reference healthy1 sample and test sample, healthy2, are ranked by their Jeffrey's Divergence. For each aligned pair, the following are displayed: mean gene expression states (μ$_i$) in terms of features, shifts in abundance (Δw), shifts in mean gene expression state (Δμ), shifts in population spread (ΔΣ), and log 10 (Jeffrey's Divergence).
Figure 27:
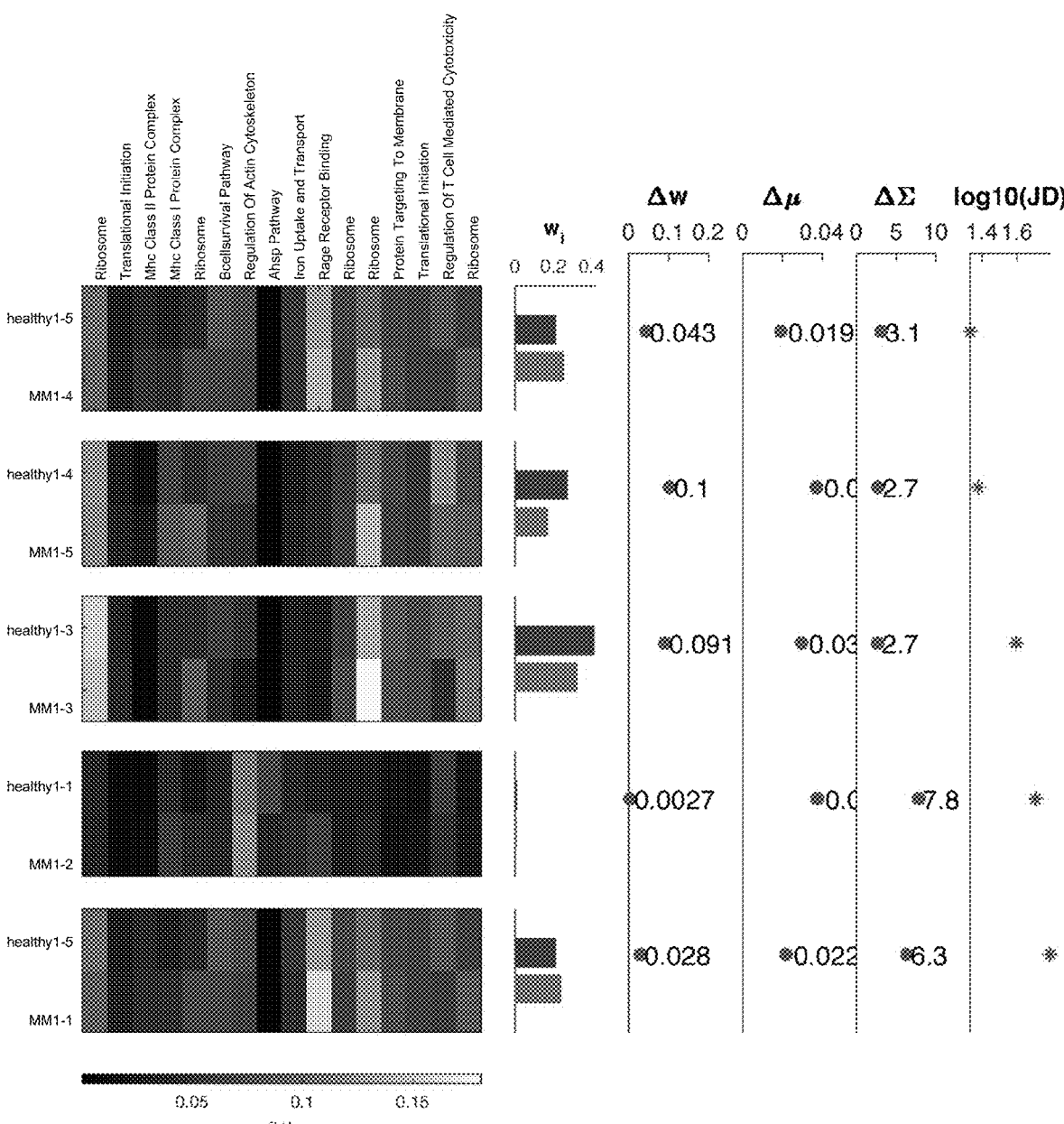
FIG. 27: Pairwise alignments between PopAlign models of healthy1 and MM1. See caption for FIG. 26.
Figure 28:
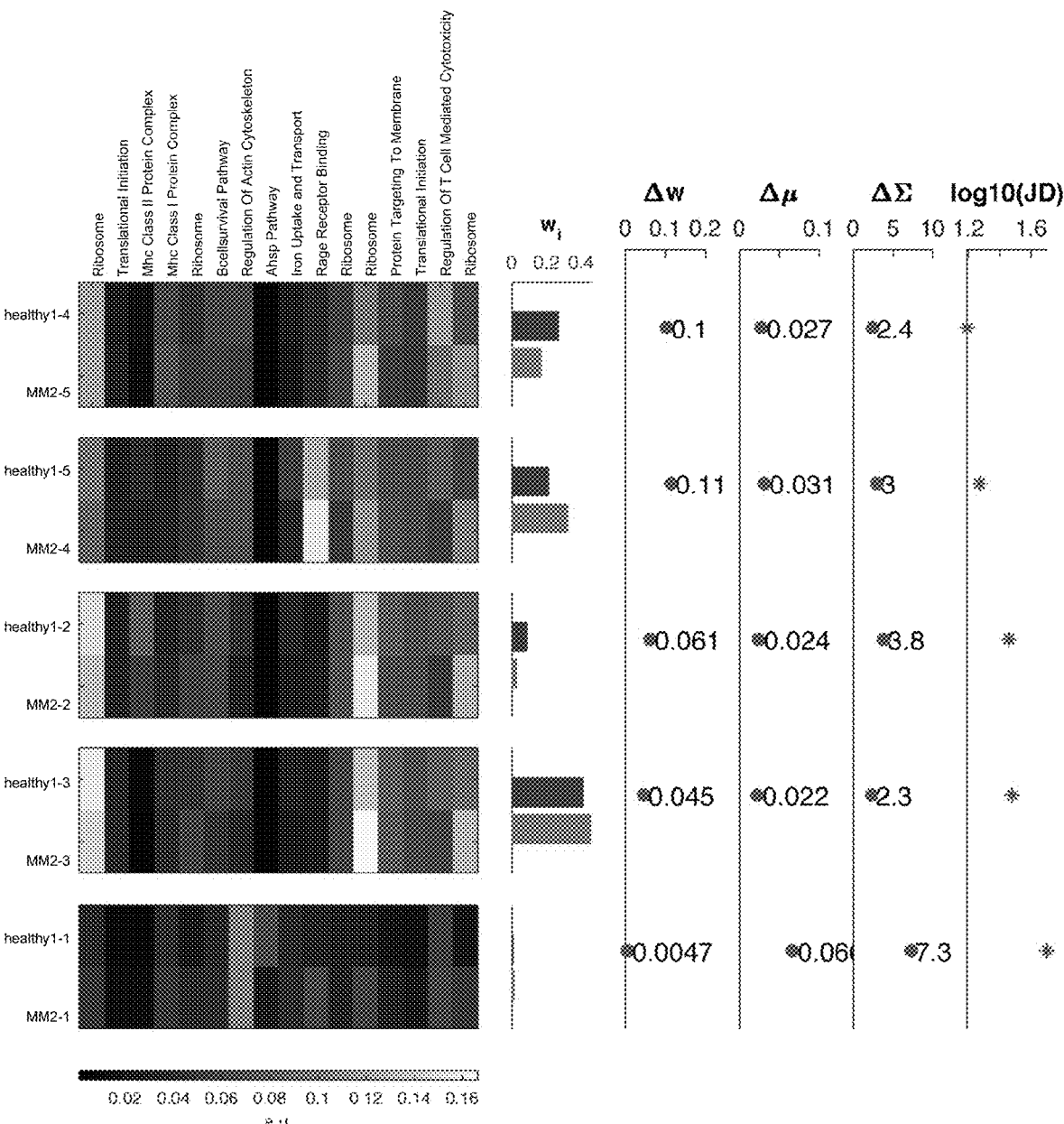
FIG. 28: Pairwise alignments between PopAlign models of healthy1 and MM2. See caption for FIG. 26.
Figure 29:
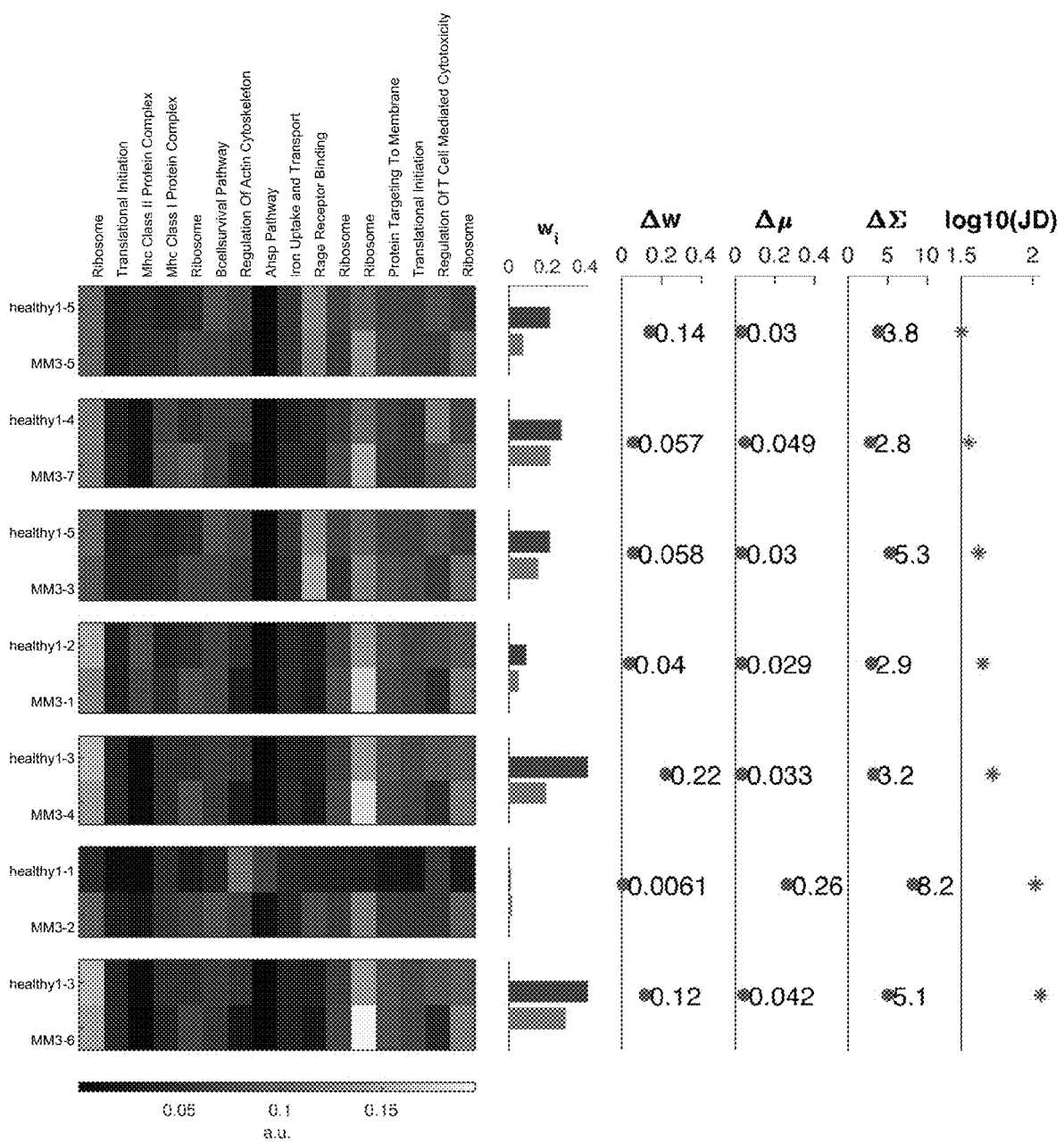
FIG. 29: Pairwise alignments between PopAlign models of healthy1 and MM3. See caption for FIG. 26.
Figure 30:
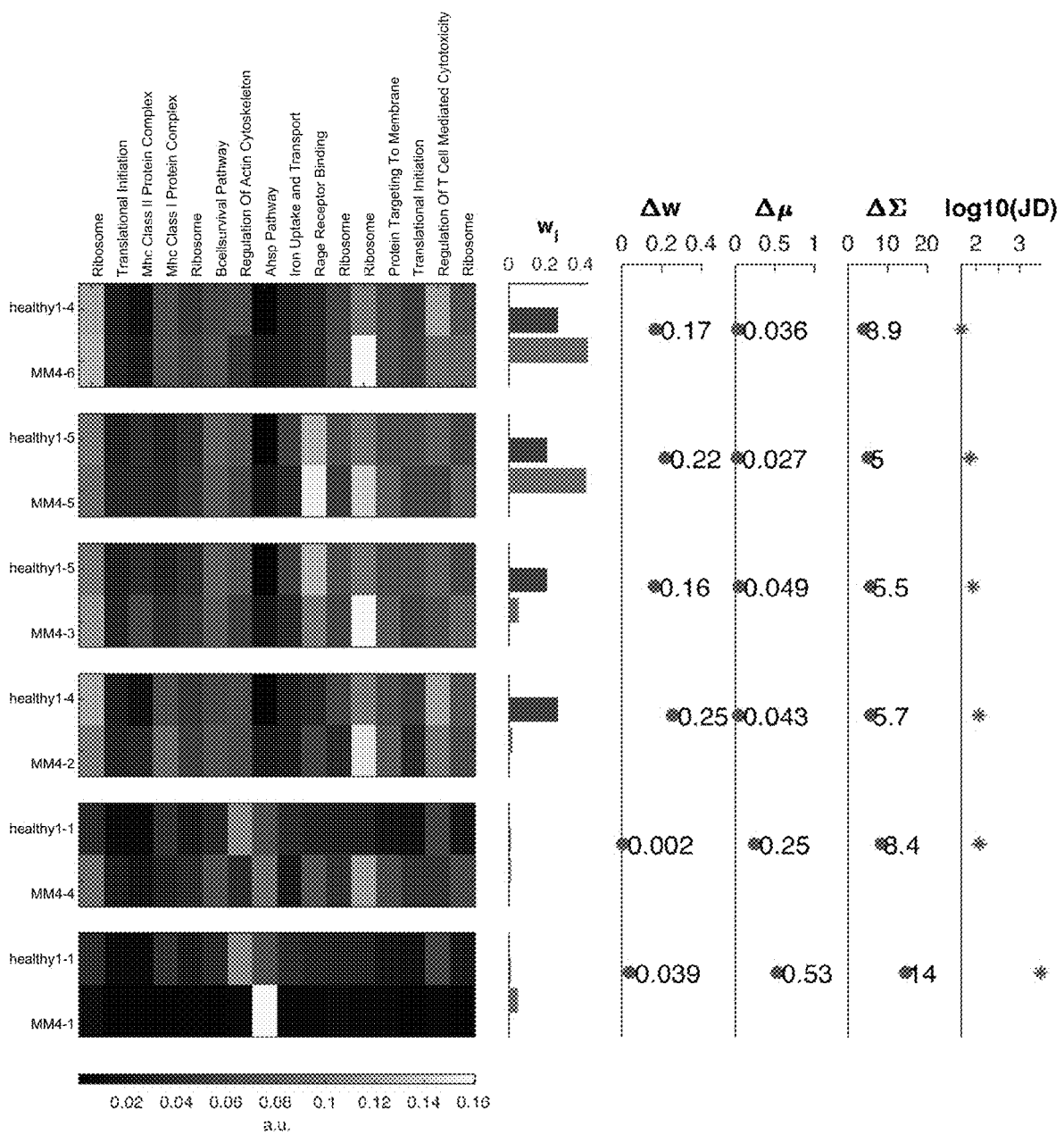
FIG. 30: Pairwise alignments between PopAlign models of healthy1 and MM4. See caption for FIG. 26.

Through alignment of model components across tissues, PopAlign enabled high-level comparisons of tissue composition. By aligning Mammary Gland to Limb Muscle (FIG. 15E), "common" cell-types between the two tissues including B-cells (p=0.0006), T-cells (p=0.001), endothelial cells (p=0.0013), and macrophages (p=0.004, 0.0076) (FIG. 22) were identified, and tissue scale differences in relative abundance were also revealed. T-cells are highly prevalent (w=0.3 in the mammary gland but rare in the limb muscle w=0.05) (FIG. 15G); endothelial cells are highly abundant in the limb muscle (w=0.32), but rare in the mammary gland (w=0.06) (FIG. 15G). Between shared cell types, such as macrophages, common programs such as FC-receptor Signaling and Lysosome, as well as tissue-specific gene expression programs such as TGF-Beta, Phagocytosis, and Leukocyte Chemotaxis (FIG. 15H) were revealed. PopAlign can, thus, give insight into the underlying composition of a tissue, shedding light onto principles of tissue organization with respect to tissue function.

PopAlign can Perform Global Comparisons of Cell State Across Tens to Hundreds of Samples The ability of PopAlign to compare large numbers of samples was tested, using synthetic collections of samples bootstrapped from Tabula Muris data survey. It was found that PopAlign runtime scales linearly with sample number and can analyze 100 samples in approximately 100 minutes on a typical workstation with 8 cores and 64 GB RAM (FIG. 16A). By first building models, PopAlign front-loads the computation to produce a low-error (FIGS. 14A-14C) representation of the data that achieves a 50-100× reduction in the memory footprint. Memory efficiency speeds up downstream tasks, such as the calculation of pairwise divergences between subpopulations (FIG. 16B) necessary for aligning them across samples.

Applying PopAlign to compare all 12 tissues of Tabula Muris shows the PopAlign method is general across many types of experiments, including comparisons of disparate tissues that do not contain overlapping populations. PopAlign achieves generality because PopAlign aligns subpopulations by performing a local computation for each test subpopulation (i.e., the minimization of Jeffrey's Divergence relative to reference subpopulations), that can be accepted or rejected by a hypothesis test. Other methods for comparing samples across experiments essentially perform batch correction to align multiple datasets, before pooling data and jointly identifying clusters. These alignment methods discover a global transformation to bring together cells that are known or inferred to be transcriptionally similar. Not only are these alignment methods computationally slow, scaling exponentially with cell/sample number (FIG. 16A), but they also require overlapping populations or force them to overlap, thus limiting the generality of the approach.

Figure 16G:
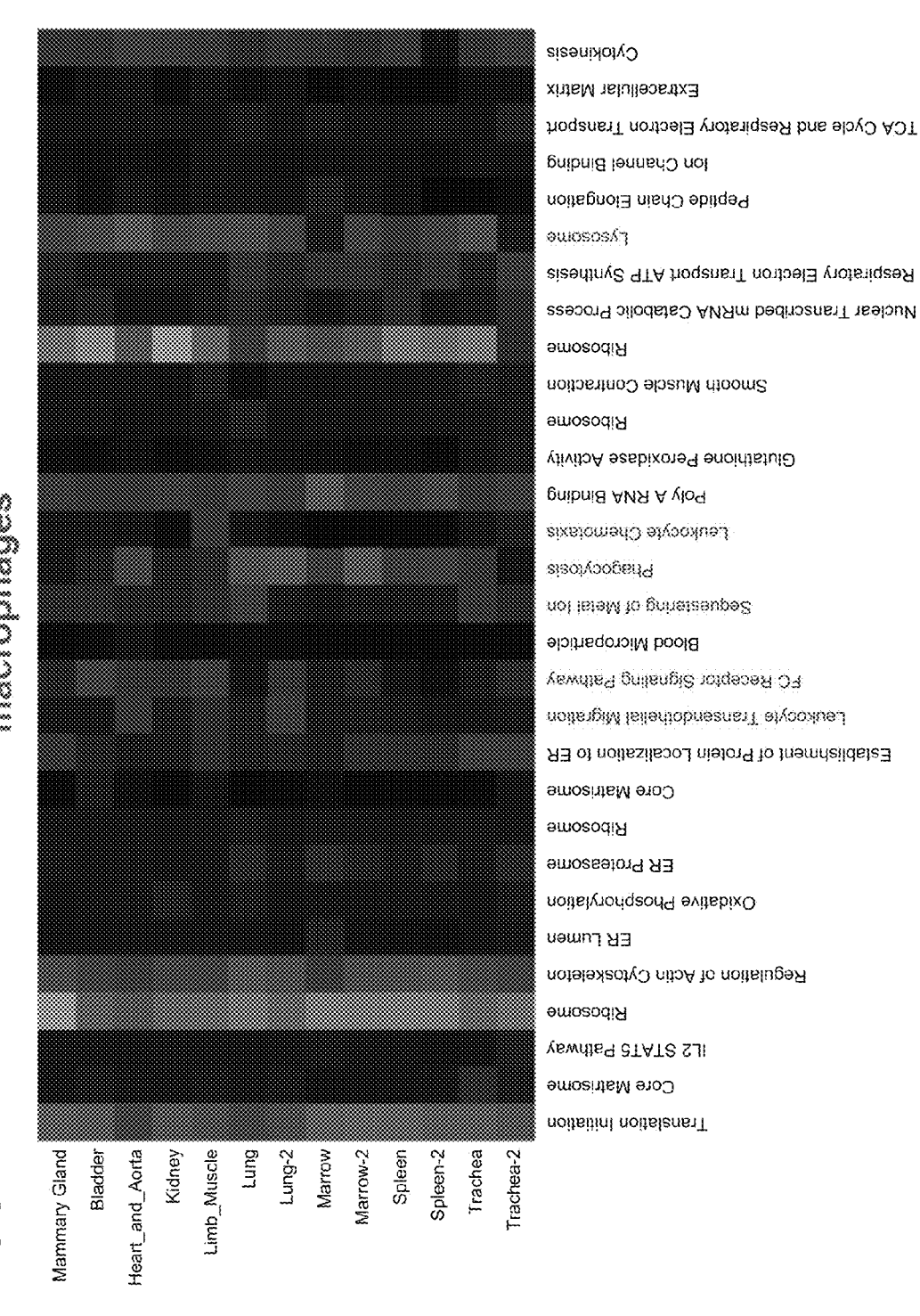

In the 12-sample Tabula Muris comparison, PopAlign uncovered meaningful signatures of cell distributions and gene expression patterns that reflect and expand upon known biology. For example, it was found that T cells (FIG. 16C) and B cells (FIG. 16D) are most abundant in organs where they are known to mature developmentally (the thymus and spleen respectively), endothelial cells (FIG. 16E) are most prevalent in highly vascularized tissues (Kidney and Limb Muscle), and macrophages (FIG. 16F) are highly prevalent in the Lung, which accumulates debris and bacteria that must be engulfed and destroyed. The analysis also highlighted surprising results, such as the observation that T cells are very abundant in the mammary gland (FIG. 16C). It was also found distinct patterns of gene program activation (e.g. Lung macrophages are highly phagocytic) in macrophage populations across tissues (FIG. 16G), consistent with previous reports of functional diversity among macrophages. These results demonstrate that PopAlign is an efficient computational framework for extracting meaningful shifts in abundance and gene expression that scales to large numbers of samples, and is not constrained by requirements for overlapping cell populations between samples.

PopAlign Identifies Subpopulation Specific Responses to Cytokines in Primary Immune Cell Populations One non-limiting application of PopAlign is to study heterogeneous cell populations in the human body as they respond to environmental change, drug treatments, and disease. The human immune system is an extremely heterogeneous physiological system that is central for disease and cell engineering applications. As a test case, PopAlign was tested for its ability to identify subtype-specific signaling responses in a complex mixture of primary human immune cells. Thus, primary human peripheral blood mononuclear cells (PBMCs) (FIG. 17A) were treated with two lymphokines—granulocyte-macrophage colony-stimulating factor (GM-CSF) (FIG. 17C) and interferon-gamma (IFNG) (FIG. 17D) that are known to have a specific impact on monocytes (See Experimental Methods).

Broadly, PopAlign found that both lymphokine signals impact gene expression in monocytes (canonical and non-canonical) while driving minimal gene expression changes in T-cells. In the reference PBMCs, five independent cell densities (FIG. 17A) were identified and classified using canonical markers from the literature (FIG. 17B). The signal treated cell-populations (FIGS. 17C-17D) were aligned to the PBMC data (FIG. 17A), finding that, for both signals, the monocyte populations (mixtures PBMC-1, PBMC-3) had the largest shifts in their average gene expression state ($|\Delta\mu| > 0.04$) (FIG. 17F). While T-cell abundances changed (numbers), their mean cell states ($\mu$) had the lowest magnitude of gene expression shift.

Additionally, the PopAlign framework exposed that GM-CSF and IFNG exerted on qualitatively different classes of transcriptional effects. In the GM-CSF condition, both canonical and non-canonical monocytes (mixture 1 and 3) responded to the signal "additively" by activating a new gene expression program called Chemokine Secretion/Leukocyte Migration pathway (FIG. 17H bottom, blue arrows) that includes genes such as CCL2 (FIG. 17J panel iii), and cystatin B (CSTB) while losing the expression of "Lysosome" program, which includes genes such as LYZ and granulysin (GRN) (FIG. 17J, panels v, vi). The GM-CSF induced change in gene expression was called "additive" because both classes of monocytes responded with the same transcriptional changes, but these changes were induced in addition to their baseline gene expression state (FIG. 17H— black arrows).

Alternately, IFNG signaling generated a "convergent" signaling response inducing both canonical and non-canonical monocytes to a single new transcriptional state. IFNG led to a single new monocyte subpopulation that aligned most closely with "non-classical" monocyte population (FIG. 17B), but also had a high secondary alignment score for the "classical" monocyte population (FIGS. 17C, 17E—red x). Based on the disappearance of the "classical monocytes" and the high score of the secondary alignment, it was inferred that IFNG drove both subtypes towards a new transcriptional state that had up-regulation of pathways involved in antigen presentation and phagocytosis—"ER Phagosome," "IFN-Gamma signaling," "Antigen Processing and Presentation". Genes upregulated include the known targets of IFNG STAT1 (FIG. 17J panel i) and also PSME2 (FIG. 17J panel ii), a proteasome gene involved in the non-lysosomal protein degradation pathway. The induced programs are consistent with literature showing that IFNG converts monocytes to macrophages, cells that recycle cellular debris within the body. In this way PopAlign revealed cell-type specific signaling responses within a complex cell mixture subject to a globally applied signal. PopAlign, further, enabled defining distinct categories of signaling responses, "additive" and "convergent," within a highly heterogeneous population of primary cells.

tSNE Obscures Association Between Cell-States Following Signal Addition

Figures 31A, 31B, 31C:
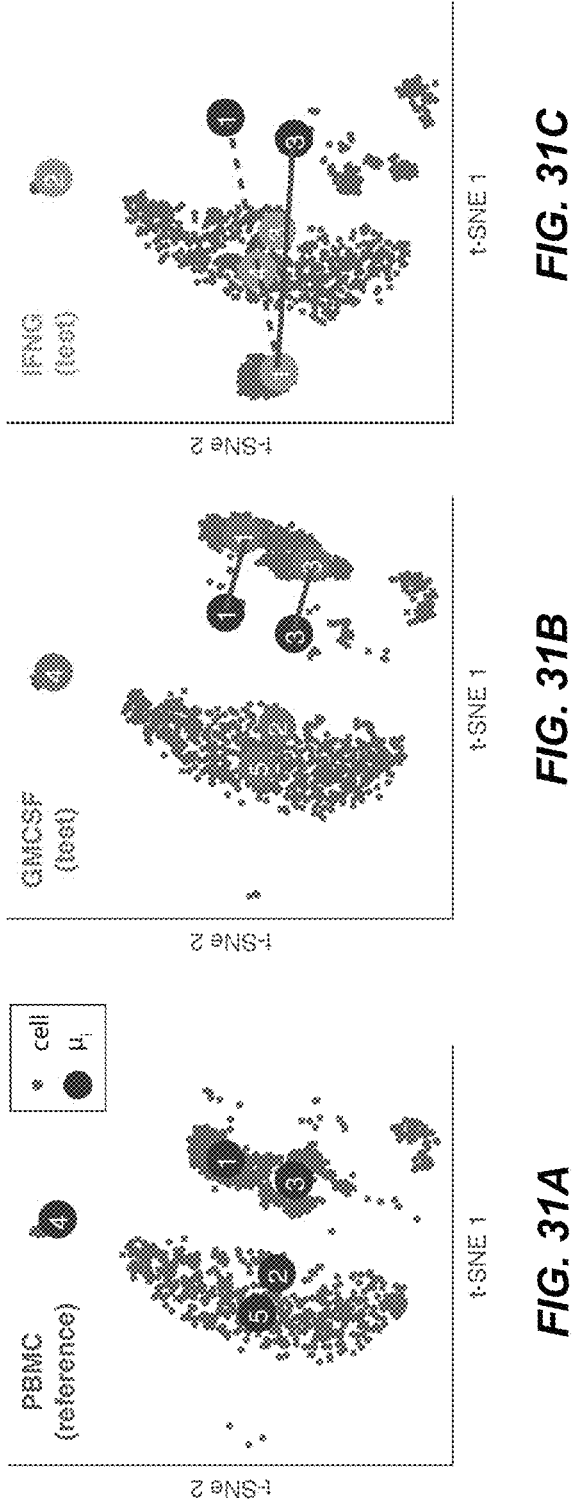
FIGS. 31A-31C: t-SNE analysis obscures the relationships between aligned subpopulations (a-c) tSNE plots of single cell data for three signaling conditions from FIGS. 16A-16G.
Figures 32A, 32B, 32C, 32D, 32E, 32F, 32G, 32H, 32I:
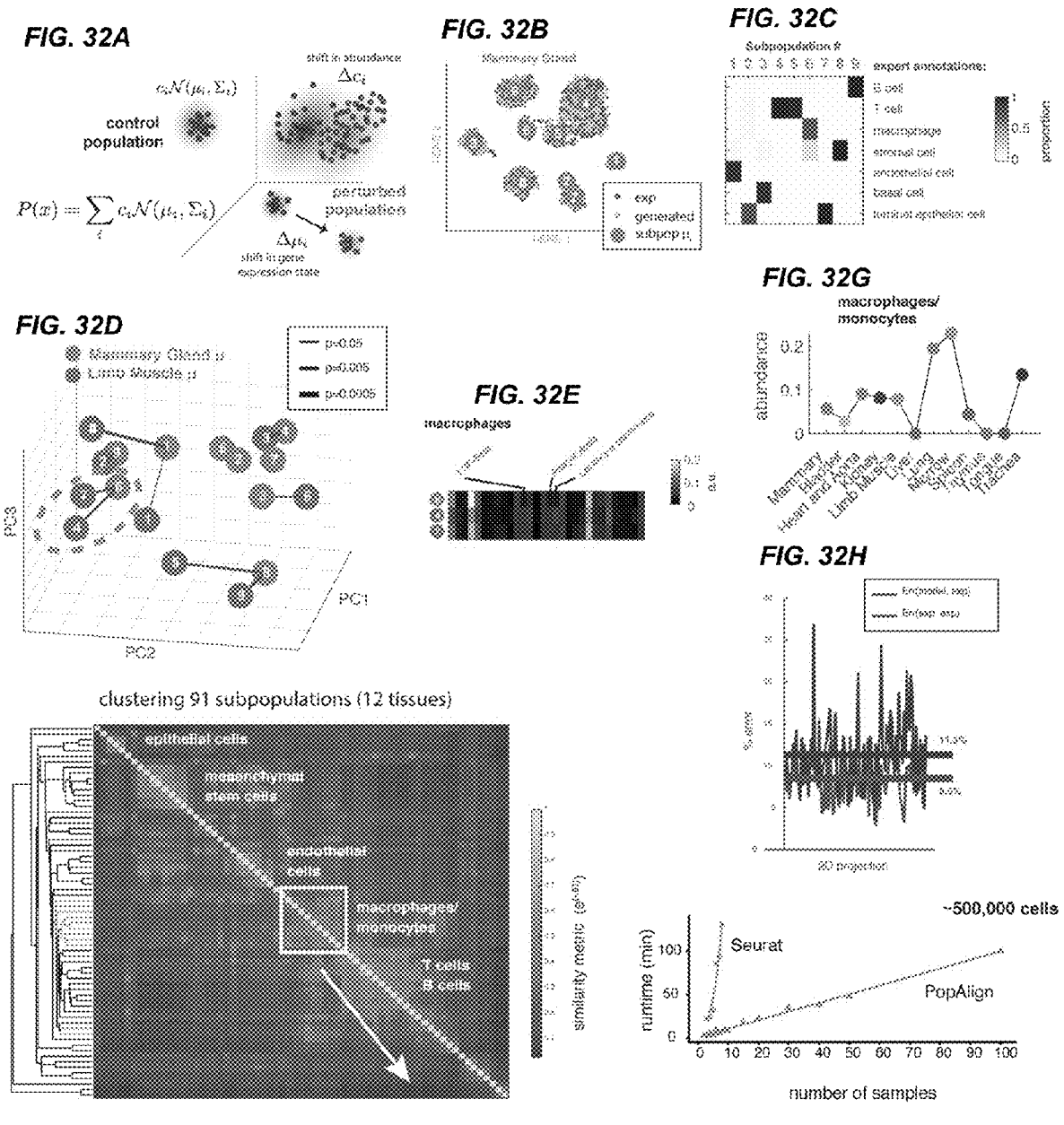
FIGS. 32A-32I: PopAlign framework and validation.
Figures 34A, 34B, 34C, 34D:
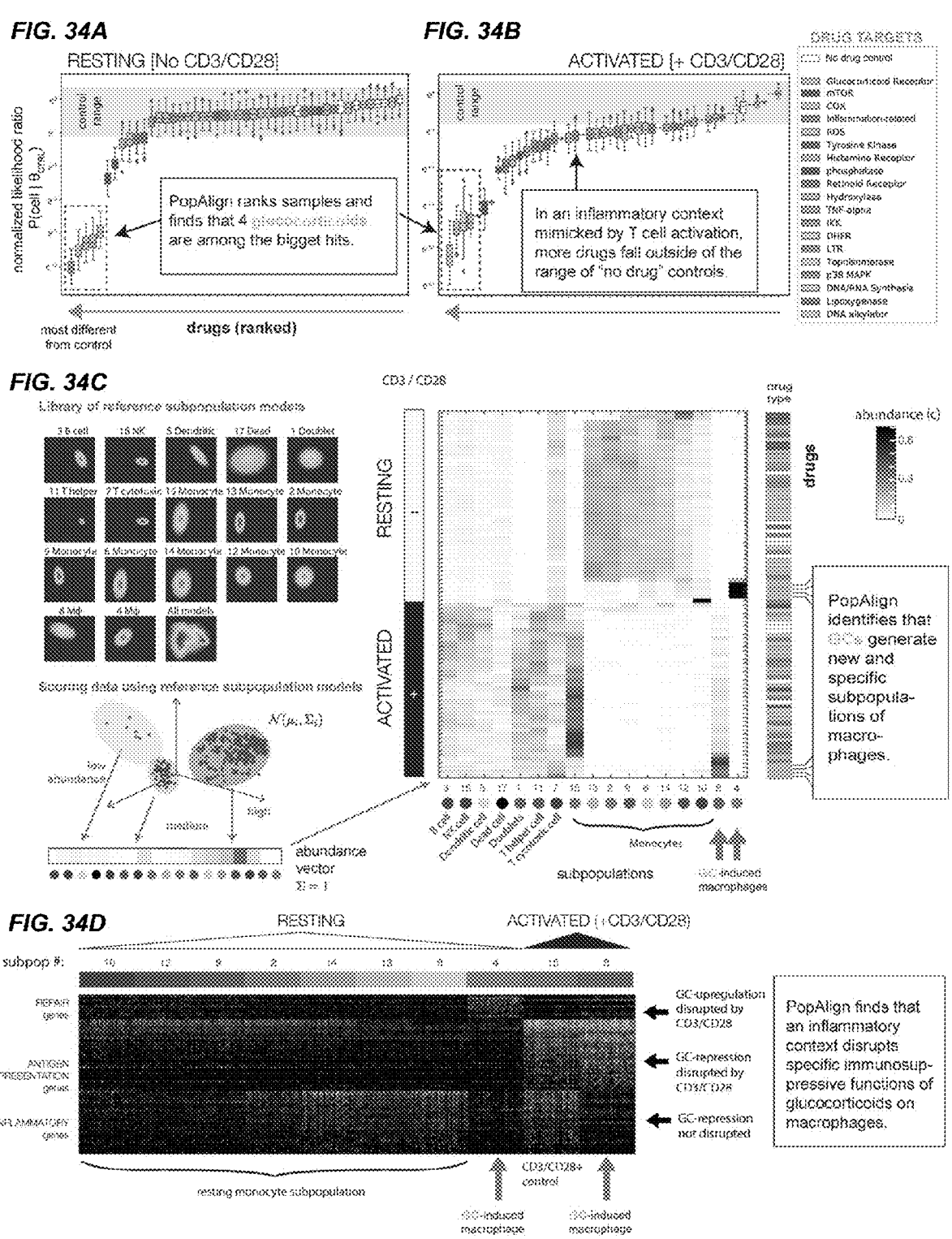
FIGS. 34A-34D: PopAlign discovered that inflammatory context disrupted drug response.

PopAlign extracts and quantifies population level changes in the signaling data set that are obscured by existing geometric techniques like tSNE. tSNE provides a low dimensional but non-linear embedding of data points that seeks to preserve geometric features of the high dimensional data while separating distinct cell-states into clusters. Thus, in the tSNE embedding of the signaling data, the relationships between cell-states (subpopulations) is often obscured because gene expression changes can result in the formation of new, separate, and "distant" clusters (FIGS. 31A-31C). For example, in response to IFNG, the monocyte populations become separated in the two-dimensional embedding (FIG. 31C) making association of these clusters pre- and post-signal complicated. Further, tSNE does not provide natural metrics for quantifying distinct parameters of a point cluster, so that abundance, mean, and shape all must be defined and quantified through heuristic approaches. Unlike tSNE, PopAlign provides a precise framework for defining populations of cells and also for calculating statistical similarity scores for individual subpopulations across samples by using the Jeffrey's divergence to measure changes in gene expression state, abundance, and covariance.

PopAlign Discovers General and Treatment-Specific Signatures of Multiple Myeloma Given the success of the PopAlign framework in extracting cell-type specific responses in the immune signaling data, the PopAlign method was applied to study underlying changes in cell state due to a disease process. PopAlign was applied to compare human PBMC samples from healthy donors to patients being treated for multiple myeloma (MM). Multiple myeloma is an incurable malignancy of blood plasma cells in the bone marrow. Both the disease and associated treatments result in broad disruptions in cell function across the immune system further contributing to disease progression and treatment relapse. In MM patients, immune cells with disrupted phenotypes can be detected in the peripheral blood. An ability to monitor disease progression and treatment in the peripheral blood could therefore provide a powerful new substrate for making clinical decisions.

Samples of frozen PBMCs were obtained from two healthy and four multiple myeloma patients undergoing various stages of treatment (Table 2.1). >5,000 cells from each patient were profiled, and probabilistic models were constructed and aligned to one reference healthy population (FIGS. 18A-18F).

TABLE 2.1

Patient information for PBMC donors with Age, Gender, Ethnicity, Disease Status, and Medications.

| Patient Label | Age | Gender | Ethnicity | Disease | Medications |
|---|---|---|---|---|---|
| healthy1 | 58 | Male | African American | none | N.D. |
| healthy2 | 43 | Female | Caucasian | none | N.D. |
| MM1 | 51 | Male | Caucasian | multiple myeloma | N.D. |
| MM2 | 43 | Female | African American | multiple myeloma | N.D. |
| MM3 | 65 | Male | Caucasian | multiple myeloma | Carizomib/Zometa every 3 months Lisinopril Acyclovir |

TABLE 2.1-continued

Patient information for PBMC donors with Age, Gender, Ethnicity, Disease Status, and Medications.

| Patient Label | Age | Gender | Ethnicity | Disease | Medications |
|---|---|---|---|---|---|
| MM4 | 67 | Male | Hispanic | multiple myeloma | Revlimid and Dexamethasone Hydrocodone Acetaminophen Vitamin D3 Diphenoxylate- atropine Calcium Alendronate Acyclovir Amlodipine Feno_brate Warfarin |

PopAlign identified several common global signatures in the MM samples at the level of cell-type abundance and gene expression. Across all samples, previously known signatures of multiple myeloma were found, including a deficiency in B cells, and an expansion of monocyte/myeloid derived cells, and importantly, new impairments in T-cell functions.

Plotting $\Delta w$ across all patients, high-level changes were found in subpopulation abundances, which are known to be prognostic of disease progression. It was found that all MM patients experience a contraction in B cell numbers (FIG. 16B), and 2 out of 4 see a dramatic expansion ($\Delta w >> 0.10$) of monocytes (FIG. 16C). Changes in T cell levels, however, can be highly variable, with outlier patient MM4 experiencing a large increase in effector T cell ($\Delta w = 0.2$), and a complete elimination of resting T cells ($\Delta w = 0.2$). For this patient, who was receiving a thalidomide-derived drug therapy, these deviations are consistent with thalidomide's known stimulatory effects on T-cells.

Especially in patients with apparently normal abundances (i.e., $\Delta w$ were small), uncovering subpopulation-specific changes in transcription can point to specific modes of immune dysfunction. PopAlign was used to find that monocyte subpopulations in patients acquire immunosuppressive phenotypes, evidenced by upregulated expression of CD11b and CD33. Both genes are specific markers of myeloid derived suppressor cells which are negative regulators of immune function associated with cancer. By plotting the monocyte-specific mean gene expression values for both CD11b and CD33, it was observed that all patients except patient MM3 score highly for both MSDC markers (FIG. 18K). Patients with high MDSC populations typically have a poor prognosis, underscoring the need to monitor MDSC populations in patients.

Figure 18A:
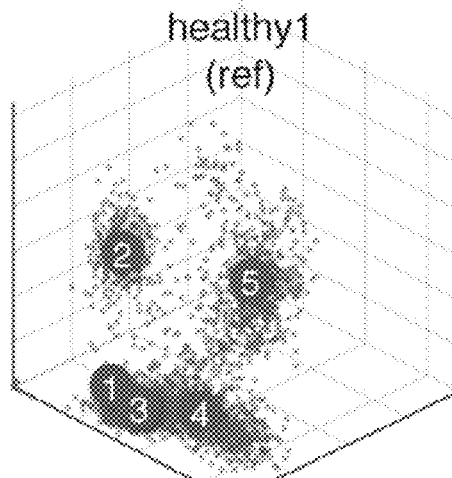
Figure 18B:
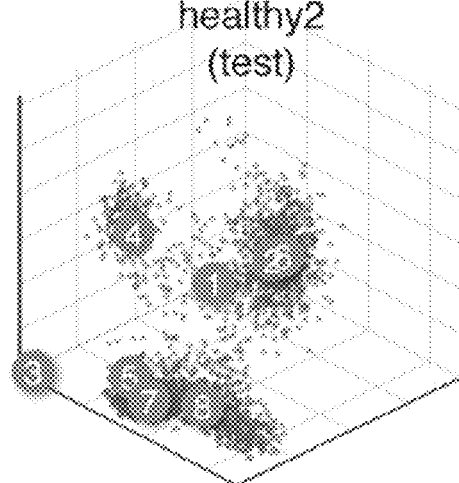
Figure 18C:
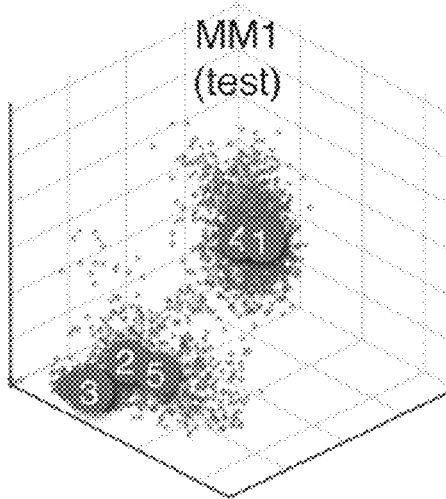
Figure 18D:
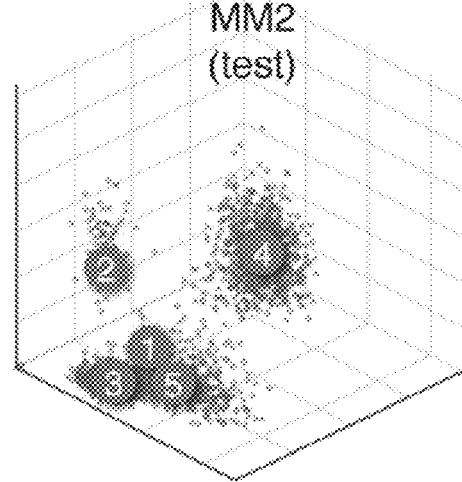
Figure 18E:
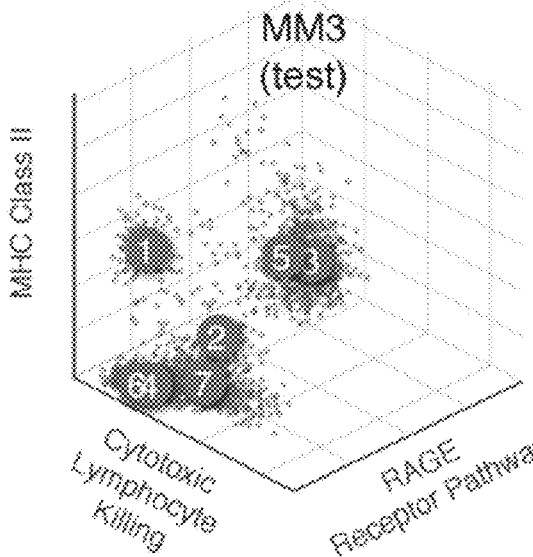
Figure 18F:
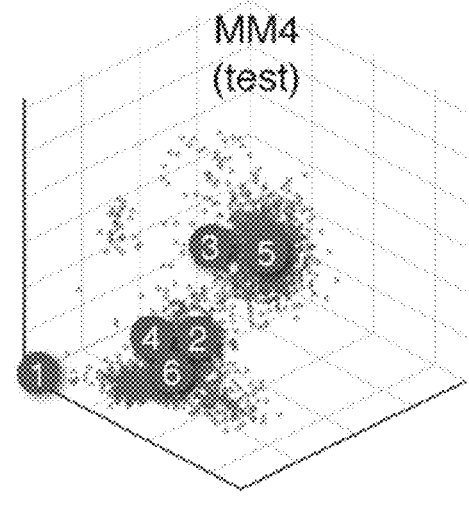
Figures 18I, 18J, 18M, 18N:
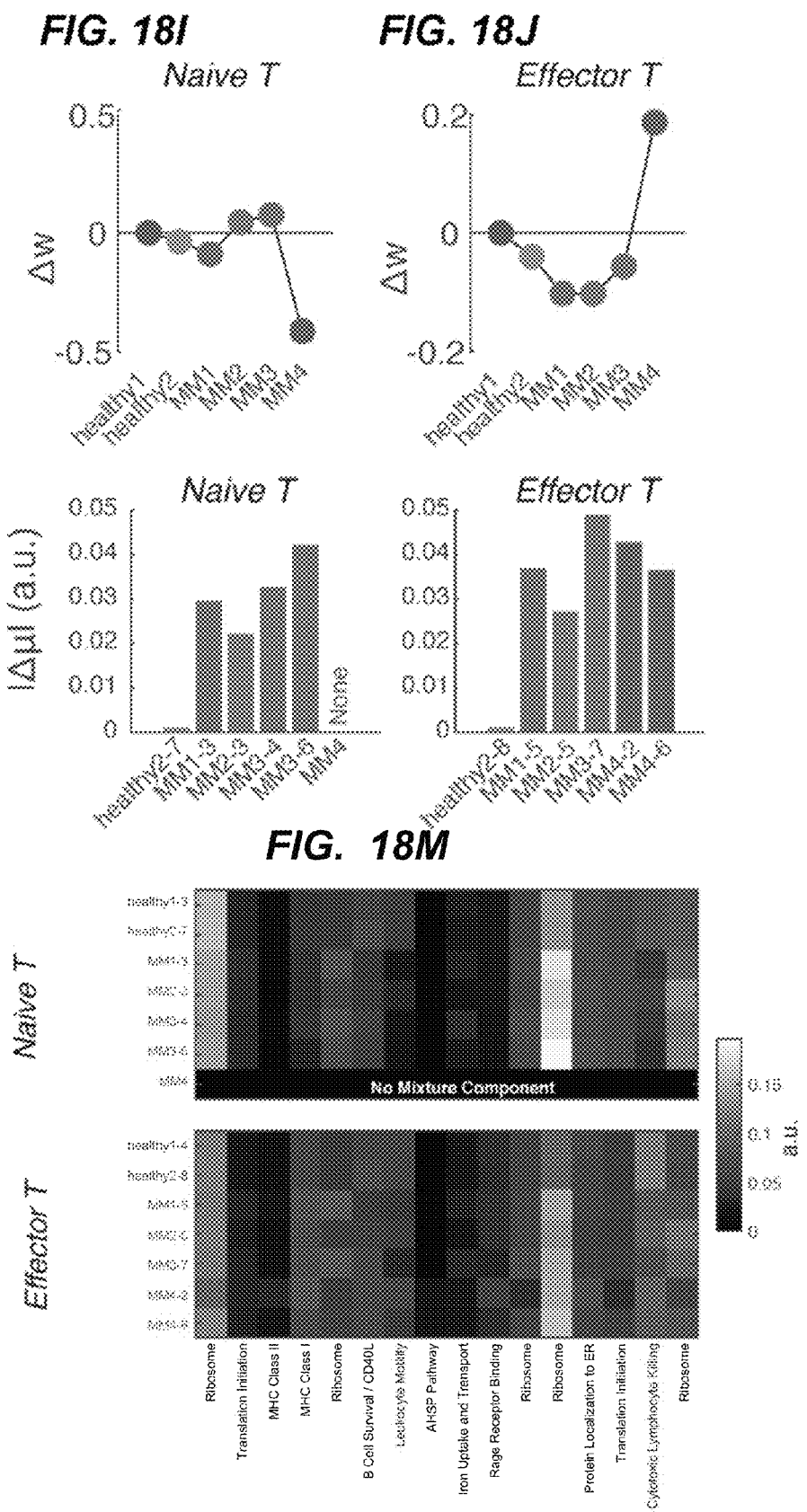

Importantly, it was also found that naive and effector T cells across all multiple myeloma patients have transcriptional defects in pathways essential for T cell function. By plotting $\Delta\mu$, it was shown that both populations of T cells experience large mean transcriptional shifts, compared to T cells from the second healthy donor, healthy2 (FIG. 18M). By examining the $\mu$'s in terms of gene expression vectors (FIG. 18N), it was found that in multiple myeloma, T cells reduce their expression of two key features—Leukocyte Motility, and Cytotoxic Lymphocyte Killing. Surprisingly, the impact on motility is apparent even on the expression of beta-actin (ACTB) (FIG. 18O), a core subunit of the actin cytoskeleton, and which was the top hit in the Leukocyte Motility feature. Similar declines was found in the distribution of Perforin 1 (PFN1), a pore-forming cytolytic protein that was found as a top hit in the Cytotoxic Lymphocyte program (FIG. 18P).

The analysis establishes that consistent and also patient-specific transcriptional signatures of human disease and treatment response can be extracted from PBMCs. Interpreting these signatures in the context of disease progression or drug response can provide insight into treatment efficacy and can form the basis of a personalized medicine approach. The PopAlign framework enables new applications by providing a highly scalable way of extracting, aligning, and comparing these disease signatures, across many patients at one time.

Discussion

As described in this example, PopAlign can be used for tracking changes in gene expression state and cell abundance in a heterogeneous cell populations across experimental conditions. The central advance in the method is a probabilistic modeling framework that represents a cell population as a mixture of Gaussian probability densities within a low dimensional space of gene expression features. Models are aligned and compared across experimental samples, and by analyzing shifts in model parameters, gene expression and cell abundance changes in individual cell populations can be identified.

PopAlign constitutes a conceptual advance over existing single cell analytical methods. PopAlign is explicitly designed to track changes within complex cell populations. Since human diseases like cancer and neurodegeneration arise due to interactions between a wide variety of cell-types within a tissue, population level models can be important for building a single cell picture of human disease and for understanding how disease interventions like drug treatments impact the wide range of cell-types within a tissue.

Mathematically, existing single cell analysis methods rely on heuristic cluster-based analysis to extract subpopulations of cells. Fundamentally, such approaches lack well defined statistical metrics for making comparisons across samples. By conceptualizing a single-cell population as a probability distribution in gene expression space, discrete mathematical objects whose parameters can be interpreted, and which can be used to explicitly calculate quantitative statistical metrics for subpopulation alignment is defined. The probabilistic representation described herein allows quick and scalable learning of drug responses even on a complex mixture of cells, in "one shot." Computationally, PopAlign scales to analyze many samples that each contain thousands of single cells. The PopAlign method can be used to analyze data from drug screens where the goal is to identify cell-population specific transcriptional responses.

PopAlign can be used as a part of a work-bench for single cell analysis and treatment of human disease. Based on the application of PopAlign on data sets from the human immune system, PopAlign can be used for identifying drug/signal targets and for deconstructing single cell disease states. PopAlign identified cell-type specific signatures of disease treatment in multiple myeloma patients exposing a potential defect in T-cell activation and motility in three patient samples. This result shows that PopAlign can be used for guiding treatment interventions by exposing the spectrum of transcriptional states within a diseased tissue and revealing the impact of drug treatments on diseased cell-states as well as the cellular microenvironment and immune cell-types. Such insights can lead to single cell targeting of drug combinations to treat human disease as an essentially population level phenomena.

Methods

Mathematical Framework.

Two populations of cells, a reference population and a test population ($D^{ref}$ and $D^{test}$) were considered. Following profiling by single cell mRNA-seq, each population of cells is a set of gene expression vectors, $$D = \{g_i\}_{i=1}^k,$$

where k is the number of cells in the population, and $g=(g_1, g_2, \ldots, g_n)$, is an n dimensional vector that quantifies the abundance of each mRNA species. While raw mRNA-seq measurements generate integer valued gene count data, due to measurement noise and data normalization, g was considered to be embedded in an n dimensional Euclidean vector space, gene expression space, $g \in \mathbb{R}^n$. The high dimensional nature of gene expression space poses the key challenge for construction and interpretation of statistical models.

The gene expression vectors, $\{g_k\}$ are considered as being distributed according to an underlying probability density function, P(g), that quantifies the probability of observing a particular joint gene expression state, $g=(g_1, g_2, \ldots, g_n)$, in a given cell population. One goal was to estimate a statistical model of P(g), based upon single cell measurements. The model provides a parametric representation of the gene expression density in each condition. Then, this representation can be used to track changes in the structure of the cell population across conditions.

A mathematical challenge is model estimation in the high dimensional nature of gene expression space. For human cells n>20,000, and single cell profiling experiments can routinely probe 10,000 cells per sample. The number of parameters in the probabilistic models described herein scales quadratically with n, and mixture model learning has data requirements that are exponential in n. Therefore, the dimensionality of the problem was first reduced by building models in a common low dimensional space defined by gene expression programs discovered from pooled data across all samples.

Data Normalization.

Single cell gene expression data can be normalized to (1) to account for the variation in the number of transcripts captured per cell and (2) to balance the wide disparity in the scale of values across different genes due to measurement noise and gene drop-out.

The total number of transcripts captured for each single cell can vary from 1000 to 100,000 unique transcripts per cell. Technical variability in reagents and library prep steps can have a large impact on the number of transcripts retrieved per cell. To scale out these differences, each gene expression value $g_i$ was divided by the total number of transcripts and then multiply by a scaling factor $\beta$.

Additionally, across genes, mean transcript values can span 5 orders of magnitude. Transforming the data using the logarithm brings values across all genes close in scale, while also reducing the skew in the data distributions. The equation for transforming a raw gene expression value $g_i$ (for a single gene) into a normalized gene expression value, $g_i'$ is:

$$g_i' = \log\left(\beta \frac{g_i}{\sum_i^n g_i} + 1\right), \tag{2.6}$$

where n is the total number of genes, and $\beta$ is a scaling factor, and a 1 pseudo-count was added to each gene expression value. It was found that by setting $\beta=1000$ to be roughly the minimum number of total transcript counts in a cell (1000 transcripts), a smooth transition was achieved in the distribution of transformed $g'_i$ when raw $g_i$ values step from 0 to 1. Gene expression values are thus denoted in units of $\log(TPT+1)$ where TPT is transcripts per thousand.

Extraction of Gene Feature Vectors with Matrix Factorization.

The curse of dimensionality was circumvented by building models in a common low-dimensional space defined by gene expression features or programs. Mathematically, the transcriptional state of each single cell, g, was represented as a linear combination of gene expression feature vectors, $\{f_i\}$:

$$g = \Sigma_{i=1}^{m} c_i f_i, \qquad (2.7)$$

where $f_i \in R^n$ specifies a gene expression feature, and $c_i$ is a coefficient that encodes the weighting of vector $f_i$ in g, the gene expression state of a single cell. One major result in is that a cell's gene expression state, g can be represented as a linear combination of m gene expression module vectors, $f_i$ where $m \ll n$. This insight allows construction of a low dimensional representation of a cell population and, then, to estimate statistical models within the low dimensional space.

The gene features, $\{f_i\}$ can be extracted using a wide range of matrix factorization and machine learning techniques including Singular Value Decomposition, and its matrix factorization relatives like sparse PCA as well as methods like layered neural networks. A technique called orthogonal non-negative matrix factorization (oNMF) was used to define a space of orthogonal gene expression features vectors. Like other linear dimensionality reduction techniques, such as PCA, oNMF factors the original data matrix, $D^{train}$ (FIG. 19A) into two matrices $D \approx F$ C (FIGS. 19B-19C). Factorization occurs through minimization of an objective function with positivity and orthogonality constraints:

$$\arg \min_{F,C} \left\| D^{train} - FC \right\|_2 \qquad (2.8)$$

$$\text{subject to } F^T F = I, \, C_{ij} \geq 0, \, F_{ij} \geq 0,$$

The optimization minimizes the (Frobenius) norm of the difference between the training data, $D^{train}$, and its factored representation FC. The columns of F contain gene features, $f_i$. The matrix C is m by k, where k is the number of single cells in $D^{train}$. Each column of C encodes the weighting of the m gene features across a given single cell. The entries of F and C; are constrained to be positive, and the columns of F (the gene features) are constrained to be orthogonal. F is an n by m matrix (genes by features). Each column contains n weights where each weight corresponds to the weight of a given gene in that feature, $f_i$. Because feature vectors have positive entries, the gene expression state of a cell, g, can be considered as being assembled as a linear sum of positive gene expression programs.

In PopAlign, orthogonality in F is incorporated as a secondary constraint to aid interpretation. Empirically, it was found that orthogonality aids in interpretation of the features as well as in model construction because the orthogonal gene expression features are interpretable as non-overlapping sets of genes (FIG. 19B) that can individually be analyzed by gene set enrichment analysis (FIG. 19F) (see Methods—Gene Set Enrichment Analysis). Second, orthogonality tended to force individual cell states to be represented by more than one feature which aided stability during model parameter estimation.

To perform oNMF, m, the number of features to be extracted was selected through an optimization that balances accuracy and dimensionality explicitly. In oNMF (as opposed to PCA and SVD), m is a parameter given to the optimization. Choosing m involves balancing the tension between the "expressiveness" in the feature set and its dimensionality. Higher m reduces the error in the representation while also breaking up blocks of genes into smaller modules that represent independent gene expression pathways with finer granularity. However, as m increases, the typical computational and sampling challenges associated with high dimensionality emerge.

This tension was balanced in PopAlign by constructing a loss function with a penalty that increases with m:

$$\arg \min_m f(m) = \left\| D^{train} - F_m C_m \right\|_2 + m^\alpha. \qquad (2.9)$$

Figure 20:
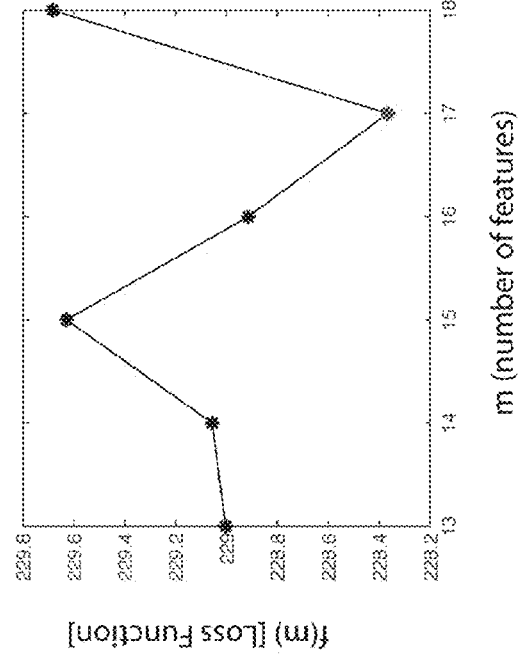
FIG. 20. Choosing dimensionality of feature set Plot of loss function for different feature sets, built by sweeping over many values of m (x-axis). Feature set with lowest loss is chosen. This example uses data from FIGS. 16A-16G. Loss function is a function of the residual error and a penalty on m. For loss function equation, see Methods—Extraction of gene feature vectors with matrix factorization.

For each value of m, oNMF was performed on $D^{train}$ yielding $F_m$ and $C_m$, and thus an error $\|D^{train} - F_m C_m\|^2$. This error is, then, incremented by the term ma which penalizes higher values of m and hence the dimensionality of the feature set. $\alpha=0.7$ was set based upon numerical experimentation on model data sets (FIG. 20). For any choice of m, the accuracy of the representation can be estimated by plotting reconstructed data FC (FIG. 19D) against normalized data D (FIG. 19A). FIGS. 19A and 19D show such plots and the PopAlign software package outputs these plots by default.

Practically, given data sampled a set of cell populations, (e.g., $D^{test_1}$, $D^{test_2}$, $D^{ref}$) data were pooled from all cell populations into a training data set, $D^{train}$, and oNMF was performed on $D^{train}$. In analyzing a large number of data sets or sets with many single cells, $D^{train}$ was generated by sampling 500-1,000 cells uniformly at random from the reference and test cell populations and selecting a m using Equation 2.9.

Because the feature vectors are not always purely orthogonal, the complete dataset was recast into the feature space using a non-negative least squares. Specifically, for each gene expression profile, $g_i$, $c_i$ is found via:

$$\arg \min_{c_i} \|g_i - F \, c_i\|_2 \qquad (2.10)$$

$$c_i \geq 0$$

where F is a fixed feature set learned from oNMF on $D^{train}$. The gene expression vector $g_i$ is thus compressed into a m-dimensional vector $c_i$ that provides a high-level programmatic representation of cell state in terms of gene expression "features." Finally, the biological meaning of the feature vectors was interpreted in terms of annotated gene expression programs using gene set enrichment analysis (see Methods—Gene Set Enrichment Analysis).

Using matrix factorization, a cell population, D={g_i}, was mapped from an n~20,000 dimensional gene expression space into a gene feature space that is often of order 10-20 dimensions $$D = \{g_i\} \rightarrow \{c_i\},$$

where $\{c_i\}$ are m×1 dimensional vectors that now represent the cell population in the reduced gene feature space.

Gene Set Enrichment Analysis.

To interpret the gene features in terms of annotated gene sets, gene set enrichment analysis was performed using the cumulative hypergeometric distribution. Each feature vector was defined by the collection of genes that have weightings greater than 4 times the standard deviation (>4σ). Using this collection of genes, the null probability of drawing k genes (P(X>k)) was then calculated from a specific annotated gene set using the hypergeometric cumulative probability distribution:

$$P(X > k) = \sum_{i=1}^{k} \frac{\binom{Y}{i}\binom{N-Y}{Z-i}}{\binom{N}{Z}},$$

where N is the total number of genes, Z is the number of genes in the feature that are >4σ, Y is the number of genes in each annotated gene set, and k is the number of genes that overlap with annotated gene set.

Gene sets are sorted by their associated null probability; the 10 gene sets with the lowest null probabilities are reported for each feature. The gene sets are pulled from GO, KEGG, and REACTOME. FIG. 19F shows an example of gene set enrichment results for two features.

oNMF Error Analysis.

The error associated with each feature set $F_m$ was assessed by comparing data entries between a cross validation dataset $D_x$ and its reconstructed matrix $F_mC_x$. The data in $D_x$ was binned into bins of equal width ~0.1 (in units of log(TPT+1)). Data values were retrieved from each bin, $(D_x)_{bin}$, and then their means were plotted against the means of corresponding data values in the reconstructed matrix, $(F_mC_x)_{bin}$ (FIG. 19D). The standard error in each bin is calculated as the mean squared deviation of the reconstructed data from the original data:

$$\sigma_{bin} = \sqrt{\frac{\sum_i^n ((F_mC_x)_i - (D_x)_i)^2}{n}}, \forall i \in bin$$

To quantify the amount of dispersion relative to the mean, the coefficient of variation for each bin was calculated:

$$CV_{bin} = \frac{\sigma_{bin}}{(D_x)_i}, \forall i \in bin$$

It was found empirically that the average CV is ~30-35% across all bins for most feature sets.

Representing a Cell Population as a Gaussian Mixture Model in Gene Feature Space.

Following the feature based representation, a statistical model of each was constructed given cell population within the reduced gene feature space. Mathematically, a probability distribution in gene expression space was exchanged for or transformed into a probability distribution in gene feature space:

$$P(g) \rightarrow P(c), \qquad (2.11)$$

where g is n×1 and c is m×1, and m<<n. A statistical model of P(c) can now be estimated.

To account for the heterogeneity of cell-states within a tissue, cell-populations were modeled using Gaussian mixture models. Gaussian densities provide a natural representation of a transcriptional state in gene expression space which is consistent with measured gene expression distributions as well as empirical models of transcription. Theoretical models of stochastic transcription commonly yield univariate gene expression distributions where mRNA counts are Poisson or Gamma distributed. Normal distributions provide a reasonable approximation to these distributions with a computationally tractable inference procedure.

The cell population was represented as a mixture of Gaussian densities, so that for a given cell population D, it was constructed:

$$\overline{P(c)} = \sum_{k=1}^{l} w_i \phi_i(c) \qquad (2.12)$$

$$\phi(c) = \mathcal{N}(c; \mu_i, \Sigma_i)$$

where $\overline{P(c)}$ is a mixture of Gaussian densities, $\mathcal{N}(c; \mu_i, \Sigma_i)$, with centroid, $\mu_i$; covariance matrix, $\Sigma_i$; and scalar weighting $w_i$. $\mu_i$ is a vector in the m dimensional feature space, and $\Sigma_1$ is a symmetric m×m matrix. l is the number of Gaussian mixtures or components in the statistical model. The Gaussian mixture model (GMM) represents a cell population as a mixture of individual Gaussian densities. Biologically, each density can be considered as parameterizing a subpopulation of cells.

The parameters $\mu_i$, $\Sigma_i$, and $w_i$ can be estimated based upon training data, using maximum likelihood estimation with likelihood function:

$$\mathcal{L}(\{\mu_i, \Sigma_i, \pi_i\} | D') = \sum_{j=1}^{k} \log P(c_j; \{\mu_i, \Sigma_i, w_i\}), \qquad (2.13)$$

where $c_j$ are single cell profiles drawn from a cell population D' and cast into feature space; k is the number of single cells in the cell population D'. For a given experimental data set, $\mathcal{L}$ defines a function over the space of model parameters. To select model parameters given data, the value of $\mathcal{L}$ was maximized. In general for Gaussian Mixture models, likelihood maximum is complicated by the geometry of $\mathcal{L}$ which is not concave and can have multiple local and global maxima. $\mathcal{L}$ can be maximized approximately using expectation maximization (EM).

Expectation-maximization is a heuristic algorithm that finds (local) maximum likelihood parameters. Although it is known to have fundamental problems—including weak performance guarantees and a propensity to overfit data, new methods place constraints that are invalid for the application described herein (such as shared covariance matrices). It was found empirically that the EM algorithm performs well, learning low-error representations of c (FIG. 20), and that fitting instabilities could be overcome by algorithmically merging components. Expectation maximization was performed using sci-kit learn. The variance of individual mixtures was regularized to constrain variance to be non-zero to avoid fitting instabilities. Mixtures number was determined through the Bayesian Information Criterion (BIC) which optimizes a trade-off between model complexity and accuracy on training data.

Merging of Redundant Mixture Components.

One drawback of the EM algorithm is its propensity to fit "redundant" mixture components to the same local density with significant overlap. For the application described herein, this redundancy complicates interpretation and comparisons across samples. This problem was overcome by taking advantage of mixture model properties to algorithmically merge redundant mixtures using the Jeffrey's divergence.

For multivariate Gaussian distributions, the Jeffrey's divergence has a closed analytic form.

$$D_{JD}(\phi_i\|\phi_j) = \frac{1}{2}(D_{KL}(\phi_i\|\phi_j) + D_{KL}(\phi_j\|\phi_i)), \quad (2.14)$$

where $\phi_0$ and $\phi_1$ are two independent components from the same mixture model, and $\mu$ and $\Sigma$ are their associated parameters. $D_{KL}$ is the Kullback Leibler divergence and has a convenient parametric form for Gaussian distributions:

$$D_{KL}\left(N_i\left(c;\mu_i,\sum_i\right)\middle\|N_j\left(c;\mu_j,\sum_j\right)\right) =$$
$$\frac{1}{2}\left(tr\left(\sum_i^{-1}\sum_j\right) + (\mu_i-\mu_j)^T\sum_i^{-1}(\mu_i-\mu_j) - k + \ln\left(\frac{\det\sum_i}{\det\sum_j}\right)\right).$$

For each mixture model, iterative attempts were made to merge component pairs with the lowest Jeffrey's divergence and mergers that increase the BIC of the model given the data were accepted. With each merge step, model parameters for candidate pair are recalculated, and the updated model is accepted or rejected based on the new BIC. Mergers are performed until the first rejection. This procedure removes redundant mixture components from the model.

Sampling Data from Gaussian Mixture Models.

Given parameters, $$\left\{\left(\mu_i,\sum_i,w_i\right)\right\}_{i=1}^l$$

for a given mixture model. synthetic data can be generated from the model through a simple sampling procedure. A given model has, l mixtures, and a mixture from the set of l mixtures was first selected with probabilities weighted by $w_i$. Following selection of a mixture, j, standard methods were used to draw a "point" in the m dimensional feature space from $N$ (c, $\mu_j$, $\Sigma_j$).

Analysis of Model Error.

Model error was assessed by comparing the distribution of model generated data to the empirical data. To avoid under-sampling, error analysis was performed within two dimensional projections of the data and averaged error over all 105 projections. Briefly, each projection was binned into 25 bins. In each bin, the deviation between the model generated data and empirical data was calculated in terms of percent error in each bin. Total error within each projection was calculated as a weighted average of this percent error over all bins in a projection:

$$error = \sum_i \frac{N_i}{N_T}\frac{|N_i-\hat{N}_i|}{N_i},$$

where $N_i$ is the number of experimental data points in bin i, $\hat{N}_i$ is the number of model generated data points in bin i and, $N_T$ is the total number of experimental data points. This metric weights the per-bin fractional error by the probability density of each binned region in the projection.

Alignment of Models Across Reference and Test Populations.

To compare the test and reference models, each mixture component in the test population model, $$\phi_i^{test}(c) \in \{\phi_i^{test}(c)\},$$

was aligned to a mixture component, $$\{\phi_i^{ref}(c)\},$$

in the reference population model (FIG. 19C). Alignment was performed by finding the "closest" reference mixture in gene feature space. Mathematically, to define closeness, Jeffrey's divergence, a statistical metric of similarity on probability distributions was used. Specifically, for each $$\phi_i^{test} \in \{\phi_i^{test}(c)\}, \text{ an } \phi_j^{ref} \in \{\phi_j(c)\}^{ref},$$

the closest mixture in the reference set, was found:

$$arg\min_{\phi_j^{ref}(c)\in\{\phi_j^{ref}(c)\}}D_{JD}\left(\phi_i^{test}(c)\middle\|\phi_j^{ref}(c)\right), \quad (2.15)$$

where the minimization is performed over each $$\{\phi_i^{ref}(c)\}$$

in the set of reference mixtures, and $D_{JD}$ is the Jeffrey's divergence (JD). Intuitively, for each test mixture, the reference mixture $\phi_j$ that is closest in terms of position and shape in feature space was found.

For each alignment, an explicit p-value was calculated from an empirical null distribution $P(D_{JD})$ that estimates the probability of observing a given value of $D_{JD}$ in an empirical data set of all subpopulation pairs within a single cell tissue database. Aligning subpopulations using Jeffrey's divergence incorporates information about the shape and position of the probability distributions (i.e., covariance), while disregarding the relative abundance of each subpopulation.

Scoring Alignments.

To assign a p-value to alignments, the probability of observing two cell-states with a given Jeffrey's divergence by chance was calculated using an empirical null distribution generated from the tissue data set. Specifically, a mixture model for all tissue pairs was constructed in Tabula Muris. Then, all pair-wise Jeffrey's divergence scores were calculated for all the underlying mixtures. This calculation provided a global distribution over $D_{JD}$ for cell-states in the mouse. This distribution provided a null distribution for typical statistical closeness between cell-states in feature space.

Model Interpretation Through Parameter Analysis.

Following mixture alignment, quantitative differences in mixture parameters between the reference and test sample were analyzed to track shifts in gene expression state, gene expression covariance, and cellular abundances across the identified cell-states in the cell population.

Specifically, for each aligned mixture pair, $$(\phi_i^{test}, \phi_j^{ref})$$

with parameters $$\{\mu_i^{ref}, \Sigma_i^{ref}, w_i^{ref}\} \text{ and } \{\mu_j^{test}, \Sigma_j^{test}, w_j^{test}\},$$

the below were calculated:

$$\Delta\mu_i = \|\mu_i^{ref} - \mu_j^{test}\|_2,$$
$$\Delta\Sigma_i = D_C(\Sigma_i^{ref}, \Sigma_j^{test}), \text{ and}$$
$$\Delta w_i = |w_i^{ref} - w_i^{test}|,$$

where $\Delta\mu_i$ measures shifts in mean gene expression; $\Delta w_i$ quantifies shifts in cell-state abundance; $\Delta\Sigma_i$ quantifies shifts in the shape of each mixture including rotations and changes in gene expression variance. These shift parameters were calculated for all mixture pairs, and the shifts were analyzed to assess the impact of signaling conditions or environmental changes on the underlying cell population.

$$D_C(\Sigma_i, \Sigma_j) = \sqrt{\sum_{z=1}^m \ln^2 \lambda_z(\Sigma_i, \Sigma_j)},$$

where $\lambda_z$ is a generalized eigenvalue of $\Sigma_i$ and $\Sigma_j$ or a solution to $\Sigma_i$ v=$\lambda_z \Sigma_j$v, and m is the number of gene features.

Classification of Mixtures Using Marker Genes.

For the Tabula Muris data set, cells and mixtures were classified using cell-type annotations provided by the study. Mixtures were classified according to the cell-type with the maximum abundance within a given mixture (FIGS. 14A-14C).

For immune cell experiments, the independent mixture components were classified as effector T cells (CD3+/CD57+), naive T-cells(CD3+/CD28+), erythrocytes (HBB+), canonical monocytes (CD14+/CD16low), and non-classical monocytes(CD14low/CD16++) (FIG. 16E). Populations in the test samples—GM-CSF (FIG. 16B) and IFNG (FIG. 15C)—were aligned to the reference populations (control) by finding pairs of components that minimize the Jeffrey's divergence (FIG. 16D).

Software Implementation.

PopAlign has been implemented within the LOWMIX software infrastructure package described herein. It is written in Python3 and requires common scientific computing libraries (numpy, matplotlib, pandas, seaborn, tables, MulticoreTSNE, adjustText) that can be easily installed with pip and the requirements file. A guide on how to get set up and install dependencies is provided on the package's Github page. The software runs on local machines, as well as on Amazon Web Services headless EC2 instances, providing a powerful setting for large-scale analyses. The architecture of this package is built around classes that store experimental samples as objects and provide a set of specific methods to perform tasks such as normalization, dimensionality reduction, model construction, model alignment, and parameter comparison.

Experimental Methods

Single-Cell RNA-Sequencing.

Cryopreserved PBMCs (healthy and disease samples) from Hemacare were thawed in a 37° C. waterbath for 2 minutes after which the cells were transferred to a 15 mL conical tube. Prewarmed RPMI 1640 was then added to the 15 mL conical to a final volume of 10 mL and centrifuged for 2 minutes at 300RCF to pellet the cells. Supernatant was removed and cells were resuspended to 1 million cells/mL in RPMI1640 supplemented with 10% FBS and 17,400 cells were loaded into each TENX lane.

PBMC Signaling Experiment.

Cryopreserved PBMCs sourced from Hemacare (~10 million cells, source ID: D23127, Lot: 17043194) were thawed in a 37° C. waterbath for 2 minutes after which the cells were transferred to a 15 mL conical tube. Prewarmed RPMI1640 was then added to the 15 mL conical to a final volume of 10 mL and centrifuged for 2 minutes at 300RCF to pellet the cells. Supernatant was removed and cells were resuspended in 10 mL of RPMI1640 supplemented with 10% FBS and 1% pen/strep. The cell suspension was then plated onto a 100 mm low attachment plate and placed in a CO2 incubator at 37° C. for 5 hours for the cells to recover.

For each condition, 700,000 cells were aliquoted into a well of a 96 well plate. These cells were cultured for 13 hours under two different conditions: 1) IFN-γ@ 1 ng/mL, 2) GM-CSF 1 ng/mL, each with a single additional replicate. After incubation, the plate was sealed with an aluminum adhesive and centrifuged for 3 minutes at 300RCF. Supernatant was removed and replaced with 40 μL of TrypLE and incubated for 2 minutes before transferring cells to two 1.5 mL Eppendorf tubes, one for each culture condition.

Both tubes were centrifuged and the cells were resuspended to 5 million cells/mL in PBS+1% FBS. 180 μL from each cell suspension processed using BDgenomic's multiplexing kit and 8,000 cells from each condition were combined and run through a single TENX lane.

Example 3

PopAlign Identifies Novel Mechanism of Immunomodulatory Compounds in 96-Plex Drug Screen A key application of PopAlign (See Example 2 for details) is to study heterogeneous cell populations from the human body as they respond to environmental change, drug treatments, and disease. The human immune system is an important application domain for PopAlign as an extremely heterogeneous physiological system that is central for disease and cell engineering applications. Being able to screen the effects of different drugs on complex immune cell populations, and understand how they affect cell function, is important to design drug therapies for disease treatment. Thus, a 96-plex screen of immunological compounds was performed on human immune cells and PopAlign was used to discover how compounds affect distinct subpopulation in terms of gene expression.

It was found that a class of commonly used glucocorticoid drugs generate a new population of monocytes that permanently suppress genes involved in neutrophil recruitment. PopAlign enabled discovery of this by providing a framework to drill into the data hierarchically, first by (1) using quantitative statistical metrics to rank samples and identify interesting drug hits, and then (2) dissecting the impact of these hits on subpopulation composition and gene expression programs.

The screen was performed using 42 drugs from a commercially available compound library (Selleck Chem) on peripheral blood mononuclear cells (PBMCs) from a healthy 22-year old male donor. A part of the design of this experiment was that the drugs were tested in both a quiet and an activated signaling context because many drugs inhibit an inflammatory response, and thus an inflammatory response is to be activated to observe the effects of these drugs. For the quiet context, a basal medium (10% FBS in RPMI) in which PBMCs are known to persist but not proliferate was used. For the activated context, CD3/CD28 Antibody conjugated beads, which are known to activate T-lymphocyte killing programs and promote T-lymphocyte proliferation, were used. Cells were incubated in drugs and signals for 24 hours before pooling using a lipid-based experimental multiplexing technique (Multi-Seq), and then assayed by standard single-cell profiling techniques.

Figures 33A, 33B, 33C:
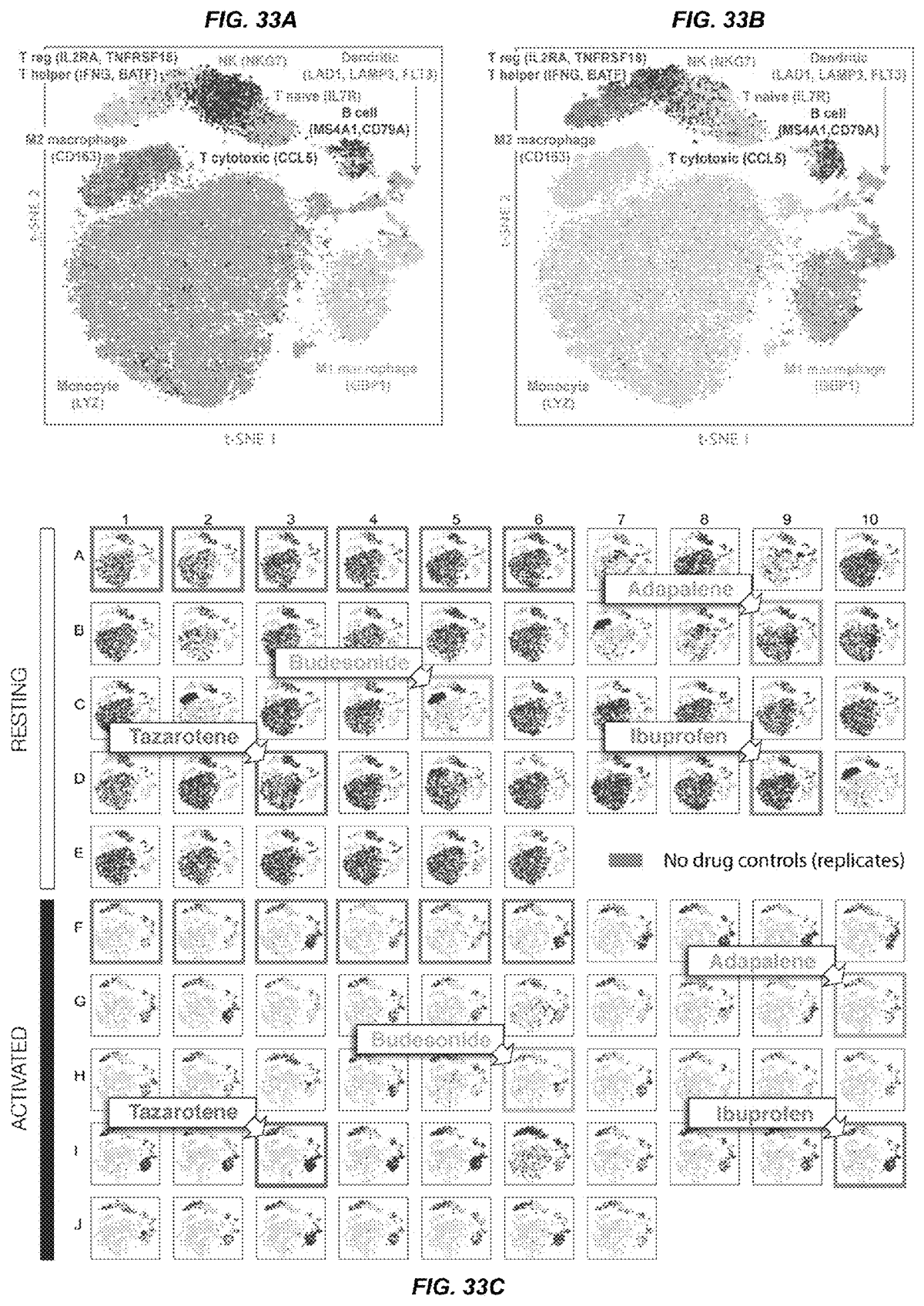

First, the probabilistic modeling framework described herein was used to identify hits by ranking all of the experimental samples in terms of a likelihood metric. A probabilistic model of the control population was built, separately for the quiet (FIG. 32A-32I) and activated (FIGS. 33A-33C) contexts. The control model was then used to calculate for each drug sample, a mean likelihood value $L(\theta_{ctrl}|D_{drug})$, which serves as a quantitative measure of how similar the drug-exposed cells are to the control sample. By ranking these likelihood scores, it was found that the biggest hits included a group of corticosteroid drugs known to impact the glucocorticoid receptor, in both the activated and the quiet contexts (compounds labeled in pink in FIGS. 34A-34D).

Next, to identify whether these drugs altered PBMCs by modulating population structure or by directly affecting gene expression, the subpopulation structure across all drug conditions was first examined by conducting a "query" operation in the PopAlign framework [See Methods—Query in Example 2]. For the "query" operation, a subsample of data pooled across experiments was used to build a global probabilistic model that can be used to dissect into distinct subpopulations. Then by scoring individual samples against subpopulation models, an abundance vector was computed for each drug sample.

Example 4

Combinatorial Signals Steer the Population Structure of Stem Cells Along a Single-Cell Reference Atlas The ability to grow and manipulate functional stem cells is fundamentally important for cell-based therapeutics.

However, there is a very limited understanding of in vitro stem cells growing in culture compared to stem cells residing within living tissues. This example illustrates using single-cell RNA-seq to profile cultured neural stem cells and comparing these lab-grown cells against a reference atlas of the developing brain. A probabilistic modeling analysis framework was used for analysis, which provided quantitative statistical metrics for comparing heterogeneous populations of cells. Although many progenitor states were present in the developing brain, only a major dominant population persisted in culture long-term. This example shows that this diversity was only progressively lost in culture, with the alternative neuroblast population giving way to the dominant stem cell state over seven days of growth. By screening over 20 combinations of additional signals, conditions that reshape population structure by shifting the relative abundances of progenitor subpopulations were identified. Importantly, the addition of BMP4 caused the dominant stem cell population to become more in-vivo like, by rejuvenating the expression of genes lost in culture as well as cortical layer-specific genes. The results show how signaling molecules can selectively amplify specific cell states within a stem cell population, altering population structure, and causing transcriptional shifts that impact the differentiation potential of the population.

The ability to derive, grow, and manipulate functional stem cells from natural mammalian tissues is a fundamental building block in regenerative medicine. Manipulating cells in artificial environments enables amplifying their numbers, steering their fates using signals and drugs, and engineering their genomes to correct mutations or to endow cells with novel functions before re-transplantation into a patient. However despite decades of research, the precise and quantitative control over stem cell derivation and differentiation remains a fundamental challenge.

Historically, engineered stem cells were either assessed by complex functional assays that are difficult to scale, or a limited number of single marker genes that are often unreliable and fail to describe the functional state of the cell. Single-cell RNA-sequencing technology allows the measurement of 20,000-dimensional transcriptional profiles of single cells. This technology has enabled the construction of high-resolution molecular maps of cellular states within complex tissues, thus providing precise transcriptional definitions of cellular phenotypes found in vivo.

This example illustrates a paradigm in which single-cell atlases were used as reference maps to understand and control heterogeneous stem cell populations in vitro. A single-cell atlas from the natural tissue provided a dictionary of cell states, as well as information about lineage relationships and the activity of signaling pathways. A mathematical framework that uses probabilistic models to describe complex cell populations in gene expression space was developed. The models provide statistical metrics for aligning in vitro populations to the reference maps to associate transcriptional states between natural and laboratory systems. This framework was used to define transcriptional states that occur in vivo and to compare the population structure of the natural and lab system. Signaling interventions were used to learn how to steer in vitro cell population relative to the reference atlas.

The paradigm used in this example can be applied to any stem cell population and reference atlas. In this example, the paradigm was applied to a canonical model system: mouse neural stem cells compared to states present in the developing brain. Applying this method to neural stem cells, the fundamental importance of population structure for stem cell function was discovered. Although the developing brain contained diverse progenitor states that give rise to mature cell types, only a single dominant stem cell population persisted in culture. This in vitro population showed loss in a diverse set of functions including genes driving both neuronal and glial differentiation, compared to the living stem cell population in the brain. A timecourse of cells in culture showed that the collapse of diversity to this dominant state happened progressively over the span of seven days, while the alternative neuroblast state slowly fades away.

To determine whether and how these states can be manipulated, 20 different combinations of canonical signaling factors added during the NSC derivation process were screened. Titrating in three factors (EGF, FGF, BMP4) shifted the population structure towards the alternative neuroblast state by changing the relative abundances of neuroblasts and progenitor cells. Importantly, although the addition of BMP4 reduced the relative proportion of stem cells, these cells were rejuvenated in their expression of neuronally important genes, including genes known to be specific to distinct layers of the mature cortex. These results highlight the transcriptional diversity existing in stem cell populations within developing embryos, and the importance for analyzing, tracking, and manipulating population structure in vitro.

Mapping Neural Stem Cells to a Neurodevelopmental Cell Atlas

First, commercially available neural stem cells grown in vitro (ivNSCs) were compared to their corresponding in vivo states, by seeing where inNSCs fall on a reference map of cells from the developing mouse brain. Using single-cell profiling methods, a reference map was constructed using cells from the developing mouse brain at four different developmental stages: embryonic day 15 (E15), embryonic day 18 (E18), postnatal day 4 (P4) and also cells from the adult cortex at 8 weeks (AdCo) (FIG. 35A).

Visualized on a low-dimensional PCA projection (FIG. 35B), this developmental reference map was seen to be comprised of three main branches. To orient around this map, publicly available annotated data (FIG. 35C) was used to classify all of the cells in the data. The three branches are marked by the major neural lineages of the brain (neurons, astrocytes, and oligodendrocytes). Importantly, these three main terminal branches stem from progenitor states that form a broad cup-like structure, suggesting high variability within the progenitor populations.

To compare cells against the reference map, the population on the reference map to which ivNSCs correspond most closely needed to be determined. To do this, a probabilistic modeling framework was used to dissect each dataset into a set of distinct subpopulations that were modeled by local probability densities (FIG. 35D). These densities were mapped in a low-dimensional linear feature space determined using orthogonal nonnegative matrix factorization (NMF), which mapped blocks of co-expressed genes onto linear basis vectors (FIGS. 40A-40C—model building and feature space). Once the Gaussian mixture models were constructed, the models can then be aligned across datasets by determining pairs of subpopulations across datasets which have the minimum statistical divergence (FIG. 35E) [See Method—Probabilistic models and alignment in this example]. In this example, the term population is used to refer to the overall density of the entire population within an experimental sample, and the term subpopulation is used to refer to a local density and its associated cluster of cells.

Using this framework, many features were discovered. ivNSCs were found to be aligned most closely to a population of cells from the E18 brain (pop1) (FIG. 35F) which was confirmed by their gene expression patterns. Gene expression pattern across all subpopulations in the E18 brain as well as in vitro neural stem cells were examined, using a mixture of established markers from the literature as well as genes extracted using unsupervised clustering. The analysis split the E18 brain into three categories that describe known states in the literature: radial glia-like neural progenitors (PAX6, FABP7 (also BLBP), SLC1A3 (also GLAST), SOX2), neuron-committed neuroblasts (SOX4, SOX11) and also an intermediate state expressing both sets of markers. Using the alignment approach, the ivNSCs were found to align most closely to the radial-glia like neural progenitors from brain, which is confirmed by the gene expression program (FIG. 35G).

In Vitro Neural Stem Cells Lost Population Entropy and Core Neural Functions

However, ivNSCs were seen to have considerable deficiencies relative to the in vivo Neural Progenitors (NProgs) (FIGS. 36A-36I). The PopAlign framework revealed that the subpopulation of ivNSCs was much less diverse than its corresponding E18 NProgs using two measures.

First, the models allowed quantifying the heterogeneity of these tissues and cell types through the entropy measure. Entropy is a statistical measure from information theory that describes the average information content of each observation. As measured in bits, the quantity describes the average number of possible states that a system can take on. Entropy is defined as $\Sigma P \log(P)$, and for an entire population, both an analytical upper bound, as well as an empirical estimate can be computed. The entropy of each subpopulation, modeled as an independent Gaussian, has an exact analytical solution which was computed directly.

Figure 36B:
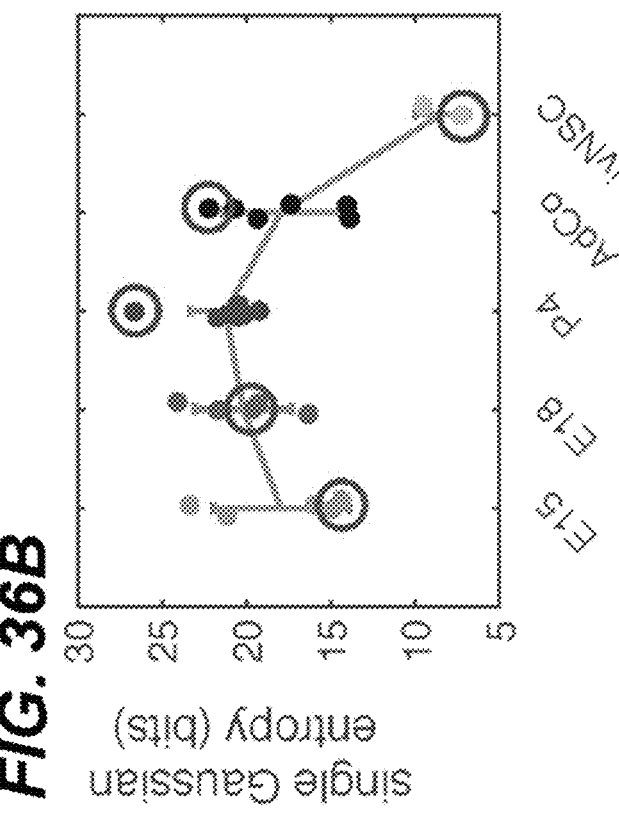
Figure 36A:
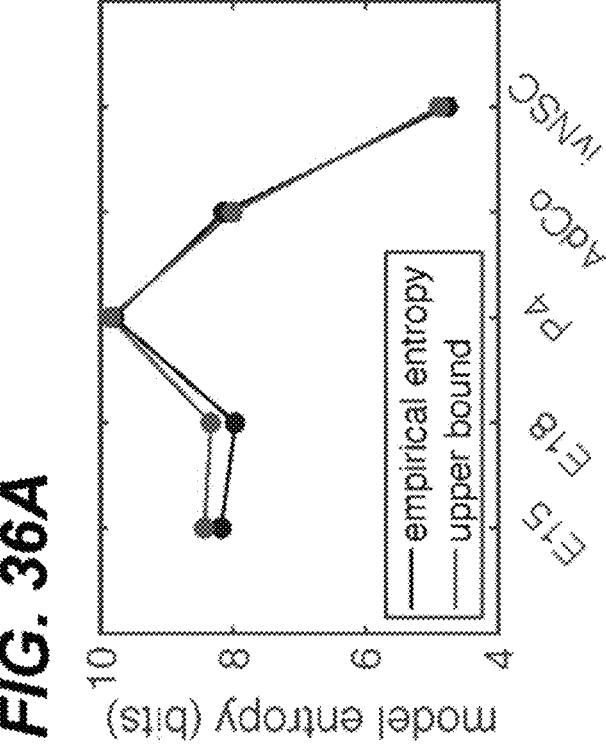
Figures 36C, 36D:
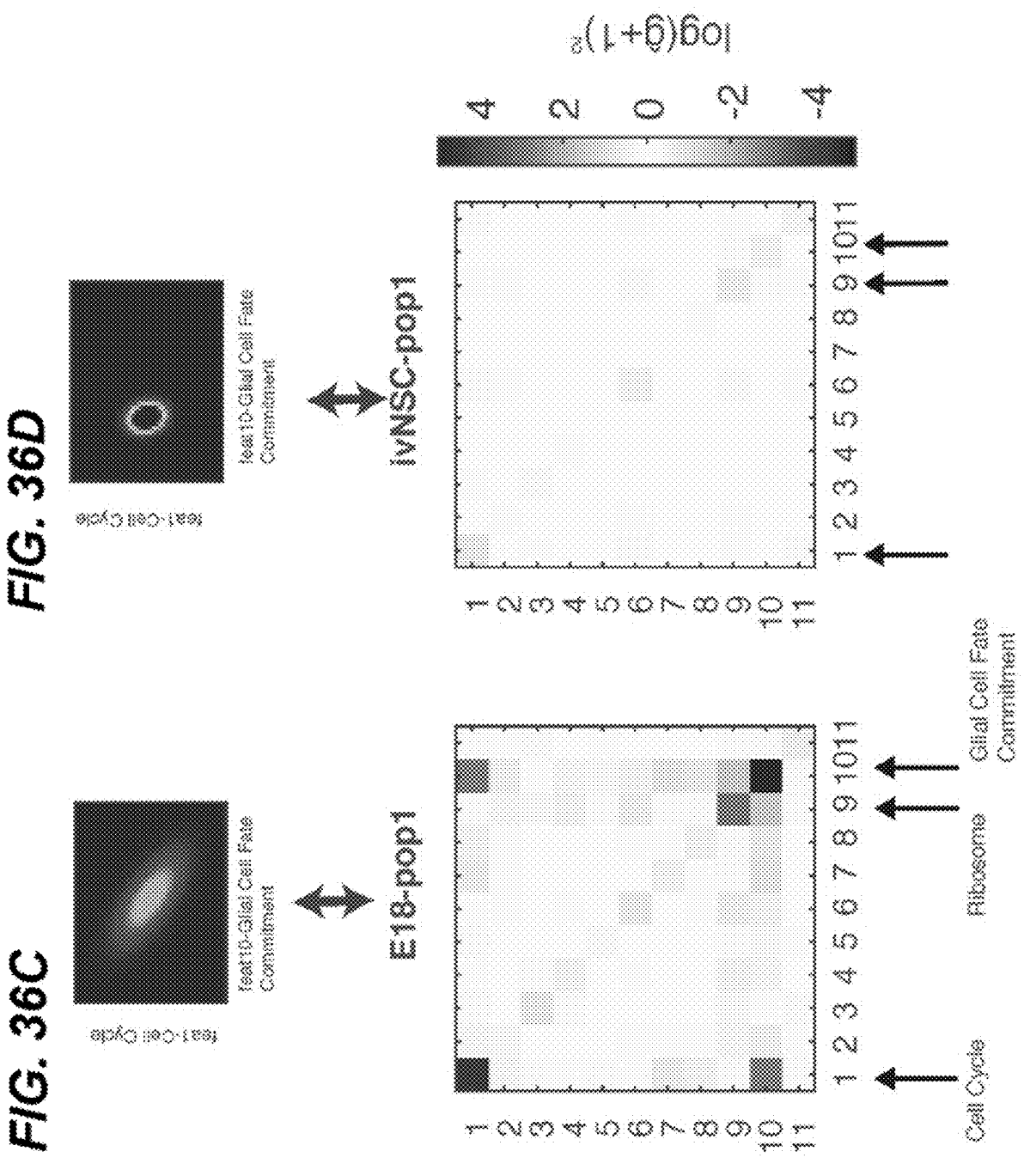
Figure 36F:
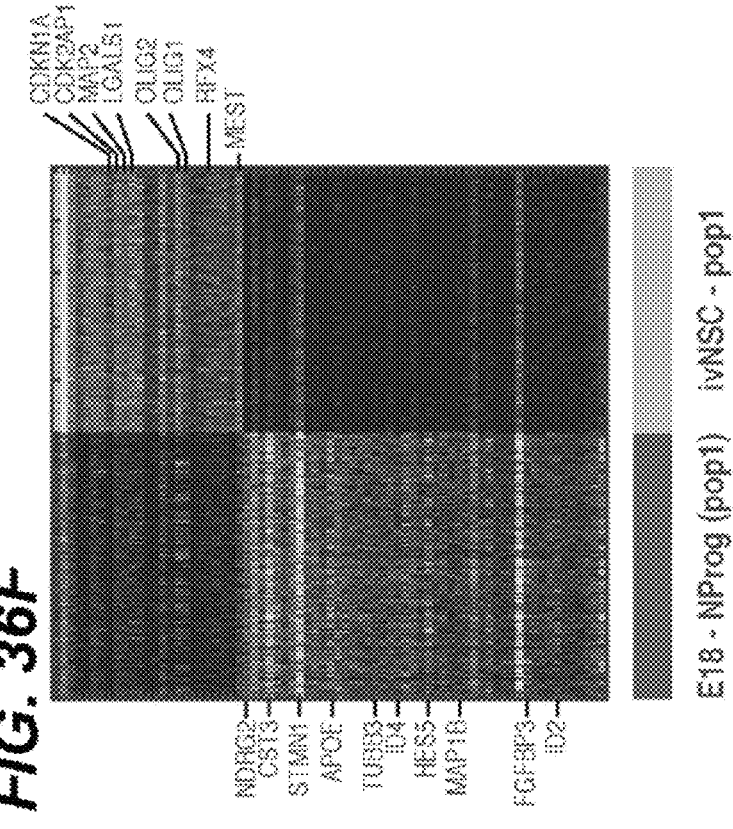

A tissue with high entropy encodes a larger range of possible cell states than a tissue with lower entropy. Since the ivNSC culture included only one cell type, it is unsurprising that the entropy of the entire ivNSC population (FIG. 36A) was much lower than the entropies of the populations at four stages of brain development, which naturally contained a multitude of cell types. However, even at the subpopulation level, the corresponding neural progenitor cells from the in vivo tissues had much higher entropy than the ivNSC population (FIG. 36B).

Secondly, the in vivo Nprog population was seen to be more diverse by examining the covariance matrix $\Sigma$, that parameterizes the subpopulation within the model. Each diagonal value in $\Sigma$ indicates the subpopulation variance along a specific feature. Examining the $\Sigma$ for Neural Progenitors, $\Sigma$ was observed to have high variances for the Cell Cycle and Glial Fate Commitment features, while the $\Sigma$ for ivNSCs had low values along all features. This showed that the ivNSC population was very narrowly focused around its mean, while the NProgs had high variance along many features. The tight distributions of ivNSCs can also be seen in arrayed pairwise scatterplots of the cells across all features (FIG. 41B). By contrast, NProg populations had higher dispersion in Features 1, 9, and 10 (FIG. 41A).

Figure 36E:
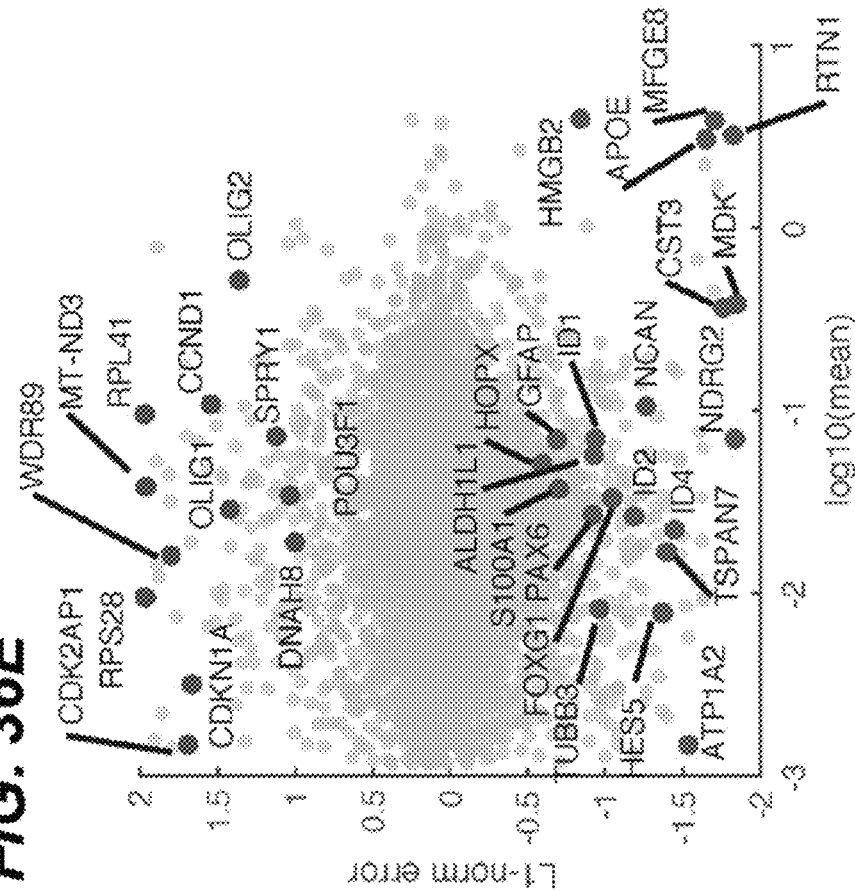
Figure 36I:
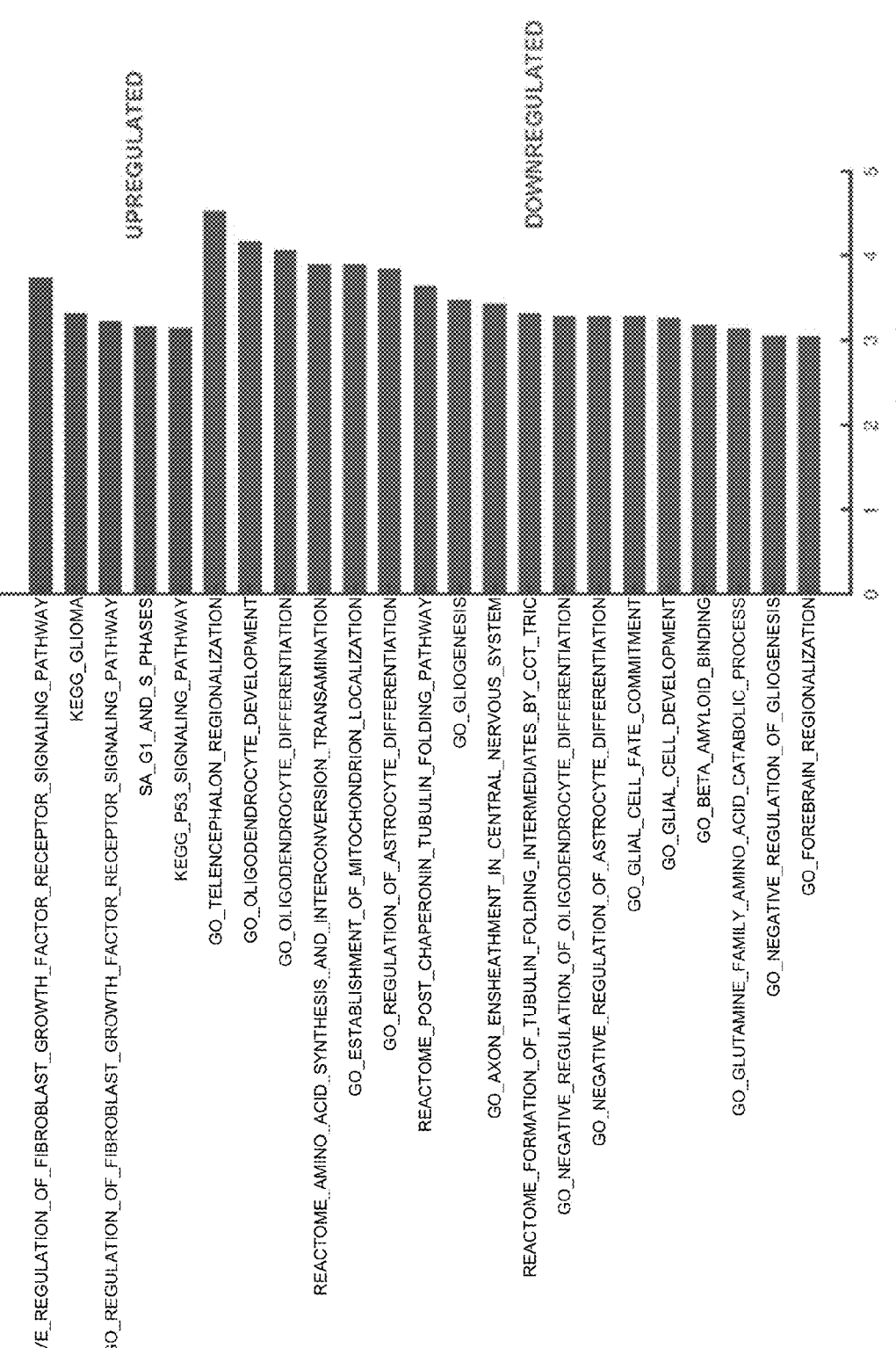

Finally, large shifts were seen in the specific genes that are regulated. An L1-norm metric was used to find genes that differ between the two states [See Method—L1-norm error metric in this example] (FIG. 36E). Roughly 174 genes were upregulated in ivNSCs relative to the E18 population, while 190 genes are downregulated (Tables 3.1A-3.1B). Gene set enrichment analysis (FIG. 36I) of the genes upregulated by ivNSCs showed that many are related to FGF signaling, metabolism, or cell cycle (such as CDKN1A, CDK2AP1, CCND1, TOP2A). The main exceptions were OLIG1 and OLIG2 which are transcription factors associated with both oligodendrocyte and neuron differentiation, and whose upregulation in neurospheres has been previously reported.

However, the genes that were downregulated in ivNSC have diverse functional roles in the brain (FIG. 36E). These include neural stem cell quiescence markers (ID1,ID2, ID4, HOPX, HES5), Neuronal differentiation genes (DCX, NEUROG2), astrocytic genes (ALDH1L1, GFAP, S100A1), Ion channels and transporters (ATP1A2), neurite-promoting factors (MDK, NDRG2, TSPAN7, NCAN, netrin G1 (NTNG1)), and many signaling pathways (PDGFRB, NOTCH2, DKK1) (Tables 3.2A-3.2B, FIGS. 36E-36G). Gene set enrichment analysis showed that programs which get downregulated in vitro include programs for amino acid synthesis (such as for neurotransmitter production), repression of astrocyte and oligodendrocyte differentiation, as well as programs involved in tubulin folding, which is a vital component of neuron cytoarchitecture. Taken together, these results indicate that there was mainly loss of functionally important programs when ivNSCs were grown in an artificial environment.

FIGS. 41A-41B illustrate non-limiting exemplary arrays of 2D renderings of data from E18 and ivNSC samples showing that ivNSCs were less heterogeneous in the feature space. FIG. 41A show that E18 data with NProg cells (pop1) highlighted. FIG. 41B ivNSC data with corresponding subpopulation (pop1) highlighted. For each plot tile, the feature number is displayed on the axis. Corresponding plots in both arrays are matched in terms of both the x- and y-axis scale.

TABLE 3.1A

| Downregulated genes of ivNSC vs. E18-pop1 | |
| --- | --- |
| MDK | −1.8444227 |
| NDRG2 | −1.833403 |
| RTN1 | −1.8225753 |
| CST3 | −1.7562677 |
| UBB | −1.7202939 |
| MFGE8 | −1.7020649 |
| PHGDH | −1.6970394 |
| APOE | −1.6460574 |
| FXYD6 | −1.639113 |
| NNAT | −1.6379822 |
| CD9 | −1.6374135 |
| GM17750 | −1.6272412 |
| PTN | −1.6270243 |
| STMN1 | −1.6195957 |
| TUBA1A | −1.6182937 |
| H1F0 | −1.6032581 |
| MMD2 | −1.597305 |
| TUBB2B | −1.5885173 |
| ATP1A2 | −1.533517 |
| RLBP1 | −1.5290786 |
| FAM210B | −1.5169305 |
| TTYH1 | −1.495067 |
| PFN2 | −1.477295 |
| NDN | −1.4761207 |
| FEZ1 | −1.4735738 |
| GSTM5 | −1.4592442 |
| ID4 | −1.4442175 |
| ACOT1 | −1.4295682 |
| TSPAN7 | −1.3984762 |
| LHX2 | −1.3931535 |
| MT2 | −1.3930941 |
| PPP1R1A | −1.3823074 |
| CNN3 | −1.3753084 |
| HES5 | −1.3690765 |
| TST | −1.3689143 |
| ITM2B | −1.3451505 |
| DDAH1 | −1.3329703 |
| SFRP1 | −1.328205 |
| EIF1B | −1.3268026 |
| CTSL | −1.3103896 |

TABLE 3.1A-continued

| Downregulated genes of ivNSC vs. E18-pop1 | |
| --- | --- |
| MAP1B | −1.2878956 |
| SERPINH1 | −1.2838958 |
| SCP2 | −1.2791971 |
| PAFAH1B3 | −1.2775498 |
| MFAP2 | −1.2714071 |
| NCAN | −1.2671494 |
| MT3 | −1.2620781 |
| PDPN | −1.2580622 |
| GNAO1 | −1.2520793 |
| FGFBP3 | −1.2448563 |
| CCDC80 | −1.2439037 |
| ENO1 | −1.2437326 |
| SLC9A3R1 | −1.2378252 |
| PDIA6 | −1.2236281 |
| BEX1 | −1.2191826 |
| ADH5 | −1.2024249 |
| OAT | −1.1972942 |
| SCRN1 | −1.1950212 |
| SLC1A3 | −1.1918895 |
| ACAT2 | −1.1886663 |
| ID2 | −1.1886182 |
| TRIM2 | −1.1766162 |
| PRKCDBP | −1.1744461 |
| CLU | −1.172598 |
| HIST3H2BA | −1.16948 |
| ALDOC | −1.1667548 |
| TSPAN13 | −1.162579 |
| JUN | −1.156841 |
| FABP7 | −1.1490237 |
| ASRGL1 | −1.1421798 |
| PGRMC1 | −1.1416705 |
| TSC22D1 | −1.1415998 |
| LDHB | −1.1369831 |
| MEIS2 | −1.1322018 |
| PRDX4 | −1.1239965 |
| PSPH | −1.1234415 |
| SAP30 | −1.1183975 |
| DBN1 | −1.1181485 |
| CYB5A | −1.1145213 |
| HMGN2 | −1.1073072 |
| ATXN10 | −1.1059297 |
| SLCO1C1 | −1.1046342 |
| MID1IP1 | −1.1026655 |
| TKT | −1.0924956 |
| HSD17B10 | −1.0903872 |
| HBB-BS | −1.0900099 |
| VCAM1 | −1.0895577 |
| GLUD1 | −1.0880548 |
| NFIX | −1.0866179 |
| EZR | −1.0844751 |
| MAGED2 | −1.0785404 |
| GPX8 | −1.0728113 |
| ECI2 | −1.0594229 |
| TUBB3 | −1.0516924 |
| FOXG1 | −1.049013 |
| UBC | −1.048168 |
| IDH2 | −1.0369451 |
| DMRTA2 | −1.0367894 |
| EFHD2 | −1.0319421 |
| SIN3B | −1.0309052 |
| CBS | −1.0284812 |
| IGFBPL1 | −1.0281134 |
| CDH2 | −1.0263342 |
| HMGCS1 | −1.0248813 |
| PDLIM4 | −1.0148368 |
| PTBP2 | −1.0108417 |
| UCHL1 | −1.0100787 |
| SAR1B | −1.0088819 |
| MPPED2 | −1.0050098 |
| SLC1A2 | −1.0039086 |
| PTX3 | −0.9964319 |
| KCNE1L | −0.9956118 |
| 2310022B05RIK | −0.9951893 |
| FSTL1 | −0.9878201 |
| KCNK2 | −0.984446 |
| PLPP3 | −0.981609 |
| PSMC5 | −0.9729652 |
| AI854517 | −0.9724327 |

TABLE 3.1A-continued

| Downregulated genes of ivNSC vs. E18-pop1 | |
| --- | --- |
| YPEL3 | −0.9716287 |
| EMID1 | −0.9714047 |
| PPP2R2B | −0.9696023 |
| SOX9 | −0.9636201 |
| PYGB | −0.9583497 |
| DHRS1 | −0.9571208 |
| D030056L22RIK | −0.9548502 |
| PDCD10 | −0.9537081 |
| DOK5 | −0.9521933 |
| GABBR1 | −0.9513596 |
| 6330403K07RIK | −0.9510672 |
| SCRG1 | −0.9483991 |
| EPHA4 | −0.9481661 |
| PCBP4 | −0.9471155 |
| RRAGA | −0.9458248 |
| GRB10 | −0.9436202 |
| ADGRB1 | −0.9436089 |
| ID1 | −0.9405182 |
| CYR61 | −0.9383617 |
| APRT | −0.938001 |
| ALDH1L1 | −0.9301837 |
| OXCT1 | −0.9289322 |
| NKAIN4 | −0.927591 |
| UBALD2 | −0.9259991 |
| ATP1B1 | −0.9193287 |
| TGFB2 | −0.9176291 |
| PSMC2 | −0.9164733 |
| EFNB1 | −0.9143465 |
| CDO1 | −0.9114704 |
| UNC119 | −0.9051019 |
| SAE1 | −0.9042842 |
| RCN3 | −0.9042313 |
| TPRGL | −0.8956243 |
| E130114P18RIK | −0.8932966 |
| REEP5 | −0.8879466 |
| CLIP3 | −0.8861098 |
| HTRA1 | −0.8859018 |
| MYL12B | −0.8825212 |
| ALDH7A1 | −0.8763487 |
| DARS | −0.8757664 |
| POLR3H | −0.87467 |
| PAX6 | −0.872356 |
| CTSB | −0.8698638 |
| TUBB2A | −0.866725 |
| MPST | −0.8658294 |
| AKTIP | −0.8606738 |
| EMX2 | −0.858106 |
| HSD17B4 | −0.8578868 |
| STMN3 | −0.8542684 |
| GSTP1 | −0.853695 |
| NPDC1 | −0.8530966 |
| 1500015O10RIK | −0.8514356 |
| SPARC | −0.8468831 |
| VEPH1 | −0.8460857 |
| HMGB2 | −0.8412182 |
| MLC1 | −0.836453 |
| FOS | −0.8358451 |
| FAM171B | −0.8337848 |
| MYCN | −0.8310364 |
| TFAP2C | −0.8269041 |
| SPARCL1 | −0.8254262 |
| B3GAT2 | −0.8252206 |
| ARL6IP1 | −0.8244718 |
| PDLIM7 | −0.8221162 |
| PSME1 | −0.8175453 |
| RGCC | −0.8117318 |
| GM9493 | −0.8111881 |
| CSTB | −0.8079488 |
| H2AFY2 | −0.8065874 |
| SCG3 | −0.8048968 |
| SAMD14 | −0.8025394 |
| ACAA1A | −0.8025121 |

TABLE 3.1B

| Upregulated genes of ivNSC vs. E18-pop1 | |
| --- | --- |
| Upregulated genes | L1error |
| RPL41 | 1.97045893 |
| RPS28 | 1.96742531 |
| MT-ND3 | 1.964876 |
| MT-ATP6 | 1.91008608 |
| RPS26 | 1.89962381 |
| MT-ND2 | 1.89579985 |
| MT-CYTB | 1.89428988 |
| MT-CO2 | 1.88096989 |
| MT-ND1 | 1.86238906 |
| TRP53I11 | 1.81727343 |
| TMSB4X | 1.80949062 |
| WDR89 | 1.80447876 |
| PCP4L1 | 1.80289807 |
| RPS27RT | 1.76980936 |
| TXN1 | 1.71701372 |
| RPS27L | 1.7029741 |
| CDK2AP1 | 1.69384592 |
| SERPINE2 | 1.67469164 |
| CDKN1A | 1.6692026 |
| MAP2 | 1.62564925 |
| LGALS1 | 1.57233959 |
| SNHG6 | 1.56987942 |
| CCND1 | 1.54753167 |
| RPS12-PS3 | 1.51957367 |
| RASSF3 | 1.51442038 |
| PPP1R14B | 1.50600231 |
| IGFBP3 | 1.49765556 |
| GNG11 | 1.47965946 |
| MT-ATP8 | 1.47333849 |
| RPL23A-PS3 | 1.47096983 |
| KCNC1 | 1.46134129 |
| OLIG1 | 1.42417487 |
| BEX2 | 1.42062069 |
| HIP1 | 1.38857369 |
| SLC25A39 | 1.38712076 |
| GRM5 | 1.38539389 |
| NPTX1 | 1.37778043 |
| AES | 1.36830699 |
| OLIG2 | 1.36365584 |
| METRN | 1.34753993 |
| SULF2 | 1.34551178 |
| CYCS | 1.33152445 |
| SPTAN1 | 1.33138065 |
| DUSP6 | 1.32803862 |
| CDKN2A | 1.31723407 |
| DDX21 | 1.31649126 |
| FYN | 1.31540617 |
| DOCK10 | 1.2960445 |
| AMD1 | 1.28872044 |
| SNHG9 | 1.28800319 |
| ERDR1 | 1.28673091 |
| RFX4 | 1.28259854 |
| NAV2 | 1.27735136 |
| AK1 | 1.26796527 |
| CDC34 | 1.25884362 |
| DPF3 | 1.24683513 |
| E030030I06RIK | 1.24395245 |
| LMO4 | 1.22772185 |
| CAMKK2 | 1.22479104 |
| RHOQ | 1.21849086 |
| AMOTL1 | 1.20442153 |
| MEST | 1.20238387 |
| AGAP1 | 1.18368657 |
| EPHX1 | 1.17987449 |
| PRKCB | 1.17830271 |
| RRBP1 | 1.17666438 |
| RPS2-PS6 | 1.16756412 |
| ANK2 | 1.16577961 |
| TAF10 | 1.1652543 |
| TRAF4 | 1.14104478 |
| RAB31 | 1.12901312 |
| VAV3 | 1.12605319 |
| SPRY1 | 1.12351279 |
| GM10263 | 1.12064378 |
| PIK3R1 | 1.11609306 |
| SEC11C | 1.11590112 |

TABLE 3.1B-continued

Upregulated genes of ivNSC vs. E18-pop1

| Upregulated genes | L1error |
|---|---|
| PHLDA3 | 1.11137595 |
| CAMK2B | 1.10533189 |
| CCNG1 | 1.0981451 |
| SPATS2L | 1.08706838 |
| EPN2 | 1.07826881 |
| ARAP2 | 1.05890714 |
| LRRFIP1 | 1.04557111 |
| DENND2A | 1.0443648 |
| PGAP1 | 1.03991509 |
| POU3F1 | 1.03722436 |
| FAM212B | 1.03436188 |
| MAP4K4 | 1.03392749 |
| NUCKS1 | 1.02630928 |
| TNRC6A | 1.0254708 |
| NMT1 | 1.01330899 |
| SDC3 | 1.00890505 |
| ADAM12 | 1.00813788 |
| YBX3 | 1.00777182 |
| DNAH8 | 1.00331796 |
| PLEKHA2 | 0.99861452 |
| NTN1 | 0.99834949 |
| TMEM176B | 0.99498428 |
| PEG3 | 0.98469791 |
| SLC25A18 | 0.98337096 |
| B930036N10RIK | 0.98293479 |
| PELI1 | 0.97554893 |
| JMJD1C | 0.97364616 |
| MT-ND4L | 0.96799905 |
| GM26917 | 0.96453164 |
| MMP15 | 0.96408417 |
| HOXA5 | 0.96064884 |
| TPD52 | 0.95935101 |
| KITL | 0.95634711 |
| SETD8 | 0.95553359 |
| CSNK1G2 | 0.95294565 |
| PISD | 0.94875801 |
| GOLPH3 | 0.94407537 |
| PURB | 0.94312042 |
| RORB | 0.94281676 |
| ZEB1 | 0.93941055 |
| CCSER2 | 0.93856316 |
| ID3 | 0.93833913 |
| DPYSL2 | 0.93552479 |
| SRGAP2 | 0.92771047 |
| FMNL2 | 0.92327444 |
| PRR18 | 0.92101988 |
| TCF12 | 0.92018556 |
| ETV5 | 0.91460501 |
| CALD1 | 0.91051602 |
| EBF1 | 0.90742832 |

TABLE 3.1B-continued

Upregulated genes of ivNSC vs. E18-pop1

| Upregulated genes | L1error |
|---|---|
| WNT5A | 0.90411125 |
| EIF4EBP1 | 0.90137891 |
| BTG1 | 0.90110675 |
| SPSB4 | 0.9007918 |
| PPP3CA | 0.89132073 |
| FDPS | 0.89106699 |
| GATAD1 | 0.89088218 |
| ACAP3 | 0.88981135 |
| EGFR | 0.88756333 |
| RRM2B | 0.87973059 |
| NEURL1A | 0.87516204 |
| SLC6A1 | 0.87427959 |
| ATP2B1 | 0.86796337 |
| CALCRL | 0.86708686 |
| MYH9 | 0.86570702 |
| NME2 | 0.86218434 |
| LPIN1 | 0.85863017 |
| CPNE8 | 0.85684149 |
| TNIK | 0.85619674 |
| REV3L | 0.85537252 |
| PTGDS | 0.85370507 |
| NES | 0.85240011 |
| TLE4 | 0.84764675 |
| ELK3 | 0.8422421 |
| SPRY4 | 0.8414565 |
| IGFBP2 | 0.83638225 |
| WLS | 0.83619566 |
| DDT | 0.83227721 |
| PTPRZ1 | 0.83107327 |
| CAR8 | 0.82845622 |
| KCNJ16 | 0.82661525 |
| CTNNBIP1 | 0.82535783 |
| RGS7 | 0.82287805 |
| 2700094K13RIK | 0.82162538 |
| TMEM229A | 0.82064607 |
| ZFP36L1 | 0.81849134 |
| ADM | 0.81668068 |
| IDH1 | 0.81519269 |
| NCOR2 | 0.81473393 |
| GM29666 | 0.8141587 |
| RAB26OS | 0.81243361 |
| ZFOS1 | 0.81061938 |
| PBXIP1 | 0.81019925 |
| PITPNC1 | 0.80962818 |
| 5930412G12RIK | 0.80799104 |
| GNL3 | 0.80543638 |
| CHN2 | 0.80376953 |
| ZMYND19 | 0.80308853 |

TABLE 3.2A

| Genes | |
|---|---|
| feat_1_genes | H2AFZ, TUBA1B, RAN, H2AFV, HMGB1, SLC25A5, PTMA, HMGB2, HMGN2, NPM1, EIF5A, UBE2S, GAPDH, CKB, HSPA8, CCND2, VIM, TUBB5, 2810417H13RIK, TMPO, EIF4A1, PFN1, H2AFX, CALM1, TOP2A, HSP90AA1, DYNLL1, UBE2C, CALM2, RPS11, RPL3, CKS2, TPM4, CENPA, TUBB4B, CENPF, HIST1H2AP, RPLP0, RPL13, RPS4X, SMC4, BIRC5, GNG5, RPS19, RRM2, RPL14, CDCA3, RPS9, SMC2, H3F3A, HES6, RPSA, CDCA8, RPS8, LOCKD, PBK, RPL22L1, CDK1, CBX3, RPL32, RACGAP1, RPS18, SPC25, RPS27A, CCNA2, ELOF1, NUSAP1, CCNB1, FTL1, RPS3, RPS5, TPX2, RPL13A, PRC1, CLIC1, RPS3A1, ARL6IP1, RPL10A, MKI67, CDCA7, RPL18A, CDC20, RPL6, EEF1A1, NUDT4, RPS27L, KNSTRN, POLR3K, RPL4, FAM64A, CENPE, CCNB2, ASCL1, GAS1, PAX6, RPL7, DBI, RPS16, MIS18BP1, GADD45G, KPNA2, YWHAQ, RPL23A, PLK4, NUF2, UHRF1, SUPT16, HMMR, MYL12A, H1F0, HIST1H4I |
| feat_2_genes | PPIA, RPS6, HNRNPA1, RPS24, MYL6, RPL35A, RPL38, RPL19, FAU, GAPDH, TPT1, RPS23, GNB1, RPS25, TMSB4X, MT-CO3, RPL39, ACTB, RPL37, RPS29, RPS27, RPL10, RPS27A |
| feat_3_genes | MT-ATP6, MT-CO3, MT-CO2, MT-CO1, MT-CYTB, MT-ND1, MT-ND3, MT-ND4, RPL27A, MT-ND2, ACTG1, RPS29, RPS28, RPL38, FTH1, CBX3, RPL35A, MT-ATP8, RPL41, MT-ND4L, RPL37, RPS27, UBE2S, RPL37A, YWHAQ, SCD2 |

TABLE 3.2A-continued

| Genes |
| --- |

| | |
| --- | --- |
| feat_4_genes | TUBA1A, TUBB3, TUBB2B, RTN1, NNAT, STMN2, MAP1B, TUBB5, NSG1, STMN1, MLLT11, TUBB2A, BASP1, STMN3, DPYSL3, ACTB, ELAVL3, PFN2, CRMP1, GAP43, HSP90AA1, TTC3, UCHL1, NDN, HN1, MARCKSL1, UBC, CALM2, HSPA8, FEZ1, FXYD6, NCAM1, STMN4, CALM1, HSP90AB1, MAPT, TMSB10, DYNLL1, DCX, INA, MT-CYTB, ISLR2, UBB, MALAT1, SEPW1, LY6H, RAC3, BCL11B, PRDX2, TMSB4X, HMGCS1, CELF2, ARL6IP1, CELF4, ZEB2, EIF4A1, FRMD4A, MT-ND4, RUNX1T1, APLP1, EIF1B, BHLHE22, CD200, SNRPN, BCL11A, JUND, TMEM108, AP1S2, SP9, DLX6OS1, HBB-BS, BEX2, GAD2, PLPPR1, CADM1, MEG3, DLX5, RPRM |
| feat_5_genes | MEG3, SNHG11, CAMK2N1, PCSK1N, SNAP25, MT-ND1, CALM2, SEPW1, MEF2C, PPP3CA, GRIA2, GPM6A, ATP1B1, NRGN, SYT1, APP, SNRPN, SERINC1, ATP2B1, VAMP2, CLSTN1, OLFM1, PSAP, SNCB, CALM1, NDRG4, SYP, SLC17A7, R3HDM1, CCK, GNG3, NRXN1, 1110008P14RIK, CELF2, ARPP21, APLP1, PPP3R1, SNCA, PCP4, CHCHD10, RTN1, ATP1A1, CHN1, NTM, PISD, PCSK2, STXBP1, SCN1B, CPLX2, CX3CL1, CAMK2A, NPTN, MT-ND4, CPE, THY1, MT-ND4L, VPS8, DCLK1, ATP1A3, DNM1, CADM2, LY6H, ATP2B2, GNB1, LMO4, MT-ND5, ENC1, NPTXR, GRIN2B, PRKCB, PTPRD, NCDN, TSPAN7, GAS7, ATP6V1G2, PRKAR1B, CELF4, NRXN3, FTH1, NELL2, SYT4, ADGRB1, TTC3, EEF1A2, SLC1A2, FAIM2, NAP1L5, PGM2L1, KALRN, MT-CO1, MT3, C1QTNF4, SYN1, OPCML, MALAT1, PTPRN, MATK, VSNL1, STMN3, SPOCK2, TSC22D1, ENO2, MT-ATP8, GRIN1, RGS4, CNTN1, NRN1, NRSN1, MT-CYTB, SYNGR1, GABRA1, MAPT, HPCA, SLC12A5, NCALD, BASP1, TCF4, FOXP1, CLSTN3, SLC24A2, PHYHIP, EPHA4, AI593442, STMN4, CALY, PFN2, SV2B, SLC6A17, PPP2R2C, GNG13, SCN2B, CHGB, FXYD7, GRM5, GRIA3, MT-ND2, MIAT, TMEM151A, SPOCK1, CADM1, 3110035E14RIK, SIRPA, NTRK2, ADCY1, NAT8L, 2900055J20RIK, TUBB4A, RASGRP1, BRINP3, PAM, NPTX1, ID2, RPRML, NEFL, GPM6B, HPCAL4, UCHL1, VGF, EPHA5, GDA, TMSB10, DYNLL1, EGR1, LY6E, ARL6IP1, RPL41, RPL38, DKK3, SYT13, NCAM1, TRANK1, C1QL3, PLK2, TMEM158, LGI1, LAMP5, BEX2, RPH3A, SERPINI1, LRFN5, SELM, CAR10, NFIX, LYNX1, TMSB4X, GRIA1, PFKP, SLC30A3, PDE1A, CTSB, RPL37, FRY, MYL6, EIF5A, TPM1, GUCY1B3, SCG2, NFASC, MLLT11, ACTB, CHL1, CUX2, ABHD2, BSG, GAPDH, RPLP1, IGFBP6, CACNG3, MBP, CALB1, FAM19A1, SLC6A6, GPCPD1, ELMO1, RESP18 |
| feat_6_genes | HSP90AB1, EEF2, XIST, RPL4, RPS9, RPS5, EEF1A1, RPL3, MARCKS, RPLP0, NFIB, RPS4X, ZBTB20, RPS14, HSPA8, RPS3, RPL13A, RPS18, TCF4, NPM1, RPS7, RPL32, RPL18A, NFIA, RPS3A1, RPL23A, ACTB, RPS8, LDHA, RPL23, RPL14, RPS19, ENAH, RPS24, RPS2, TRAF4, CALM1, RPS15A, RPS11, RPL10 |
| feat_7_genes | FTH1, CST3, ITM2B, CD81, FTL1, JUND, PLP1, JUN, MBP, PTGDS, CTSD, RHOB, FAU, SEPP1, RNF7, SPARC, RPS24, PFN1, TMSB4X, NPC2, ACTB, CTSB, UBC, GLUL, GATM, B2M, MOBP, QDPR, CNP, JUNB, CRYAB, TRF, CSRP1, LGMN, SIRT2, H3F3B, RPS29, CLDN11, SERINC3, C1QA, C1QB, BIN1, C1QC, CTSL, BTG2, HEXB, RNF13, GPX1, DUSP1, BTG1, TYROBP, ARPC1B, MAL, NFKBIA, JOSD2, CD9, CTSZ, RPS27, SEPT4, SAT1, GLTP, TUBB4A, PSAP, SLC38A2, CTSS, SEPW1, CAR2, FCER1G, TALDO1, DESI1, UBB, GRN, APOE, HEXA, ZEB2, RGS10, RPS14, CCL4, CYBA, MALAT1, RPLP1, CCL3, TSPAN2, DCAF17, PLLP, CSF1R, P2RY12, ENPP2, LITAF, MAG, SGK1, GRB14, APOD, PPP1R14A, CEBPB, CX3CR1, MOG, FCRLS, ERMN, KLF6, COMT, LAPTM5, HIST1H2BC, TREM2, PLEKHB1, GSTP1, NEAT1, PPP1R16B, SELPLG, IER5, RPL10, MT-ND1, CD63, S100A13, CLIC1, FCGR3, H2-D1, RPL13A, EVI2A, TMEM119, LY86, ITGB5, ZFP36, PPP1R15A, ETV1, TGFBR1, OPALIN, ATF3, NR4A1, GPR34, UGT8A, AIF1, NDRG1, KCTD12, VAMP8, HIST1H1C, GJC3, OSTF1, SLC3A2, RPL18A, CD83, OLFML3, CPOX, TMEM176B, TPPP3, TTYH2, NFE2L2, MAF, NKX6-2, RPL13, CTSH, LTC4S, SOX10, PMP22, UNC93B1, RPS3, MT-ND5, IER3, RPS23, UCP2, LPAR1, BCAS1, TMEM88B, TXNIP, TTLL7, HSPA1A, SOCS3, GSN, SIGLECH, PDLIM2, IER2, RPLP2, CD53, GPR37, IFNGR1, RNASE4, GM42418, ZFP36L1, PTPN18, LY6E, SNX2, ANXA3, EFNB3, RPS9, CD68, MAFB, SPI1, PYCARD, VSIR, CRYBB1, QK, MID1IP1, RPL3, ARHGDIB, CTSC, RPS11, FA2H, IL33, BMP2K, PLD4, H2-K1, BCL2A1B, TPT1, ASPA, LPCAT2, MT-ND4, ST3GAL6, CHN2, CCL2, TGFB1, CMTM7, LMO2 |
| feat_8_genes | H3F3B, UBB, PTMA, TMSB10, H3F3A, SOX11, SOX4, STMN1, ACTG1, MARCKSL1, CD24A, PRDX2, IGFBPL1, EIF4A1, FTL1, YWHAQ, TUBB5, FABP5, HIST3H2BA, HN1, MEIS2, TSC22D1, PANTR1, HNRNPA1, H1F0, NEUROD6, TUBA1A, GM17750, DYNLL1, MDK, HBB-BS, MPPED2, EEF1A1, CITED2, EIF1B, TCF4, LHX2, NFIB, RPS11, HSPA8, HBA-A1, ID2, TMSB4X, CELF2, RPS14, MFAP2, NRP1, CDKN1C, RPL13, LMO1, HBA-A2, RPS24, RPL18A, BCL11A, RPS5, HBB-Y, GM3764, CSRP2, BTG1, HBB-BT, TALDO1, EPHA5, POU3F2, RND2, TPT1, SEPW1, NNAT, RPL7, POLR3K, SEMA3C, GADD45G, RPS15A, HSP90AA1, NEUROD1, RPL6, RPS27A, RPL32, EZR, HES6, TTC3, RPS23, ACTB, NEUROG2, SSTR2, NPC2 |
| feat_9_genes | RPL41, TMSB4X, RPL37A, RPS2, RPLP2, RPS15, RPS16, RPS26, RPS12, RPL31, RPL23, RPLP1, RPS19, RPL21, RPS20, RPS15A, RPS8, RPL39, RPS27A, RPL28, RPL7, RPL37, RPS23, RPSA, RPL23A, RPL6, RPL13, RPS27, RPS28, RPL10A, RPL32, RPS25, RPL18A, RPS3A1, RPL14, EEF1A1, RPS18, TPT1, RPL19, RPS29, RPLP0, RPL13A, RPS11, RPL10, RPS4X, RPL35A, RPS3, RPS7, RPS5, TXN1, RPS14, RPS27L, BEX2, RPL27A, FAU, RPL38, RPL22L1, PPP1R14B, RPL3, |

TABLE 3.2A-continued

| Genes |
|---|
| RPL4, RPS9, TRP53I11, LGALS1, MEST, FTL1, CCND1, RPS24, GNG5, CDKN1A, FYN, PCP4L1 | feat_10_genes FABP7, DBI, PTN, CKB, APOE, GPM6B, MT1, PTPRZ1, MT-CYTB, MT3, MT-ND4, SLC1A3, MT-ND1, MT-ND2, SERPINE2, SCD2, PRDX6, ALDOC, FOS, CSPG5, QK, CPE, PEA15A, OLIG1, ATP1A2, ID3, PLPP3, BCAN, NDRG2, IGFBP2, MALAT1, MFGE8, CD63, SPARCL1, GM3764, HMGCS1, FABP5, DDAH1, GLUD1, MARCKS, HES1, HES5, GSTM5, MMD2, SOX2, TSC22D4, PHGDH, VIM, S100A16, MT2, TTYH1, CLU, EDNRB, GLUL, ACOT1, CST3, GSTM1, DCLK1, CD81, NCAN, PANTR1, CD9, SOX9, LXN, LUZP2, SLC6A1, MLC1, SLC25A5, GJA1, LDHA, FJX1, PLA2G7, RGCC, SLC1A2, S100A1, OLIG2, TSPAN7, TST, ACSBG1, SLC4A4, AQP4, TXN1, RPL22L1, ATP1B2, ID4, ARL6IP1, TNC, GPR37L1, SLC6A11, CYR61, GAS1, HTRA1, SLC9A3R1, RPL41, FEZ1, MID1IP1, ID1, NRARP, RPLP1, NTRK2, CHST2, RAMP1, TMEM47, CCND2, SFXN5, BTBD17, TIMP3, NKAIN4, ZFP36L1, EIF1B, RLBP1, RPS2, CXCL14, SCRG1, S1PR1, SLC27A1, TRIL, RORB, INSIG1, NFIA, CLDN10, FGFBP3, ENHO, MGST1, FOSB, CHPT1, ZBTB20, KLF6, SELM, SLC3A2, SLC25A18, MT-ND5, TIMP4, TMEM176B, IGFBP5, HADHB, EGR1, TMEM100, PLAT, E130114P18RIK, ALDH1L1, S100A6, FTH1, SPRY2, GFAP, FBXO2, FGFR3, LFNG, SLC38A3, CMTM5, CDO1, HIST1H2BC, PDPN, CAR8, SLC7A10, S100B, MDK, TLCD1, RPL14, APPL2, GPM6A, NTSR2, RFX4 feat_11_genes MALAT1, ACTB, BSG, MT-CYTB, MT-ND1, RPS14, MYL12A, DYNLL1, RPL13A, CALD1, MT-ND4, CALM1, GNG11, CLIC4, FTL1, IFITM2, SERPINH1, MPZL1, TAGLN2, RBP1, RPS19, GM13889, IER2, DNAJB1, JUND, EBF1, KLF2, RPS27, TPM1, PHLDA1, RPS18, RPL21, CXCL12, RPL13, RPL14, S100A10, WLS, ITM2A, SLC7A5, NBL1, RPL18A, IFITM3, KLF4, RAMP2, FSTL1, ZIC1, JUN, ANXA5, S100A11, RPL3, CRIP1, VTN, IGFBP7

TABLE 3.2B

| Gene Sets | |
|---|---|
| feat_1 | pval_1 |
| KEGG_RIBOSOME | 7.68262E−16 |
| GO_CYTOSOLIC_RIBOSOME | 5.75547E−13 |
| GO_ESTABLISHMENT_OF_PROTEIN_LOCALIZATION_TO_ENDOPLASMIC_RETICULUM | 4.92125E−12 |
| GO_NUCLEAR_TRANSCRIBED_MRNA_CATABOLIC_PROCESS_NONSENSE_MEDIATED_DECAY | 8.92724E−11 |
| GO_PROTEIN_LOCALIZATION_TO_ENDOPLASMIC_RETICULUM | 2.25381E−10 |
| GO_TRANSLATIONAL_INITIATION | 1.68419E−09 |
| GO_MULTI_ORGANISM_METABOLIC_PROCESS | 2.74398E−09 |
| GO_RIBOSOMAL_SUBUNIT | 3.69714E−09 |
| REACTOME_PEPTIDE_CHAIN_ELONGATION | 4.69471E−09 |
| GO_PROTEIN_TARGETING_TO_MEMBRANE | 8.19615E−09 |
| GO_CYTOSOLIC_SMALL_RIBOSOMAL_SUBUNIT | 2.44621E−08 |
| REACTOME_INFLUENZA_VIRAL_RNA_TRANSCRIPTION_AND_REPLICATION | 3.8985E−08 |
| REACTOME_3_UTR_MEDIATED_TRANSLATIONAL_REGULATION | 9.02531E−08 |
| GO_CYTOSOLIC_LARGE_RIBOSOMAL_SUBUNIT | 2.32151E−07 |
| GO_STRUCTURAL_CONSTITUENT_OF_RIBOSOME | 2.58415E−07 |
| REACTOME_NONSENSE_MEDIATED_DECAY_ENHANCED_BY_THE_EXON_JUNCTION_COMPLEX | 3.8293E−07 |
| REACTOME_INFLUENZA_LIFE_CYCLE | 4.06897E−07 |
| REACTOME_SRP_DEPENDENT_COTRANSLATIONAL_PROTEIN_TARGETING_TO_MEMBRANE | 5.29892E−07 |
| GO_CYTOSOLIC_PART | 7.44498E−07 |
| REACTOME_TRANSLATION | 2.42511E−06 |
| GO_RIBOSOME | 3.42934E−06 |
| GO_KINETOCHORE_ORGANIZATION | 5.35244E−06 |
| GO_SMALL_RIBOSOMAL_SUBUNIT | 5.93586E−06 |
| GO_RNA_CATABOLIC_PROCESS | 1.2325E−05 |
| PID_AURORA_B_PATHWAY | 3.69827E−05 |
| PID_FOXM1_PATHWAY | 4.59425E−05 |
| GO_LARGE_RIBOSOMAL_SUBUNIT | 5.78869E−05 |
| GO_ESTABLISHMENT_OF_PROTEIN_LOCALIZATION_TO_MEMBRANE | 6.03857E−05 |
| REACTOME_ACTIVATION_OF_THE_MRNA_UPON_BINDING_OF_THE_CAP_BIND-ING_COMPLEX_AND_EIFS_AND_SUBSEQUENT_BINDING_TO_43S | 6.43679E−05 |
| REACTOME_FORMATION_OF_THE_TERNARY_COMPLEX_AND_SUBSEQUENTLY_THE_43S_COMPLEX | 7.84557E−05 |
| feat_2 | pval_2 |
| KEGG_RIBOSOME | 2.19171E−17 |
| GO_ESTABLISHMENT_OF_PROTEIN_LOCALIZATION_TO_ENDOPLASMIC_RETICULUM | 3.13312E−16 |
| GO_CYTOSOLIC_RIBOSOME | 1.15518E−15 |
| GO_NUCLEAR_TRANSCRIBED_MRNA_CATABOLIC_PROCESS_NONSENSE_MEDIATED_DECAY | 2.27239E−15 |
| GO_PROTEIN_LOCALIZATION_TO_ENDOPLASMIC_RETICULUM | 4.33519E−15 |
| GO_MULTI_ORGANISM_METABOLIC_PROCESS | 2.56659E−14 |
| GO_TRANSLATIONAL_INITIATION | 6.09181E−14 |
| REACTOME_PEPTIDE_CHAIN_ELONGATION | 1.24543E−13 |

TABLE 3.2B-continued

| Gene Sets | |
| --- | --- |
| GO_PROTEIN_TARGETING_TO_MEMBRANE | 1.84475E-13 |
| GO_RIBOSOMAL_SUBUNIT | 3.25998E-13 |
| REACTOME_INFLUENZA_VIRAL_RNA_TRANSCRIPTION_AND_REPLICATION | 5.63384E-13 |
| REACTOME_3_UTR_MEDIATED_TRANSLATIONAL_REGULATION | 1.03917E-12 |
| REACTOME_NONSENSE_MEDIATED_DECAY_ENHANCED_BY_THE_EXON_JUNCTION_COMPLEX | 1.03917E-12 |
| REACTOME_SRP_DEPENDENT_COTRANSLATIONAL_PROTEIN_TARGETING_TO_MEMBRANE | 1.34012E-12 |
| REACTOME_INFLUENZA_LIFE_CYCLE | 8.79843E-12 |
| REACTOME_TRANSLATION | 3.31253E-11 |
| GO_CYTOSOLIC_PART | 3.53966E-11 |
| GO_RIBOSOME | 4.31052E-11 |
| GO_RNA_CATABOLIC_PROCESS | 4.60021E-11 |
| GO_CYTOSOLIC_SMALL_RIBOSOMAL_SUBUNIT | 5.22228E-11 |
| GO_VIRAL_LIFE_CYCLE | 1.01856E-10 |
| GO_RRNA_METABOLIC_PROCESS | 2.52851E-10 |
| GO_STRUCTURAL_CONSTITUENT_OF_RIBOSOME | 3.20157E-10 |
| GO_ESTABLISHMENT_OF_PROTEIN_LOCALIZATION_TO_MEMBRANE | 4.18794E-10 |
| REACTOME_METABOLISM_OF_MRNA | 1.20483E-09 |
| GO_SMALL_RIBOSOMAL_SUBUNIT | 3.20335E-09 |
| GO_RIBOSOME_BIOGENESIS | 3.86142E-09 |
| REACTOME_FORMATION_OF_THE_TERNARY_COMPLEX_AND_SUBSEQUENTLY_THE_43S_COMPLEX | 6.96216E-09 |
| REACTOME_METABOLISM_OF_RNA | 1.03141E-08 |
| REACTOME_ACTIVATION_OF_THE_MRNA_UPON_BINDING_OF_THE_CAP_BIND-ING_COMPLEX_AND_EIFS_AND_SUBSEQUENT_BINDING_TO_43S | 2.20036E-08 |

| feat_3 | pval_3 |
| --- | --- |
| KEGG_RIBOSOME | 6.58776E-09 |
| GO_ESTABLISHMENT_OF_PROTEIN_LOCALIZATION_TO_ENDOPLASMIC_RETICULUM | 3.45524E-08 |
| GO_CYTOSOLIC_RIBOSOME | 7.77844E-08 |
| GO_NUCLEAR_TRANSCRIBED_MRNA_CATABOLIC_PROCESS_NONSENSE_MEDIATED_DECAY | 1.18401E-07 |
| GO_PROTEIN_LOCALIZATION_TO_ENDOPLASMIC_RETICULUM | 1.76743E-07 |
| GO_MULTI_ORGANISM_METABOLIC_PROCESS | 5.3095E-07 |
| GO_TRANSLATIONAL_INITIATION | 9.04486E-07 |
| REACTOME_PEPTIDE_CHAIN_ELONGATION | 1.40383E-06 |
| GO_PROTEIN_TARGETING_TO_MEMBRANE | 1.78643E-06 |
| GO_CYTOSOLIC_LARGE_RIBOSOMAL_SUBUNIT | 1.80455E-06 |
| GO_RIBOSOMAL_SUBUNIT | 2.53167E-06 |
| REACTOME_INFLUENZA_VIRAL_RNA_TRANSCRIPTION_AND_REPLICATION | 3.5364E-06 |
| REACTOME_3_UTR_MEDIATED_TRANSLATIONAL_REGULATION | 5.13551E-06 |
| REACTOME_NONSENSE_MEDIATED_DECAY_ENHANCED_BY_THE_EXON_JUNCTION_COMPLEX | 5.13551E-06 |
| REACTOME_SRP_DEPENDENT_COTRANSLATIONAL_PROTEIN_TARGETING_TO_MEMBRANE | 5.99453E-06 |
| REACTOME_INFLUENZA_LIFE_CYCLE | 1.87049E-05 |
| GO_STRUCTURAL_CONSTITUENT_OF_RIBOSOME | 2.75323E-05 |
| GO_LARGE_RIBOSOMAL_SUBUNIT | 3.61545E-05 |
| REACTOME_TRANSLATION | 4.13745E-05 |
| GO_CYTOSOLIC_PART | 4.30424E-05 |
| GO_RIBOSOME | 4.83996E-05 |
| GO_RNA_CATABOLIC_PROCESS | 5.03087E-05 |
| GO_RRNA_METABOLIC_PROCESS | 0.000137633 |
| GO_ESTABLISHMENT_OF_PROTEIN_LOCALIZATION_TO_MEMBRANE | 0.00018488 |
| REACTOME_METABOLISM_OF_MRNA | 0.000341366 |
| GO_VIRAL_LIFE_CYCLE | 0.000406028 |
| GO_RIBOSOME_BIOGENESIS | 0.000665518 |
| GO_RIBOSOMAL_SMALL_SUBUNIT_ASSEMBLY | 0.000762252 |
| GO_CYTOSOLIC_SMALL_RIBOSOMAL_SUBUNIT | 0.000986324 |
| REACTOME_METABOLISM_OF_RNA | 0.001159941 |

| feat_4 | pval_4 |
| --- | --- |
| GO_ESTABLISHMENT_OF_MITOCHONDRION_LOCALIZATION | 7.69131E-06 |
| REACTOME_PREFOLDIN_MEDIATED_TRANSFER_OF_SUBSTRATE_TO_CCT_TRIC | 0.000177274 |
| REACTOME_POST_CHAPERONIN_TUBULIN_FOLDING_PATHWAY | 0.00022738 |
| GO_SUBSTANTIA_NIGRA_DEVELOPMENT | 0.000413163 |
| REACTOME_FORMATION_OF_TUBULIN_FOLDING_INTERMEDIATES_BY_CCT_TRIC | 0.000477966 |
| REACTOME_TETRAHYDROBIOPTERIN_BH4_SYNTHESIS_RECYCLING_SALVAGE_AND_REGULATION | 0.000530875 |
| GO_MICROTUBULE_DEPOLYMERIZATION | 0.000530875 |
| GO_MITOCHONDRION_LOCALIZATION | 0.000749018 |
| GO_PROTEIN_DEPOLYMERIZATION | 0.000895155 |
| GO_MHC_CLASS_II_PROTEIN_COMPLEX_BINDING | 0.001256947 |
| GO_MHC_PROTEIN_COMPLEX_BINDING | 0.002490359 |
| GO_NITRIC_OXIDE_SYNTHASE_BINDING | 0.002490359 |
| REACTOME_ENOS_ACTIVATION_AND_REGULATION | 0.003039016 |
| GO_NEURAL_NUCLEUS_DEVELOPMENT | 0.004158009 |
| PID_P38_GAMMA_DELTA_PATHWAY | 0.004169029 |
| REACTOME_IONOTROPIC_ACTIVITY_OF_KAINATE_RECEPTORS | 0.004169029 |
| GO_PHOSPHATASE_ACTIVATOR_ACTIVITY | 0.004169029 |
| GO_INOSITOL_TRISPHOSPHATE_KINASE_ACTIVITY | 0.004169029 |
| BIOCARTA_GCR_PATHWAY | 0.004373218 |

TABLE 3.2B-continued

| Gene Sets | |
|---|---|
| GO_NEGATIVE_REGULATION_OF_RYANODINE_SENSITIVE_CALCIUM_RELEASE_CHANNEL_ACTIVITY | 0.005433199 |
| GO_CLATHRIN_SCULPTED_VESICLE | 0.005433199 |
| GO_AXON_EXTENSION | 0.005459306 |
| REACTOME_PROTEIN_FOLDING | 0.005758644 |
| GO_SITE_OF_POLARIZED_GROWTH | 0.006178831 |
| GO_POSITIVE_REGULATION_OF_PROTEIN_IMPORT_INTO_NUCLEUS_TRANSLOCATION | 0.006903896 |
| GO_REGULATION_OF_CELL_COMMUNICATION_BY_ELECTRICAL_COUPLING | 0.006903896 |
| GO_ACTIN_MONOMER_BINDING | 0.007038238 |
| REACTOME_CRMPS_IN_SEMA3A_SIGNALING | 0.008588916 |
| GO_POSITIVE_REGULATION_OF_MRNA_SPLICING_VIA_SPLICEOSOME | 0.008588916 |
| GO_POSITIVE_REGULATION_OF_CELL_SIZE | 0.008588916 |

| feat_5 | pval_5 |
|---|---|
| REACTOME_UNBLOCKING_OF_NMDA_RECEPTOR_GLUTAMATE_BINDING_AND_ACTIVATION | 1.09609E−05 |
| GO_TERMINAL_BOUTON | 1.72784E−05 |
| REACTOME_CREB_PHOSPHORYLATION_THROUGH_THE_ACTIVATION_OF_CAMKII | 0.000121035 |
| REACTOME_DOPAMINE_NEUROTRANSMITTER_RELEASE_CYCLE | 0.000129627 |
| REACTOME_ACTIVATION_OF_NMDA_RECEPTOR_UPON_GLUTAMATE_BINDING_AND_POSTSYNAPTIC_EVENTS | 0.000189402 |
| REACTOME_RAS_ACTIVATION_UOPN_CA2_INFUX_THROUGH_NMDA_RECEPTOR | 0.000314131 |
| BIOCARTA_NOS1_PATHWAY | 0.000626124 |
| GO_IONOTROPIC_GLUTAMATE_RECEPTOR_SIGNALING_PATHWAY | 0.000626124 |
| REACTOME_ACETYLCHOLINE_NEUROTRANSMITTER_RELEASE_CYCLE | 0.000837634 |
| REACTOME_NOREPINEPHRINE_NEUROTRANSMITTER_RELEASE_CYCLE | 0.000837634 |
| GO_EXTRACELLULAR_GLUTAMATE_GATED_ION_CHANNEL_ACTIVITY | 0.00099712 |
| REACTOME_GLUTAMATE_NEUROTRANSMITTER_RELEASE_CYCLE | 0.001041067 |
| GO_REGULATION_OF_SYNAPTIC_PLASTICITY | 0.001694445 |
| GO_AXON_PART | 0.001705895 |
| GO_GLUTAMATE_SECRETION | 0.001947649 |
| GO_EXOCYTIC_VESICLE_MEMBRANE | 0.00247168 |
| GO_SYNTAXIN_1_BINDING | 0.003088853 |
| GO_REGULATION_OF_LONG_TERM_NEURONAL_SYNAPTIC_PLASTICITY | 0.003290326 |
| REACTOME_POST_NMDA_RECEPTOR_ACTIVATION_EVENTS | 0.005942304 |
| KEGG_LONG_TERM_POTENTIATION | 0.006170841 |
| GO_NEURON_PROJECTION_TERMINUS | 0.006709215 |
| REACTOME_CREB_PHOSPHORYLATION_THROUGH_THE_ACTIVATION_OF_RAS | 0.00673657 |
| GO_GLUTAMATE_RECEPTOR_ACTIVITY | 0.00673657 |
| GO_LONG_TERM_SYNAPTIC_DEPRESSION | 0.006942415 |
| GO_GLUTAMATE_RECEPTOR_SIGNALING_PATHWAY | 0.007205735 |
| BIOCARTA_BARRESTIN_PATHWAY | 0.007713584 |
| REACTOME_TRAFFICKING_OF_AMPA_RECEPTORS | 0.008332876 |
| GO_LONG_TERM_MEMORY | 0.008332876 |
| REACTOME_TRAFFICKING_OF_GLUR2_CONTAINING_AMPA_RECEPTORS | 0.009395298 |
| REACTOME_IONOTROPIC_ACTIVITY_OF_KAINATE_RECEPTORS | 0.011305551 |

| feat_6 | pval_6 |
|---|---|
| KEGG_RIBOSOME | 1.33572E−24 |
| GO_ESTABLISHMENT_OF_PROTEIN_LOCALIZATION_TO_ENDOPLASMIC_RETICULUM | 2.30271E−24 |
| GO_CYTOSOLIC_RIBOSOME | 2.03968E−23 |
| REACTOME_PEPTIDE_CHAIN_ELONGATION | 5.34525E−23 |
| GO_NUCLEAR_TRANSCRIBED_MRNA_CATABOLIC_PROCESS_NONSENSE_MEDIATED_DECAY | 6.29259E−23 |
| GO_PROTEIN_LOCALIZATION_TO_ENDOPLASMIC_RETICULUM | 1.8398E−22 |
| GO_MULTI_ORGANISM_METABOLIC_PROCESS | 3.48387E−21 |
| GO_TRANSLATIONAL_INITIATION | 1.44579E−20 |
| GO_PROTEIN_TARGETING_TO_MEMBRANE | 8.90949E−20 |
| GO_RIBOSOMAL_SUBUNIT | 2.26278E−19 |
| REACTOME_INFLUENZA_VIRAL_RNA_TRANSCRIPTION_AND_REPLICATION | 5.53254E−19 |
| REACTOME_TRANSLATION | 1.17811E−18 |
| REACTOME_3_UTR_MEDIATED_TRANSLATIONAL_REGULATION | 1.50212E−18 |
| REACTOME_NONSENSE_MEDIATED_DECAY_ENHANCED_BY_THE_EXON_JUNCTION_COMPLEX | 1.50212E−18 |
| REACTOME_SRP_DEPENDENT_COTRANSLATIONAL_PROTEIN_TARGETING_TO_MEMBRANE | 2.27344E−18 |
| GO_RIBOSOME | 3.63831E−17 |
| REACTOME_INFLUENZA_LIFE_CYCLE | 4.83406E−17 |
| GO_STRUCTURAL_CONSTITUENT_OF_RIBOSOME | 1.37125E−16 |
| GO_CYTOSOLIC_PART | 4.59136E−16 |
| GO_CYTOSOLIC_SMALL_RIBOSOMAL_SUBUNIT | 5.71786E−16 |
| GO_RNA_CATABOLIC_PROCESS | 7.00768E−16 |
| GO_VIRAL_LIFE_CYCLE | 1.17218E−15 |
| REACTOME_METABOLISM_OF_MRNA | 1.00828E−14 |
| GO_RRNA_METABOLIC_PROCESS | 1.08748E−14 |
| GO_ESTABLISHMENT_OF_PROTEIN_LOCALIZATION_TO_MEMBRANE | 2.44314E−14 |
| GO_RIBOSOME_BIOGENESIS | 7.13485E−14 |
| REACTOME_METABOLISM_OF_RNA | 3.70214E−13 |
| GO_SMALL_RIBOSOMAL_SUBUNIT | 4.8131E−13 |
| REACTOME_FORMATION_OF_THE_TERNARY_COMPLEX_AND_SUBSEQUENTLY_THE_43S_COMPLEX | 1.676E−12 |
| GO_ESTABLISHMENT_OF_PROTEIN_LOCALIZATION_TO_ORGANELLE | 3.07623E−12 |

TABLE 3.2B-continued

Gene Sets

| feat_7 | pval_7 |
| --- | --- |
| GO_COMPACT_MYELIN | 0.000965532 |
| GO_NEUTROPHIL_ACTIVATION_INVOLVED_IN_IMMUNE_RESPONSE | 0.001338532 |
| GO_ENSHEATHMENT_OF_NEURONS | 0.001437205 |
| GO_OLIGODENDROCYTE_DEVELOPMENT | 0.001672633 |
| KEGG_RIBOSOME | 0.002655364 |
| GO_CYTOSOLIC_SMALL_RIBOSOMAL_SUBUNIT | 0.00322906 |
| GO_CELLULAR_RESPONSE_TO_LIPOPROTEIN_PARTICLE_STIMULUS | 0.00323098 |
| GO_CELLULAR_RESPONSE_TO_THYROID_HORMONE_STIMULUS | 0.00323098 |
| GO_OLIGODENDROCYTE_DIFFERENTIATION | 0.004032856 |
| REACTOME_TRAFFICKING_AND_PROCESSING_OF_ENDOSOMAL_TLR | 0.004679559 |
| GO_ESTABLISHMENT_OF_PROTEIN_LOCALIZATION_TO_ENDOPLASMIC_RETICULUM | 0.006222822 |
| GO_CYTOSOLIC_RIBOSOME | 0.006496563 |
| GO_MYELOID_CELL_ACTIVATION_INVOLVED_IN_IMMUNE_RESPONSE | 0.006572505 |
| GO_GRANULOCYTE_ACTIVATION | 0.006749582 |
| REACTOME_CREATION_OF_C4_AND_C2_ACTIVATORS | 0.007334172 |
| GO_REGULATION_OF_SUPEROXIDE_ANION_GENERATION | 0.015072472 |
| GO_NEGATIVE_REGULATION_BY_HOST_OF_VIRAL_TRANSCRIPTION | 0.015072472 |
| GO_REGULATION_OF_CHEMOKINE_SECRETION | 0.015072472 |
| GO_AXON_ENSHEATHMENT_IN_CENTRAL_NERVOUS_SYSTEM | 0.015072472 |
| GO_MICROGLIAL_CELL_ACTIVATION | 0.015072472 |
| GO_PERK_MEDIATED_UNFOLDED_PROTEIN_RESPONSE | 0.015072472 |
| GO_RESPONSE_TO_REDOX_STATE | 0.015072472 |
| GO_PARANODE_REGION_OF_AXON | 0.015072472 |
| GO_TAU_PROTEIN_BINDING | 0.015072472 |
| GO_PROTEIN_LOCALIZATION_TO_ENDOPLASMIC_RETICULUM | 0.015476652 |
| GO_ENDOSOME_LUMEN | 0.019934591 |
| GO_MACROPHAGE_CHEMOTAXIS | 0.020335357 |
| GO_NUCLEAR_TRANSCRIBED_MRNA_CATABOLIC_PROCESS_NONSENSE_MEDIATED_DECAY | 0.021270971 |
| GO_RESPONSE_TO_LIPOPROTEIN_PARTICLE | 0.023691045 |
| GO_GLIAL_CELL_DEVELOPMENT | 0.026197199 |

| feat_8 | pval_8 |
| --- | --- |
| KEGG_RIBOSOME | 2.47805E−06 |
| GO_ESTABLISHMENT_OF_PROTEIN_LOCALIZATION_TO_ENDOPLASMIC_RETICULUM | 3.75923E−06 |
| GO_CYTOSOLIC_RIBOSOME | 1.08339E−05 |
| GO_TRANSLATIONAL_INITIATION | 1.58859E−05 |
| GO_NUCLEAR_TRANSCRIBED_MRNA_CATABOLIC_PROCESS_NONSENSE_MEDIATED_DECAY | 1.85824E−05 |
| GO_CYTOSOLIC_SMALL_RIBOSOMAL_SUBUNIT | 2.25914E−05 |
| GO_PROTEIN_LOCALIZATION_TO_ENDOPLASMIC_RETICULUM | 3.09069E−05 |
| REACTOME_PEPTIDE_CHAIN_ELONGATION | 0.000111935 |
| GO_MULTI_ORGANISM_METABOLIC_PROCESS | 0.000121164 |
| REACTOME_INFLUENZA_VIRAL_RNA_TRANSCRIPTION_AND_REPLICATION | 0.000364231 |
| GO_PROTEIN_TARGETING_TO_MEMBRANE | 0.000515899 |
| REACTOME_3_UTR_MEDIATED_TRANSLATIONAL_REGULATION | 0.000579375 |
| GO_SMALL_RIBOSOMAL_SUBUNIT | 0.000749113 |
| GO_RIBOSOMAL_SUBUNIT | 0.000772505 |
| REACTOME_ACTIVATION_OF_THE_MRNA_UPON_BINDING_OF_THE_CAP_BINDING_COMPLEX_AND_EIFS_AND_SUBSEQUENT_BINDING_TO_43S | 0.000890267 |
| REACTOME_FORMATION_OF_THE_TERNARY_COMPLEX_AND_SUBSEQUENTLY_THE_43S_COMPLEX | 0.001396522 |
| REACTOME_NONSENSE_MEDIATED_DECAY_ENHANCED_BY_THE_EXON_JUNCTION_COMPLEX | 0.001719153 |
| GO_RNA_POLYMERASE_II_TRANSCRIPTION_COACTIVATOR_ACTIVITY | 0.001793002 |
| GO_DENTATE_GYRUS_DEVELOPMENT | 0.00179799 |
| REACTOME_SRP_DEPENDENT_COTRANSLATIONAL_PROTEIN_TARGETING_TO_MEMBRANE | 0.002040437 |
| REACTOME_TRANSLATION | 0.002703161 |
| REACTOME_INFLUENZA_LIFE_CYCLE | 0.002720744 |
| GO_VENTRICULAR_SEPTUM_MORPHOGENESIS | 0.003207289 |
| KEGG_PATHOGENIC_ESCHERICHIA_COLI_INFECTION | 0.005555645 |
| GO_SYMPATHETIC_NERVOUS_SYSTEM_DEVELOPMENT | 0.006640471 |
| GO_CARDIAC_CHAMBER_FORMATION | 0.006648259 |
| GO_CYTOSOLIC_LARGE_RIBOSOMAL_SUBUNIT | 0.006687025 |
| GO_E_BOX_BINDING | 0.007612288 |
| GO_RNA_CATABOLIC_PROCESS | 0.008258415 |
| GO_ADRENAL_GLAND_DEVELOPMENT | 0.009280876 |

| feat_9 | pval_9 |
| --- | --- |
| KEGG_RIBOSOME | 2.60172E−74 |
| GO_CYTOSOLIC_RIBOSOME | 6.92538E−68 |
| GO_ESTABLISHMENT_OF_PROTEIN_LOCALIZATION_TO_ENDOPLASMIC_RETICULUM | 2.82028E−66 |
| GO_NUCLEAR_TRANSCRIBED_MRNA_CATABOLIC_PROCESS_NONSENSE_MEDIATED_DECAY | 2.78396E−62 |
| GO_PROTEIN_LOCALIZATION_TO_ENDOPLASMIC_RETICULUM | 5.16508E−61 |
| GO_MULTI_ORGANISM_METABOLIC_PROCESS | 1.36429E−57 |
| GO_RIBOSOMAL_SUBUNIT | 1.49752E−56 |
| REACTOME_PEPTIDE_CHAIN_ELONGATION | 1.67613E−56 |
| GO_TRANSLATIONAL_INITIATION | 5.82924E−56 |

TABLE 3.2B-continued

| Gene Sets | |
| --- | --- |
| GO_PROTEIN_TARGETING_TO_MEMBRANE | 6.75104E−54 |
| REACTOME_INFLUENZA_VIRAL_RNA_TRANSCRIPTION_AND_REPLICATION | 7.62495E−52 |
| REACTOME_3_UTR_MEDIATED_TRANSLATIONAL_REGULATION | 9.94978E−51 |
| REACTOME_NONSENSE_MEDIATED_DECAY_ENHANCED_BY_THE_EXON_JUNCTION_COMPLEX | 9.94978E−51 |
| REACTOME_SRP_DEPENDENT_COTRANSLATIONAL_PROTEIN_TARGETING_TO_MEMBRANE | 2.87947E−50 |
| GO_CYTOSOLIC_PART | 1.03188E−47 |
| GO_STRUCTURAL_CONSTITUENT_OF_RIBOSOME | 2.11708E−47 |
| GO_RIBOSOME | 2.38758E−47 |
| REACTOME_INFLUENZA_LIFE_CYCLE | 6.95016E−47 |
| REACTOME_TRANSLATION | 3.64538E−46 |
| GO_RNA_CATABOLIC_PROCESS | 5.96315E−44 |
| GO_RRNA_METABOLIC_PROCESS | 1.64672E−42 |
| GO_ESTABLISHMENT_OF_PROTEIN_LOCALIZATION_TO_MEMBRANE | 4.43488E−40 |
| REACTOME_METABOLISM_OF_MRNA | 3.05131E−38 |
| GO_VIRAL_LIFE_CYCLE | 1.01546E−37 |
| GO_RIBOSOME_BIOGENESIS | 1.15733E−37 |
| GO_CYTOSOLIC_SMALL_RIBOSOMAL_SUBUNIT | 5.30837E−35 |
| REACTOME_METABOLISM_OF_RNA | 1.57338E−34 |
| GO_ESTABLISHMENT_OF_PROTEIN_LOCALIZATION_TO_ORGANELLE | 2.38388E−32 |
| GO_NCRNA_PROCESSING | 4.7719E−32 |
| GO_PROTEIN_LOCALIZATION_TO_MEMBRANE | 2.27205E−31 |

| feat_10 | pval_10 |
| --- | --- |
| GO_GLIAL_CELL_FATE_COMMITMENT | 0.000983734 |
| GO_AMINO_ACID_IMPORT | 0.002059284 |
| KEGG_PROXIMAL_TUBULE_BICARBONATE_RECLAMATION | 0.002969313 |
| GO_NEGATIVE_REGULATION_OF_SODIUM_ION_TRANSPORT | 0.004188427 |
| GO_OLIGODENDROCYTE_DIFFERENTIATION | 0.00503803 |
| GO_AXON_ENSHEATHMENT_IN_CENTRAL_NERVOUS_SYSTEM | 0.005963034 |
| GO_SODIUM_AMINO_ACID_SYMPORTER_ACTIVITY | 0.005963034 |
| GO_GLIAL_CELL_DIFFERENTIATION | 0.006808624 |
| GO_REGULATION_OF_ASTROCYTE_DIFFERENTIATION | 0.006983976 |
| GO_NEGATIVE_REGULATION_OF_OLIGODENDROCYTE_DIFFERENTIATION | 0.008176056 |
| GO_NEGATIVE_REGULATION_OF_ASTROCYTE_DIFFERENTIATION | 0.008176056 |
| GO_DERMATAN_SULFATE_METABOLIC_PROCESS | 0.008176056 |
| GO_S100_PROTEIN_BINDING | 0.008176056 |
| GO_CHONDROITIN_SULFATE_CATABOLIC_PROCESS | 0.010866734 |
| GO_POSITIVE_REGULATION_OF_AMINO_ACID_TRANSPORT | 0.010866734 |
| GO_METALLOENDOPEPTIDASE_INHIBITOR_ACTIVITY | 0.010866734 |
| GO_ASTROCYTE_DIFFERENTIATION | 0.012237497 |
| GO_NEUROTRANSMITTER_UPTAKE | 0.014069443 |
| GO_CELL_COMMUNICATION_BY_ELECTRICAL_COUPLING | 0.014069443 |
| GO_CAMERA_TYPE_EYE_PHOTORECEPTOR_CELL_DIFFERENTIATION | 0.014069443 |
| GO_REGULATION_OF_NEUROTRANSMITTER_UPTAKE | 0.014069443 |
| GO_GLIAL_CELL_PROJECTION | 0.014069443 |
| GO_FIBROBLAST_GROWTH_FACTOR_BINDING | 0.014998891 |
| GO_DERMATAN_SULFATE_PROTEOGLYCAN_METABOLIC_PROCESS | 0.017813441 |
| GO_DICARBOXYLIC_ACID_CATABOLIC_PROCESS | 0.017813441 |
| GO_CATION_AMINO_ACID_SYMPORTER_ACTIVITY | 0.017813441 |
| GO_NEGATIVE_REGULATION_OF_MYOBLAST_DIFFERENTIATION | 0.017960081 |
| GO_INSULIN_LIKE_GROWTH_FACTOR_BINDING | 0.021283881 |
| REACTOME_AMINO_ACID_SYNTHESIS_AND_INTERCONVERSION_TRANSAMINATION | 0.022122754 |
| GO_BRANCH_ELONGATION_OF_AN_EPITHELIUM | 0.022122754 |

| feat_11 | pval_11 |
| --- | --- |
| GO_ESTABLISHMENT_OF_PROTEIN_LOCALIZATION_TO_ENDOPLASMIC_RETICULUM | 7.5572E−06 |
| KEGG_RIBOSOME | 1.09486E−05 |
| GO_CYTOSOLIC_RIBOSOME | 1.70293E−05 |
| GO_NUCLEAR_TRANSCRIBED_MRNA_CATABOLIC_PROCESS_NONSENSE_MEDIATED_DECAY | 2.58459E−05 |
| GO_PROTEIN_LOCALIZATION_TO_ENDOPLASMIC_RETICULUM | 3.8385E−05 |
| GO_PROTEIN_TARGETING_TO_MEMBRANE | 7.83225E−05 |
| GO_MULTI_ORGANISM_METABOLIC_PROCESS | 0.000112275 |
| GO_TRANSLATIONAL_INITIATION | 0.000187432 |
| GO_CYTOSOLIC_LARGE_RIBOSOMAL_SUBUNIT | 0.000250487 |
| REACTOME_PEPTIDE_CHAIN_ELONGATION | 0.000284965 |
| GO_RIBOSOMAL_SMALL_SUBUNIT_ASSEMBLY | 0.000463734 |
| GO_RIBOSOMAL_SUBUNIT | 0.000496873 |
| REACTOME_INFLUENZA_VIRAL_RNA_TRANSCRIPTION_AND_REPLICATION | 0.000678705 |
| BIOCARTA_CCR5_PATHWAY | 0.000711197 |
| REACTOME_3_UTR_MEDIATED_TRANSLATIONAL_REGULATION | 0.000958427 |
| REACTOME_NONSENSE_MEDIATED_DECAY_ENHANCED_BY_THE_EXON_JUNCTION_COMPLEX | 0.000958427 |
| REACTOME_SRP_DEPENDENT_COTRANSLATIONAL_PROTEIN_TARGETING_TO_MEMBRANE | 0.001104786 |
| REACTOME_SMOOTH_MUSCLE_CONTRACTION | 0.001714778 |
| GO_CYTOSOLIC_SMALL_RIBOSOMAL_SUBUNIT | 0.002165699 |
| GO_RESPONSE_TO_LAMINAR_FLUID_SHEAR_STRESS | 0.002877245 |
| GO_ESTABLISHMENT_OF_PROTEIN_LOCALIZATION_TO_MEMBRANE | 0.002910323 |

TABLE 3.2B-continued

| Gene Sets | |
|---|---|
| REACTOME_INFLUENZA_LIFE_CYCLE | 0.003084206 |
| GO_LARGE_RIBOSOMAL_SUBUNIT | 0.003614374 |
| GO_STRUCTURAL_CONSTITUENT_OF_RIBOSOME | 0.004335214 |
| GO_RIBOSOME_ASSEMBLY | 0.005361165 |
| REACTOME_TRANSLATION | 0.006174664 |
| GO_CYTOSOLIC_PART | 0.006388408 |
| GO_RIBOSOME | 0.007065184 |
| GO_CELLULAR_RESPONSE_TO_FLUID_SHEAR_STRESS | 0.007099793 |
| GO_NEGATIVE_REGULATION_OF_VIRAL_ENTRY_INTO_HOST_CELL | 0.007099793 |

In Vitro Culture Caused Collapse of Population to a Dominant Progenitor State within Days Stem cells intended for therapeutic or research purposes are often expanded aggressively in vitro, to produce a consistent lot of cells that can be used repeatedly. Specifically, the ivNSCs in this example came from a commercial lot that was banked at passage 8 after approximately 2-3 weeks in culture. Whether the functional changes observed—reduced diversity and significant transcriptional downregulation—were the gradual result of this long-term culture or happened instantaneously after isolation from the living tissue were determined. Thus, a fresh derivation of neural stem cells (NSCs) from the ventricular zone region of the E18 mouse brain were performed (See Methods—NSC derivation in this example), and these populations were tracked over 18 days in culture using single-cell profiling (FIG. 37A).

Figures 37A, 37B, 37C, 37D, 37E:
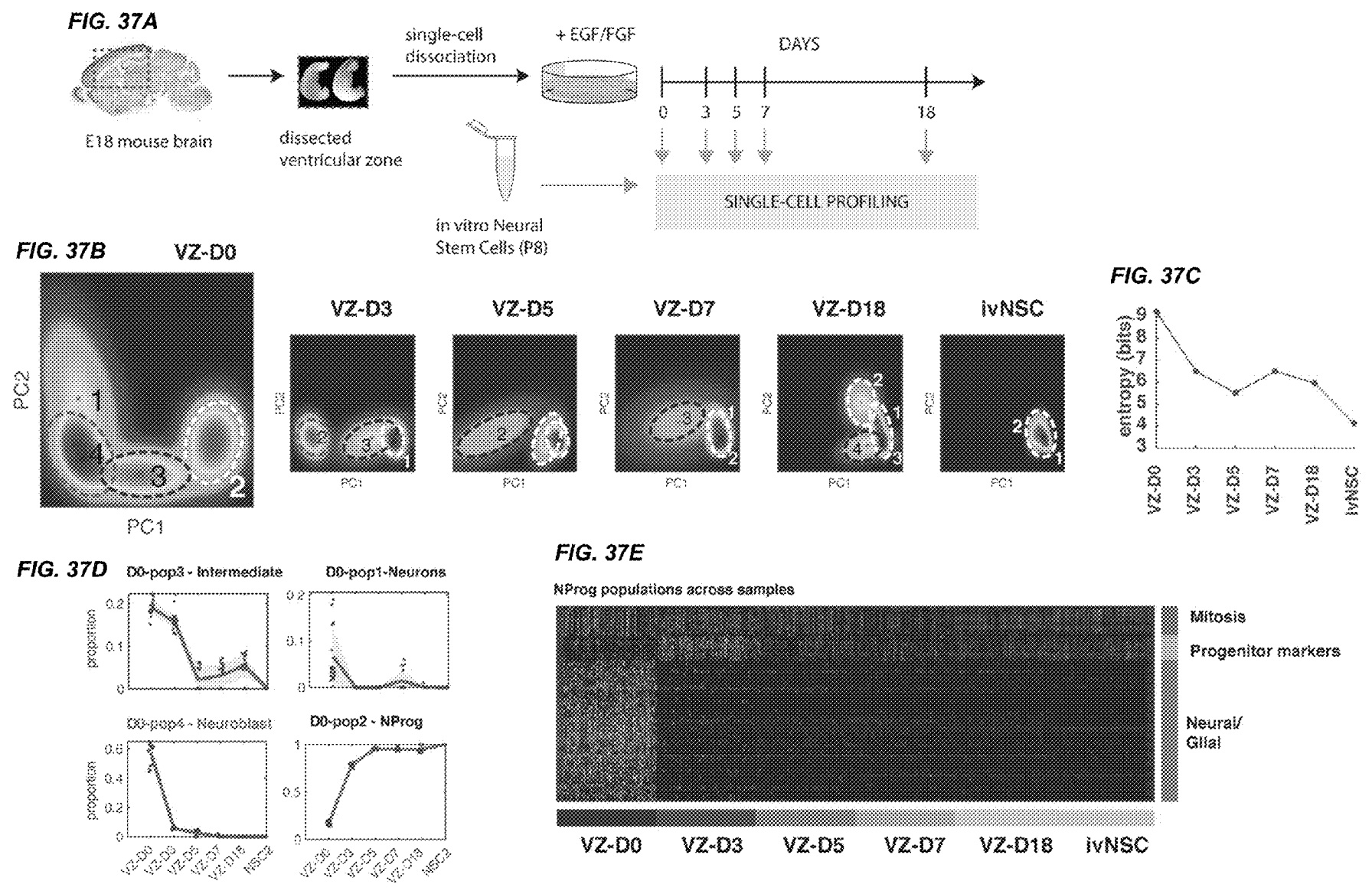

First, models of the populations from each time point were built, and the subpopulations were aligned across samples, using the VZ-D0 model as the reference (FIG. 37B). As in the E18 whole brain, the ventricular zone of the E18 brain contained multiple populations of progenitors including a Committed Neuroblast (CN) [oval on the left], neural progenitor (Neural Progenitor) [oval on the right], as well as an Intermediate Progenitor (IP) population [oval in the middle] and Neurons (only found in the D0 sample). Over the course of 18 days, the entire population was observed to collapse to a single dominant population—the NProgs—within about 7 days. This observation is also reflected in the decline of the total population entropy (FIG. 37C).

This population collapse was quantified by extracting the abundances for each set of the aligned subpopulations across timepoints (FIG. 37D). To bolster against potential brittleness in model fitting for any single model, 20 models were built for each timepoint, and all models were aligned to the same reference population. Every point represents the abundance parameter w for the mixture component within the model that was optimally aligned to the reference subpopulation. While Neurons, intermediate progenitors (IPs), and Committed Neuroblasts declined very rapidly, within 3 to 5 days, the NProg population continued to rise asymptotically to 100% of the population by day 5.

Transcriptional changes occurred even faster. By examining gene expression patterns of only the Nprog populations extracted from all samples (FIG. 37E), key neural and glial genes found in FIGS. 36A-36I were observed to decline very rapidly, within less than 3 days after establishing cells in culture. These results show that although canonical stem cell markers (such as Pax6 and Sox2) were maintained in culture over time, the expression of genes that are important for later functional diversity were erased immediately after cells were grown and manipulated in in vitro culture.

Combinatorial Signals Titrated the Relative Balance of Progenitor Subpopulations Next, whether and how signaling interventions can preemptively bias the transcriptional state of neural stem cells, potentially restoring lost functionality, were determined. Given the finding that transcriptional changes happened in less than three days after in vitro culture, signals were added immediately after dissociation from the brain. Signals known to be important in neural stem cell differentiation into astrocytes (BMP4), neurons (Wnt pathway through CHIR activation), or oligodendrocytes (PDGF-AA), were chosen. A combinatorial screen, in which these signals were added together with EGF/FGF at varying concentrations to dissociated cells from the brain, were performed. The cells were grown for 5 days before profiling. To profile all of these samples, a multiplexing approach, in which cells were methanol fixed and then covalently labeled with a separate exogenous DNA barcode for each experimental condition, was used. A total of 8691 cells were profiled across 19 conditions [See Methods—Experimental multiplexing using Clicktags in this example].

First, how the populations responded at a high-level were examined by using the PopAlign framework to build new models of populations, and the populations were ranked against a control population using a Log-likelihood ratio score (FIG. 38A). In this case, the control population was defined as the 20 ng/mL EGF/FGF condition, which is the concentration of growth factors normally used to propagate neural stem cells in culture. The log-likelihood ratio score is a single metric that measures the extent to which an entire population model diverges from a control population.

Low concentrations of EGF/FGF (0.8 ng/mL) were observed to generate populations that were highly divergent from the control, based on the large effect that EGF/FGF concentration had on the log-likelihood ratio (LLR) score. However, subtler patterns suggested that other signals also influenced population structure: within each of the three tiers of EGF/FGF concentration, the samples containing high concentrations of BMP4 and CHIR consistently had the lowest LLR score.

To investigate this more deeply, how the population structure of these progenitor cells responded to the signaling cues was determined. For this analysis the query function [See Methods—Query in this example] of the modeling framework was used to score all cells in each sample using a standard model built from the control population. For this combinatorial screen, some conditions suffered from poor sampling (roughly 100 cells vs. 1000 cells for most samples) due to variation in proliferation rates. Thus, querying all samples using the same model was more robust than building separate models (which can be of poor quality with severe undersampling). The first 3 principal components (PCs) were used as the feature vectors in order to improve the sampling within the gene expression space.

In this new analysis, the population were segmented into more fine-grained subpopulations (FIG. 38B). While there was a committed neuroblast population, the neural progenitor population now split into three subpopulations: (1) a proliferating progenitor (PP) population that actively expressed mitotic genes, (2) a non-proliferating progenitor population (NPP), as well as (3) a basal progenitor (BP) that only expressed the progenitor program (Prog), but not glial genes like ALDOC or SPARCL1. Using the control model, individual cells from each sample were scored and assigned into one of the four subpopulations, and abundances of each individual subpopulation across all experimental samples were (FIG. 38D).

To dissect how the abundances of these individual populations responded to signals, a multinomial logistic regression analysis was performed. Multinomial logistic regression models were used to determine the probability of each cell belonging to one of K mutually exclusive classes (in this case, the four subpopulations defined above) based on m independent predictor variables (in this case, the concentrations of each signal) [See Methods—Multinomial logistic regression in this example].

By examining the regression coefficients β, the relationship between each signal and how the signal regulates the proportions of each cell type can be determined. Importantly, the regression model only computed coefficients for K−1 of the outcome classes, while the $K^{th}$ class was treated as a reference. In this case, the "non-proliferating progenitor" was chosen as the reference class because the "non-proliferating progenitor" had the least variance across all samples. By taking the exponent of each coefficient $e^{\beta_{k,m}}$ (whose values are displayed in FIG. 38E), a quantity called the "odds ratio" was determined, which is the relative chance of a cell choosing class k over the reference class K for every unit increase of predictor variable m.

From this analysis, some signals having very strong effects on regulating the abundances of specific subpopulations were determined. The strongest effect was the coefficient relating EGF/FGF to proliferating progenitors (PP), which corresponded to an odds ratio of 3.47, which means that for every extra unit of EGF/FGF that was added to the cells, 3.47× as many PP, compared to non-proliferating progenitors (NPP), resulted. This strongest effect may be because EGF and FGF stimulate proliferation and served to confirm that the approach discovers biologically meaningful results.

Other results demonstrate interesting new relationships: for instance, the coefficient relating PDGF to basal progenitors corresponded to an odds ratio of 1.75. The activation of the Wnt pathway, through CHIR, seemed to inhibit the PP population; each additional unit of CHIR (3 uM) resulted in 0.6× the number of PP. Finally the coefficient relating BMP4 to committed neuroblasts corresponded to an odds ratio of 2.2, suggesting that BMP4 increased neuroblast populations, while decreasing PP and NPP populations. The results highlight the potential for using signals as a way to steer stem cell composition, and thus fate propensity.

Additional Signals Rescued Transcriptional Defects of Cultured ivNSCs and Reinvigorates Layer-Specific Genes Having seen that these signals can control population structure, whether these additional signals induced major transcriptional changes in neural stem cells was determined. Further, whether any changes restored the functional defects observed in response to in vitro culture was determined. To learn these transcriptional changes, a new experiment was performed using high concentrations of signaling factors for two reasons: 1) the original combinatorial screen required the cells to be fixed in methanol, which may disrupt gene expression values thus making comparing that data directly to the in vivo data difficult and 2) the original combinatorial screen suffered from low sample number for some of the conditions, due to variation in proliferation rate. This new experiment was performed by adding high concentrations of additional signals (BMP4 (20 ng/mL), CHIR (3 uM), PDGF-AA (20 ng/mL) and DLL1 (surface-coated)) in addition to high concentrations of EGF/FGF immediately after dissociation of cells from the VZ, and all cells were grown for five days in these signal cocktails before profiling.

First, models were built for all of the new samples, aligned each to the VZ-D0 sample (which served as the control), and then only the subpopulations across all samples that aligned to the neural progenitor population were pulled out (FIG. 39B). By plotting the Jeffreys Divergence between these aligned populations (FIG. 39C), all the in vivo populations (E15, E18, and VZ-D0) were seen to be close to each other, while in vitro populations were very distant (VZ-D18 and ivNSC). Interestingly, the BMP4 sample was closest to the in vivo populations, compared to other samples at that timepoint (VZ-D5, VZ-D5-CHIR, VZ-D5-DLL, VZ-D5-PDGF), suggesting that BMP4 induced stem cells may be more similar to neural progenitors from the brain.

To confirm this possibility, the genes that were differentially expressed in the BMP4-, DLL-, PDGF-, and CHIR-containing cells were examined, and these genes were compared to the genes discovered in FIG. 36A-36I. Twenty of the BMP4-upregulated genes overlapped with the 190 genes downregulated in ivNSCs (relative to E18 NProgs), suggesting that BMP4 may be restoring functionality that is lost during in vitro culture. By contrast, CHIR only rescued 3 of the lost genes, while DLL and PDGF had only one differentially regulated gene each (FIG. 39D). The heatmap of these BMP4 overlap genes show that the pattern of gene expression induced by BMP4 mirrored that of population from the in vivo stages (E15, E18, and VZ=D0). Similarly, BMP4 suppressed the expression of 22 genes that are upregulated in ivNSCs (FIG. 39F), and their expression patterns are shown in FIG. 39G.

Normally in development, these neural progenitors give rise to neurons that form six distinct layers in the cortex. These cortical layers have distinct functions, connectivity patterns, and gene expression patterns, which have been characterized in the literature. The gene expression patterns of these layer-specific genes were examined in neural progenitor populations aligned across all samples (FIGS. 39H-39I). Expression of these genes, while noisy, was very extensive in the in vivo populations, but that culture in vitro erased their expression. BMP4 was the only signal that could rescue the expression of these genes.

CONCLUSIONS/DISCUSSION

The probabilistic models enabled aligning subpopulations across many experimental samples and datasets, and tracking concurrent shifts in subpopulation gene expression, abundance, and population dynamics. Drilling down into this representation enabled reasoning about complex populations at the level of single subpopulations and individual gene programs.

The utility of transplantable cell-based therapeutics for tissue regeneration hinges on the ability to produce functional cells matched to native tissue. The inability to generate functional differentiated neurons from neurosphere cultured NSCs in tissue culture and following transplantation had indicated the possibility that NSCs themselves were missing core functions. The PopAlign framework provides a way to engineer stem cell populations by identifying and explicitly comparing subpopulations, pinpointing their molecular defects, and then screening experimental conditions that maintain or grow subpopulations without those defects.

The results point to three major conclusions about the nature of neural stem cells. First, it is striking that progenitor cells from the developing brain occupy a broad transcriptional landscape, with extensive expression of background genes that are important for downstream differentiation states. The fact that these genes are lost when cells are transferred to in vitro culture, within a matter of days not weeks, suggest possible mechanisms for why these cultured stem cells fail to differentiate into functional neurons.

Secondly, a novel mechanism was demonstrated for altering stem cell fate propensity by reshaping population structure via adjusting the relative abundances of distinct progenitor subpopulations. The ability to control the demographics of cell populations by titrating potent developmental signals (such as Wnt pathway activation and BMP4) suggests that the developing brain may be employing similar mechanisms to maintain or steer population diversity.

Finally the finding that BMP4 can reinvigorate genes specific to different layers of the cortex raises the possibility that environmental signals naturally optimize the preservation of stochastic gene expression that will later be necessary for differentiation. In contrast, historical approaches to handling and manipulating stem cells in culture have optimized for preservation of a few marker genes, whose expression can actually be fairly easily maintained. Without single-cell profiling, the erasure of these noisy genes upon in vitro culture, nor their rescue upon supplementation with BMP4 signal, cannot be observed.

The example shows a path forward for cell engineering—via comparisons of large-scale screens of signals or other perturbations that can alter population structure and revitalize the patterns of gene expression found in living tissue.

Methods

Mouse Brain Tissue Dissociation.

Tissue from mouse brain was purchased from Brainbits or acquired, and digested using 6 mg of Papain (Brainbits) at 2 mg/mL in Hibernate E medium (Brainbits) for 30 minutes at 30° C. After incubation, tissue was triturated for one minute using a silzanized pasteur pipet. Dissociation medium containing the dissociated cells were centrifuged for 1 minute at 200x g and the cell pellet was resuspended in NPgrow media (Brainbits), which contains 20 ng/mL EGF/FGF, or 1×PBS+0.04% BSA for subsequent culturing or single-cell profiling through the 10× Genomics platform respectively. Data from the E18 mouse brain was obtained from 10× Genomics.

ivNSC Culture

Cryopreserved mouse neural stem cells (Millipore) were thawed at 37° C. then the cells were pelleted via centrifugation for 2 minutes at 200x g. Cells were resuspended in pre-warmed Neural Stem Cell Basal Medium (Millipore), which contains 20 ng/mL EGF/FGF, and counted on the Countess II Automated Cell Counter (Thermofisher). Cells were then plated onto poly-L-ornithine (Millipore) and laminin (Thermofisher) coated 100 mm culture plates at 700,000 cells per plate in 10 mL of Neural Stem Cell Basal Medium supplemented with EGF (Millipore) and bFGF (Millipore) at 20 ng/mL, heparin (Sigma) at 2 ug/mL, and 1% Penicillin-Streptomycin (Thermofisher). Cells were cultured at 37° C. and 5% CO2 and supplemented medium was changed the next day and every other day thereafter until confluent.

NSC Derivation.

Neuroprogenitors are dissociated from the combined cortex, hippocampus and ventricular zone of E18 mice (Brainbits). After dissociation and resuspension of the cells in NPgrow, cells were counted and plated onto ultra-low attachment 100 mm culture plates (Corning) at one million cells per plate in 10 mL of NPgrow supplemented with 1% Penicillin-Streptomycin. Cells were cultured at 37° C. and 5% CO2 and supplemented medium was changed every 3 to 4 days. In some experiments, subventricular zone (SVZ) stem cells were derived with supplemental factors during derivation. PDGF-AA and BMP4 (Peprotech) were used at 4 ng/mL, and 20 ng/mL. CHIR99021 (Stem Cell) was used at 3 uM. DLL1 ligand was coated onto tissue culture plastic for one hour before plating cells.

Experimental Multiplexing Using Clicktags.

Cultured cells were dissociated in Accutase into a single cell suspension. Cells were then fixed in ice-cold 80% methanol. Prior to cell labeling, two methyltetrazine (MTZ) activated barcoding oligos were combined for each labeling sample, NHS-trans-cyclooctene (NHS-TCO) was then added and left to reaction for 5 minutes. The previously fixed cells were then mixed thoroughly with the barcode oligo solution and incubated for 30 minutes at room temperature. Labeling reaction was then quenched with the addition of Tris-HCl and methyltetrazine-DBCO. After the quenching step, cells from all labeling samples were pooled together along with the addition of two volumes of PBS-BSA then centrifuged at 800×g for 5 minutes followed by two more cycles of PBS-BSA washes and centrifugation steps. After the final centrifugation step, the cell pellet was resuspended in 100 uL of PBS-BSA and counted on a hemocytometer. Cells were then loaded onto 3-4 lanes, targeting 10,000 cells per lane, of the Chromium Controller and processed as recommended by the 10× Genomics v2 Single Cell 3' reagent kit protocol until completion of the cDNA amplification PCR step. At this step, SPRI size-selection was used to separate the barcode oligos from the cDNA which were then processed separately.

Barcode Demultiplexing.

The 10× cDNA library was sequenced and the sequence reads aligned them to a mouse reference (mm10) using the Cellranger count pipeline. This generated a list of cell barcodes that was used as a whitelist to parse the clicktags data (FASTQ files). When parsing a read from the clicktags data, the cell barcode was extracted and compared to the cell barcode whitelist. If a match was found, the clicktag sequence was extracted and aligned to the list of known clicktag sequences. Counts for clicktags were stored in cell barcodes by tags matrix. For each clicktag, the counts distribution was computed and the optimal threshold was found using Otsu's method. The counts distribution for a clicktag was a bimodal distribution, and the threshold helped separating the cells with low counts and the cells with high counts for a given clicktag. The clicktag counts matrix was binarized using the clicktag threshold values: the values for a clicktag under its respective threshold became 0, and the values greater than the threshold became 1. From this binary matrix, only the singly-called cells were retained.

Probabilistic Models and Alignment.

To compare single-cell datasets, probabilistic models were constructed that estimate the underlying joint probability distribution of cells within gene expression space. Probabilistic models are useful because they are a highly-compressed, conceptually meaningful representations of single-cell data, and their sub-components can be quantitatively compared using well-defined statistical metrics. In this example, the probabilistic model-based comparisons allowed automatically determination of which cells from the natural brain were closest to in vitro-grown cells, and statistically ranking the cells.

Models were constructed as described in the PopAlign example (Example 2). Briefly, single-cell gene expression data was first normalized by the total number of transcripts per cell, and then log-transformed in order to bring all genes close in scale. The genes were then filtered and only highly variable genes (e.g. supra-Poisson genes) were kept.

Gene expression data was compressed into a set of m features, which are gene expression programs extracted from the data using matrix factorization techniques (e.g. oNMF). Using these features, a compressed representation of each cell was constructed as a vector $c=(c_1, c_2, \ldots, c_m)$ of m feature coefficients, which weight the magnitude of gene expression programs within a given cell.

For each sample a mixture model was built that factors the population into a set of distinct subpopulations, each represented by a distinct mixture component (e.g. a Gaussian probability density):

$$P(c) = \sum_{j=1}^{l} w_j \phi_j(c)$$

where $\phi_j(c) = N(c; \mu_j, \Sigma_j)$.

Aligning Probabilistic Models.

To determine which subpopulations to compare between samples, an alignment was performed between models based on statistical "closeness." The population was denoted to be compared as the "reference" population, and the other populations as "test" populations. For each mixture component in the "test" population, the closest mixture component was found within the reference set by minimizing the Jeffrey Divergence, a symmetrized version of the Kullback-Leibler (KL)-divergence:

$$\operatorname{argmin}_j D_{JD}\left(\phi_i^{test}(c) \parallel \phi_j^{ref}(c)\right).$$

L1-Norm Error Metric.

Up- and down-regulated genes were discovered between any two subpopulations by measuring the L1 distance between their distributions. For each gene, two empirical distributions $P_1(g)$, $P_2(g)$, one for each subpopulation, were determined. These distributions were discretized over identical histogram binnings, a, over the gene's entire range of expression, $\Omega$. Then the L1 distance was defined as:

$$d = \operatorname{sign}(\overline{g_2} - \overline{g_1}) \Sigma_{a \in \Omega} \|P_1(a) - P_2(a)\|_1,$$

where $\overline{g_1}$ and $\overline{g_2}$ denote the respective means of subpopulations 1 and 2. The sign allowed distinguishing whether a gene was down-regulated in population 2 (negative) or upregulated in population 2 (positive). The L1 distance ranged from −2 to +2, both of which corresponded to completely non-overlapping distributions. Genes with L1 distances of high magnitude ($\gtrsim 0.5$) always had distributions which, by eye, were in obvious agreement with the labeled directionality. A value of 0.8 was used to threshold up- and down-regulated genes in subpopulation comparisons.

Query.

In samples where the number of cells was too small to build a standalone model, an existing model was used to classify cells into different subpopulations. For the combinatorial signaling screen, some samples had roughly 100 cells, which would not adequately sample the feature space. For these experiments, each datapoint $c_i$ was queried against a control model built from the reference population. The control model included a collection of mixture components $\{\phi_j(c)\}$. A class $Y_i$ was assigned for each specific cell $c_i$:

$$Y_i = \operatorname{arg\,max}_j(\phi_i(c_i))$$

Each cell in each sample received a class label Y, these class labels can then be used to compute sample-specific subpopulation parameters—$\mu_j$, $\Sigma_j$ and $w_j$. The resulting abundances $w_j$ were used in a multinomial logistic regression model to learn how population structure was steered by signals.

Multinomial Logistic Regression.

A multinomial logistic regression model was used to understand how signals affected the relative proportions of K subpopulations within a sample. Each datapoint i (e.g., a single cell) was associated with a set of independent predictor variables describing the concentrations of M signals $x_i = \{x_{i,1}, x_{i,2}, \ldots, x_{i,M}\}$ as well as the corresponding categorical outcome $Y_i$ (e.g., the subpopulation class), which can take on one of K values. A multinomial logistic regression model uses a linear predictor function to predict the probability that observation i has outcome k. The multinomial model extends the binary logistic regression model by using one subpopulation K as the "pivot," while the other K−1 outcomes are regressed independently against this pivot.

$$\ln\frac{P(Y_i = 1)}{P(Y_i = K)} = \beta_1 * x_i$$

$$\ln\frac{P(Y_i = 2)}{P(Y_i = K)} = \beta_2 * x_i$$

$$\ldots$$

$$\ln\frac{P(Y_i = K - 1)}{P(Y_i = K)} = \beta_{K-1} * x_i$$

where the coefficients are an M-dimensional vector $\beta_k = \{\beta_{k,1}, \beta_{k,2}, \ldots, \beta_{k,M}\}$. From this equation, the coefficients $\beta_k$ can be seen as related to the relative probability of getting subpopulation k vs. the pivot subpopulation K. Taking the exponent of both sides, a quantity known as the odds ratio on the right was determined: $e^{\beta_{k,j}}$.

$$\frac{P(Y_i = k)}{P(Y_i = K)} = e^{(\beta_k * x_i)}$$

This quantity means that for every unit increase in signal j, it is X times as likely to get subpopulation k vs. the pivot subpopulation K, where $X = e^{\beta_k}$. For each subpopulation, the odds ratio was interpreted to relate how its abundance (relative to the pivot) responds to specific signaling inputs.

ADDITIONAL CONSIDERATIONS

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Accordingly, phrases such as "a device configured to" are intended to include one or more recited devices. Such one or more recited devices can also be collectively configured to carry out the stated recitations. For example, "a processor configured to carry out recitations A, B and C can include a first processor configured to carry out recitation A and working in conjunction with a second processor configured to carry out recitations B and C. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc."

is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for single cell analysis comprising:
performing single-cell RNA-sequencing on a plurality of test cells to obtain single cell gene expression profiles of the plurality of test cells, wherein the plurality of test cells represents a heterogeneous cell population;
under control of a hardware processor:
receiving single cell gene expression data comprising a plurality of normalized reference gene expression vectors and a plurality of normalized test gene expression vectors representing single cell gene expression profiles of a plurality of reference cells and the plurality of test cells respectively;
determining (i) a gene feature matrix, comprising a plurality of gene features, and, for each of the plurality of normalized reference gene expression vectors and the plurality of normalized test gene expression vectors, (ii) a reference gene feature weighting vector or a test gene feature weighting vector using a training matrix comprising a plurality normalized training gene expression vectors, wherein the plurality of reference gene feature weighting vectors and the plurality of test gene feature weighting vectors represent gene feature profiles of the plurality of reference cells and the plurality of test cells, respectively, wherein a size of a reference gene feature weighting vector is less than a size of a reference gene expression vector and a size of a test gene feature weighting vector is less than a size of a test gene expression vector, thereby reducing a dimension of the single cell gene expression data;
determining (i) a reference Gaussian mixture model comprising a plurality of reference Gaussian densities each associated with a reference weight and (ii) a test Gaussian mixture model comprising a plurality of test Gaussian densities each associated with a test weight from the plurality of reference gene feature weighting vectors and the plurality of test gene expression vectors, respectively, wherein each of (i) the plurality of reference Gaussian densities and associated reference weights and (ii) the plurality of test Gaussian densities and the associated test weights represents a subpopulation of the plurality of reference cells or the plurality of test cells, respectively, thereby modeling a distribution of gene expression states within the heterogeneous cell population;
aligning each of the plurality of test Gaussian densities to an aligned reference Gaussian density of the plurality of reference Gaussian densities;
determining a Gaussian density difference between one of the plurality of test Gaussian densities and the aligned reference Gaussian density the test Gaussian density is aligned to; and
determining a difference between the plurality of test cells, or a subpopulation thereof, and the plurality of reference cells, or a subpopulation thereof, using the Gaussian density difference.

2. The method of claim 1, wherein receiving the single cell gene expression data comprises:
receiving single cell gene expression data comprising a plurality of reference gene expression vectors and a plurality of test gene expression vectors representing single cell gene expression profiles of a plurality of reference cells and a plurality of test cells respectively;
for each of the plurality of reference gene expression vectors and the plurality of test gene expression vectors, normalizing gene expression values of the reference gene expression vector or the test gene expression vector to generate a normalized reference gene expression vector or a normalized test gene expression vector comprising normalized gene expression values.

3. The method of claim 1, wherein the gene expression profiles comprise mRNA expression profiles and/or protein expression profiles.

4. The method of claim 1, wherein the normalizing comprises:

normalizing the gene expression values of the reference gene expression vector or the test gene expression vector relative to a sum of the gene expression values to generate the normalized reference gene expression vector or the normalized test gene expression vector comprising the normalized gene expression values, adjusting the gene expression values of the reference gene expression vector or the test gene expression vector with a scaling factor to generate the normalized reference gene expression vector or the normalized test gene expression vector comprising the normalized gene expression values, increasing the gene expression values of the reference gene expression vector or the test gene expression vector by a pseudo-count value to generate the normalized reference gene expression vector or the normalized test gene expression vector comprising the normalized gene expression values, wherein the pseudo-count value is one, and/or changing the gene expression values of the reference gene expression vector or the test gene expression vector to a logarithmic scale to generate the normalized reference gene expression vector or the normalized test gene expression vector comprising the normalized gene expression values.

5. The method of claim 4, wherein the scaling factor is about a sum of the gene expression values of one of the plurality of reference gene expression vectors or one the plurality of test gene expression vectors, wherein the scaling factor is about a smallest sum of the gene expression values of any of the plurality of reference gene expression vectors and any of the plurality of test gene expression vectors, and/or wherein the scaling factor is about 1000.

6. The method of 1, wherein the plurality of normalized training gene expression vectors comprises: one or more of the plurality of normalized reference gene expression vectors and/or one or more of the plurality of test gene expression vectors, wherein the plurality of normalized training gene expression vectors comprises one or more of the plurality of normalized reference gene expression vectors sampled and/or one or more of the plurality of test gene expression vectors, wherein the plurality of normalized training gene expression vectors comprises two or more the plurality of normalized reference gene expression vectors randomly and/or uniformly sampled and/or two or more of the plurality of test gene expression vectors randomly and/or uniformly sampled, and/or wherein the plurality of normalized training gene expression vectors comprises the plurality of normalized reference gene expression vectors and/or the plurality of test gene expression vectors.

7. The method of claim 1, wherein determining the gene feature matrix comprises:

determining the gene feature matrix from the plurality of normalized training gene expression vectors using machine learning, wherein the machine learning is based on a layered neural network, and/or determining the gene feature matrix using matrix factorization, wherein the matrix factorization comprises singular value decomposition, principal component analysis, non-negative matrix factorization, sparse non-negative matrix factorization, and/or orthogonal non-negative matrix factorization.

8. The method of claim 1 wherein the gene feature matrix is an orthogonal matrix, wherein each, or at least one, element of the gene feature matrix is greater than or equal to zero, and/or wherein each, or at least one, element of at least one of the plurality of reference gene feature weighting vectors and/or at least one of the plurality of test gene feature weighting vectors is greater than or equal to zero.

9. The method of claim 1, wherein a number of the plurality of gene features is predetermined, and/or wherein a ratio of a size of a gene expression vector of the plurality of reference gene expression vectors and the plurality of test gene expression vectors to a number of the plurality of gene features is at least 10, 20, 30, 40, 50, 100, 500, or 1000.

10. The method of claim 1 wherein determining the gene feature matrix comprises:

determining the gene feature matrix comprising the plurality of gene features using a plurality normalized training gene expression vectors; and for each of the plurality of normalized reference gene expression vectors and the plurality of normalized test gene expression vectors, determining a reference gene feature weighting vector or a test gene feature weighting vector using the gene feature matrix, wherein determining the gene feature matrix comprises:

determining the gene feature matrix and a gene feature weighting matrix comprising a plurality of gene feature weighting vectors using the plurality of normalized training gene expression vectors, wherein each, or at least one, element of the gene feature weighting matrix is greater than or equal to zero, wherein determining the gene feature matrix and the gene feature weighting matrix comprises: determining the gene feature matrix and the gene feature weighting matrix by minimizing a loss function comprising a difference of the training matrix and a product of the gene feature matrix and the gene feature weighting matrix, wherein determining the gene feature matrix and the gene feature weighting matrix comprises: determining the gene feature matrix and the gene feature weighting matrix by minimizing a loss function comprising a norm of the training matrix and a product of the gene feature matrix and the gene feature weighting matrix, and/or wherein determining the gene feature matrix and the gene feature weighting matrix comprises: determining the gene feature matrix and the gene feature weighting matrix by minimizing a loss function comprising a Frobenius norm of the training matrix and a product of the gene feature matrix and the gene feature weighting matrix, wherein the loss function comprises a penalty comprising a number of the plurality of gene features in the gene feature matrix, wherein the loss function comprises a penalty comprising to a number of the plurality of gene features in the gene feature matrix exponentiated with an exponentiation factor, and/or wherein the exponentiation factor is about 0.7.

11. The method of claim 10 wherein determining the reference gene feature weighting vector or the test gene feature weighting vector comprises: determining the reference gene feature weighting vector or the test gene feature weighting vector by minimizing a loss function comprising a difference of the corresponding normalized reference gene expression vector or normalized test gene expression vector and a product of the gene feature matrix and the reference gene feature weighting vector or the test gene feature weighting vector, wherein determining the reference gene feature weighting vector or the test gene feature weighting vector comprises:

determining the reference gene feature weighting vector or the test gene feature weighting vector by minimizing a loss function comprising a norm of the corresponding normalized reference gene expression vector or normalized test gene expression vector and a product of the gene feature matrix and the reference gene feature weighting vector or the test gene feature weighting vector, and/or wherein determining the reference gene feature weighting vector or the test gene feature weighting vector comprises: determining the reference gene feature weighting vector or the test gene feature weighting vector by minimizing a loss function comprising a Frobenius norm of the corresponding normalized reference gene expression vector or normalized test gene expression vector and a product of the gene feature matrix and the reference gene feature weighting vector or the test gene feature weighting vector.

12. The method of claim 1 wherein determining (i) the reference Gaussian mixture model and (ii) the test Gaussian mixture model comprises: determining (i) one or more reference parameters and the reference weight of or associated with each of the plurality of reference Gaussian densities and (ii) one or more test parameters and the test weight of each of the plurality of test Gaussian densities, respectively, from (i) the plurality of reference gene feature weighting vectors and (ii) the plurality of test gene feature weighting vectors, respectively, wherein each of the plurality of reference Gaussian densities and/or each of the plurality of test Gaussian densities comprises a normal distribution, and wherein parameters of the normal distribution comprise the one or more reference parameters or the one or more test parameters of the reference Gaussian density or the test Gaussian density, respectively, wherein the one or more parameters of each, or at least one, of the plurality of reference Gaussian densities comprises a reference centroid and a reference covariance matrix, and wherein the one or more parameters of each, or at least one, of the plurality of test Gaussian densities comprises a test centroid and a test covariance matrix, wherein the reference centroid, the reference covariance matrix, and the reference weight of or associated with a reference Gaussian density of the plurality of Gaussian densities represent an average of reference gene features of a subpopulation of the plurality of reference cells represented by the reference Gaussian density, a spread of the reference gene features, an abundance of the subpopulation of the plurality of reference cells represented by the reference Gaussian density, and wherein the test centroid, the test covariance matrix, and the test weight of or associated with a test Gaussian density of the plurality of Gaussian densities represent an average of test gene features of a subpopulation of the plurality of test cells represented by the test Gaussian density, a spread of the test gene features, an abundance of the subpopulation of the plurality of test cells represented by the test Gaussian density, wherein determining (i) the reference Gaussian mixture model and (ii) the test Gaussian mixture model comprises: determining (i) the reference Gaussian mixture model and (ii) the test Gaussian mixture model by maximum likelihood estimation and a likelihood function, and/or wherein the maximum likelihood estimation comprises an expectation maximization method.

13. The method of claim 1 wherein a number of the plurality of reference Gaussian densities and/or a number of the plurality of test Gaussian densities are pre-determined, or wherein a number of the plurality of reference Gaussian densities and/or a number of the plurality of test Gaussian densities is about 10, 15, 20, 30, 40, or 50, or wherein determining (i) the reference Gaussian mixture model and (ii) the test Gaussian mixture model comprises determining a number of the plurality of reference Gaussian densities and/or a number of the plurality of test Gaussian densities by penalizing the number of the plurality of reference Gaussian densities and/or the number of the plurality of test Gaussian densities, or wherein determining (i) the reference Gaussian mixture model and (ii) the test Gaussian mixture model comprises: determining a number of the plurality of reference Gaussian densities and/or a number of the plurality of test Gaussian densities using Bayesian Information Criterion.

14. The method of claim 1 wherein determining (i) the reference Gaussian mixture model comprises: determining a pair of reference Gaussian densities of the plurality of reference Gaussian densities with a divergence smaller than a divergence of any other pair of reference Gaussian densities of the plurality of reference Gaussian densities to be redundant in the reference Gaussian model; merging the pair reference Gaussian densities to generate a merged reference Gaussian density; determining merging the pair of reference Gaussian densities results in increasing a Bayesian Information Criterion of the reference Gaussian mixture model; and accepting the merged reference Gaussian density, and wherein determining (i) the test Gaussian mixture model comprises: determining a pair of test Gaussian densities of the plurality of test Gaussian densities with a divergence smaller than a divergence of any other pair of test Gaussian densities of the plurality of test Gaussian densities to be redundant in the test Gaussian model; merging the pair test Gaussian densities to generate a merged test Gaussian density; determining merging the pair of test Gaussian densities results in increasing a Bayesian Information Criterion of the test Gaussian mixture model; and accepting the merged test Gaussian density, wherein determining (i) the reference Gaussian mixture model comprises: iterative merging a pair of reference Gaussian densities of the plurality of reference Gaussian densities with a divergence smaller than a divergence of any other pair of reference Gaussian densities of the plurality of reference Gaussian densities to be redundant until merging the pair of reference Gaussian densities does not result in increasing a Bayesian Information Criterion of the reference Gaussian mixture model after merging, and wherein determining (i) the test Gaussian mixture model comprises: iterative merging a pair of test Gaussian densities of the plurality of test Gaussian densities with a divergence smaller than a divergence of any other pair of test Gaussian densities of the plurality of test Gaussian densities to be redundant until merging the pair of test Gaussian densities does not result in increasing a Bayesian Information Criterion of the test Gaussian mixture model after merging, wherein the divergence of the pair of reference Gaussian densities or test Gaussian densities comprises a Jeffrey's divergence of the pair of reference Gaussian densities or test Gaussian densities, and/or wherein the divergence of the pair of reference Gaussian densities or test Gaussian densities comprises a Kullback Leibler divergence of the pair of reference Gaussian densities or test Gaussian densities.

15. The method of claim 1, comprising: determining a reference diversity comprising a reference heterogeneity of the plurality of reference cells or a subpopulation of the plurality of reference cells and/or a test diversity comprising a test heterogeneity of the plurality of test cells or a subpopulation of the plurality of test cells, wherein the reference heterogeneity comprises: (i) an entropy of one, at least one, or each, of the plurality of reference Gaussian mixtures and/or associated reference weights and/or (ii) a reference covariance matrix of one, at least one, or each, the plurality of reference Gaussian mixtures, wherein the test heterogeneity comprises (i) an entropy of one, at least one, or each, of the plurality of test Gaussian mixtures and/or associated test weights and/or (ii) a test covariance matrix of one, at least one, or each, the plurality of test Gaussian mixtures, and/or wherein the subpopulation of the plurality of reference cells comprises 50%, 60%, 70%, 80%, 90%, 95%, 99%, or 100% cells of a cell type, and/or wherein the subpopulation of the plurality of test cells comprises 50%, 60%, 70%, 80%, 90%, 95%, 99%, or 100% cells of a cell type.

16. The method of claim 1, comprising: determining if a gene is upregulated or downregulated in a subpopulation of the plurality of test cells relative to a subpopulation of the plurality of reference cells, wherein determining if the gene is upregulated or downregulated comprises: determining if the gene is upregulated or downregulated in a subpopulation of the plurality of test cells relative to a subpopulation of the plurality of reference cells using a L1 distance between a test distribution of the single cell gene expression profiles of the gene in the subpopulation of the plurality of test cells and a reference distribution of the single cell gene expression profiles of the gene in the subpopulation of the plurality of reference cells, and/or wherein the subpopulation of the plurality of reference cells comprises 50%, 60%, 70%, 80%, 90%, 95%, 99%, or 100% cells of a cell type, and/or wherein the subpopulation of the plurality of test cells comprises 50%, 60%, 70%, 80%, 90%, 95%, 99%, or 100% cells of a cell type.

17. A system for single cell analysis comprising:
non-transitory memory configured to store executable instructions and single cell gene expression data comprising a plurality of reference gene expression vectors and a plurality of test gene expression vectors representing single cell gene expression profiles of a plurality of reference cells and a plurality of test cells respectively, wherein the plurality of test cells represents a heterogeneous cell population; and
a hardware processor in communication with the non-transitory memory, the hardware processor is programmed by the executable instructions to:
for each of the plurality of reference gene expression vectors and the plurality of test gene expression vectors, normalize gene expression values of the reference gene expression vector or the test gene expression vector to generate a normalized reference gene expression vector or a normalized test gene expression vector comprising normalized gene expression values;
determine (i) a gene feature matrix, comprising a plurality of gene features, and, for each of the plurality of normalized reference gene expression vectors and the plurality of normalized test gene expression vectors, (ii) reference gene feature weighting vector or a test gene feature weighting vector using a training matrix comprising a plurality normalized training gene expression vectors, wherein the plurality of reference gene feature weighting vectors and the plurality of test gene feature weighting vectors represent gene feature profiles of the plurality of reference cells and the plurality of test cells, respectively, wherein a size of a reference gene feature weighting vector is less than a size of a reference gene expression vector and a size of a test gene feature weighting vector is less than a size of a test gene expression vector, thereby reducing a dimension of the single cell gene expression data;
determine (i) a reference Gaussian mixture model comprising a plurality of reference Gaussian densities each associated with a reference weight and (ii) a test Gaussian mixture model comprising a plurality of test Gaussian densities each associated with a test weight from the plurality of reference gene feature weighting vectors and the plurality of test gene expression vectors, respectively, wherein each of (i) the plurality of reference Gaussian densities and associated reference weights and (ii) the plurality of test Gaussian densities and the associated test weights represents a subpopulation of the plurality of reference cells or the plurality of test cells, respectively, thereby modeling a distribution of gene expression states within the heterogeneous cell population;
align each of the plurality of test Gaussian densities to an aligned reference Gaussian density of the plurality of reference Gaussian densities; and
perform an analysis of the plurality of test cells relative to the plurality of reference cells using one, at least one, or each, of the plurality of test Gaussian densities and the aligned reference Gaussian density the test Gaussian density is aligned to.

18. A system for single cell analysis comprising:
non-transitory memory configured to store executable instructions and single cell gene expression data comprising a plurality of normalized reference gene expression vectors and a plurality of normalized test gene expression vectors representing single cell gene expression profiles of a plurality of reference cells and a plurality of test cells respectively, wherein the plurality of test cells represents a heterogeneous cell population; and
a hardware processor in communication with the non-transitory memory, the hardware processor is programmed by the executable instructions to:
determine (i) a gene feature matrix, comprising a plurality of gene features, and, for each of the plurality of normalized reference gene expression vectors and the plurality of normalized test gene expression vectors, (ii) reference gene feature weighting vector or a test gene feature weighting vector using a training matrix comprising a plurality normalized training gene expression vectors, wherein the plurality of reference gene feature weighting vectors and the plurality of test gene feature weighting vectors represent gene feature profiles of the plurality of reference cells and the plurality of test cells, respectively, wherein a size of a reference gene feature weighting vector is less than a size of a reference gene expression vector and a size of a test gene feature weighting vector is less than a size of a test gene expression vector, thereby
reducing a dimension of the single cell gene expres-
sion data;
determine (i) a reference Gaussian mixture model com-
prising a plurality of reference Gaussian densities
each associated with a reference weight and (ii) a test
Gaussian mixture model comprising a plurality of
test Gaussian densities each associated with a test
weight from the plurality of reference gene feature
weighting vectors and the plurality of test gene
expression vectors, respectively, wherein each of (i)
the plurality of reference Gaussian densities and
associated reference weights and (ii) the plurality of
test Gaussian densities and the associated test
weights represents a subpopulation of the plurality of
reference cells or the plurality of test cells, respec-
tively, thereby modeling a distribution of gene
expression states within the heterogeneous cell
population;
align each of the plurality of test Gaussian densities to
an aligned reference Gaussian density of the plurality
of reference Gaussian densities;
determine a Gaussian density difference between one of
the plurality of test Gaussian densities and the
aligned reference Gaussian density the test Gaussian
density is aligned to; and
determine a difference between the plurality of test
cells, or a subpopulation thereof, and the plurality of
reference cells, or a subpopulation thereof, using the
Gaussian density difference.

19. The system of claim 17
wherein to perform the analysis, the hardware processor
is programmed by the executable instructions to: per-
form the analysis of the plurality of test cells relative to
the plurality of reference cells using one of the plurality
of test Gaussian densities and the associated test weight
and the aligned reference Gaussian density the test
Gaussian density is aligned to and the associated ref-
erence weight, wherein to determine the difference, the
hardware processor is programmed by the executable
instructions to: determine the difference of the plurality
of test cells and the plurality of reference cells using
one of the plurality of test Gaussian densities and the
associated test weight and the aligned reference Gauss-
ian density the test Gaussian density is aligned to and
the associated reference weight, or wherein to deter-
mine the Gaussian density difference, the hardware
processor is programmed by the executable instructions
to: determine the Gaussian density difference between
one of the plurality of test Gaussian densities and the
associated test weight and the aligned reference Gauss-
ian density the test Gaussian density is aligned to and
the associated reference weight.

20. The system of claim 17
wherein to perform the analysis, the hardware processor
is programmed by the executable instructions to: per-
form the analysis of the plurality of test cells relative to
the plurality of reference cells using a test centroid and
a test covariance matrix of one of the plurality of test
Gaussian densities and the associated test weight and a
reference centroid and a reference covariance matrix of
the aligned reference Gaussian density the test Gauss-
ian mixture component is aligned to and the associated
reference weight, wherein to determine the difference,
the hardware processor is programmed by the execut-
able instructions to: determine the difference between
one of the plurality of test cells and to the plurality of reference cells using a test centroid and a test covari-
ance matrix of one of the plurality of test Gaussian
densities and the associated test weight and a reference
centroid and a reference covariance matrix of the
aligned reference Gaussian density the test Gaussian
mixture component is aligned to and the associated
reference weight, wherein to determine the Gaussian
density difference, the hardware processor is pro-
grammed by the executable instructions to: determine
the Gaussian density difference comprising a test cen-
troid and a test covariance matrix of one of the plurality
of test Gaussian densities and the associated test weight
and a reference centroid and a reference covariance
matrix of the aligned reference Gaussian density the
test Gaussian mixture component is aligned to and the
associated reference weight, wherein to perform the
analysis, or to determine the difference, the hardware
processor is programmed by the executable instructions
to: determine a centroid delta of the test centroid and
the reference centroid; determine a covariance matrix
delta of the test covariance matrix and the reference
covariance matrix; determine a weight delta of the test
weight and the reference weight; and perform the
analysis of the plurality of test cells relative to the
plurality of reference cells using the centroid delta, the
covariance matrix delta, and the weight delta, or deter-
mine the difference between the plurality of test cells
and the plurality of reference cells using the centroid
delta, the covariance matrix delta, and the weight delta,
or wherein the Gaussian density difference comprises a
centroid delta of the test centroid and the reference
centroid, and/or a weight delta of the test weight and
the reference weight, wherein the centroid delta repre-
sents a change in gene features of a subpopulation of
cells represented by the test Gaussian densities or the
aligned reference Gaussian density, wherein the cova-
riance matrix delta represents a change in a spread of
the gene features of the subpopulation of cells, and
wherein the weight delta represents a change in abun-
dance of the subpopulation of cells, and/or wherein the
centroid delta comprises a difference, a norm, or a
Frobenius norm of the test centroid and the reference
centroid, wherein the covariance matrix delta com-
prises a difference or a norm of the test covariance
matrix and the reference covariance matrix, and a
weight delta comprises a difference or a norm of the test
weight and the reference weight.

21. The system of claim 17
wherein each, or at least one, of the plurality of reference
cells is associated with a first annotation, and wherein
the hardware processor is programmed by the execut-
able instructions to: determine a second annotation of
each, or at least one, of the plurality of reference
Gaussian densities using the first annotation associated
with each, or at least one, of the plurality of reference
cells, wherein the first annotation and/or the second
annotation comprises a function annotation, a pathway
annotation, a cell-type annotation, and/or a tissue-type
annotation, and/or wherein the hardware processor is
programmed by the executable instructions to:
determine a third annotation of each, or at least one, of the
plurality of test Gaussian densities using the second
annotation associated with the aligned reference Gauss-
ian density the test Gaussian density is aligned to.

22. The system of claim 17
wherein the plurality of reference cells comprises healthy
cells and the plurality of test cells comprises diseased cells, wherein the plurality of reference cells comprises cells cultured in the absence of a drug or a signal and wherein the plurality of test cells comprises cells cultured in the presence of the drug or the signal, wherein the plurality of reference cells comprises cells from a first subject not treated with a drug and wherein the plurality of test cells comprises cells from the first subject treated with the drug, and/or wherein the plurality of reference cells comprises cells from a first tissue type and wherein the plurality of test cells comprises cells from a second tissue type.

23. The system of claim 17 wherein to perform the analysis, the hardware processor is programmed by the executable instructions to: determine similarities of and difference between the plurality of reference cells and the plurality of test cells, wherein to perform the analysis, the hardware processor is programmed by the executable instructions to: determine a gene feature of the plurality of gene features absent or present in the plurality of reference cells is present or absent in the plurality of test cells, and/or wherein to perform the analysis, the hardware processor is programmed by the executable instructions to: determine a similarity between the plurality of reference cells and the plurality of test cells using a log-likelihood ratio score of (i) one, at least one, or each of, the plurality of reference Gaussian mixtures and associated reference weights and (ii) one, at least one, or each of, the plurality of test Gaussian mixtures and associated test weights.

24. The system of claim 17 wherein the single cell gene expression data comprises a plurality of second reference gene expression vectors representing single cell gene expression profiles of a plurality of second reference cells, wherein to normalize, the hardware processor is programmed by the executable instructions to: for each of the plurality of second reference gene expression vectors, normalize gene expression values of the second reference gene expression vector to generate a normalized second reference gene expression vector comprising normalized gene expression values, wherein to determine the gene feature matrix, the hardware processor is programmed by the executable instructions to: for each of the plurality of normalized second reference gene expression vectors, determine a second reference gene feature weighting vector using the training matrix, wherein the plurality of second reference gene feature weighting vectors represent second gene feature profiles of the plurality of second reference cells, wherein to determine (i) the reference Gaussian mixture model, the hardware processor is programmed by the executable instructions to: determine a second reference Gaussian mixture model comprising a plurality of second reference Gaussian densities each associated with a second reference weight, wherein each of the plurality of second reference Gaussian densities and associated reference weights represents a second subpopulation of the plurality of second reference cells, and wherein to perform the analysis, the hardware processor is programmed by the executable instructions to: perform the analysis of the plurality of test cells relative to the plurality of reference cells and the plurality of second reference cells using the plurality of reference Gaussian densities, the plurality of second reference Gaussian densities, and the plurality of test Gaussian densities, wherein the plurality of gene expression vectors comprises a plurality of first reference gene expression vectors and a plurality of second reference gene expression vectors representing single cell gene expression profiles of a plurality of first reference cells and a plurality of second reference cells of the plurality of cells, wherein the plurality of first reference cells comprises healthy cells, and wherein the plurality of second reference cells comprises diseased cells, wherein the plurality of first reference cells is from a first tissue, and wherein the plurality of second reference cells is from a second tissue, and/or wherein the first tissue and the second tissue are of different tissue types.

25. The system of claim 24, wherein to perform the analysis, the hardware processor is programmed by the executable instructions to:
determine a first similarity between the plurality of first reference cells and the plurality of test cells using a first log-likelihood ratio score of (i) one, at least one, or each of, the plurality of first reference Gaussian mixtures and associated first reference weights and (ii) one, at least one, or each of, the plurality of test Gaussian mixtures and associated test weights;
determine a second similarity between the plurality of second reference cells and the plurality of test cells using a second log-likelihood ratio score of (i) one, at least one, or each of, the plurality of second reference Gaussian mixtures and associated second reference weights and (ii) one, at least one, or each of, the plurality of test Gaussian mixtures and associated test weights; and
determine the plurality of test cells to be more similar to the plurality of first reference cells and the plurality of second reference cells based on the first similarity and the second similarity.

26. The system of claim 24 wherein to perform the analysis, the hardware is processor is programmed by the executable instructions to: determine a probability of the plurality of test cells, or a subpopulation thereof, to be a first reference cell type of the plurality of first reference cells, or a subpopulation thereof, relative to the a second reference cell type of the plurality of second reference cells, or a subpopulation thereof, with respect to a difference in a first condition for culturing the plurality of first reference cells and a second condition for culturing the plurality of second reference cells, wherein to determine the probability, the hardware is processor programmed by the executable instructions to: determine the probability using multinomial logistic regression, and/or wherein the plurality of first reference cells comprises a first reference type of cells and is associated with a first reference label, wherein the plurality of second reference cells comprises a second reference type of cells and is associated with a second reference label, and wherein to perform the analysis, the hardware processor is programmed by the executable instructions to: determine a probability of the plurality of test cells to be the reference type of cells using (i) the plurality of first reference Gaussian densities and/or the associated first reference weights and (ii) the plurality of test Gaussian densities and/or the associated test weights; determine a probability of the plurality of test cells to be the second reference type of cells using (i) the plurality of second reference Gaussian densities and/or the associated second reference weights and (ii) the plurality of test Gaussian densities and/or the associated test weights; and determine a test label of the plurality of test cells to be the reference label or the second reference label based on the probability and the second probability.

27. The system of claim 17 wherein the single cell gene expression data comprises a plurality of second test gene expression vectors representing single cell gene expression profiles of a plurality of second test cells, wherein to normalize, the hardware processor is programmed by the executable instructions to: for each of the plurality of second test gene expression vectors, normalize gene expression values of the second test gene expression vector to generate a normalized second test gene expression vector comprising normalized gene expression values, wherein to determine the gene feature matrix, the hardware processor is programmed by the executable instructions to: for each of the plurality of normalized second test gene expression vectors, determine a second test gene feature weighting vector using the training matrix, wherein the plurality of second test gene feature weighting vectors represent second gene feature profiles of the plurality of second test cells, wherein to determine (i) the reference Gaussian mixture model, the hardware processor is programmed by the executable instructions to: determine a second test Gaussian mixture model comprising a plurality of second test Gaussian densities each associated with a second test weight, wherein each of the plurality of second test Gaussian densities and associated test weights represents a second subpopulation of the plurality of second test cells, and wherein to perform the analysis, the hardware processor is programmed by the executable instructions to: perform an analysis of the plurality of second test cells relative to the plurality of reference cells using the plurality of reference Gaussian densities and the plurality of second test Gaussian densities, wherein to perform the analysis, the hardware processor is programmed by the executable instructions to: perform an analysis of the plurality of test cells relative to the plurality of second test cells using the plurality of test Gaussian densities and the plurality of second test Gaussian densities, wherein the plurality of gene expression vectors comprises a plurality of first test gene expression vectors and a plurality of second test gene expression vectors representing single cell gene expression profiles of a plurality of first test cells and a plurality of second test cells of the plurality of cells, wherein to perform the analysis, the hardware processor is programmed by the executable instructions to: perform an analysis of the plurality of first test cells and the plurality of second test cells relative to the plurality reference cells using the plurality of reference Gaussian densities and a plurality of first test Gaussian densities and the plurality of second test Gaussian densities of the plurality of test Gaussian densities, wherein the plurality of first test cells is originally of a first test cell type or from a first test tissue type and cultured under a first test condition, wherein the plurality of second test cells is originally of a second test cell type or from a second test tissue type and cultured under a second test condition, and wherein the plurality of reference cells is originally of a reference cell type or from a reference tissue type and cultured under a reference condition, wherein the plurality of first test cells is cultured under a first test condition and of a first test cell type and, wherein the plurality of second test cells is cultured under a second test condition and of a second test cell type, and wherein the plurality of reference cells is cultured under a reference condition and of a reference cell type, wherein the first test cell type, the second test cell type, and/or the reference cell type are identical, wherein the first tissue type, the second test tissue type, and/or the reference tissue type are identical, and/or wherein the first test condition, the second test condition, and/or the reference condition are identical, wherein the first test cell type, the second test cell type, and/or the reference cell type are different, wherein the first tissue type, the second test tissue type, and/or the reference tissue type are different, and/or wherein the first test condition, the second test condition, and/or the reference condition are different, wherein the first test condition comprises presence of a first drug, signal, or environmental condition, and wherein the second test condition comprises presence of a second drug, signal, or environmental condition, wherein the reference condition comprises no first drug, signal, and environmental condition and/or no second drug, signal, and environmental condition, wherein the first test condition, second test condition, and/or the reference condition comprise different concentrations or extents of a drug, signal, or environmental condition, and/or wherein the plurality of first test cells is from a first sample of a subject at a first time, and wherein the plurality of second test cells is from a second sample of the subject at a second time.

28. The system of claim 27 wherein to perform the analysis, the hardware processor is programmed by the executable instructions to: determine a first similarity between the plurality of first test cells and the plurality of reference cells using a first log-likelihood ratio score of (i) one, at least one, or each of, the plurality of first test Gaussian mixtures and associated first test weights and (ii) one, at least one, or each of, the plurality of reference Gaussian mixtures and associated reference weights; determine a second similarity between the plurality of second test cells and the plurality of reference cells using a second log-likelihood ratio score of (i) one, at least one, or each of, the plurality of second test Gaussian mixtures and associated second test weights and (ii) one, at least one, or each of, the plurality of reference Gaussian mixtures and associated reference weights; and determine the plurality of first test cells or the plurality of second test cells to be more similar to the plurality of reference cells based on the first similarity and the second similarity.

29. The system of claim 27 wherein the hardware processor is programmed by the executable instructions to: separate the plurality of test gene expression vectors to generate a plurality of first test gene expression vectors and a plurality of second gene expression vectors.

30. The method of claim 1, wherein the size of the reference gene feature weighting vector and the size of the test gene feature weighting vector are from 5 to 30 and the size of the reference gene expression vector and the size of the test gene expression vector are from 1000 to 20000.

* * * * *